US012583900B2

(12) United States Patent
Shen et al.

(10) Patent No.: US 12,583,900 B2
(45) Date of Patent: Mar. 24, 2026

(54) PEPTIDE CONJUGATES AND METHODS OF USE

(71) Applicant: The Scripps Research Institute, La Jolla, CA (US)

(72) Inventors: Weijun Shen, San Diego, CA (US); Elsa Pflimlin, San Diego, CA (US); Sam Lear, Del Mar, CA (US); Zaid Amso, El Cajon, CA (US); Peter G. Schultz, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 855 days.

(21) Appl. No.: 17/782,573

(22) PCT Filed: Dec. 3, 2020

(86) PCT No.: PCT/US2020/063149
§ 371 (c)(1),
(2) Date: Jun. 3, 2022

(87) PCT Pub. No.: WO2021/113535
PCT Pub. Date: Jun. 10, 2021

(65) Prior Publication Data
US 2023/0071371 A1      Mar. 9, 2023

Related U.S. Application Data

(60) Provisional application No. 62/994,791, filed on Mar. 25, 2020, provisional application No. 62/943,667, filed on Dec. 4, 2019.

(51) Int. Cl.
| | |
|---|---|
| *C07K 14/605* | (2006.01) |
| *A61K 38/00* | (2006.01) |
| *A61K 47/54* | (2017.01) |
| *A61K 47/60* | (2017.01) |
| *A61P 3/04* | (2006.01) |
| *A61P 25/16* | (2006.01) |
| *A61P 25/28* | (2006.01) |

(52) U.S. Cl.
CPC .......... *C07K 14/605* (2013.01); *A61K 47/542* (2017.08); *A61K 47/60* (2017.08); *A61P 3/04* (2018.01); *A61P 25/16* (2018.01); *A61P 25/28* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 3,854,480 | A | 12/1974 | Zaffaroni |
| 3,887,699 | A | 6/1975 | Yolles |
| 4,452,775 | A | 6/1984 | Kent |
| 4,485,045 | A | 11/1984 | Regen |
| 4,544,545 | A | 10/1985 | Ryan et al. |
| 4,675,189 | A | 6/1987 | Kent et al. |
| 5,133,974 | A | 7/1992 | Paradissis et al. |
| 5,407,686 | A | 4/1995 | Patel et al. |
| 5,654,010 | A | 8/1997 | Johnson et al. |
| 5,736,152 | A | 4/1998 | Dunn |
| 5,750,497 | A | 5/1998 | Havelund et al. |
| 5,759,807 | A | 6/1998 | Breece et al. |
| 5,811,395 | A | 9/1998 | Schwabe et al. |
| 5,863,552 | A | 1/1999 | Yue |
| 5,866,538 | A | 2/1999 | Norup et al. |
| 6,011,007 | A | 1/2000 | Havelund et al. |
| 6,051,551 | A | 4/2000 | Hughes et al. |
| 6,268,343 | B1 | 7/2001 | Knudsen et al. |
| 6,372,716 | B1 | 4/2002 | Bush et al. |
| 6,444,641 | B1 | 9/2002 | Flora |
| 6,566,329 | B1 | 5/2003 | Meyn et al. |
| 6,685,940 | B2 | 2/2004 | Andya et al. |
| 6,869,930 | B1 | 3/2005 | Havelund et al. |
| 6,890,518 | B2 | 5/2005 | Patton et al. |
| 7,563,770 | B2 | 7/2009 | Larsen et al. |

(Continued)

FOREIGN PATENT DOCUMENTS

| | | |
|---|---|---|
| CA | 1176565 A | 10/1984 |
| CA | 2924109 A1 | 3/2015 |

(Continued)

OTHER PUBLICATIONS

Lear et al. "Engineering of a Potent, Long-Acting NPY2R Agonist for Combination with a GLP-1R Agonist as a Multi-Hormonal Treatment for Obesity" J. Med. Chem. 63:9660-9671. (Year: 2020).*

(Continued)

*Primary Examiner* — Sudhakar Katakam
*Assistant Examiner* — Zachary J Miknis
(74) *Attorney, Agent, or Firm* — WILSON SONSINI GOODRICH & ROSATI

(57) ABSTRACT

Peptide conjugates comprising a peptide selected from a peptide that modulates the PYY receptor, a peptide that modulates both the GLP-1 receptor and the GCG receptor, a peptide that modulates both the GLP-1 receptor and the GIP receptor, and a peptide that modulates the GLP-1 receptor; and a staple attached to the peptide at a first amino acid and a second amino acid are disclosed herein. Also provided are peptide conjugates comprising prolactin-releasing peptide. The peptide conjugates may be used for treating conditions such as obesity. Further provided are stapled prolactin-releasing peptide.

5 Claims, 36 Drawing Sheets

Specification includes a Sequence Listing.

(56) References Cited

U.S. PATENT DOCUMENTS

| | | | |
|---|---|---|---|
| 7,781,567 | B2 | 8/2010 | Wagner et al. |
| 7,928,058 | B2 | 4/2011 | Sinha Roy et al. |
| 7,960,506 | B2 | 6/2011 | Nash |
| 7,981,998 | B2 | 7/2011 | Nash |
| 7,981,999 | B2 | 7/2011 | Nash |
| 8,071,541 | B2 | 12/2011 | Arora et al. |
| 8,129,343 | B2 | 3/2012 | Lau et al. |
| 8,217,145 | B2 | 7/2012 | Wang et al. |
| 8,288,339 | B2 | 10/2012 | Gegg, Jr. et al. |
| 8,399,405 | B2 | 3/2013 | Nash et al. |
| 8,420,598 | B2 | 4/2013 | Lee et al. |
| 8,454,971 | B2 | 6/2013 | Day et al. |
| 8,486,384 | B2 | 7/2013 | Shen et al. |
| 8,507,428 | B2 | 8/2013 | DiMarchi et al. |
| 8,524,653 | B2 | 9/2013 | Nash et al. |
| 8,637,686 | B2 | 1/2014 | Nash |
| 8,703,701 | B2 | 4/2014 | Dimarchi |
| 8,735,539 | B2 | 5/2014 | Kraynov et al. |
| 8,808,694 | B2 | 8/2014 | Nash et al. |
| 9,062,124 | B2 | 6/2015 | DiMarchi et al. |
| 9,156,901 | B2 | 10/2015 | Riber et al. |
| 9,254,311 | B2 | 2/2016 | Bancel et al. |
| 9,474,780 | B2 | 10/2016 | Bokvist et al. |
| 10,039,809 | B2 * | 8/2018 | Shen .................... A61P 3/04 |
| 10,286,078 | B2 | 5/2019 | Shen et al. |
| 10,683,353 | B2 | 6/2020 | Wang et al. |
| 10,987,427 | B2 | 4/2021 | Shen et al. |
| 11,007,252 | B2 * | 5/2021 | Shen ............. A61K 38/2278 |
| 11,865,160 | B2 * | 1/2024 | Shen ............. A61K 47/554 |
| 12,329,823 | B2 | 6/2025 | Shen et al. |
| 12,337,028 | B2 | 6/2025 | Shen et al. |
| 2003/0158376 | A1 | 8/2003 | Schwabe et al. |
| 2005/0176108 | A1 | 8/2005 | Kim et al. |
| 2005/0192217 | A1 | 9/2005 | Muhlradt et al. |
| 2007/0212355 | A1 | 9/2007 | Baker et al. |
| 2008/0262200 | A1 | 10/2008 | Nash |
| 2008/0305519 | A1 | 12/2008 | Lin et al. |
| 2009/0047711 | A1 | 2/2009 | Nash |
| 2009/0088553 | A1 | 4/2009 | Nash |
| 2009/0117104 | A1 | 5/2009 | Baker et al. |
| 2009/0186817 | A1 | 7/2009 | Ghosh et al. |
| 2009/0239784 | A1 | 9/2009 | Jonassen et al. |
| 2009/0275519 | A1 | 11/2009 | Nash et al. |
| 2009/0326192 | A1 | 12/2009 | Nash et al. |
| 2010/0029554 | A1 | 2/2010 | Ghosh et al. |
| 2010/0093086 | A1 | 4/2010 | Lin et al. |
| 2010/0184133 | A1 | 7/2010 | Norgaard et al. |
| 2010/0184628 | A1 | 7/2010 | Nash |
| 2010/0210515 | A1 | 8/2010 | Nash et al. |
| 2010/0216688 | A1 | 8/2010 | Nash et al. |
| 2010/0239554 | A1 | 9/2010 | Schellenberger et al. |
| 2010/0292172 | A1 | 11/2010 | Ghosh et al. |
| 2010/0298201 | A1 | 11/2010 | Nash et al. |
| 2011/0046056 | A1 | 2/2011 | Bianchi et al. |
| 2011/0144303 | A1 | 6/2011 | Nash et al. |
| 2011/0166321 | A1 | 7/2011 | Garibay et al. |
| 2011/0223149 | A1 | 9/2011 | Nash et al. |
| 2011/0243942 | A1 | 10/2011 | Wang |
| 2011/0263815 | A1 | 10/2011 | Nash |
| 2012/0040889 | A1 | 2/2012 | Nash et al. |
| 2012/0046229 | A1 | 2/2012 | Kraynov et al. |
| 2012/0149648 | A1 | 6/2012 | Nash et al. |
| 2012/0172311 | A1 | 7/2012 | Nash et al. |
| 2012/0178700 | A1 | 7/2012 | Nash et al. |
| 2012/0190818 | A1 | 7/2012 | Nash |
| 2012/0264674 | A1 | 10/2012 | Nash et al. |
| 2013/0023646 | A1 | 1/2013 | Nash et al. |
| 2013/0040884 | A1 | 2/2013 | Lau et al. |
| 2013/0123169 | A1 | 5/2013 | Kawahata et al. |
| 2013/0203673 | A1 | 8/2013 | Drucker et al. |
| 2013/0210745 | A1 | 8/2013 | Guerlavais et al. |
| 2013/0237481 | A1 | 9/2013 | Kraynov et al. |
| 2014/0057857 | A1 | 2/2014 | Lin et al. |
| 2014/0128581 | A1 | 5/2014 | Darlak et al. |
| 2014/0135255 | A1 | 5/2014 | Nash et al. |
| 2014/0135473 | A1 | 5/2014 | Nash |
| 2014/0148390 | A1 | 5/2014 | Haupts et al. |
| 2014/0309168 | A1 | 10/2014 | Rosendahl |
| 2014/0329742 | A1 | 11/2014 | Dock et al. |
| 2016/0317623 | A1 | 11/2016 | Shen et al. |
| 2017/0260248 | A1 | 9/2017 | Walensky et al. |
| 2018/0118758 | A1 | 5/2018 | Jacques |
| 2018/0207276 | A1 | 7/2018 | Shen |
| 2018/0228907 | A1 | 8/2018 | Crew et al. |
| 2019/0000928 | A1 | 1/2019 | Shen et al. |
| 2020/0024322 | A1 | 1/2020 | Abraham et al. |
| 2022/0000981 | A1 | 1/2022 | Shen et al. |
| 2022/0072104 | A1 | 3/2022 | Shen et al. |
| 2023/0057847 | A1 | 2/2023 | Shen et al. |
| 2024/0148884 | A1 | 5/2024 | Shen et al. |
| 2024/0207363 | A1 | 6/2024 | Shen et al. |
| 2025/0235508 | A1 | 7/2025 | Shen et al. |

FOREIGN PATENT DOCUMENTS

| | | | |
|---|---|---|---|
| CA | 2933701 | A1 | 6/2015 |
| CN | 101568350 | A | 10/2009 |
| CN | 103201285 | A | 7/2013 |
| DE | 3218121 | A1 | 11/1983 |
| EP | 0133988 | A2 | 3/1985 |
| JP | 2008533105 | A | 8/2008 |
| WO | WO-9315722 | A1 | 8/1993 |
| WO | WO-9420069 | A1 | 9/1994 |
| WO | WO-9607399 | A1 | 3/1996 |
| WO | WO-9629998 | A1 | 10/1996 |
| WO | WO-9633193 | A1 | 10/1996 |
| WO | WO-9640072 | A2 | 12/1996 |
| WO | WO-9703692 | A1 | 2/1997 |
| WO | WO-2004100997 | A2 | 11/2004 |
| WO | WO-2006066258 | A2 | 6/2006 |
| WO | WO-2006097537 | A2 | 9/2006 |
| WO | WO-2007109135 | A2 | 9/2007 |
| WO | WO-2008057298 | A2 | 5/2008 |
| WO | WO-2010096052 | A1 | 8/2010 |
| WO | WO-2010096142 | A1 | 8/2010 |
| WO | WO-2011039096 | A1 | 4/2011 |
| WO | WO-2012003995 | A1 | 1/2012 |
| WO | WO-2012006598 | A2 | 1/2012 |
| WO | WO-2012011752 | A2 | 1/2012 |
| WO | WO-2012024452 | A2 | 2/2012 |
| WO | WO-2012088116 | A2 | 6/2012 |
| WO | WO-2012088379 | A2 | 6/2012 |
| WO | WO-2012149563 | A1 | 11/2012 |
| WO | WO-2013004607 | A1 | 1/2013 |
| WO | WO-2013007563 | A1 | 1/2013 |
| WO | WO-2013100704 | A1 | 7/2013 |
| WO | WO-2013130683 | A2 | 9/2013 |
| WO | WO-2014059213 | A1 | 4/2014 |
| WO | WO-2015038938 | A1 | 3/2015 |
| WO | WO-2015095406 | A1 | 6/2015 |
| WO | WO-2016111971 | A1 | 7/2016 |
| WO | WO-2016149501 | A2 | 9/2016 |
| WO | WO-2016205488 | A1 | 12/2016 |
| WO | WO-2017007612 | A1 | 1/2017 |
| WO | WO-2017024317 | A2 | 2/2017 |
| WO | WO-2017024318 | A1 | 2/2017 |
| WO | WO-2017210600 | A1 | 12/2017 |
| WO | WO-2018119448 | A1 | 6/2018 |
| WO | WO-2018148440 | A1 | 8/2018 |
| WO | WO-2018148443 | A1 | 8/2018 |
| WO | WO-2018187401 | A1 | 10/2018 |
| WO | WO-2019165229 | A1 | 8/2019 |
| WO | WO-2019203645 | A1 | 10/2019 |
| WO | WO-2020077278 | A1 | 4/2020 |
| WO | WO-2021113524 | A2 | 6/2021 |
| WO | WO-2021113535 | A1 | 6/2021 |
| WO | WO-2022257979 | A1 | 12/2022 |

OTHER PUBLICATIONS

Eppstein et al. Biological activity of liposome-encapsulated murine interferon gamma is mediated by a cell membrane receptor. PNAS USA 82(11):3688-92 (1985).

(56)            References Cited

OTHER PUBLICATIONS

Langer. Controlled release of macromolecules. Chem. Tech. 12:98-105 (1982).
Langer, et al. Biocompatibility of polymeric delivery systems for macromolecules. J Biomed Mater Res. 15(2):267-277 (1981).
Lear et al. Recombinant Expression and Stapling of a Novel Long-Acting GLP-1R Peptide Agonist. Molecules 25(11):2508 (2020).
U.S. Appl. No. 17/317,631 Office Action dated May 12, 2023.
U.S. Appl. No. 17/485,171 Office Action dated May 10, 2023.
U.S. Appl. No. 17/485,171 Office Action dated Nov. 3, 2023.
Yang et al. Stapled, Long-Acting Glucagon-like Peptide 2 Analog with Efficacy in Dextran Sodium Sulfate Induced Mouse Colitis Models. J Med Chem 61(7):3218-3223 (2018).
Dermatitis from Merck Manual, (2020). Accessed on Aug. 30, 2020, pp. 1-4.
Inflammation from Merck Manual, (2020). Accessed on Aug. 30, 2020, pp. 1-3.
Inflammatory disorders from Merck Manual, (2020). Accessed on Aug. 30, 2020, pp. 1-4.
U.S. Appl. No. 18/514,838 Office Action dated Jan. 22, 2025.
Das, Shinjita. Psoriasis. Merck Manual, Professional Version, Sep. 2023; [retrieved on Sep. 28, 2024]. Available at URL:merckmanuals.com/professional/dermatologic-disorders/psoriasis-and-scaling-diseases/psoriasis? query=psoriasis pp. 1-20.
Kontzias, Apostolos. Osteoarthritis. Merck Manual, Professional Version, May 2020; [retrieved on Oct. 14, 2020]. Available at URL:https://www.merckmanuals.com/professional/musculoskeletal-and-connective-tissue-disorders/joint-disorders/osteoarthritis-oa pp. 1-10.
Korczyn, Amos D, and Miri Nussbaum. Emerging therapies in the pharmacological treatment of Parkinson's disease. Drugs 62(5):775-786 (2002).
Margolis, Russell L et al. Diagnosis of Huntington disease. Clinical chemistry 49(10): 1726-1732 (2003).
Nguyen, Minhhuyen. Colorectal Cancer. Merck Manual, Consumer Version, Jul. 2019; [retrieved on Oct. 24, 2020]. Available at URL:https://www.merckmanuals.com/home/digestive-disorders/tumors-of-the-digestive-system/colorectal-cancer pp. 1-8.
Obesity. NHS, May 2019; [retrieved on Oct. 24, 2020]. Available at URL:https://www.nhs.uk/conditions/obesity/ pp. 1-6.
Prevention of Cardiovascular Disease: Guidelines for assessment and management of cardiovascular risk. World Health Organization, Jan. 2007; [retrieved on Mar. 16, 2015]. Available at URL:who.intJcardiovascular_diseases/guidelines/Full%20text.pdf pp. 1-92.
U.S. Appl. No. 17/485,171 Office Action dated May 28, 2024.
U.S. Appl. No. 18/514,838 Office Action dated Sep. 29, 2024.
Druce et al. Investigation of Structure-Activity Relationships of Oxyntomodulin (Oxm) Using Oxm Analogs. Endocrinology 150(4):1712-1721 (Apr. 2009).
Muppidi et al. Rational design of proteolytically stable, cell-permeable peptide-based selective Mcl-1 inhibitors. J. Am. Chem. Soc. 134:14734-14737 (Aug. 2012).
Patterson et al. Functional association of the N-terminal residues with the central region in glucagon-related peptides. J. Pept. Sci. 17:659-666 (2011).
PCT/US2016/037834 International Search Report and Written Opinion dated Oct. 26, 2016.
U.S. Appl. No. 17/317,631 Non-Final Office Action dated Dec. 23, 2022.
Co-pending U.S. Appl. No. 19/169,978, inventors Shen; Weijun et al., filed Apr. 3, 2025.
Co-pending U.S. Appl. No. 19/208,499, inventors Shen; Weijun et al., filed May 14, 2025.
Aicart-Ramos C. et al. Protein palmitoylation and subcellar trafficking. Biochim Biophys Acta 1808:2981-2994 (2011).
Altschul et al., Gapped BLAST and PSI-BLAST: a new generation of protein database search programs. Nucleic Acids Res. Sep. 1, 1997;25(17):3389-402.
Amso et al., A Peptide Engineering Platform for PEG-FA Stapled Long-acting Peptide Hormones. (2020).

Backer, et al. Chapter 16: Cysteine-Containing Fusion Tag for Site-Specific Conjugation of Therapeutic and Imaging Agents to Targeting Proteins, Peptide-Based Drug Design Methods and Protocols, Springer Protocols, pp. 275-294 (2008).
Bader, et al., Bioorganic synthesis of lipid-modified proteins for the study of signal transduction. Nature, 403:223-226 (Jan. 13, 2000).
Baosheng, Liu, Peptide PEGylation: The Next Generation Linking peptides to polythylene glycol, or PEGylation, has helped improve pharmaceutical therapeutics in several ways. A wave of new techniques is now ushering in further advances. Pharmaceutical Technology, 2011(3): 1-3 (May 1, 2011).
Bird, Gregory H. et al. Hydrocarbon double-stapling remedies the proteolytic instability of a lengthy peptide therapeutic. Proceedings of the National Academy of Sciences, 2010, vol. 107, No. 32, pp. 14093-14098.
Bloom, Stephen R. et al. Investigation of Structure-Activity Relationships of Oxyntomodulin (Oxm) Using Oxm Analogs. Endocrinology 150(4):1712-1721 (Apr. 2009).
Chalker et al. Chemical modification of proteins at cysteine: opportunities in chemistry and biology. Chem Asian J 4(5):630-640 (2009).
Chang, Y. et al. Stapled α-helical peptide drug development: A potent dual inhibitor of MDM2 and MDMX for p53-dependent cancer therapy, Proceedings of the National Academy of Sciences, e-pub. Aug. 14, 2013, vol. 110, No. 36, pp. E3445-E3454.
Cheng, W. and Lee-Yong Lim, Design, synthesis, characterization and in-vivo activity of a novel salmon calcitonin conjugate containing a novel PEG-lipid moiety. Journal of Pharmacy and Pharmacology, 62(3):296-304 (Mar. 2010).
Cheng, W. et al. Lipeo-sCT: A novel reversible lipidized salmon calcitonin derivative, its biophysical properties and hypocalcemic activity. European Journal of Pharmaceutical Sciences 37(2):151-159 (May 12, 2009).
Day et al., A new glucagon and GLP-1 co-agonist eliminates obesity in rodents. Nature Chemical Biology. 5(10): 749-757 (2009).
Day, J.W. et al. Optimization of co-agonism at GLP-1 and glucagon receptors to safely maximize weight reduction in DIO-rodents. Biopolymers, 98(5):443-450 (Apr. 2012).
DiMarchi, Richard D. et al. Functional association of the N-terminal residues with the central region in glucagon-related peptides. J. Pept. Sci. 17:659-666 (2011).
Finan et al., Unimolecular Dual Incretins Maximize Metabolic Benefits in Rodents, Monkeys, and Humans. Science Translational Medicine 5(209): 1-17 (2013).
Guldenhaupt, et al. Secondary structure of lipidated Ras bound to lipid bilayer. FEBS Journal275:5910-5918 (2008).
Havelund, S. The mechanism of protraction of insulin detemir, a long-acting, acylated analog of human insulin. Pharmaceutical Research, 21(9):1498-1504 (Aug. 2004).
Hossain; et al, "The Minimal Active Structure of Human Relaxin-2. Journal of Biological Chemistry, vol. 286, No. 43, pp. 37555-37565. Published Oct. 28, 2011.".
Hossain, Mohammed A. et al. Chimeric relaxin peptides highlight the role of the A-chain in the function of H2 relaxin. Peptides 35:102-106 (May 2012).
International Application No. PCT/US16/37834 International Search Report Issued Oct. 26, 2016.
International Application No. PCT/US2014/055457 International Preliminary Report on Patentability Issued Mar. 15, 2016.
International Application No. PCT/US2014/055457 International Search Report and Written Opinion Mailed Dec. 23, 2014.
International Application No. PCT/US2014/070977 International Preliminary Report on Patentability Mailed Jun. 30, 2016.
International Application No. PCT/US2014/070977 International Search Report and Written Opinion Mailed Mar. 27, 2015.
International Application No. PCT/US2016/022880 International Search Report and Written Opinion Mailed Oct. 7, 2016.
International Application No. PCT/US2016/037834 International Preliminary Report on Patentability Mailed Dec. 28, 2017.
Janout et al., Bioconjugate-Based Molecular Umbrellas. Bioconjugate Chemistry, 20(2): 183-192 (E-Pub Nov. 20, 2008).

(56) References Cited

OTHER PUBLICATIONS

Joregensen et al., Oxyntomodulin differentially affects glucagon-like peptide-1 receptor beta-arrestin recruitment and signaling throughGαs. The Journal of Pharmacology and Experimental Therapeutics. 322(1):148-154 (2007).

Karlin et al., Applications and statistics for multiple high-scoring segments in molecular sequences. Proc Natl Acad Sci U S A. Jun. 15, 1993;90(12):5873-7.

Koonin et al., Chapter 2: Evolutionary Concept in Genetics and Genomics. Sequence—Evolution—Function: Computational Approaches in Comparative Genomics. Boston: Kluwer Academic; 2003.

Lau et al., Peptide stapling techniques based on different macrocyclisation chemistries. Chemical Society Reviews. 44(1):91-102 (2015).

Lear et al., Engineering of a Potent, Long-Acting NPY2R Agonist for Combination with a GLP-1R Agonist as a Multi-Hormonal Treatment for Obesity. J Med Chem 63(17):9660-9671 (2020).

Lear et al., Engineering PEG-fatty acid stapled, long-acting peptide agonist for G protein-coupled receptors. Methods in Enzymology 622: 183-200 (2019).

Lear et al., Engineering PEG-fatty acid stapled, long-acting peptide agonists for G protein-coupled receptors. Methods in Enzymology 622: 183-200 (2019).

Lear et al., Peptide Engineering Strategies for Long-Acting Peptide Hormones. (2019) Abstract.

Lin, Q. et al. rational Design of Proteolytically Stable, Cell-Permeable peptide-Based Selective Mcl-1 Inhibitors. J. Am. Chem. Soc. 134:14734-14737 (Aug. 2012).

Lorenz, Martin et al. Recent progress and future options in the development of GLP-1 receptor agonists for the treatment of diabesity. Bioorganic & Medicinal Chemistry Letters 23(14): 4011-4018 (May 16, 2013).

Metra, M. et al. Effect of Serelaxin on Cardiac, Renal, and Hepatic Biomarkers in the Relaxin in Acute Heart Failure (RELAX-AHF) Development Program. Journal of the American College of Cardiology 61(2): 196-206 (Jan. 15, 2013).

Muller, et al. Chapter 2: Peptide carrier conjugation, Synthetic Peptides as Antigens, Laboratory Techniques in Biochemstry and Molecular Biology. 28:79-131 (1999).

Muppidi et al., Design and Synthesis of Potent, Long-Acting Lipidated Relaxin-2 Analogs. Bioconjugate Chem. 30: 83-89 (Dec. 2018).

Muppidi et al., Design of Potent and Proteolytically Stable Oxyntomodulin Analogs. ACS Chem. Biol. 11: 324-328 (2016).

Pan, et al. Design of a Long Acting Peptide Functioning as Both a Glucagon-like Peptide-1 Receptor Agonist and a Glucagon Receptor Antagonist. The Journal of Biological Chemistry 281(18):12506-12515 (May 5, 2008).

PCT/US2020/063130 International Search Report and Written Opinion dated May 24, 2021.

PCT/US2020/063149 International Search Report and Written Opinion dated Apr. 29, 2021.

Pflimlin et al., Design of a Long-Acting and Selective MEG-Fatty Acid Stapled Prolactin-Releasing Peptide Analog. ACS Med. Chem. Lett. 10: 1166-1172 (2019).

Pflimlin et al., Engineering a Potent, Long Acting and Periphery-Restricted Oxytocin Receptor Agonist with Anorexigenic and Body Weight Reducing Effects. J. Med. Chem. 63(1):382-390 (2020).

Pollaro et al., Strategies to prolong the plasma residence time of peptide drugs. Med. Chem. Commun. 1:319-324 (2010).

Rost, B. Twilight zone of protein sequence alignments. Protein engineering 12.2 (1999): 85-94.

Santoprete, A. et al. DPP-IV-resistant, long-acting oxyntomodulin derivatives. Journal Peptide Science, 17:270-280 (2011).

Schultz, P.G. et al. General Approach to the Synthesis of Short a-Helical Peptides. J. Am. Chem. Soc. 113:9391-9392 (1991).

Shah, Trishul, Bioconjugates: The Adaptable Challenge. BioPharm International The Science & Business of Biopharmaceuticals, 26(1):1-4 (Jan. 1, 2013).

Soloff, M. et al. Cloning, characterization, and expression of the rat relaxin gene. Gene 323:149-155 (2003).

Teerlink, et al. Serelaxin, recombinant human relaxin-2, for treatment of acute heart failure (RELAX-AHF): a randomised, placebo-controlled trial. Lancet 381:29-39 (Jan. 2013).

Trussel, et al. New strategy for the extension of the serum half-life of antibody fragments. Bioconjug Chem. Dec. 2009;20(12):2286-92. doi: 10.1021/bc9002772.

Underwood, Christina R. et al. Crystal Structure of Glucagon-like Peptide-1 in Complex with the Extracellular Domain of the Glucagon-like Peptide-1 Receptor. The Journal of Biological Chemistry 285(1): 723-730 (Jan. 1, 2010).

U.S. Appl. No. 14/917,689 Final Office Action Mailed Dec. 22, 2017.

U.S. Appl. No. 14/917,689 Non-Final Office Action Mailed May 30, 2017.

U.S. Appl. No. 14/917,689 Restriction Requirement Mailed Feb. 6, 2017.

U.S. Appl. No. 15/104,807 Non-final Office Action mailed Nov. 27, 2017.

U.S. Appl. No. 15/104,807 Notice of Allowance Mailed Apr. 26, 2018.

U.S. Appl. No. 15/104,807 Notice of Allowance Mailed May 10, 2018.

U.S. Appl. No. 15/104,807 Restriction Requirement Mailed Mar. 14, 2017.

U.S. Appl. No. 15/735,898 Final Office Action dated May 25, 2021.

U.S. Appl. No. 15/735,898 Final Office Action dated Jun. 22, 2020.

U.S. Appl. No. 15/735,898 Non-Final Office Action dated Jan. 8, 2020.

U.S. Appl. No. 16/000,829 Non-Final Office Action dated Aug. 27, 2020.

U.S. Appl. No. 16/000,829 Non-Final Office Action dated Mar. 5, 2020.

U.S. Appl. No. 16/405,594 Office Action dated Aug. 12, 2020.

Verdine, Gregory L. et al. Stapled Peptides for Intracellular Drug Targets. Methods in Enzymology, vol. 503, Chapter 1, pp. 1-31 (Dec. 2012).

Wade, John D. et al. The Chemical Synthesis of Relaxin and Related peptides: A Historical Perspective. Ann. N.Y. Acad. Sci. 1160: 11-15 (2009).

Walensky, Loren D. et al. Hydrocarbon-Stapled Peptides: Principles, Practice, and Progress, Journal of Medicinal Chemistry 57:6275-6288 (2014).

Webber et al., Genes and homology. Current Biology 14(9):R332-R333 (2004).

Wisniewski et al., Synthesis and Pharmacological Characterization of Novel Glucagon-like Peptide-2 (GLP-2) Analogues with Low Systemic Clearance. J Med Chem 59: 3129-3139 (2016).

Wisniewski et al., Synthesis and Pharmacological Characterization of Novel Glucagon-like Peptide-2 (GLP-2) Analogues with Low Systemic Clearance. J Med Chem 59: 3129-3139 (Mar. 2016).

Wu, Ye-Lin, et al. Addition of a cysteine to glucagon-like peptide-1 (GLP-1) conjugates GLP-1 to albumin in serum and prolongs GLP-1 action in vivo, Regulatory Peptides, 2010, vol. 164, No. 2, pp. 83-89.

Yang et al. Engineering a long-acting, potent GLP-1 analog for microstructure-based transdermal delivery. PNAS 113(15):4140-4145 (2016).

Yang et al., New Generation Oxyntomodulin Peptides with Improved Pharmacokinetic Profiles Exhibit Weight Reducing and Anti-Steatotic Properties in Mice. Bioconjugate Chem. 31(4):1167-1176 (2020).

Backus et al. Proteome-wide covalent ligand discovery in native biological systems. Nature 534(7608):570-574 (2016).

Bondeson, et al., Catalytic in vivo protein knockdown by small-molecule PROTACs. Nat Chem Biol 11(8):611-617 (Aug. 2015).

Bondeson et al. Lessons in PROTAC Design from Selective Degradation with a Promiscuous Warhead. Cell Chem Biol 25:78-87.e5 (2018).

Buckley et al. Small-molecule inhibitors of the interaction between the E3 ligase VHL and HIF1α. Angew Chem Int Ed Engl 51:11463-11467 (2012).

(56)          References Cited

OTHER PUBLICATIONS

Cal et al. Cysteine-selective reactions for antibody conjugation. Angewandte Chemi International Edition 53:10585-10587 (2014).

Chen et al. Plant E3 Ligases: Flexible Enzymes in a Sessile World. Molecular Plant 6(5):1388-1404 (2013).

Co-pending U.S. Appl. No. 15/104,807, inventors Shen; Weijun et al., filed Jun. 15, 2016.

Co-pending U.S. Appl. No. 15/735,898, inventors Shen; Weijun et al., filed Dec. 12, 2017.

Co-pending U.S. Appl. No. 16/000,829, inventors Shen; Weijun et al., filed Jun. 5, 2018.

Co-pending U.S. Appl. No. 17/317,631, inventors Shen; Weijun et al., filed May 11, 2021.

Co-pending U.S. Appl. No. 17/485,171, inventors Shen; Weijun et al., filed Sep. 24, 2021.

Co-pending U.S. Appl. No. 17/782,560, inventors Shen; Weijun et al., filed Jun. 3, 2022.

Co-pending U.S. Appl. No. 18/366,653, inventors Shen; Weijun et al., filed Aug. 7, 2023.

Co-pending U.S. Appl. No. 18/514,838, inventors Shen; Weijun et al., filed Nov. 20, 2023.

Co-pending U.S. Appl. No. 18/568,244, inventors Shen; Weijun et al., filed Dec. 7, 2023.

Deshaies et al.RING Domain E3 Ubiquitin Ligases. Annual Review Of Biochemistry 78(1):399-434 (2009).

Filippakopoulos et al.: Selective inhibition of BET bromodomains. Nature 468:1067-1073 (2010).

Gadd et al. Structural basis of PROTAC cooperative recognition for selective protein degradation. Nat Chem Biol 13:514-521 (2017).

Huang et al. A Chemoproteomic Approach to Query the Degradable Kinome Using a Multi-kinase Degrader. Cell Chem Biol 25:88-99 (2018).

Ito et al. Identification of a primary target of thalidomide teratogenicity. Science 327:1345-1350 (2010).

Jin et al., A family of diverse Cul4-Ddb1-interacting proteins includes Cdt2, which is required for S phase destruction of the replication factor Cdt1. Molecular Cell. 23(5):709-721 (2006).

Nabet et al. The dTAG system for immediate and target-specific protein degradation. Nat Chem Biol 14:431-441 (2018).

PCT/US2019/055958 International Search Report and Written Opinion dated Feb. 3, 2020.

Raina et al. PROTAC-induced BET protein degradation as a therapy for castration-resistant prostate cancer. PNAS USA 113:7124-7129 (2016).

Soucy et al. An inhibitor of NEDD8-activating enzyme as a new approach to treat cancer. Nature 458:732-736 (2009).

U.S. Appl. No. 16/600,326 Office Action dated Apr. 27, 2021.

U.S. Appl. No. 16/600,326 Office Action dated Dec. 2, 2021.

U.S. Appl. No. 16/600,326 Office Action dated May 23, 2022.

Vassilev et al. In vivo activation of the p53 pathway by small-molecule antagonists of MDM2. Science 303:844-848 (2004).

Weerapana et al. Quantitative reactivity profiling predicts functional cysteines in proteomes. Nature 468:790-795 (2010).

Winter et al. Drug Development. Phthalimide conjugation as a strategy for in vivo target protein degradation. Science 348:1376-1381 (2015).

Xu et al. ProLuCID: An improved SEQUEST-like algorithm with enhanced sensitivity and specificity. J Proteomics 129:16-24 (2015).

Zhang et al. Electrophilic PROTACs that degrade nuclear proteins by engaging DCAF16. Nature Chemical Biology 15:737-746 (2019).

* cited by examiner

FIG. 1A                              FIG. 1B

| | 0% FBS | 10% FBS |
|---|---|---|
| SEQ ID NO. 1 | | |
| SEQ ID NO. 2 | | |
| Conjugate 40 | | |
| Conjugate 62 | | |

* vehicle
* 187, 0.01 mg/kg
* 40, 0.04 mg/kg
* 40, 0.2 mg/kg
* 187, 0.01 mg/kg + 40, 0.04 mg/kg
* 187, 0.01 mg/kg+ 40, 0.02 mg/kg ▱ vehicle ▨ 187, 0.01 mg/kg ◰ 40, 0.04 mg/kg ▩ 40, 0.2 mg/kg ▢ 187, 0.01 mg/kg + 40, 0.04 mg/kg ▰ 187, 0.01 mg/kg+ 40, 0.02 mg/kg vehicle 187, 0.01 mg/kg 40, 0.04 mg/kg 40, 0.2 mg/kg 187, 0.01 mg/kg + 40, 0.04 mg/kg 187, 0.01 mg/kg+ 40, 0.02 mg/kg ⬜ vehicle ▨ 187, 0.01 mg/kg ▨ 40, 0.04 mg/kg ▨ 40, 0.2 mg/kg ⬜ 187, 0.01 mg/kg + 40, 0.04 mg/kg ⬛ 187, 0.01 mg/kg+ 40, 0.02 mg/kg -✕- vehicle
-◼- 187, 0.01 mg/kg
-△- 40, 0.04 mg/kg
-▼- 40, 0.2 mg/kg
-◇- 187, 0.01 mg/kg + 40, 0.04 mg/kg
-◆- 187, 0.01 mg/kg+ 40, 0.02 mg/kg
-○- Expected additivity 187 + 40, 0.04 mg/kg
-●- Expected additivity 187 + 40, 0.02 mg/kg

FIG. 4D

Legend:

- ✳ vehicle
- ◼ 187, 0.01 mg/kg
- △ 40, 0.04 mg/kg
- ▼ 40, 0.2 mg/kg
- ◇ 187, 0.01 mg/kg + 40, 0.04 mg/kg
- ◆ 187, 0.01 mg/kg + 40, 0.02 mg/kg

FIG. 4F

Stability in 2% plasma over 50 hours

CRE-GLP-1R stability

CRE-GLP-1R PK

CRE-GLP-1R PK

FIG. 7A
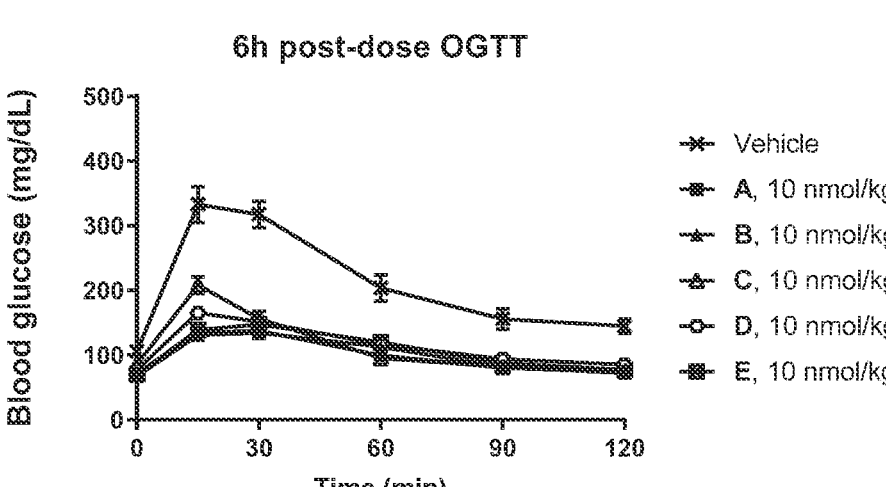
FIG. 7B
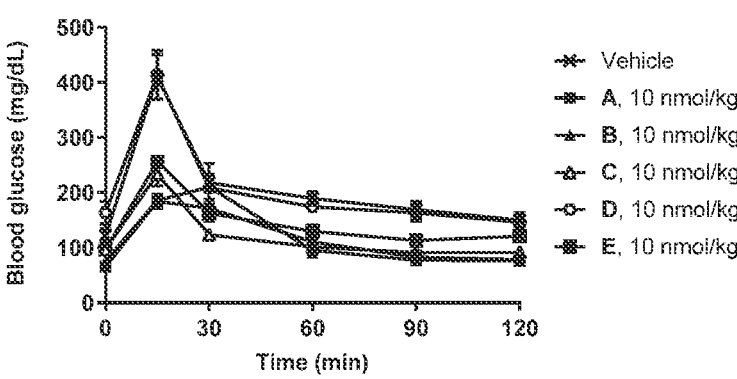
FIG. 7C
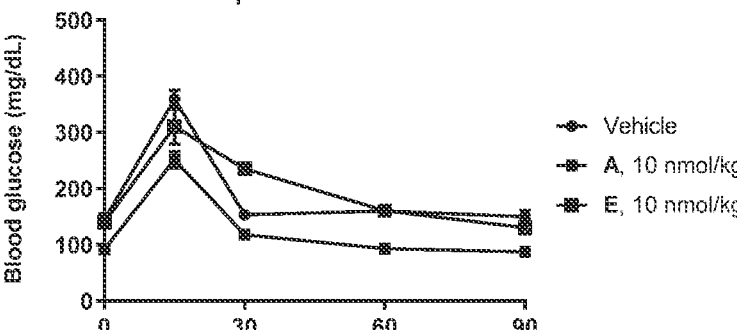

FIG. 7D
6h post-dose OGTT
FIG. 7E
48h post-dose OGTT AUC
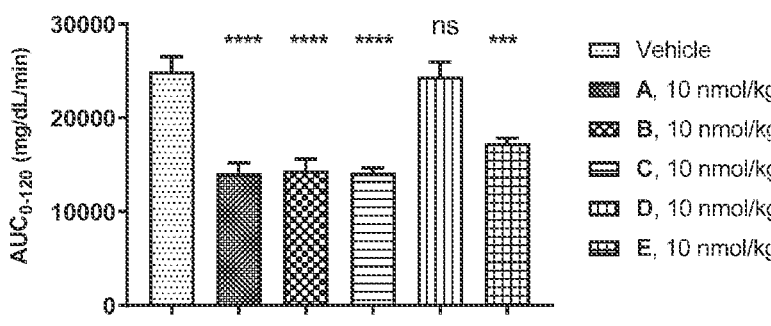
FIG. 7F
96h post-dose OGTT AUC
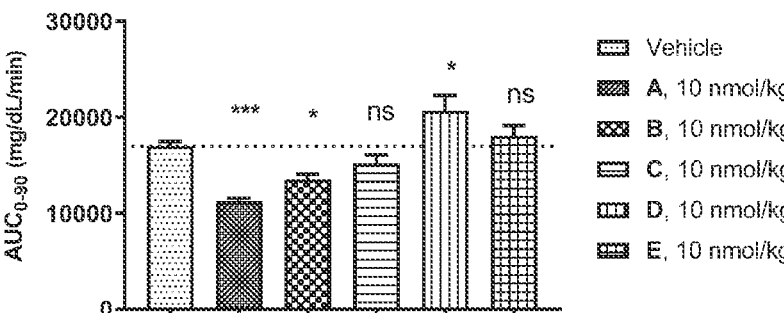

2h post-dose OGTT 72h post-dose OGTT 96h post-dose OGTT 144h post-dose OGTT

AUC 96h post-dose OGTT

AUC 144h post-dose OGTT

Fasted glucose 2h post

Fasted glucose 72h post

Fasted glucose 96h post

Fasted glucose 144h post

FIG. 10D
D8 OGTT
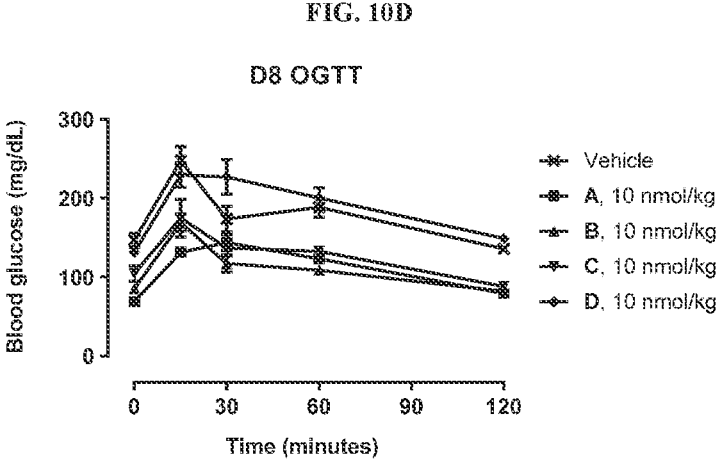
FIG. 10E
D8 OGTT AUC
FIG. 10F
O/N fasted glucose D8
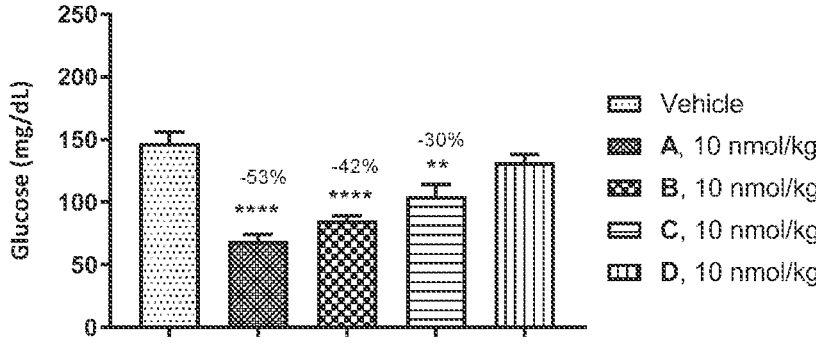

A    Vehicle

B    PrRP31, 5mg/kg

C    97-L5, 0.5 mg/kg

SEQUENCE LISTING

```
<160> NUMBER OF SEQ ID NOS: 120

<210> SEQ ID NO 1
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 2
<211> LENGTH: 34
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ile Lys Pro Glu Ala Pro Gly Cys Asp Ala Ser Pro Glu Glu Cys Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ile Lys Pro Glu Ala Pro Gly Glu Asp Ala Ser Pro Glu Glu Leu Asn
1               5                   10                  15

Arg Tyr Tyr Ala Cys Leu Arg His Tyr Leu Asn Cys Val Thr Arg Gln
            20                  25                  30

Arg Tyr

<210> SEQ ID NO 5
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Pro Lys Pro Glu Ala Pro Gly Cys Asp Ala Ser Pro Glu Glu Cys Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 6
<211> LENGTH: 34
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 6

Pro Lys Pro Glu Ala Pro Gly Lys Asp Ala Ser Pro Glu Glu Trp Asn
1               5                   10                  15

Arg Tyr Tyr Ala Cys Leu Arg His Tyr Leu Asn Cys Leu Thr Arg Gln
            20                  25                  30

Arg Tyr

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Lys Pro Glu Ala Pro Gly Lys Asp Ala Ser Pro Glu Glu Lys Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 8
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Pro Lys Pro Glu Ala Pro Gly Lys Asp Ala Ser Pro Glu Glu Trp Asn
1               5                   10                  15

Arg Tyr Tyr Ala Lys Leu Arg His Tyr Leu Asn Lys Leu Thr Arg Gln
            20                  25                  30

Arg Tyr

<210> SEQ ID NO 9
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Orn
<220> FEATURE:
<221> NAME/KEY: MOD_RES
<222> LOCATION: (28)..(28)
<223> OTHER INFORMATION: Orn

<400> SEQUENCE: 9

Pro Lys Pro Glu Ala Pro Gly Lys Asp Ala Ser Pro Glu Glu Trp Asn
1               5                   10                  15

Arg Tyr Tyr Ala Xaa Leu Arg His Tyr Leu Asn Xaa Leu Thr Arg Gln
            20                  25                  30

Arg Tyr
```

-continued

```
<210> SEQ ID NO 10
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Pro Lys Pro Glu Ala Pro Gly Cys Asp Ala Ser Pro Glu Glu Trp Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 11
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Pro Lys Pro Glu Ala Pro Gly Lys Asp Ala Ser Pro Glu Glu Cys Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 12
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Pro Lys Pro Glu Ala Pro Gly Lys Asp Ala Ser Pro Glu Glu Trp Asn
1               5                   10                  15

Arg Tyr Tyr Ala Cys Leu Arg His Tyr Leu Asn Trp Leu Thr Arg Gln
            20                  25                  30

Arg Tyr

<210> SEQ ID NO 13
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Pro Lys Pro Glu Ala Pro Gly Lys Asp Ala Ser Pro Glu Glu Trp Asn
1               5                   10                  15

Arg Tyr Tyr Ala Asp Leu Arg His Tyr Leu Asn Cys Leu Thr Arg Gln
            20                  25                  30

Arg Tyr

<210> SEQ ID NO 14
<211> LENGTH: 34
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 14

Pro Lys Pro Glu Ala Pro Gly Cys Asp Ala Ser Pro Glu Glu Trp Asn
1               5                   10                  15

Arg Tyr Tyr Ala Cys Leu Arg His Tyr Leu Asn Cys Leu Thr Arg Gln
            20                  25                  30

Arg Tyr

<210> SEQ ID NO 15
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Lys Pro Glu Ala Pro Gly Cys Asp Ala Ser Pro Glu Glu Cys Asn
1               5                   10                  15

Arg Tyr Tyr Ala Cys Leu Arg His Tyr Leu Asn Trp Leu Thr Arg Gln
            20                  25                  30

Arg Tyr

<210> SEQ ID NO 16
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

His Cys Ile Lys Pro Glu Ala Pro Cys Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

His Ile Lys Pro Glu Ala Pro Gly Cys Asp Ala Ser Pro Glu Glu Cys
1               5                   10                  15

Asn Arg Tyr Tyr Ala Ser Leu Arg His Tyr Leu Asn Leu Val Thr Arg
            20                  25                  30

Gln Arg Tyr
        35

<210> SEQ ID NO 18
<211> LENGTH: 35
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 18

His Ile Lys Pro Glu Ala Pro Gly Glu Asp Ala Ser Pro Glu Glu Cys
1               5                   10                  15

Asn Arg Tyr Tyr Ala Ser Cys Arg His Tyr Leu Asn Leu Val Thr Arg
            20                  25                  30

Gln Arg Tyr
        35

<210> SEQ ID NO 19
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ile Lys Pro Glu Ala Pro Gly Glu Asp Ala Ser Pro Glu Glu Leu Cys
1               5                   10                  15

Arg Tyr Tyr Ala Ser Leu Cys His Tyr Leu Asn Leu Val Thr Arg Gln
            20                  25                  30

Arg Tyr

<210> SEQ ID NO 20
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ile Lys Pro Glu Ala Pro Gly Glu Asp Ala Ser Pro Glu Glu Leu Asn
1               5                   10                  15

Cys Tyr Tyr Ala Ser Leu Arg Cys Tyr Leu Asn Leu Val Thr Arg Gln
            20                  25                  30

Arg Tyr

<210> SEQ ID NO 21
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

His Ile Lys Pro Glu Ala Pro Gly Glu Asp Ala Ser Pro Glu Glu Leu
1               5                   10                  15

Asn Arg Cys Tyr Ala Ser Leu Arg His Cys Leu Asn Leu Val Thr Arg
            20                  25                  30

Gln Arg Tyr
        35

<210> SEQ ID NO 22
<211> LENGTH: 34
<212> TYPE: PRT
<213> ORGANISM: Artificial Sequence
<220> FEATURE:
```

-continued

<223> OTHER INFORMATION: Description of Artificial Sequence: Synthetic
polypeptide

<400> SEQUENCE: 22

Ile Lys Pro Glu Ala Pro Gly Glu Asp Ala Ser Pro Glu Glu Leu Asn
1               5                   10                  15

Arg Tyr Cys Ala Ser Leu Arg His Tyr Cys Asn Leu Val Thr Arg Gln
            20                  25                  30

Arg Tyr

<210> SEQ ID NO 23
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

Ile Lys Pro Glu Ala Pro Gly Glu Asp Ala Ser Pro Glu Glu Leu Asn
1               5                   10                  15

Arg Tyr Tyr Cys Ser Leu Arg His Tyr Leu Cys Leu Val Thr Arg Gln
            20                  25                  30

Arg Tyr

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

His Ile Lys Pro Glu Ala Pro Gly Glu Asp Ala Ser Pro Glu Glu Leu
1               5                   10                  15

Asn Arg Tyr Tyr Ala Ser Cys Arg His Tyr Leu Asn Leu Cys Thr Arg
            20                  25                  30

Gln Arg Tyr
        35

<210> SEQ ID NO 25
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Ile Lys Pro Glu Ala Pro Gly Cys Asp Ala Ser Pro Glu Glu Leu Asn
1               5                   10                  15

Arg Tyr Cys Ala Ser Leu Arg His Tyr Leu Asn Leu Val Thr Arg Gln
            20                  25                  30

Arg Tyr

<210> SEQ ID NO 26
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Ile Lys Pro Glu Ala Pro Gly Glu Asp Ala Cys Pro Glu Glu Leu Asn
1               5                   10                  15

Arg Tyr Tyr Ala Ser Cys Arg His Tyr Leu Asn Leu Val Thr Arg Gln
            20                  25                  30

Arg Tyr

<210> SEQ ID NO 27
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ile Lys Pro Glu Ala Pro Cys Glu Asp Ala Ser Pro Glu Glu Leu Asn
1               5                   10                  15

Arg Tyr Tyr Ala Ser Cys Arg His Tyr Leu Asn Leu Val Thr Arg Gln
            20                  25                  30

Arg Tyr

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ile Lys Pro Glu Ala Pro Gly Glu Asp Ala Ser Pro Cys Glu Leu Asn
1               5                   10                  15

Arg Tyr Tyr Ala Ser Leu Arg His Tyr Leu Asn Cys Val Thr Arg Gln
            20                  25                  30

Arg Tyr

<210> SEQ ID NO 29
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ile Lys Pro Glu Ala Pro Gly Glu Asp Ala Ser Cys Glu Glu Leu Asn
1               5                   10                  15

Arg Tyr Tyr Ala Ser Leu Arg His Tyr Leu Asn Cys Val Thr Arg Gln
            20                  25                  30

Arg Tyr

<210> SEQ ID NO 30
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

-continued

```
Ile Lys Pro Glu Ala Pro Gly Glu Asp Ala Ser Pro Glu Glu Leu Asn
1               5                   10                  15

Cys Tyr Tyr Ala Ser Leu Arg His Tyr Leu Asn Cys Val Thr Arg Gln
            20                  25                  30

Arg Tyr

<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: N-MeR

<400> SEQUENCE: 31

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 32
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: N-MeR

<400> SEQUENCE: 32

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 33
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: N-MeR

<400> SEQUENCE: 33

Ile Lys Pro Glu Ala Pro Gly Cys Asp Ala Ser Pro Glu Glu Cys Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 34
```

-continued

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: N-MeR

<400> SEQUENCE: 34

Ile Lys Pro Glu Ala Pro Gly Glu Asp Ala Ser Pro Glu Glu Leu Asn
1               5                   10                  15

Arg Tyr Tyr Ala Cys Leu Arg His Tyr Leu Asn Cys Val Thr Arg Gln
            20                  25                  30

Arg Tyr

<210> SEQ ID NO 35
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: N-MeR

<400> SEQUENCE: 35

Pro Lys Pro Glu Ala Pro Gly Cys Asp Ala Ser Pro Glu Glu Cys Asn
1               5                   10                  15

Arg Tyr Tyr Ala Asp Leu Arg His Tyr Leu Asn Trp Leu Thr Arg Gln
            20                  25                  30

Arg Tyr

<210> SEQ ID NO 36
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ile Lys Pro Glu Ala Pro Gly Cys Asp Ala Ser Leu Glu Glu Cys Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 37
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ile Lys Pro Glu Ala Pro Gly Cys Asp Ala Ser Val Glu Glu Cys Asn
1               5                   10                  15

Arg Tyr Tyr Ala Ser Leu Arg His Tyr Leu Asn Leu Val Thr Arg Gln
            20                  25                  30
```

-continued

Arg Tyr

<210> SEQ ID NO 38
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: beta-hArg

<400> SEQUENCE: 38

Ile Lys Pro Glu Cys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 39
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: beta-hArg

<400> SEQUENCE: 39

His Ile Lys Pro Glu Cys Pro Gly Glu Asp Ala Ser Pro Glu Glu Leu
1               5                   10                  15

Gln Arg Tyr Tyr Ala Ser Leu Arg His Tyr Leu Asn Trp Val Thr Arg
            20                  25                  30

Gln Arg Tyr
        35

<210> SEQ ID NO 40
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: beta-hArg

<400> SEQUENCE: 40

Arg Pro Glu Cys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 41
<211> LENGTH: 12
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: N-MeR

<400> SEQUENCE: 41

Arg His Tyr Leu Asn Trp Val Thr Arg Gln Arg Tyr
1               5                   10

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ahx
<220> FEATURE:
<221> NAME/KEY: MOD_RES
<222> LOCATION: (22)..(22)
<223> OTHER INFORMATION: N-MeR

<400> SEQUENCE: 42

Ile Lys Xaa Cys Asn Arg Tyr Tyr Ala Ser Cys Arg His Tyr Leu Asn
1               5                   10                  15

Trp Val Thr Arg Gln Arg Tyr
            20

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: N-MeR

<400> SEQUENCE: 43

Cys Asn Arg Tyr Tyr Ala Ser Cys Arg His Tyr Leu Asn Trp Val Thr
1               5                   10                  15

Arg Gln Arg Tyr
            20

<210> SEQ ID NO 44
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ahx

<400> SEQUENCE: 44

Tyr Glu Ser Lys Xaa Cys Ala Arg Tyr Tyr Ser Ala Cys Arg His Tyr
1               5                   10                  15

Ile Asn Leu Ile Thr Arg Gln Arg Tyr
            20                  25
```

<210> SEQ ID NO 45
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ahx

<400> SEQUENCE: 45

Tyr Glu Ser Lys Xaa Cys Glu Asp Leu Ala Arg Tyr Cys Ser Ala Leu
1               5                   10                  15

Arg His Tyr Ile Asn Leu Ile Thr Arg Gln Arg Tyr
            20                  25

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Pro Lys Pro Glu His Pro Gly Lys Asp Ala Ser Pro Glu Glu Trp Ala
1               5                   10                  15

Lys Tyr Tyr Ala Ala Leu Arg His Tyr Ile Asn Trp Val Thr Arg Gln
            20                  25                  30

Arg Tyr

<210> SEQ ID NO 47
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 47

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 48
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 48

His Ser Gln Gly Thr Phe Thr Ser Asp Tyr Ser Lys Tyr Leu Asp Glu
1               5                   10                  15

```
Lys Ala Ala Lys Glu Phe Ile Lys Trp Leu Leu Asn Gly Gly Pro Ser
            20              25              30

Ser Gly Ala Pro Pro Pro Ser
        35
```

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid

<400> SEQUENCE: 49

```
His Ser Gln Gly Thr Phe Thr Ser Asp Tyr Ser Lys Tyr Leu Asp Glu
1               5               10              15

Lys Ala Ala Lys Glu Phe Ile Lys Trp Leu Leu Arg Ala
            20              25
```

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 50

```
His Xaa Gln Gly Thr Phe Thr Ser Asp Tyr Ser Lys Tyr Leu Asp Glu
1               5               10              15

Lys Ala Ala Lys Glu Phe Ile Lys Trp Leu Leu Asn Gly Arg Asn Arg
            20              25              30

Asn Asn Ile Ala
        35
```

<210> SEQ ID NO 51
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib

<400> SEQUENCE: 51

```
His Xaa Gln Gly Thr Phe Thr Ser Asp Tyr Ser Lys Tyr Leu Asp Ser
1               5               10              15

Lys Lys Ala Lys Glu Phe Val Lys Trp Leu Leu Asn Xaa Gly Pro Ser
            20              25              30

Ser Gly Ala Pro Pro Pro Ser
        35
```

```
<210> SEQ ID NO 52
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 52

His Xaa Gln Gly Thr Phe Thr Ser Asp Tyr Ser Lys Tyr Leu Asp Ser
1               5                   10                  15

Lys Lys Ala Gln Glu Phe Val Lys Trp Leu Leu Asn Gly Pro Ser Ser
            20                  25                  30

Gly Ala Pro Pro Pro Ser
        35

<210> SEQ ID NO 53
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 53

His Xaa Gln Gly Thr Phe Thr Ser Asp Tyr Ser Lys Tyr Leu Asp Lys
1               5                   10                  15

Lys Ala Ala Lys Glu Phe Lys Gln Trp Leu Leu Asn Gly Pro Ser Ser
            20                  25                  30

Gly Ala Pro Pro Pro Ser
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib

<400> SEQUENCE: 54

His Xaa Gln Gly Thr Phe Thr Ser Asp Tyr Ser Lys Tyr Leu Asp Lys
1               5                   10                  15

Lys Lys Ala Lys Glu Phe Lys Gln Trp Leu Leu Asn Xaa Gly Arg Asn
            20                  25                  30

Arg Asn Asn Ile Ala
        35

<210> SEQ ID NO 55
<211> LENGTH: 39
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 55

His Ser Gln Gly Thr Phe Thr Ser Asp Tyr Ser Glu Tyr Leu Asp Glu
1               5                   10                  15

Lys Ala Ala Lys Glu Phe Ile Lys Trp Leu Leu Asn Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 56

His Ser Gln Gly Thr Phe Thr Ser Asp Tyr Ser Glu Tyr Leu Asp Glu
1               5                   10                  15

Lys Ala Ala Arg Glu Phe Ile Lys Trp Leu Leu Ala Gly Gly Pro Ser
            20                  25                  30

Ser Gly Ala Pro Pro Pro Ser
        35

<210> SEQ ID NO 57
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (6)..(6)
<223> OTHER INFORMATION: Nle

<400> SEQUENCE: 57

His Ser Gln Gly Thr Leu Thr Ser Asp Tyr Ser Glu Tyr Leu Asp Glu
1               5                   10                  15

Lys Ala Ala Lys Glu Phe Ile Lys Trp Leu Leu Asn Gly Gly Pro Ser
            20                  25                  30

Ser Gly Ala Pro Pro Pro Ser
```

US 12,583,900 B2

247

248

-continued

35

<210> SEQ ID NO 58
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 58

His Ser Gln Gly Thr Leu Thr Ser Asp Tyr Ser Glu Tyr Leu Asp Glu
1               5                   10                  15

Lys Ala Ala Lys Glu Phe Ile Lys Trp Leu Leu Asn Gly Gly Pro Ser
            20                  25                  30

Ser Gly Ala Pro Pro Pro Ser
        35

<210> SEQ ID NO 59
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 59

His Ser Gln Gly Thr Leu Thr Ser Asp Tyr Ser Glu Tyr Leu Asp Ser
1               5                   10                  15

Lys Arg Ala Arg Glu Phe Val Lys Trp Leu Glu Ala Gly Gly Pro Ser
            20                  25                  30

Ser Gly Ala Pro Pro Pro Ser
        35

<210> SEQ ID NO 60
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 60

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Leu Asn Gly Gly Pro Ser
            20                  25                  30

Ser Gly Ala Pro Pro Pro Ser
        35

<210> SEQ ID NO 61
<211> LENGTH: 29
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid

<400> SEQUENCE: 61

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Leu Arg Ala
            20                  25

<210> SEQ ID NO 62
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 62

Tyr Xaa Glu Gly Thr Phe Thr Ser Asp Tyr Ser Ile Tyr Leu Asp Lys
1               5                   10                  15

Lys Ala Ala Xaa Glu Phe Val Lys Trp Leu Leu Ala Gly Gly Pro Ser
            20                  25                  30

Ser Gly Ala Pro Pro Pro Ser
        35

<210> SEQ ID NO 63
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 63

Tyr Xaa Glu Gly Thr Phe Thr Ser Asp Tyr Ser Ile Tyr Lys Asp Lys
1               5                   10                  15

Gln Ala Ala Xaa Lys Phe Val Asn Trp Leu Leu Ala Gly Gly Pro Ser
            20                  25                  30

Ser Gly Ala Pro Pro Pro Ser
        35

<210> SEQ ID NO 64
<211> LENGTH: 39
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 64

Tyr Xaa Glu Gly Thr Phe Thr Ser Asp Tyr Ser Ile Tyr Lys Asp Lys
1               5                   10                  15

Gln Ala Ala Xaa Lys Phe Lys Asn Trp Leu Lys Ala Gly Gly Pro Ser
            20                  25                  30

Ser Gly Ala Pro Pro Pro Ser
        35

<210> SEQ ID NO 65
<211> LENGTH: 39
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 65

Tyr Xaa Glu Gly Thr Phe Thr Ser Asp Tyr Ser Ile Tyr Leu Asp Lys
1               5                   10                  15

Lys Ala Gln Xaa Ala Phe Val Lys Trp Leu Ile Ala Gln Gly Pro Ser
            20                  25                  30

Ser Gly Ala Pro Pro Pro Ser
        35

<210> SEQ ID NO 66
<211> LENGTH: 39
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 66

Tyr Xaa Glu Gly Thr Phe His Ser Asp Tyr Asp Ile Tyr Lys Asp Lys
1               5                   10                  15

Gln Ala Ala Xaa Lys Phe Val Gln Trp Leu Leu Ala Gly Gly Pro Ser
            20                  25                  30

Ser Gly Ala Pro Pro Pro Ser
        35

<210> SEQ ID NO 67
```

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Nle

<400> SEQUENCE: 67

Tyr Xaa Glu Gly Thr Phe His Ser Asp Tyr Asp Ile Tyr Lys Asp Lys
1               5                   10                  15

Gln Ala Ala Leu Lys Phe Val Ala Trp Leu Leu Ala Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (11)..(11)
<223> OTHER INFORMATION: D-amino acid
<220> FEATURE:
<221> NAME/KEY: MOD_RES
<222> LOCATION: (20)..(20)
<223> OTHER INFORMATION: Nle

<400> SEQUENCE: 68

Tyr Xaa Glu Gly Thr Phe Thr Ser Asp Tyr Ser Ile Tyr Lys Asp Lys
1               5                   10                  15

Gln Ala Ala Leu Lys Phe Val Ala Trp Leu Leu Ala Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib
```

```
<400> SEQUENCE: 69

Tyr Xaa Glu Gly Thr Phe Thr Ser Asp Tyr Ser Ile Tyr Cys Asp Lys
1               5                   10                  15

Gln Ala Ala Xaa Cys Phe Val Asn Trp Leu Leu Ala Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Tyr Gly Glu Gly Thr Phe Thr Ser Asp Tyr Ser Ile Tyr Cys Asp Lys
1               5                   10                  15

Gln Ala Ala Gln Cys Phe Val Asn Trp Leu Leu Ala Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 71

Tyr Xaa Glu Gly Thr Phe Thr Ser Asp Tyr Ser Ile Tyr Cys Asp Lys
1               5                   10                  15

Gln Ala Ala Gln Cys Phe Val Asn Trp Leu Leu Ala Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

His Gly Glu Gly Thr Phe Thr Ser Asp Leu Ser Lys Gln Met Glu Glu
1               5                   10                  15

Lys Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 73
<211> LENGTH: 39
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 73

His Gly Glu Gly Thr Phe Thr Ser Asp Leu Ser Lys Gln Leu Glu Glu
1               5                   10                  15

Lys Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 74
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Nle

<400> SEQUENCE: 74

His Gly Glu Gly Thr Phe Thr Ser Asp Leu Ser Lys Gln Leu Glu Glu
1               5                   10                  15

Lys Ala Val Arg Leu Phe Ile Lys Trp Leu Lys Asn Gly Gly Pro Ser
            20                  25                  30

Ser Gly Ala Pro Pro Pro Ser
        35

<210> SEQ ID NO 75
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 75

His Xaa Glu Gly Thr Phe Thr Ser Asp Val Ser Ser Tyr Leu Glu Gly
1               5                   10                  15

Lys Ala Ala Lys Glu Phe Ile Lys Trp Leu Val Lys Gly Arg Gly
            20                  25                  30

<210> SEQ ID NO 76
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

His Gly Glu Gly Thr Phe Thr Ser Asp Leu Ser Lys Gln Leu Glu Glu
1               5                   10                  15

Cys Ala Val Arg Leu Phe Ile Cys Trp Leu Lys Asn Gly Gly Pro Ser
            20                  25                  30

Ser Gly Ala Pro Pro Pro Ser
```

-continued

```
                   35

<210> SEQ ID NO 77
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

His Gly Glu Gly Thr Phe Thr Ser Asp Leu Ser Lys Gln Met Glu Glu
1               5                   10                  15

Cys Ala Val Arg Leu Phe Ile Cys Trp Leu Lys Asn Gly Gly Pro Ser
            20                  25                  30

Ser Gly Ala Pro Pro Pro Ser
        35

<210> SEQ ID NO 78
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

His Gly Glu Gly Thr Phe Thr Ser Asp Val Ser Ser Tyr Leu Glu Gly
1               5                   10                  15

Cys Ala Ala Lys Glu Phe Ile Cys Trp Leu Val Lys Gly Arg Gly
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 79

His Xaa Glu Gly Thr Phe Thr Ser Asp Val Ser Ser Tyr Leu Glu Gly
1               5                   10                  15

Cys Ala Ala Lys Glu Phe Ile Cys Trp Leu Val Lys Gly Arg Gly
            20                  25                  30

<210> SEQ ID NO 80
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 80

His Ser Gln Gly Thr Phe Thr Ser Asp Tyr Ser Lys Tyr Leu Asp Glu
1               5                   10                  15

Cys Ala Ala Lys Glu Phe Ile Cys Trp Leu Met Asn Thr Lys Arg Asn
```

-continued

```
              20              25              30

Arg Asn Asn Ile Ala
      35

<210> SEQ ID NO 81
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-amino acid

<400> SEQUENCE: 81

His Ser Gln Gly Thr Phe Thr Ser Asp Tyr Ser Lys Tyr Leu Asp Glu
1               5               10              15

Cys Ala Ala His Asp Phe Val Cys Trp Leu Leu Arg Ala
            20              25

<210> SEQ ID NO 82
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 82

His Ser Gln Gly Thr Phe Thr Ser Asp Tyr Ser Lys Tyr Leu Asp Glu
1               5               10              15

Cys Ala Ala Lys Glu Phe Ile Cys Trp Leu Leu Arg Ala Gly Pro Ser
            20              25              30

Ser Gly Ala Pro Pro Pro Ser
      35

<210> SEQ ID NO 83
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Pro Asp Ile Cys Pro Ala Trp Tyr Thr Gly Cys Gly Ile Arg Pro
1               5               10              15

Val Gly Arg Phe
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Thr Pro Asp Ile Asn Cys Ala Trp Tyr Thr Gly Arg Cys Ile Arg Pro
```

-continued

```
1               5               10              15

Val Gly Arg Phe
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Pro Asp Ile Asn Pro Cys Trp Tyr Thr Gly Arg Gly Cys Arg Pro
1               5               10              15

Val Gly Arg Phe
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Pro Asp Ile Asn Pro Ala Cys Tyr Thr Gly Arg Gly Ile Cys Pro
1               5               10              15

Val Gly Arg Phe
            20

<210> SEQ ID NO 87
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Pro Asp Ile Asn Pro Ala Trp Cys Thr Gly Arg Gly Ile Arg Cys
1               5               10              15

Val Gly Arg Phe
            20

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Pro Asp Ile Asn Pro Ala Trp Tyr Cys Gly Arg Gly Ile Arg Pro
1               5               10              15

Cys Gly Arg Phe
            20

<210> SEQ ID NO 89
<211> LENGTH: 31
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 89

Cys Arg Ala His Gln His Ser Cys Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 90
<211> LENGTH: 31
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 90

Ser Arg Ala His Gln Cys Ser Met Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 91

Ser Arg Ala His Gln His Ser Met Cys Thr Arg Thr Pro Asp Ile Cys
1               5                   10                  15

Pro Ala Trp Tyr Thr Gly Arg Gly Ile Arg Pro Val Gly Arg Phe
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 92

Ser Arg Ala His Gln His Ser Met Glu Thr Arg Thr Cys Asp Ile Asn
1               5                   10                  15

Pro Ala Trp Cys Thr Gly Arg Gly Ile Arg Pro Val Gly Arg Phe
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 93

Ser Arg Ala His Gln His Ser Met Glu Thr Arg Thr Pro Asp Cys Asn
1               5                   10                  15

Pro Ala Trp Tyr Thr Cys Arg Gly Ile Arg Pro Val Gly Arg Phe
            20                  25                  30

-continued

```
<210> SEQ ID NO 94
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ser Arg Ala His Gln His Ser Met Glu Thr Arg Thr Pro Asp Ile Cys
1               5                   10                  15

Pro Ala Trp Tyr Thr Gly Cys Gly Ile Arg Pro Val Gly Arg Phe
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ser Arg Ala His Gln His Ser Met Glu Thr Arg Thr Pro Asp Ile Asn
1               5                   10                  15

Pro Cys Trp Tyr Thr Gly Arg Gly Cys Arg Pro Val Gly Arg Phe
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ser Arg Ala His Gln His Ser Met Glu Thr Arg Thr Pro Asp Ile Asn
1               5                   10                  15

Pro Ala Trp Cys Thr Gly Arg Gly Ile Arg Cys Val Gly Arg Phe
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (23)..(23)
<223> OTHER INFORMATION: hArg

<400> SEQUENCE: 97

Ser Arg Ala His Gln Cys Ser Leu Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 98
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (23)..(23)
<223> OTHER INFORMATION: Beta-hArg

<400> SEQUENCE: 98

Ser Arg Ala His Gln Cys Ser Leu Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (23)..(23)
<223> OTHER INFORMATION: NMe-Arg

<400> SEQUENCE: 99

Ser Arg Ala His Gln Cys Ser Leu Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 100
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (30)..(30)
<223> OTHER INFORMATION: hArg

<400> SEQUENCE: 100

Ser Arg Ala His Gln Cys Ser Leu Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: Description of Artificial Sequence: Synthetic
```

-continued

```
        polypeptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (30)..(30)
<223> OTHER INFORMATION: Beta-hArg

<400> SEQUENCE: 101

Ser Arg Ala His Gln Cys Ser Leu Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (30)..(30)
<223> OTHER INFORMATION: NMe-Arg

<400> SEQUENCE: 102

Ser Arg Ala His Gln Cys Ser Leu Glu Thr Arg Thr Cys Asp Ile Asn
1               5                   10                  15

Pro Ala Trp Tyr Thr Gly Arg Gly Ile Arg Pro Val Gly Arg Phe
            20                  25                  30

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Cys Asp Ile Asn Pro Ala Trp Cys Thr Gly Arg Gly Ile Arg Pro
1               5                   10                  15

Val Gly Arg Phe
            20

<210> SEQ ID NO 104
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Pro Cys Ile Asn Pro Ala Trp Tyr Cys Gly Arg Gly Ile Arg Pro
1               5                   10                  15

Val Gly Arg Phe
            20

<210> SEQ ID NO 105
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Pro Asp Cys Asn Pro Ala Trp Tyr Thr Cys Arg Gly Ile Arg Pro
1               5                   10                  15

Val Gly Arg Phe
            20

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Thr Pro Asp Ile Asn Pro Ala Trp Tyr Thr Gly Arg Gly Ile Arg Pro
1               5                   10                  15

Val Gly Arg Phe
            20

<210> SEQ ID NO 107
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 108
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib

<400> SEQUENCE: 108

His Xaa Gln Gly Thr Phe Thr Ser Asp Tyr Ser Glu Tyr Leu Asp Ser
1               5                   10                  15

Lys Lys Ala Lys Glu Phe Val Lys Trp Leu Leu Asn Xaa Gly Pro Ser
            20                  25                  30

Ser Gly Ala Pro Pro Pro Ser
        35

<210> SEQ ID NO 109
```

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib

<400> SEQUENCE: 109

His Xaa Gln Gly Thr Phe Thr Ser Asp Tyr Ser Glu Tyr Leu Asp Ser
1               5                   10                  15

Lys Lys Ala Gln Glu Phe Val Lys Trp Leu Leu Asn Gly Gly Pro Ser
            20                  25                  30

Ser Gly Ala Pro Pro Pro Ser
        35

<210> SEQ ID NO 110
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 110

His Ser Gln Gly Thr Phe Thr Ser Asp Tyr Ser Glu Tyr Leu Asp Glu
1               5                   10                  15

Lys Ala Ala Lys Glu Phe Ile Lys Trp Leu Leu Asn Gly Gly Pro Ser
            20                  25                  30

Ser Gly Ala Pro Pro Pro Ser
        35

<210> SEQ ID NO 111
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-amino acid

<400> SEQUENCE: 111

His Ser Gln Gly Thr Phe Thr Ser Asp Tyr Ser Lys Gln Leu Asp Glu
1               5                   10                  15

Cys Ala Ala Lys Glu Phe Ile Cys Trp Leu Leu Gln Gly Gly Pro Ser
            20                  25                  30

Ser Gly Ala Pro Pro Pro Ser
        35

<210> SEQ ID NO 112

<400> SEQUENCE: 112

000

<210> SEQ ID NO 113
```

<400> SEQUENCE: 113

000

<210> SEQ ID NO 114
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 114

```
Tyr Xaa Glu Gly Thr Phe Thr Ser Asp Tyr Ser Ile Tyr Leu Asp Lys
1               5                   10                  15

Cys Ala Ala Xaa Glu Phe Val Cys Trp Leu Leu Ala Gly Gly Pro Ser
            20                  25                  30

Ser Gly Ala Pro Pro Pro Ser
        35
```

<210> SEQ ID NO 115
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 115

```
Tyr Xaa Glu Gly Thr Phe Thr Ser Asp Tyr Ser Ile Tyr Leu Asp Lys
1               5                   10                  15

Cys Ala Gln Xaa Ala Phe Val Cys Trp Leu Ile Ala Gln Gly Pro Ser
            20                  25                  30

Ser Gly Ala Pro Pro Pro Ser
        35
```

<210> SEQ ID NO 116
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 116

```
Tyr Xaa Glu Gly Thr Phe Thr Ser Asp Tyr Ser Ile Tyr Cys Asp Lys
1               5                   10                  15

Gln Ala Ala Xaa Cys Phe Val Asn Trp Leu Ile Ala Gly Gly Pro Ser
            20                  25                  30

Ser Gly Ala Pro Pro Pro Ser
        35
```

```
<210> SEQ ID NO 117
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 117
```

```
Tyr Xaa Glu Gly Thr Phe Ile Ser Asp Val Ser Ile Tyr Cys Asp Lys
1               5                   10                  15

Gln Ala Ala Xaa Cys Phe Val Asn Trp Leu Ile Ala Gly Gly Pro Ser
            20                  25                  30

Ser Gly Ala Pro Pro Pro Ser
        35
```

```
<210> SEQ ID NO 118
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 118
```

```
Tyr Xaa Glu Gly Thr Phe Ile Ser Asp Val Ser Ile Tyr Leu Asp Lys
1               5                   10                  15

Cys Ala Ala Xaa Glu Phe Val Cys Trp Leu Ile Ala Gly Gly Pro Ser
            20                  25                  30

Ser Gly Ala Pro Pro Pro Ser
        35
```

-continued

```
<210> SEQ ID NO 119
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 119

Tyr Xaa Glu Gly Thr Phe Ile Ser Asp Leu Ser Ile Tyr Cys Asp Lys
1               5                   10                  15

Gln Ala Ala Xaa Cys Phe Val Gln Trp Leu Ile Ala Gly Gly Pro Ser
            20                  25                  30

Ser Gly Ala Pro Pro Pro Ser
        35

<210> SEQ ID NO 120
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (20)..(20)
<223> OTHER INFORMATION: Aib

<400> SEQUENCE: 120

Tyr Xaa Glu Gly Thr Phe Ile Ser Asp Leu Ser Ile Tyr Leu Asp Lys
1               5                   10                  15

Cys Ala Ala Xaa Glu Phe Val Cys Trp Leu Ile Ala Gly Gly Pro Ala
            20                  25                  30

Ser Gly Ala Pro Pro Pro Ser
        35
```

PEPTIDE CONJUGATES AND METHODS OF USE

CROSS-REFERENCE

This patent application is a national stage entry of PCT/US2020/063149, filed on Dec. 3, 2020, which claims the benefit of U.S. Provisional Application No. 62/994,791, filed Mar. 25, 2020; and U.S. Provisional Application No. 62/943,667 filed Dec. 4, 2019; which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jan. 12, 2021, is named 36271-707 831 SL.txt, and is 57,279 bytes in size.

BACKGROUND OF THE INVENTION

The development of therapeutic agents is often hampered by short half-lives. The biological half-life of an agent is the time it takes for the agent to lose half of its pharmacologic, physiologic, or radiologic activity. As a result, patients are often administered higher dosages of a therapeutic agent more frequently, which can lead to reduced compliance, higher costs and greater risk of side effects.

Accordingly, there is a need for generation of therapeutic agents with extended half-lives.

SUMMARY OF THE INVENTION

Disclosed herein is a peptide conjugate comprising:
a) a peptide selected from a peptide that modulates the PYY receptor, a peptide that modulates both the GLP-1 receptor and the GCG receptor, a peptide that modulates both the GLP-1 receptor and the GIP receptor, and a peptide that modulates the GLP-1 receptor; and
b) a staple attached to the peptide at a first sulfhydryl-containing amino acid and a second sulfhydryl-containing amino acid;
wherein the staple is of Formula (I):

Formula (I)

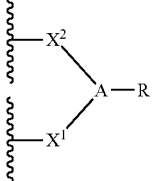

wherein
A is —N—;
$X^1$ and $X^2$ are a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;
wherein $X^1$ is attached to a sulfhydryl-containing amino acid of the peptide, $X^2$ is attached to a sulfhydryl-containing amino acid of the peptide, and $X^1$ and $X^2$ are identical;

R is hydrogen or -(L)$_s$-Y;
each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;
v is 2-20;
each R$^1$ or R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
or R$^1$ and R$^2$ are taken together to form a C$_1$-C$_6$ cycloalkyl or C$_1$-C$_6$ heterocycloalkyl; each R$^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;
Y is hydrogen, C$_1$-C$_6$ alkyl, —CO$_2$H, —CO$_2$(C$_1$-C$_6$ alkyl), —CO$_2$NH$_2$, —CO$_2$N(alkyl)$_2$, or —CO$_2$NH(alkyl);
s is 0-20;
R$^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;
R$^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$; and
each R$^c$ and R$^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$.

Also provided herein is a peptide conjugate comprising:
a) a peptide that modulates the PYY receptor comprising a peptide sequence having at least about 95% identity to any one of SEQ ID NOs: 3, 5, 6, 8, 14-30, 36, or 37; and
b) a staple attached to the peptide at a first amino acid and a second amino acid.

Also provided herein is a peptide conjugate comprising:
a) a peptide that modulates both the GLP-1 receptor and the GCGR receptor comprising a peptide sequence having at least about 95% identity to any one of SEQ ID NOs: 50-59; and b) a staple attached to the peptide at a first amino acid and a second amino acid.

Also provided herein is a peptide conjugate comprising:
a) a peptide that modulates both the GLP-1 receptor and the GIP receptor comprising a peptide sequence having at least about 95% identity to any one of SEQ ID NOs: 62-71; and b) a staple attached to the peptide at a first amino acid and a second amino acid.

Also provided herein is a peptide conjugate comprising:
a) a peptide that modulates the GLP-1 receptor comprising a peptide sequence having at least about 95% identity to any one of SEQ ID NOs: 74 and 79; and
b) a staple attached to the peptide at a first amino acid and a second amino acid.

Also provided herein is a pharmaceutical composition comprising the peptide conjugate described herein and a pharmaceutically acceptable excipient.

Also provided herein is a method for treating a disease or condition in a subject in need thereof, the method comprising administering to the subject a composition comprising a therapeutically effective amount of a peptide conjugate described herein.

BRIEF DESCRIPTION OF FIGURES

FIG. 4D illustrates the glucose levels in an oral-glucose tolerance test given to diet-induced obese mice treated with conjugate 187, conjugate 40, a combination of conjugate 187 and 40, or vehicle alone after 14 days of treatment.

FIG. 4F illustrates the fasted blood glucose of diet-induced obese mice treated with conjugate 187, conjugate 40, a combination of conjugate 187 and 40, or vehicle alone after 14 days of treatment.

FIG. 7A depicts the effects of the compounds in an oral glucose tolerance test on blood glucose levels over time at 6 hours post dose. A: 122, B: 135, C: 138, D: Cotadutide, E: Semaglutide.

FIG. 7B depicts the effects of the compounds in an oral glucose tolerance test on blood glucose levels over time at 48 hours post dose. A: 122, B: 135, C: 138, D: Cotadutide, E: Semaglutide.

FIG. 7C depicts the effects of the compounds in an oral glucose tolerance test on blood glucose levels overtime at 96 hours post dose. A: 122 and E: Semaglutide.

FIG. 7D depicts the effects of treatment with the compounds in an oral glucose tolerance test on blood glucose levels as measured by the area under the curve (AUC) at 6 hours post dose. A: 122, B: 135, C: 138, D: Cotadutide, E: Semaglutide.

FIG. 7E depicts the effects of treatment with the compounds in an oral glucose tolerance test on blood glucose levels as measured by the area under the curve (AUC) at 48 hours post dose. A: 122, B: 135, C: 138, D: Cotadutide, E: Semaglutide.

FIG. 7F depicts the effects of treatment with the compounds in an oral glucose tolerance test on blood glucose levels as measured by the area under the curve (AUC) at 96 hours post dose. A: 122, B: 135, C: 138, D: Cotadutide, E: Semaglutide.

FIG. 10D displays the results of the compounds in an oral glucose tolerance test (OGTT) on blood glucose levels over time. A: 142 (7×/wk), B: 142 (2×/wk), C: Tirzepatide (2×/wk), D: Semaglutide (2×/wk).

FIG. 10E displays the results of the compounds in an oral glucose tolerance test (OGTT) on blood glucose levels as measured by the area under the curve (AUC). A: 142 (7×/wk), B: 142 (2×/wk), C: Tirzepatide (2×/wk), D: Semaglutide (2×/wk).

FIG. 10F displays the results of the compounds in an oral glucose tolerance test (OGTT) on fasted glucose at day 8. A: 142 (7×/wk), B: 142 (2×/wk), C: Tirzepatide (2×/wk), D: Semaglutide (2×/wk).

DETAILED DESCRIPTION OF THE INVENTION

Figure 1:
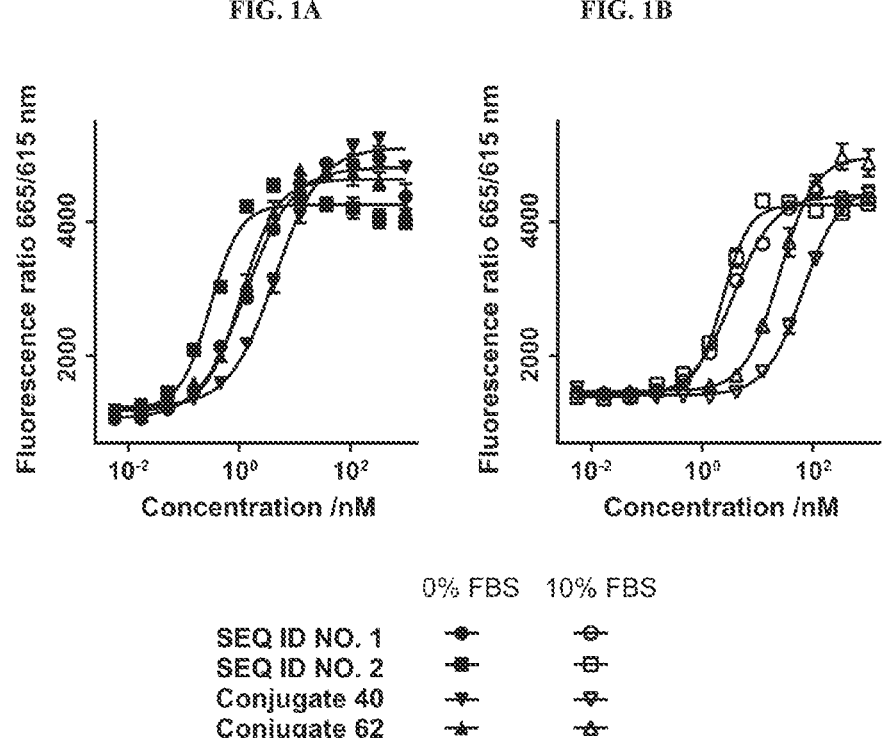
FIG. 1A displays dose-response curves for symmetrically-stapled PYY analogues in the absence of fetal bovine serum.
FIG. 1B displays dose-response curves for symmetrically-stapled PYY analogues in the presence of fetal bovine serum (10%).

Peptide YY (PYY) and glucagon like peptide (GLP)-1 are peptides secreted from intestinal L cells in response to a meal. Increased plasma levels of each peptide have been shown to reduce appetite and inhibit food intake. For rodents dosed with a PYY compound and a GLP-1 compound, an additive effect on feeding inhibition was observed over individual doses of either compound. This additive inhibition of feeding was also observed in genetic obese models, ob/ob and db/db mice. Additional studies on healthy human volunteers also showed an additive effect of a PYY compound and GLP-1 compound on decreasing energy intake (27%) at a buffet. This reduction in energy intake was greater for individuals dosed with the combination, then either PYY compound or GLP-1 compound alone. Thus, PYY, optionally in combination with a GLP-1 or similar compound, is a promising therapeutic for the treatment of conditions associated with weight loss.

The neuropeptide Y family regulates signaling between the brain and the gut through neuropeptide Y receptors, and includes peptides PYY, NPY (neuropeptide Y), and PP (pancreatic polypeptide). PYY is a naturally secreted, 36 amino acid peptide PYY(1-36) that is cleaved to PYY(3-36). However, PYY(3-36) is rapidly eliminated and has been reported to have a half-life in pigs of less than 30 minutes. Accordingly, the pharmacokinetic properties of naturally occurring PYY compounds are suboptimal for therapeutic use.

G protein-coupled receptors (GPCRs) are membrane-bound proteins that have seven transmembrane domains linked by three intracellular and three extracellular loops. Their ligand-binding sites are highly specialized so that each receptor responds only to a limited variety of chemicals which bind with high affinity. Examples of GPCR ligands are peptides, proteins, lipid-derived molecules, small organic compounds and ions. GPCRs have been of long-standing interest as pharmaceutical drug targets, as they are involved in a plethora of pathophysiological processes, including the regulation of neuronal excitability, metabolism, reproduction, hormonal homeostasis, and behavior. It is estimated that around 34% of all Food and Drug Administration (FDA) approved drugs target 108 members of the GPCR family. GPCRs are generally classified into multiple superfamilies. Family B GPCRs, or the so-called secretin receptor family, are a small but structurally and functionally diverse set of receptors. These proteins are vital to many physiological functions and serve as key drug targets for several human diseases such as type II diabetes mellitus (T2DM), migraine, osteoporosis, depression, and anxiety. Members of this family include receptors for polypeptide hormones of 27-141 residues in length. Nine of these receptors are targeted by ligands that are structurally related to one another, examples of which include glucagon-like peptides (GLP-1 and GLP-2), glucagon, glucose-dependent insulinotropic polypeptide (GIP), vasoactive intestinal peptide (VIP), pituitary adenylate cyclase-activating polypeptide (PACAP) and growth hormone-releasing hormone (GHRH).

Glucagon-like peptide 1 (GLP-1) is a naturally-occurring incretin hormone released into the circulation by the L cells of the gut in response to ingested nutrients. By binding to its cognate receptor (GLP-1R) GLP-1 is able to promote insulin secretion while suppressing glucagon secretion, but only when glucose levels are raised, thus offering the potential to lower plasma glucose levels while reducing the risk of hypoglycemia. Furthermore, GLP-1 decreases the rate of gastric emptying, and reduces appetite, thus resulting in weight loss.

GLP-1 receptor agonists (GLP-1RAs) represent a unique approach to the treatment of diabetes, with benefits beyond glucose control, including favorable effects on body weight, blood pressure, cholesterol levels, and beta-cell function. Two short-acting (exenatide and liraglutide; once- or twice-daily administration) and three long-acting (albiglutide, dulaglutide, and exenatide LAR; weekly administration) GLP-1RAs are currently approved in the United States. In particular, exenatide, a GLP-1 analog originally isolated from the saliva of the Gila monster, has a half-life of 30 min after i.v. administration and a half-life of 2-3 h after s.c. administration in humans. These drugs mimic the effects of the naturally occurring incretin hormone GLP-1 by activating GLP-1 receptors in the pancreas, which leads to enhanced insulin release and reduced glucagon release in a glucose-dependent manner—with a consequently low risk of hypoglycemia. The effects of these GLP-1RAs on GLP-1 receptors in the CNS and the gastrointestinal tract also lead to reduced appetite and delayed glucose absorption, with concomitant weight loss. Given their limited oral bioavailability, these GLP-1RAs are currently given as an s.c.

injection. In some aspects, provided herein are GLP-1RAs connected to a fatty-acid derived side-chain staple to increase half-life.

Incretin-based peptides are effective therapeutics for treating type 2 diabetes mellitus (T2DM). Oxyntomodulin (OXM), a dual agonist of GLP-1R and GCGR, has shown superior weight loss and glucose lowering effects, compared to single GLP-1R agonists. To overcome the short half-life and rapid renal clearance of OXM, which limit its therapeutic potential, both lipid and PEG modified OXM analogs have been reported. However, these approaches often result in reduced potency or PEG-associated toxicity. In certain embodiments, provided herein are GLP-1R and GCGR dual agonists having increased plasma stability and higher potency in activating both GLP-1R and GCGR.

GIP is also characterized as an incretin that stimulates insulin secretion in a glucose-dependent manner. A GIP and GLP-1 receptor dual agonist has been shown to reduce fasting serum glucose compared to placebo and to reduce body weight. This dual agonist, LY3298176, is administered once-weekly subcutaneously. In certain embodiments, further provided herein are GIPR and GLP-1R dual agonists comprising a stapled feature to increase serum stability and half-life.

Prolactin-releasing peptide (PrRP) was initially discovered from hypothalamus as a novel peptide that stimulates prolactin secretion in anterior pituitary cells via activation of the orphan G-protein coupled receptor human gustatory receptor 3 (Gr3), and its rat ortholog unknown hypothalamic receptor-1 (UHR-1). However, later reports showed that PrRP does not stimulate the secretion of prolactin or other pituitary hormones, but may act as a neuromodulator and play a key role in the regulation of energy balance via activation of the prolactin-releasing peptide receptor, also known as G-protein coupled receptor 10 (GPR10, identical to hGr3). PrRP reduces body weight and food intake, and modifies body temperature when administered centrally, suggesting a role in energy homeostasis. The anorexigenic effect of PrRP is mediated by corticotropin-releasing hormone (CRH) receptors, and it also interacts with leptin to reduce food intake and body weight. PrRP-deficient mice show late onset obesity and adiposity suggesting that PrRP relays the satiety signal within the brain. A disturbance of PrRP receptor signaling can result in obesity and metabolic disorders. Thus, PrRP may offer potential as a therapeutic for diabetes and obesity, via harnessing of its anorexigenic properties for food intake and body weight reduction.

However, central administration of PrRP results in significantly increased cardiac contractility, heart rate and blood pressure. PrRP belongs to the RFamide peptide family, and in addition to activating GPR10 it also exhibits high affinity toward NPFF2R (neuropeptide FF receptor 2 or GPR74). While NPFF2R signaling exerts an additional anorexigenic effect that may augment that mediated by GPR10, NPFF2R has been linked to elevated arterial blood pressure and may be responsible for PrRP-induced cardiovascular effects. PrRP causes an increase in arterial blood pressure and heart rate, which can be abolished by co-administration of RF9, a specific NPFF2R antagonist, but not neuropeptide Y, a putative GPR10 antagonist. Direct conjugation of palmitic acid to the N-terminus of PrRP via a Lys side chain at position 11 leads to significant extension of half-life and in vivo anorexigenic effect, with reduction of food intake, body weight and glucose intolerance in rat and mouse models of obesity. Despite the benefit of exerting a central nervous system effect following peripheral administration, palmitoylated PrRP analogs seem to demonstrate increased activity toward NPFF2R. Thus, there is a need to develop GPR10-selective PrRP analogs that retain their anorectic and anti-diabetic effects, while diminishing their activity toward NPFF2R agonism and its associated cardiovascular risk.

Provided herein are peptide conjugates comprising a therapeutic peptide stapled to a molecule, such as a half-life extending molecule.

In certain embodiments, the stapled peptides comprise incretin peptides or incretin peptide mimetics. Incretin peptides generally bind to their cognate receptors in an α-helical conformation, therefore certain embodiments herein provide for modifications that stabilize the α-helix, which in some cases may increase binding affinity to their receptors. Moreover, proteolytic stability may also be enhanced in a helical rather than an extended conformation. In some aspects, provided herein are such conjugated peptides having increased circulatory half-life and potency toward their cognate receptors.

In some aspects, described herein is a peptide engineering strategy used to generate stapled long-acting peptide analogs with comparable potency as native peptides and significantly enhanced pharmacokinetic properties.

Peptide that Modulates the PYY Receptor

In one aspect, provided herein are peptide conjugates comprising a peptide specific for a neuropeptide Y family receptor (NPY family of biologically active peptides, NPY, peptide YY (PYY) and pancreatic polypeptide (PP)) derivative. In one aspect, provided herein are peptide conjugates comprising a peptide that modulates the PYY receptor. In some embodiments, the peptide that modulates the PYY receptor is a PYY receptor agonist.

The binding affinity of the peptide conjugate as described herein may be within about 5% of the binding affinity of an unmodified form of the peptide. The binding affinity of the peptide conjugate as described herein may be within about 10% of the binding affinity of an unmodified form of the peptide. The binding affinity of the peptide conjugate as described herein may be within about 15% of the binding affinity of an unmodified form of the peptide. The binding affinity of the peptide conjugate as described herein may be within about 20% of the binding affinity of an unmodified form of the peptide.

In some cases, the NPY derivative refers to a PYY derivative. In some cases, the NPY derivative refers to a PYY derivative having an amino acid sequence that differs be fewer than 9, 8, 7, 6, 5, 4, 3, 2, or 10 amino acids from PYY having SEQ ID NO: 1 or 2.

The NPY derivative, e.g., PYY derivative, may comprise one or more sulfhydryl containing amino acid residues. The one or more sulfhydryl containing amino acid residues may be used for connecting a staple to the PYY. The one or more sulfhydryl containing amino acid residues may be used for connecting a HEM to the NPY derivative. The one or more sulfhydryl containing amino acid residues may be naturally occurring in the NPY derivative. The one or more sulfhydryl containing amino acid residues may be inserted into the PYY derivative. The one or more sulfhydryl containing amino acid residues may replace one or more amino acid residues in the PYY derivative. Methods for amino acid substitution and/or insertion are known in the art.

The NPY derivative, e.g., PYY derivative, may comprise one or more amine containing residues. Non-limiting examples of amine containing residues include lysine, ornithine, diaminobutyric acid, diaminopropionic acid and homolysine. The one or more amine containing residues may be used for connecting a staple to the PYY derivative.

The one or more one or more amine containing residues may be used for connecting a HEM to the PYY derivative. The one or more one or more amine containing residues may be naturally occurring in the PYY derivative. The one or more one or more amine containing residues may be inserted into the PYY derivative. The one or more one or more amine containing residues may replace one or more amino acid residues in the PYY derivative.

The NPY derivative, e.g., PYY derivative, may comprise at least a portion of a wild-type peptide comprising one or more amino acid mutations. The one or more amino acid mutations may comprise a deletion, substitution, addition or a combination thereof. The one or more amino acid mutations may comprise adding one or more amino acid residues to a wild-type peptide. The one or more amino acid mutations may comprise deletion of one or more amino acid residues of the wild-type peptide. The one or more amino acid mutations may comprise substitution of one or more amino acid residues of the wild-type peptide. The one or more amino acid mutations may comprise substituting one or more amino acid residues of the wild-type peptide with one or more cysteine, lysine or other sulfhydryl or amine containing residues. The one or more amino acid mutations may comprise substituting one or more amino acid residues of the wild-type peptide with one or more D-amino acid residues. The one or more amino acid residues of the wild-type peptide may comprise one or more alanines, methionines, arginines, serines, threonines, and tyrosines.

The NPY derivative, e.g., PYY derivative, may be modified with, for example, acetylation, phosphorylation, and methylation. The peptide modification may comprise a chemical modification. Peptide modifications may occur on the N-terminus of the peptide. Peptide modifications may comprise acetyling the amino group at the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

In some embodiments, the peptide derivative may be a modified PYY with a D-serine in place of L-serine. In some embodiments, the peptide derivative may be a modified PYY with an aminoisobutyric acid [Aib] in place of L-serine. In some embodiments, the peptide derivative may be a modified PYY with an neuroleucine [Nle] in place of leucine (Leu).

In some embodiments, the peptide that modulates the PYY receptor comprises a truncated version of the wild-type 36 amino acid PYY peptide. In some embodiments, the N terminus is truncated by 1, 2, 3, or 4 residues. In some embodiments, the N terminus is truncated by 2 residues. In some cases, the PYY derivative comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 1 or 2. In some cases, the peptide derivative has an amino acid sequence at least about 80% identical to any one of SEQ ID NOs: 1 or 2. In some cases, the peptide that modulates the PYY receptor comprises a peptide sequence at least about 90% identical to SEQ ID NO: 1 or 2. In some cases, the peptide that modulates the PYY receptor comprises a peptide sequence at least about 91% identical to SEQ ID NO: 1 or 2. In some cases, the peptide that modulates the PYY receptor comprises a peptide sequence at least about 92% identical to SEQ ID NO: 1 or 2. In some cases, the peptide that modulates the PYY receptor comprises a peptide sequence at least about 93% identical to SEQ ID NO: 1 or 2. In some cases, the peptide that modulates the PYY receptor comprises a peptide sequence at least about 94% identical to SEQ ID NO: 1 or 2. In some cases, the peptide that modulates the PYY receptor comprises a peptide sequence at least about 95% identical to SEQ ID NO: 1 or 2. In some cases, the peptide that modulates the PYY receptor comprises a peptide sequence at least about 96% identical to SEQ ID NO: 1 or 2. In some cases, the peptide that modulates the PYY receptor comprises a peptide sequence at least about 97% identical to SEQ ID NO: 1 or 2. In some cases, the peptide that modulates the PYY receptor comprises a peptide sequence at least about 98% identical to SEQ ID NO: 1 or 2. In some cases, the peptide that modulates the PYY receptor comprises a peptide sequence at least about 99% identical to SEQ ID NO: 1 or 2.

In some embodiments, the peptide that modulates the PYY receptor comprises a peptide sequence of any one of SEQ ID NOs: 3-45. In some cases, the peptide that modulates the PYY receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 3-45. In some cases, the peptide that modulates the PYY receptor comprises a peptide sequence at least about 90% identical to any one of SEQ ID NOs: 3-45. In some cases, the peptide that modulates the PYY receptor comprises a peptide sequence at least about 95% identical to any one of SEQ ID NOs: 3-45. In some cases, the peptide that modulates the PYY receptor comprises a peptide sequence at least about 99% identical to any one of SEQ ID NOs: 3-45. In some cases, the peptide that modulates the PYY receptor comprises an amino acid sequence having up to about 1, 2, 3, 4, or 5 amino acid insertions, deletions, modifications, or substitutions as compared to any one of SEQ ID NOS: 3-45.

In some embodiments, the peptide that modulates the PYY receptor comprises a peptide sequence that is SEQ ID NO: 6. In some cases, the peptide that modulates the PYY receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 6. In some cases, the peptide that modulates the PYY receptor comprises a peptide sequence at least about 90% identical to SEQ ID NO: 6. In some cases, the peptide that modulates the PYY receptor comprises a peptide sequence at least about 95% identical to SEQ ID NO: 6. In some cases, the peptide that modulates the PYY receptor comprises a peptide sequence at least about 99% identical to SEQ ID NO: 6. In some cases, the peptide that modulates the PYY receptor comprises an amino acid sequence having up to about 1, 2, 3, 4, or 5 amino acid insertions, deletions, modifications, or substitutions as compared to SEQ ID NO: 6.

In some embodiments, the peptide that modulates the PYY receptor comprises a peptide sequence that is SEQ ID NO: 10. In some cases, the peptide that modulates the PYY receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 10. In some cases, the peptide that modulates the PYY receptor comprises a peptide sequence at least about 90% identical to SEQ ID NO: 10. In some cases, the peptide that modulates the PYY receptor comprises a peptide sequence at least about 95% identical to SEQ ID NO: 10. In some cases, the peptide that modulates the PYY receptor comprises a peptide sequence at least about 99% identical to SEQ ID NO: 10. In some cases, the peptide that modulates the PYY receptor comprises an amino acid sequence having up to about 1, 2, 3, 4, or 5 amino acid insertions, deletions, modifications, or substitutions as compared to SEQ ID NO: 10.

In some embodiments, the peptide that modulates the PYY receptor comprises a peptide sequence that is SEQ ID NO: 20. In some cases, the peptide that modulates the PYY receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 20. In some cases, the peptide that modulates the PYY receptor comprises a peptide sequence at least about 90% identical to SEQ ID NO: 20. In some cases, the peptide that modulates the PYY receptor comprises a peptide sequence at least about 95% identical to SEQ ID NO: 20. In some cases, the peptide that modulates the PYY receptor comprises a peptide sequence at least about 99% identical to SEQ ID NO: 20. In some cases, the peptide that modulates the PYY receptor comprises an amino acid sequence having up to about 1, 2, 3, 4, or 5 amino acid insertions, deletions, modifications, or substitutions as compared to SEQ ID NO: 20.

In some cases, the PYY derivative is numbered with the last amino acid in the sequence as position 36.

Non-limiting examples of peptide derivatives are shown in Table 1.

TABLE 1

| SEQ ID NO. | Sequence |
|---|---|
| | PYY SEQ ID Table |
| 1 | IKPEAPGEDASPEELNRYYASLRHYLNLVTRQRY |
| 2 | PKPEAPGKDASPEEWNRYYADLRHYLNWLTRQRY |
| 3 | IKPEAPGCDASPEECNRYYASLRHYLNLVTRQRY |
| 4 | IKPEAPGEDASPEELNRYYACLRHYLNCVTRQRY |
| 5 | PKPEAPGCDASPEECNRYYADLRHYLNWLTRQRY |
| 6 | PKPEAPGKDASPEEWNRYYACLRHYLNCLTRQRY |
| 7 | PKPEAPGKDASPEEKNRYYADLRHYLNWLTRQRY |
| 8 | PKPEAPGKDASPEEWNRYYAKLRHYLNKLTRQRY |
| 9 | PKPEAPGKDASPEEWNRYYA[Orn]LRHYLN[Orn]LTRQRY |
| 10 | PKPEAPGCDASPEEWNRYYADLRHYLNWLTRQRY |
| 11 | PKPEAPGKDASPEECNRYYADLRHYLNWLTRQRY |

TABLE 1-continued

| SEQ ID NO. | Sequence |
|---|---|
| | PYY SEQ ID Table |
| 12 | PKPEAPGKDASPEEWNRYYACLRHYLNWLTRQRY |
| 13 | PKPEAPGKDASPEEWNRYYADLRHYLNCLTRQRY |
| 14 | PKPEAPGCDASPEEWNRYYACLRHYLNCLTRQRY(*) |
| 15 | PKPEAPGCDASPEECNRYYACLRHYLNWLTRQRY(*) |
| 16 | HCIKPEAPCEDASPEELNRYYASLRHYLNLVTRQRY |
| 17 | HIKPEAPGCDASPEECNRYYASLRHYLNLVTRQRY |
| 18 | HIKPEAPGEDASPEECNRYYASCRHYLNLVTRQRY |
| 19 | IKPEAPGEDASPEELCRYYASLCHYLNLVTRQRY |
| 20 | IKPEAPGEDASPEELNCYYASLRCYLNLVTRQRY |
| 21 | HIKPEAPGEDASPEELNRCYASLRHCLNLVTRQRY |
| 22 | IKPEAPGEDASPEELNRYCASLRHYCNLVTRQRY |
| 23 | IKPEAPGEDASPEELNRYYCSLRHYLCLVTRQRY |
| 24 | HIKPEAPGEDASPEELNRYYASCRHYLNLCTRQRY |
| 25 | IKPEAPGCDASPEELNRYCASLRHYLNLVTRQRY |
| 26 | IKPEAPGEDACPEELNRYYASCRHYLNLVTRQRY |
| 27 | IKPEAPCEDASPEELNRYYASCRHYLNLVTRQRY |
| 28 | IKPEAPGEDASPCELNRYYASLRHYLNCVTRQRY |
| 29 | IKPEAPGEDASCEELNRYYASLRHYLNCVTRQRY |
| 30 | IKPEAPGEDASPEELNCYYASLRHYLNCVTRQRY |
| 31 | IKPEAPGEDASPEELNRYYASLRHYLNLVTRQ[N-MeR]Y |
| 32 | IKPEAPGEDASPEELNRYYASLRHYLNWVTRQ[N-MeR]Y |
| 33 | IKPEAPGCDASPEECNRYYASLRHYLNWVTRQ[N-MeR]Y |
| 34 | IKPEAPGEDASPEELNRYYACLRHYLNCVTRQ[N-MeR]Y |
| 35 | PKPEAPGCDASPEECNRYYADLRHYLNWLTRQ[N-MeR]Y |
| 36 | IKPEAPGCDASLEECNRYYASLRHYLNLVTRQRY |
| 37 | IKPEAPGCDASVEECNRYYASLRHYLNLVTRQRY |
| 38 | IKPECPGEDASPEELQRYYASLRHYLNWVTRQ[beta-hArg]Y |
| 39 | HIKPECPGEDASPEELQRYYASLRHYLNWVTRQ[beta-hArg]Y |
| 40 | Isovaleryl-RPECPGEDASPEELQRYYASLRHYLNWVTRQ[beta-hArg]Y |
| 41 | Ac-IC[Pqa]RHYLNWVTRQ[N-MeR]Y |
| 42 | Ac-IK[Ahx]CNRYYASCRHYLNWVTRQ[N-MeR]Y |
| 43 | Ac-IK[Pqa]CNRYYASCRHYLNWVTRQ[N-MeR]Y |

TABLE 1-continued

PYY SEQ ID Table

| SEQ ID NO. | Sequence |
|---|---|
| 44 | YESK[Ahx]CARYYSACRHYINLITRQRY |
| 45 | YESK[Ahx]CEDLARYCSALRHYINLITRQRY |
| 46 | PKPEHPGKDASPEEWAKYYAALRHYINWVTRQRY |
| 47 | H[Aib]EGTFTSDVSSYLEGQAAKEFIAWLVRGRG(*) |

(*)indicates a C-termina

Peptide that Modulates Both the GLP-1 Receptor and the GCG Receptor

In one aspect, provided herein are peptide conjugates comprising a peptide that modulates the GLP-1 receptor and/or the GCG receptor. In some embodiments, the peptide modulates both the GLP-1 receptor and the GCG receptor. In some embodiments, a peptide that modulates the GLP-1 receptor is a GLP-1 receptor agonist. In some embodiments, a peptide that modulates the GCG receptor is a GCG receptor agonist.

The binding affinity of the peptide conjugate as described herein may be within about 5% of the binding affinity of an unmodified form of the peptide. The binding affinity of the peptide conjugate as described herein may be within about 10% of the binding affinity of an unmodified form of the peptide. The binding affinity of the peptide conjugate as described herein may be within about 15% of the binding affinity of an unmodified form of the peptide. The binding affinity of the peptide conjugate as described herein may be within about 20% of the binding affinity of an unmodified form of the peptide.

The peptide that modulates both the GLP-1 receptor and the GCG receptor may comprise one or more sulfhydryl containing amino acid residues. The one or more sulfhydryl containing amino acid residues may be used for connecting a staple. The one or more sulfhydryl containing amino acid residues may be used for connecting a HEM. The one or more sulfhydryl containing amino acid residues may be naturally occurring in the peptide that modulates both the GLP-1 receptor and the GCG receptor. The one or more sulfhydryl containing amino acid residues may be inserted into the peptide that modulates both the GLP-1 receptor and the GCG receptor. The one or more sulfhydryl containing amino acid residues may replace one or more amino acid residues in the peptide that modulates both the GLP-1 receptor and the GCG receptor. Methods for amino acid substitution and/or insertion are known in the art.

The peptide that modulates both the GLP-1 receptor and the GCG receptor may comprise one or more amine containing residues. Non-limiting examples of amine containing residues include lysine, ornithine, diaminobutyric acid, diaminopropionic acid and homolysine. The one or more amine containing residues may be used for connecting a staple. The one or more one or more amine containing residues may be used for connecting a HEM. The one or more one or more amine containing residues may be naturally occurring in the peptide that modulates both the GLP-1 receptor and the GCG receptor. The one or more one or more amine containing residues may be inserted into the peptide that modulates both the GLP-1 receptor and the GCG receptor. The one or more one or more amine containing residues may replace one or more amino acid residues in the peptide that modulates both the GLP-1 receptor and the GCG receptor.

The peptide that modulates both the GLP-1 receptor and the GCG receptor may comprise at least a portion of a wild-type peptide comprising one or more amino acid mutations. The one or more amino acid mutations may comprise a deletion, substitution, addition or a combination thereof. The one or more amino acid mutations may comprise adding one or more amino acid residues to a wild-type peptide. The one or more amino acid mutations may comprise deletion of one or more amino acid residues of the wild-type peptide. The one or more amino acid mutations may comprise substitution of one or more amino acid residues of the wild-type peptide. The one or more amino acid mutations may comprise substituting one or more amino acid residues of the wild-type peptide with one or more cysteine, lysine or other sulfhydryl or amine containing residues. The one or more amino acid mutations may comprise substituting one or more amino acid residues of the wild-type peptide with one or more D-amino acid residues. The one or more amino acid residues of the wild-type peptide may comprise one or more alanines, methionines, arginines, serines, threonines, and tyrosines.

The peptide that modulates both the GLP-1 receptor and the GCG receptor may be modified with, for example, acetylation, phosphorylation, and methylation. The peptide modification may comprise a chemical modification. Peptide modifications may occur on the N-terminus of the peptide. Peptide modifications may comprise acetyling the amino group at the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

In some embodiments, the peptide that modulates both the GLP-1 receptor and the GCG receptor may be a modified peptide with a D-serine in place of L-serine. In some embodiments, the peptide that modulates both the GLP-1 receptor and the GCG receptor may be a modified with an aminoisobutyric acid [Aib] in place of L-serine. In some embodiments, the peptide that modulates both the GLP-1 receptor and the GCG receptor may be a modified peptide with an neuroleucine [Nle] in place of leucine (Leu).

In some embodiments, the peptide that modulates both the GLP-1 receptor and the GCG receptor comprises a peptide sequence of any one of SEQ ID NOs: 48-61 or 80-82. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 48-61 or 80-82. In some cases, the peptide that modulates both the GLP-1 receptor and the GCG receptor comprises a peptide sequence at least about 90% identical to any one of SEQ ID NOs: 48-61 or 80-82. In some cases, the peptide that modulates both the GLP-1 receptor and the GCG receptor comprises a peptide sequence at least about 95% identical to any one of SEQ ID NOs: 48-61 or 80-82. In some cases, the peptide that modulates both the GLP-1 receptor and the GCG receptor comprises a peptide sequence at least about 99% identical to any one of SEQ ID NOs: 48-61 or 80-82. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 48-61 or 80-82.

In some embodiments, the peptide that modulates both the GLP-1 receptor and the GCG receptor comprises a peptide sequence of any one of SEQ ID NOs: 108-114. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 108-114. In some cases, the peptide that modulates both the GLP-1 receptor and the GCG receptor comprises a peptide sequence at least about 90% identical to any one of SEQ ID NOs: 108-114. In some cases, the peptide that modulates both the GLP-1 receptor and the GCG receptor comprises a peptide sequence at least about 95% identical to any one of SEQ ID NOs: 108-114. In some cases, the peptide that modulates both the GLP-1 receptor and the GCG receptor comprises a peptide sequence at least about 99% identical to any one of SEQ ID NOs: 108-114. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 108-114.

In some embodiments, the peptide that modulates both the GLP-1 receptor and the GCG receptor comprises a peptide sequence of any one of SEQ ID NOs: 80-82. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 80-82. In some cases, the peptide that modulates both the GLP-1 receptor and the GCG receptor comprises a peptide sequence at least about 90% identical to any one of SEQ ID NOs: 80-82. In some cases, the peptide that modulates both the GLP-1 receptor and the GCG receptor comprises a peptide sequence at least about 95% identical to any one of SEQ ID NOs: 80-82. In some cases, the peptide that modulates both the GLP-1 receptor and the GCG receptor comprises a peptide sequence at least about 99% identical to any one of SEQ ID NOs: 80-82. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 80-82.

In some embodiments, the peptide that modulates both the GLP-1 receptor and the GCG receptor comprises a peptide sequence of any one of SEQ ID NOs: 48-59. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 48-59. In some cases, the peptide that modulates both the GLP-1 receptor and the GCG receptor comprises a peptide sequence at least about 90% identical to any one of SEQ ID NOs: 48-59. In some cases, the peptide that modulates both the GLP-1 receptor and the GCG receptor comprises a peptide sequence at least about 95% identical to any one of SEQ ID NOs: 48-59. In some cases, the peptide that modulates both the GLP-1 receptor and the GCG receptor comprises a peptide sequence at least about 99% identical to any one of SEQ ID NOs: 48-59. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 48-59.

In some embodiments, the peptide that modulates both the GLP-1 receptor and the GCG receptor comprises a peptide sequence of any one of SEQ ID NOs: 108-110. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 108-110. In some cases, the peptide that modulates both the GLP-1 receptor and the GCG receptor comprises a peptide sequence at least about 90% identical to any one of SEQ ID NOs: 108-110. In some cases, the peptide that modulates both the GLP-1 receptor and the GCG receptor comprises a peptide sequence at least about 95% identical to any one of SEQ ID NOs: 108-110. In some cases, the peptide that modulates both the GLP-1 receptor and the GCG receptor comprises a peptide sequence at least about 99% identical to any one of SEQ ID NOs: 108-110. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 108-110.

In some embodiments, the peptide that modulates both the GLP-1 receptor and the GCG receptor comprises a peptide sequence of any one of SEQ ID NOs: 60-61 or 80-82. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 60-61 or 80-82. In some cases, the peptide that modulates both the GLP-1 receptor and the GCG receptor comprises a peptide sequence at least about 90% identical to any one of SEQ ID NOs: 60-61 or 80-82. In some cases, the peptide that modulates both the GLP-1 receptor and the GCG receptor comprises a peptide sequence at least about 95% identical to any one of SEQ ID NOs: 60-61 or 80-82. In some cases, the peptide that modulates both the GLP-1 receptor and the GCG receptor comprises a peptide sequence at least about 99% identical to any one of SEQ ID NOs: 60-61 or 80-82. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 60-61 or 80-82.

In some embodiments, the peptide that modulates both the GLP-1 receptor and the GCG receptor comprises a peptide sequence that is SEQ ID NO: 111. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 111. In some cases, the peptide that modulates both the GLP-1 receptor and the GCG receptor comprises a peptide sequence at least about 90% identical to SEQ ID NO: 111. In some cases, the peptide that modulates both the GLP-1 receptor and the GCG receptor comprises a peptide sequence at least about 95% identical to SEQ ID NO: 111. In some cases, the peptide that modulates both the GLP-1 receptor and the GCG receptor comprises a peptide sequence at least about 99% identical to SEQ ID NO: 111. In some cases, the peptide that modulates both the GLP-1 receptor and the GCG receptor comprises an amino acid sequence having up to about 1, 2, 3, 4, or 5 amino acid insertions, deletions, modifications, or substitutions as compared to SEQ ID NOS: 111.

In some embodiments, the peptide that modulates both the GLP-1 receptor and the GCG receptor comprises a peptide sequence of any one of SEQ ID NOs: 48-52 or 55-61 or 80-82. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 48-52 or 55-61 or 80-82. In some cases, the peptide that modulates both the GLP-1 receptor and the GCG receptor comprises a peptide sequence at least about 90% identical to any one of SEQ ID NOs: 48-52 or 55-61 or 80-82. In some cases, the peptide that modulates both the GLP-1 receptor and the GCG receptor comprises a peptide sequence at least about 95% identical to any one of SEQ ID NOs: 48-52 or 55-61 or 80-82. In some cases, the peptide that modulates both the GLP-1 receptor and the GCG receptor comprises a peptide sequence at least about 99% identical to any one of SEQ ID NOs: 48-52 or 55-61 or 80-82. In some cases, the peptide that modulates both the GLP-1 receptor and the GCG receptor comprises an amino acid sequence having up to about 1, 2, 3, 4, or 5 amino acid insertions, deletions, modifications, or substitutions as compared to any one of SEQ ID NOS: 48-52 or 55-61 or 80-82.

In some embodiments, the peptide that modulates both the GLP-1 receptor and the GCG receptor comprises a peptide sequence that is SEQ ID NO: 48. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 48. In some cases, the peptide that modulates both the GLP-1 receptor and the GCG receptor comprises a peptide sequence at least about 90% identical to SEQ ID NO: 48. In some cases, the peptide that modulates both the GLP-1 receptor and the GCG receptor comprises a peptide sequence at least about 95% identical to SEQ ID NO: 48. In some cases, the peptide that modulates both the GLP-1 receptor and the GCG receptor comprises a peptide sequence at least about 99% identical to SEQ ID NO: 48. In some cases, the peptide that modulates both the GLP-1 receptor and the GCG receptor comprises an amino acid sequence having up to about 1, 2, 3, 4, or 5 amino acid insertions, deletions, modifications, or substitutions as compared to SEQ ID NO: 48.

In some embodiments, the peptide that modulates both the GLP-1 receptor and the GCG receptor comprises a peptide sequence that is SEQ ID NO: 60. In some cases, the peptide that modulates both the GLP-1 receptor and the GCG receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 60. In some cases, the peptide that modulates both the GLP-1 receptor and the GCG receptor comprises a peptide sequence at least about 90% identical to SEQ ID NO: 60. In some cases, the peptide that modulates both the GLP-1 receptor and the GCG receptor comprises a peptide sequence at least about 95% identical to SEQ ID NO: 60. In some cases, the peptide that modulates both the GLP-1 receptor and the GCG receptor comprises a peptide sequence at least about 99% identical to SEQ ID NO: 60. In some cases, the peptide that modulates both the GLP-1 receptor and the GCG receptor comprises an amino acid sequence having up to about 1, 2, 3, 4, or 5 amino acid insertions, deletions, modifications, or substitutions as compared to SEQ ID NO: 60.

Non-limiting examples of peptide derivatives are shown in Table 2.

TABLE 2

GLP-1R/GCGR Modulators SEQ ID Table

| SEQ ID NO. | Sequence |
|---|---|
| 48 | H[D-Ser]QGTFTSDYSKYLDEKAAKEFIKWLLNGGPSSGAPPPS |
| 49 | H[D-Ser]QGTFTSDYSKYLDEKAAKEFIKWLLRA |
| 50 | H[Aib]QGTFTSDYSKYLDEKAAKEFIKWLLNGRNRNNIA |
| 51 | H[Aib]QGTFTSDYSKYLDSKKAKEFVKWLLN[Aib]GPSSGAPPPS |
| 52 | H[Aib]QGTFTSDYSKYLDSKKAQEFVKWLLNGPSSGAPPPS |
| 53 | H[Aib]QGTFTSDYSKYLDKKAAKEFKQWLLNGPSSGAPPPS |
| 54 | H[Aib]QGTFTSDYSKYLDKKKAKEFKQWLLN[Aib]GRNRNNIA |

TABLE 2-continued

| GLP-1R/GCGR Modulators SEQ ID Table | |
| --- | --- |
| SEQ ID NO. | Sequence |
| 55 | H[D-Ser]QGT[D-Phe]TSDYSEYLDEKAAKEFIKWLLNGGPSSGAPPPS |
| 56 | H[D-Ser]QGT[D-Phe]TSDYSEYLDEKAAREFIKWLLAGGPSSGAPPPS |
| 57 | H[D-Ser]QGT[Nle]TSDYSEYLDEKAAKEFIKWLLNGGPSSGAPPPS |
| 58 | H[D-Ser]QGTLTSDYSEYLDEKAAKEFIKWLLNGGPSSGAPPPS |
| 59 | H[D-Ser]QGTLTSDYSEYLDSKRAREFVKWLEAGGPSSGAPPPS |
| 60 | H[D-Ser]QGTFTSDYSKYLDECAAKEFICWLLNGGPSSGAPPPS |
| 61 | H[D-Ser]QGTFTSDYSKYLDECAAKEFICWLLRA |
| 80 | H[D-Ser]QGTFTSDYSKYLDECAAKEFICWLMNTKRNRNNIA |
| 81 | H[D-Ser]QGTFTSDYSKYLDECAAHDFVCWLLRA |
| 82 | H[D-Ser]QGTFTSDYSKYLDECAAKEFICWLLRAGPSSGAPPPS |
| 108 | H[Aib]QGTFTSDYSEYLDSKKAKEFVKWLLN[Aib]GPSSGAPPPS |
| 109 | H[Aib]QGTFTSDYSEYLDSKKAQEFVKWLLNGGPSSGAPPPS |
| 110 | H[D-Ser]QGTFTSDYSEYLDEKAAKEFIKWLLNGGPSSGAPPPS |
| 111 | H[D-Ser]QGTFTSDYSKQLDECAAKEFICWLLQGGPSSGAPPPS |

Peptide that Modulates Both the GLP-1 Receptor and the GIP Receptor

In one aspect, provided herein are peptide conjugates comprising a peptide that modulates the GLP-1 receptor and/or the GIP receptor. In some embodiments, the peptide modulates both the GLP-1 receptor and the GIP receptor. In some embodiments, a peptide that modulates the GLP-1 receptor is a GLP-1 receptor agonist. In some embodiments, a peptide that modulates the GIP receptor is a GIP receptor agonist.

The binding affinity of the peptide conjugate as described herein may be within about 5% of the binding affinity of an unmodified form of the peptide. The binding affinity of the peptide conjugate as described herein may be within about 10% of the binding affinity of an unmodified form of the peptide. The binding affinity of the peptide conjugate as described herein may be within about 15% of the binding affinity of an unmodified form of the peptide. The binding affinity of the peptide conjugate as described herein may be within about 20% of the binding affinity of an unmodified form of the peptide.

The peptide that modulates both the GLP-1 receptor and the GIP receptor may comprise one or more sulfhydryl containing amino acid residues. The one or more sulfhydryl containing amino acid residues may be used for connecting a staple. The one or more sulfhydryl containing amino acid residues may be used for connecting a HEM. The one or more sulfhydryl containing amino acid residues may be naturally occurring in the peptide that modulates both the GLP-1 receptor and the GIP receptor. The one or more sulfhydryl containing amino acid residues may be inserted into the peptide that modulates both the GLP-1 receptor and the GIP receptor. The one or more sulfhydryl containing amino acid residues may replace one or more amino acid residues in the peptide that modulates both the GLP-1 receptor and the GIP receptor. Methods for amino acid substitution and/or insertion are known in the art.

The peptide that modulates both the GLP-1 receptor and the GIP receptor may comprise one or more amine containing residues. Non-limiting examples of amine containing residues include lysine, ornithine, diaminobutyric acid, diaminopropionic acid and homolysine. The one or more amine containing residues may be used for connecting a staple. The one or more one or more amine containing residues may be used for connecting a HEM. The one or more one or more amine containing residues may be naturally occurring in the peptide that modulates both the GLP-1 receptor and the GIP receptor.

The one or more one or more amine containing residues may be inserted into the peptide that modulates both the GLP-1 receptor and the GIP receptor. The one or more one or more amine containing residues may replace one or more amino acid residues in the peptide that modulates both the GLP-1 receptor and the GIP receptor.

The peptide that modulates both the GLP-1 receptor and the GIP receptor may comprise at least a portion of a wild-type peptide comprising one or more amino acid mutations. The one or more amino acid mutations may comprise a deletion, substitution, addition or a combination thereof. The one or more amino acid mutations may comprise adding one or more amino acid residues to a wild-type peptide. The one or more amino acid mutations may comprise deletion of one or more amino acid residues of the wild-type peptide. The one or more amino acid mutations may comprise substitution of one or more amino acid residues of the wild-type peptide. The one or more amino acid mutations may comprise substituting one or more amino acid residues of the wild-type peptide with one or more cysteine, lysine or other sulfhydryl or amine containing residues. The one or more amino acid mutations may comprise substituting one or more amino acid residues of the wild-type peptide with one or more D-amino acid residues. The one or more amino acid residues of the wild-type peptide may comprise one or more alanines, methionines, arginines, serines, threonines, and tyrosines.

The peptide that modulates both the GLP-1 receptor and the GIP receptor may be modified with, for example, acetylation, phosphorylation, and methylation. The peptide modification may comprise a chemical modification. Peptide modifications may occur on the N-terminus of the peptide. Peptide modifications may comprise acetyling the amino group at the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

In some embodiments, the peptide that modulates both the GLP-1 receptor and the GIP receptor may be a modified peptide with a D-serine in place of L-serine. In some embodiments, the peptide that modulates both the GLP-1 receptor and the GIP receptor may be a modified with an aminoisobutyric acid [Aib] in place of L-serine. In some embodiments, the peptide that modulates both the GLP-1 receptor and the GIP receptor may be a modified peptide with an neuroleucine [Nle] in place of leucine (Leu).

In some embodiments, the peptide that modulates both the GLP-1 receptor and the GIP receptor comprises a peptide sequence of any one of SEQ ID NOs: 62-71. In some cases, the peptide that modulates both the GLP-1 receptor and the GIP receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 62-71. In some cases, the peptide that modulates both the GLP-1 receptor and the GIP receptor comprises a peptide sequence at least about 90% identical to any one of SEQ ID NOs: 62-71. In some cases, the peptide that modulates both the GLP-1 receptor and the GIP receptor comprises a peptide sequence at least about 95% identical to any one of SEQ ID NOs: 62-71. In some cases, the peptide that modulates both the GLP-1 receptor and the GIP receptor comprises a peptide sequence at least about 99% identical to any one of SEQ ID NOs: 62-71. In some cases, the peptide that modulates both the GLP-1 receptor and the GIP receptor comprises an amino acid sequence having up to about 1, 2, 3, 4, or 5 amino acid insertions, deletions, modifications, or substitutions as compared to any one of SEQ ID NOS: 62-71.

In some embodiments, the peptide that modulates both the GLP-1 receptor and the GIP receptor comprises a peptide sequence of any one of SEQ ID NOs: 62 or 65. In some cases, the peptide that modulates both the GLP-1 receptor and the GIP receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 62 or 65. In some cases, the peptide that modulates both the GLP-1 receptor and the GIP receptor comprises a peptide sequence at least about 90% identical to any one of SEQ ID NOs: 62 or 65. In some cases, the peptide that modulates both the GLP-1 receptor and the GIP receptor comprises a peptide sequence at least about 95% identical to any one of SEQ ID NOs: 62 or 65. In some cases, the peptide that modulates both the GLP-1 receptor and the GIP receptor comprises a peptide sequence at least about 99% identical to any one of SEQ ID NOs: 62 or 65. In some cases, the peptide that modulates both the GLP-1 receptor and the GIP receptor comprises an amino acid sequence having up to about 1, 2, 3, 4, or 5 amino acid insertions, deletions, modifications, or substitutions as compared to any one of SEQ ID NOS: 62 or 65.

In some embodiments, the peptide that modulates both the GLP-1 receptor and the GIP receptor comprises a peptide sequence of any one of SEQ ID NOs: 114-120. In some cases, the peptide that modulates both the GLP-1 receptor and the GIP receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 114-120. In some cases, the peptide that modulates both the GLP-1 receptor and the GIP receptor comprises a peptide sequence at least about 90% identical to any one of SEQ ID NOs: 114-120. In some cases, the peptide that modulates both the GLP-1 receptor and the GIP receptor comprises a peptide sequence at least about 95% identical to any one of SEQ ID NOs: 114-120. In some cases, the peptide that modulates both the GLP-1 receptor and the GIP receptor comprises a peptide sequence at least about 99% identical to any one of SEQ ID NOs: 114-120. In some cases, the peptide that modulates both the GLP-1 receptor and the GIP receptor comprises an amino acid sequence having up to about 1, 2, 3, 4, or 5 amino acid insertions, deletions, modifications, or substitutions as compared to any one of SEQ ID NOS: 114-120.

In some embodiments, the peptide that modulates both the GLP-1 receptor and the GIP receptor comprises a peptide sequence of any one of SEQ ID NOs: 62-68. In some cases, the peptide that modulates both the GLP-1 receptor and the GIP receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 62-68. In some cases, the peptide that modulates both the GLP-1 receptor and the GIP receptor comprises a peptide sequence at least about 90% identical to any one of SEQ ID NOs: 62-68. In some cases, the peptide that modulates both the GLP-1 receptor and the GIP receptor comprises a peptide sequence at least about 95% identical to any one of SEQ ID NOs: 62-68. In some cases, the peptide that modulates both the GLP-1 receptor and the GIP receptor comprises a peptide sequence at least about 99% identical to any one of SEQ ID NOs: 62-68. In some cases, the peptide that modulates both the GLP-1 receptor and the GIP receptor comprises an amino acid sequence having up to about 1, 2, 3, 4, or 5 amino acid insertions, deletions, modifications, or substitutions as compared to any one of SEQ ID NOS: 62-68. In some embodiments, the peptide that modulates both the GLP-1 receptor and the GIP receptor comprises a peptide sequence of any one of SEQ ID NOs: 69-71. In some cases, the peptide that modulates both the GLP-1 receptor and the GIP receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 69-71. In some cases, the peptide that modulates both the GLP-1 receptor and the GIP receptor comprises a peptide sequence at least about 90% identical to any one of SEQ ID NOs: 69-71. In some cases, the peptide that modulates both the GLP-1 receptor and the GIP receptor comprises a peptide sequence at least about 95% identical to any one of SEQ ID NOs: 69-71. In some cases, the peptide that modulates both the GLP-1 receptor and the GIP receptor GLP-1 receptor and the GIP receptor comprises a peptide sequence at least about 95% identical to SEQ ID NO: 63. In some cases, the peptide that modulates both the GLP-1 receptor and the GIP receptor comprises a peptide sequence at least about 99% identical to SEQ ID NO: 63. In some cases, the peptide that modulates both the GLP-1 receptor and the GIP receptor comprises an amino acid sequence having up to about 1, 2, 3, 4, or 5 amino acid insertions, deletions, modifications, or substitutions as compared to SEQ ID NO: 63.

Non-limiting examples of peptide derivatives are shown in Table 3.

TABLE 3

GLP-1R/GIPR Modulators SEQ ID Table

| SEQ ID NO. | Sequence |
|---|---|
| 62 | Y[Aib]EGTFTSDYSIYLDKKAA[Aib]EFVKWLLAGGPSSGAPPPS |
| 63 | Y[Aib]EGTFTSDYSIYKDKQAA[Aib]KFVNWLLAGGPSSGAPPPS |
| 64 | Y[Aib]EGTFTSDYSIYKDKQAA[Aib]KFKNWLKAGGPSSGAPPPS |
| 65 | Y[Aib]EGTFTSDYSIYLDKKAQ[Aib]AFVKWLIAQGPSSGAPPPS |
| 66 | Y[Aib]EGTFHSDYDIYKDKQAA[Aib]KFVQWLLAGGPSSGAPPPS |
| 67 | Y[Aib]EGTFHSDYDIYKDKQAA[Nle]KFVAWLLAGGPSSGAPPPS |
| 68 | Y[Aib]EGTFT[D-Ser]DY[D-Ser]IYKDKQAA[Nle]KFVAWLLAGGPSSGAPPPS |
| 69 | Y[Aib]EGTFTSDYSIYCDKQAA[Aib]CFVNWLLAGGPSSGAPPPS |
| 70 | YGEGTFTSDYSIYCDKQAAQCFVNWLLAGGPSSGAPPPS |
| 71 | Y[Aib]EGTFTSDYSIYCDKQAAQCFVNWLLAGGPSSGAPPPS |
| 114 | Y[Aib]EGTFTSDYSIYLDKCAA[Aib]EFVCWLLAGGPSSGAPPPS |
| 115 | Y[Aib]EGTFTSDYSIYLDKCAQ[Aib]AFVCWLIAQGPSSGAPPPS |
| 116 | Y[Aib]EGTFTSDYSIYCDKQAA[Aib]CFVNWLIAGGPSSGAPPPS |
| 117 | Y[Aib]EGTFISDVSIYCDKQAA[Aib]CFVNWLIAGGPSSGAPPPS |
| 118 | Y[Aib]EGTFISDVSIYLDKCAA[Aib]EFVCWLIAGGPSSGAPPPS |
| 119 | Y[Aib]EGTFISDLSIYCDKQAA[Aib]CFVQWLIAGGPSSGAPPPS |
| 120 | Y[Aib]EGTFISDLSIYLDKCAA[Aib]EFVCWLIAGGPASGAPPPS | comprises a peptide sequence at least about 99% identical to any one of SEQ ID NOs: 69-71. In some cases, the peptide that modulates both the GLP-1 receptor and the GIP receptor comprises an amino acid sequence having up to about 1, 2, 3, 4, or 5 amino acid insertions, deletions, modifications, or substitutions as compared to any one of SEQ ID NOS: 69-71. In some embodiments, the peptide that modulates both the GLP-1 receptor and the GIP receptor comprises a peptide sequence that is SEQ ID NO: 63. In some cases, the peptide that modulates both the GLP-1 receptor and the GIP receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 63. In some cases, the peptide that modulates both the GLP-1 receptor and the GIP receptor comprises a peptide sequence at least about 90% identical to SEQ ID NO: 63. In some cases, the peptide that modulates both the Peptide that Modulates the GLP-1 Receptor In one aspect, provided herein are peptide conjugates comprising a peptide that modulates the GLP-1 receptor. In some embodiments, the peptide that modulates the GLP-1 receptor is a GLP-1 receptor agonist.

The binding affinity of the peptide conjugate as described herein may be within about 5% of the binding affinity of an unmodified form of the peptide. The binding affinity of the peptide conjugate as described herein may be within about 10% of the binding affinity of an unmodified form of the peptide. The binding affinity of the peptide conjugate as described herein may be within about 15% of the binding affinity of an unmodified form of the peptide. The binding affinity of the peptide conjugate as described herein may be within about 20% of the binding affinity of an unmodified form of the peptide.

The peptide that modulates the GLP-1 receptor may comprise one or more sulfhydryl containing amino acid residues. The one or more sulfhydryl containing amino acid residues may be used for connecting a staple. The one or more sulfhydryl containing amino acid residues may be used for connecting a HEM. The one or more sulfhydryl containing amino acid residues may be naturally occurring in the peptide that modulates the GLP-1 receptor. The one or more sulfhydryl containing amino acid residues may be inserted into the peptide that modulates the GLP-1 receptor. The one or more sulfhydryl containing amino acid residues may replace one or more amino acid residues in the peptide that modulates the GLP-1 receptor. Methods for amino acid substitution and/or insertion are known in the art.

The peptide that modulates the GLP-1 receptor may comprise one or more amine containing residues. Non-limiting examples of amine containing residues include lysine, ornithine, diaminobutyric acid, diaminopropionic acid and homolysine. The one or more amine containing residues may be used for connecting a staple. The one or more one or more amine containing residues may be used for connecting a HEM. The one or more one or more amine containing residues may be naturally occurring in the peptide that modulates the GLP-1 receptor. The one or more one or more amine containing residues may be inserted into the peptide that modulates the GLP-1 receptor. The one or more one or more amine containing residues may replace one or more amino acid residues in the peptide that modulates the GLP-1 receptor.

The peptide that modulates the GLP-1 receptor may comprise at least a portion of a wild-type peptide comprising one or more amino acid mutations. The one or more amino acid mutations may comprise a deletion, substitution, addition or a combination thereof. The one or more amino acid mutations may comprise adding one or more amino acid residues to a wild-type peptide. The one or more amino acid mutations may comprise deletion of one or more amino acid residues of the wild-type peptide. The one or more amino acid mutations may comprise substitution of one or more amino acid residues of the wild-type peptide. The one or more amino acid mutations may comprise substituting one or more amino acid residues of the wild-type peptide with one or more cysteine, lysine or other sulfhydryl or amine containing residues. The one or more amino acid mutations may comprise substituting one or more amino acid residues of the wild-type peptide with one or more D-amino acid residues. The one or more amino acid residues of the wild-type peptide may comprise one or more alanines, methionines, arginines, serines, threonines, and tyrosines.

The peptide that modulates the GLP-1 receptor may be modified with, for example, acetylation, phosphorylation, and methylation. The peptide modification may comprise a chemical modification.

Peptide modifications may occur on the N-terminus of the peptide. Peptide modifications may comprise acetyling the amino group at the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

In some embodiments, the peptide that modulates the GLP-1 receptor may be a modified peptide with a D-serine in place of L-serine. In some embodiments, the peptide that modulates the GLP-1 receptor may be a modified with an aminoisobutyric acid [Aib] in place of L-serine. In some embodiments, the peptide that modulates the GLP-1 receptor may be a modified peptide with an neuroleucine [Nle] in place of leucine (Leu).

In some embodiments, the peptide that modulates the GLP-1 receptor comprises a peptide sequence of any one of SEQ ID NOs: 48-82 or 108-120. In some cases, the peptide that modulates the GLP-1 receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 48-82 or 108-120. In some cases, the peptide that modulates the GLP-1 receptor comprises a peptide sequence at least about 90% identical to any one of SEQ ID NOs: 48-82 or 108-120. In some cases, the peptide that modulates the GLP-1 receptor comprises a peptide sequence at least about 95% identical to any one of SEQ ID NOs: 48-82 or 108-120. In some cases, the peptide that modulates the GLP-1 receptor comprises a peptide sequence at least about 99% identical to any one of SEQ ID NOs: 48-82 or 108-120. In some cases, the peptide that modulates the GLP-1 receptor comprises an amino acid sequence having up to about 1, 2, 3, 4, or 5 amino acid insertions, deletions, modifications, or substitutions as compared to any one of SEQ ID NOS: 48-82 or 108-120.

In some embodiments, the peptide that modulates the GLP-1 receptor comprises a peptide sequence of any one of SEQ ID NOs: 72-79. In some cases, the peptide that modulates the GLP-1 receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 72-79. In some cases, the peptide that modulates the GLP-1 receptor comprises a peptide sequence at least about 90% identical to any one of SEQ ID NOs: 72-79. In some cases, the peptide that modulates the GLP-1 receptor comprises a peptide sequence at least about 95% identical to any one of SEQ ID NOs: 72-79. In some cases, the peptide that modulates the GLP-1 receptor comprises a peptide sequence at least about 99% identical to any one of SEQ ID NOs: 72-79. In some cases, the peptide that modulates the GLP-1 receptor comprises an amino acid sequence having up to about 1, 2, 3, 4, or 5 amino acid insertions, deletions, modifications, or substitutions as compared to any one of SEQ ID NOS: 72-79.

In some embodiments, the peptide that modulates the GLP-1 receptor comprises a peptide sequence of any one of SEQ ID NOs: 72-75. In some cases, the peptide that modulates the GLP-1 receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 72-75. In some cases, the peptide that modulates the GLP-1 receptor comprises a peptide sequence at least about 90% identical to any one of SEQ ID NOs: 72-75. In some cases, the peptide that modulates the GLP-1 receptor comprises a peptide sequence at least about 95% identical to any one of SEQ ID NOs: 72-75. In some cases, the peptide that modulates the GLP-1 receptor comprises a peptide sequence at least about 99% identical to any one of SEQ ID NOs: 72-75. In some cases, the peptide that modulates the GLP-1 receptor comprises an amino acid sequence having up to about 1, 2, 3, 4, or 5 amino acid insertions, deletions, modifications, or substitutions as compared to any one of SEQ ID NOS: 72-75.

In some embodiments, the peptide that modulates the GLP-1 receptor comprises a peptide sequence of any one of SEQ ID NOs: 76-79. In some cases, the peptide that modulates the GLP-1 receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to any one of SEQ ID NOs: 76-79. In some cases, the peptide that modulates the GLP-1 receptor comprises a peptide sequence at least about 90% identical to any one of SEQ ID NOs: 76-79. In some cases, the peptide that modulates the GLP-1 receptor comprises a peptide sequence at least about 95% identical to any one of SEQ ID NOs: 76-79. In some cases, the peptide that modulates the GLP-1 receptor comprises a peptide sequence at least about 99% identical to any one of SEQ ID NOs: 76-79. In some cases, the peptide that modulates the GLP-1 receptor comprises an amino acid sequence having up to about 1, 2, 3, 4, or 5 amino acid insertions, deletions, modifications, or substitutions as compared to any one of SEQ ID NOS: 76-79.

In some embodiments, the peptide that modulates the GLP-1 receptor comprises a peptide sequence that is SEQ ID NO: 76. In some cases, the peptide that modulates the GLP-1 receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 76. In some cases, the peptide that modulates the GLP-1 receptor comprises a peptide sequence at least about 90% identical to SEQ ID NO: 76. In some cases, the peptide that modulates the GLP-1 receptor comprises a peptide sequence at least about 95% identical to SEQ ID NO: 76. In some cases, the peptide that modulates the GLP-1 receptor comprises a peptide sequence at least about 99% identical to SEQ ID NO: 76. In some cases, the peptide that modulates the GLP-1 receptor comprises an amino acid sequence having up to about 1, 2, 3, 4, or 5 amino acid insertions, deletions, modifications, or substitutions as compared to SEQ ID NO: 76.

In some embodiments, the peptide that modulates the GLP-1 receptor comprises a peptide sequence that is SEQ ID NO: 77. In some cases, the peptide that modulates the GLP-1 receptor comprises a peptide sequence at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical to SEQ ID NO: 77. In some cases, the peptide that modulates the GLP-1 receptor comprises a peptide sequence at least about 90% identical to SEQ ID NO: 77. In some cases, the peptide that modulates the GLP-1 receptor comprises a peptide sequence at least about 95% identical to SEQ ID NO: 77. In some cases, the peptide that modulates the GLP-1 receptor comprises a peptide sequence at least about 99% identical to SEQ ID NO: 77. In some cases, the peptide that modulates the GLP-1 receptor comprises an amino acid sequence having up to about 1, 2, 3, 4, or 5 amino acid insertions, deletions, modifications, or substitutions as compared to SEQ ID NO: 77.

Non-limiting examples of peptide derivatives are shown in Table 4.

TABLE 4

| GLP-1R Modulators SEQ ID Table | |
| --- | --- |
| SEQ ID NO. | Sequence |
| 72 | HGEGTFTSDLSKQMEEKAVRLFIKWLKNGGPSSGAPPPS |
| 73 | HGEGTFTSDLSKQLEEKAVRLFIKWLKNGGPSSGAPPPS |
| 74 | HGEGTFTSDLSKQ[N1e]EEKAVRLFIKWLKNGGPSSGAPPPS |
| 75 | H[Aib]EGTFTSDVSSYLEGKAAKEFIKWLVKGRG(*) |
| 76 | HGEGTFTSDLSKQLEECAVRLFICWLKNGGPSSGAPPPS |
| 77 | HGEGTFTSDLSKQMEECAVRLFICWLKNGGPSSGAPPPS |
| 78 | HGEGTFTSDVSSYLEGCAAKEFICWLVKGRG(*) |
| 79 | H[Aib]EGTFTSDVSSYLEGCAAKEFICWLVKGRG(*) |

(*)indicates a C-terminal -OH group. All others have a C-terminal -NH$_2$

Prolactin-Releasing Peptide (PrRP)

In one aspect, provided herein are peptide conjugates comprising a prolactin-releasing peptide (PrRP).

The binding affinity of the peptide conjugate as described herein may be within about 5% of the binding affinity of an unmodified form of the peptide. The binding affinity of the peptide conjugate as described herein may be within about 10% of the binding affinity of an unmodified form of the peptide. The binding affinity of the peptide conjugate as described herein may be within about 15% of the binding affinity of an unmodified form of the peptide. The binding affinity of the peptide conjugate as described herein may be within about 20% of the binding affinity of an unmodified form of the peptide.

The prolactin-releasing peptide (PrRP) may comprise one or more sulfhydryl containing amino acid residues. The one or more sulfhydryl containing amino acid residues may be used for connecting a staple to the prolactin-releasing peptide (PrRP). The one or more sulfhydryl containing amino acid residues may be naturally occurring in the prolactin-releasing peptide (PrRP). The one or more sulfhydryl containing amino acid residues may be inserted into the prolactin-releasing peptide (PrRP). The one or more sulfhydryl containing amino acid residues may replace one or more amino acid residues in the prolactin-releasing peptide (PrRP). Methods for amino acid substitution and/or insertion are known in the art.

The prolactin-releasing peptide (PrRP) may comprise at least a portion of a wild-type peptide comprising one or more amino acid mutations. The one or more amino acid mutations may comprise a deletion, substitution, addition or a combination thereof. The one or more amino acid mutations may comprise adding one or more amino acid residues to a wild-type peptide. The one or more amino acid mutations may comprise deletion of one or more amino acid residues of the wild-type peptide. The one or more amino acid mutations may comprise substitution of one or more amino acid residues of the wild-type peptide. The one or more amino acid mutations may comprise substituting one or more amino acid residues of the wild-type peptide with one or more cysteine, lysine or other sulfhydryl or amine containing residues. The one or more amino acid mutations may comprise substituting one or more amino acid residues of the wild-type peptide with one or more D-amino acid residues. The one or more amino acid residues of the wild-type peptide may comprise one or more alanines, methionines, arginines, serines, threonines, and tyrosines.

The prolactin-releasing peptide (PrRP) may be modified with, for example, acetylation, phosphorylation, and methylation. The peptide modification may comprise a chemical modification.

Peptide modifications may occur on the N-terminus of the peptide. Peptide modifications may comprise acetyling the amino group at the N-terminus of the peptide. Alternatively, or additionally, peptide modifications may occur on the C-terminus of the peptide. Peptide modifications may occur at one or more internal amino acids of the peptide. Peptide modifications may comprise replacing the carboxyl group at the C-terminus of the peptide. Peptide modifications may comprise modifying the carboxyl group at the C-terminus of the peptide. The carboxyl group at the C-terminus of the peptide may be modified to produce an amide group. The carboxyl group at the C-terminus of the peptide may be modified to produce an amine group.

In some embodiments, the peptide derivative may be a modified prolactin-releasing peptide (PrRP) with a hArg in place of an Arg. In some embodiments, the peptide derivative may be a modified prolactin-releasing peptide (PrRP) with a R-hArg in place of an Arg. In some embodiments, the peptide derivative may be a modified prolactin-releasing peptide (PrRP) with a NMe-Arg in place of an Arg. In some embodiments, the peptide derivative may be a modified prolactin-releasing peptide (PrRP) with a Nle in place of a Met.

Non-limiting examples of prolactin-releasing peptide (PrRP) are shown in Table 5.

In some cases, the prolactin-releasing peptide (PrRP) has an amino acid sequence at least about 80%, about 81%, about 82%, about 83%, about 84%, about 85%, about 86%, about 87%, about 88%, about 89%, 90%, about 91%, about 92%, about 93%, about 94%, about 95%, about 96%, about 97%, about 98%, or about 99% identical to any one of SEQ ID NOS: 83-105. In some cases, the prolactin-releasing peptide (PrRP) has an amino acid sequence at least about 80% identical to any one of SEQ ID NOS: 83-105. In some cases, the prolactin-releasing peptide (PrRP) has an amino acid sequence at least about 80% identical to any one of SEQ ID NOS: 83-105. In some cases, the prolactin-releasing peptide (PrRP) has an amino acid sequence at least about 85% identical to any one of SEQ ID NOS: 83-105. In some cases, the prolactin-releasing peptide (PrRP) has an amino acid sequence at least about 90% identical to any one of SEQ ID NOS: 83-105. In some cases, the prolactin-releasing peptide (PrRP) has an amino acid sequence at least about 95% identical to any one of SEQ ID NOS: 83-105. In some cases, the prolactin-releasing peptide (PrRP) has an amino acid sequence at least about 99% identical to any one of SEQ ID NOS: 83-105. In some cases, the PrRP comprises an amino acid sequence having up to about 1, 2, 3, 4, or 5 amino acid insertions, deletions, modifications, or substitutions as compared to any one of SEQ ID NOS: 83-105.

TABLE 5

PrRP SEQ ID Table

| SEQ | Peptide sequence |
|-----|------------------|
| 103 | TCDINPAWCTGRGIRPVGRF-NH2 |
| 104 | TPCINPAWYCGRGIRPVGRF-NH2 |
| 105 | TPDCNPAWYTCRGIRPVGRF-NH2 |
| 83 | TPDICPAWYTGCGIRPVGRF-NH2 |
| 84 | TPDINCAWYTGRCIRPVGRF-NH2 |
| 85 | TPDINPCWYTGRGCRPVGRF-NH2 |
| 86 | TPDINPACYTGRGICPVGRF-NH2 |
| 87 | TPDINPAWCTGRGIRCVGRF-NH2 |
| 88 | TPDINPAWYCGRGIRPCGRF-NH2 |
| 89 | CRAHQHSCETRTPDINPAWYTGRGIRPVGRF-NH2 |
| 90 | SRAHQCSMETRTCDINPAWYTGRGIRPVGRF-NH2 |
| 91 | SRAHQHSMCTRTPDICPAWYTGRGIRPVGRF-NH2 |
| 92 | SRAHQHSMETRTCDINPAWCTGRGIRPVGRF-NH2 |
| 93 | SRAHQHSMETRTPDCNPAWYTCRGIRPVGRF-NH2 |
| 94 | SRAHQHSMETRTPDICPAWYTGCGIRPVGRF-NH2 |
| 95 | SRAHQHSMETRTPDINPCWYTGRGCRPVGRF-NH2 |
| 96 | SRAHQHSMETRTPDINPAWCTGRGIRCVGRF-NH2 |
| 97 | SRAHQCS-Nle-ETRTCDINPAWYTG-hArg-GIRPVGRF-NH2 |
| 98 | SRAHQCS-Nle-ETRTCDINPAWYTG-β-hArg-GIRPVGRF-NH2 |
| 99 | SRAHQCS-Nle-ETRTCDINPAWYTG-NMe-Arg-GIRPVGRF-NH2 |
| 100 | SRAHQCS-Nle-ETRTCDINPAWYTGRGIRPVG-hArg-F-NH2 |
| 101 | SRAHQCS-Nle-ETRTCDINPAWYTGRGIRPVG-β-hArg-F-NH2 |
| 102 | SRAHQCS-Nle-ETRTCDINPAWYTGRGIRPVG-NMe-Arg-F-NH2 |
| 106 | TPDINPAWYTGRGIRPVGRF-NH2 |
| 107 | SRAHQHSMETRTPDINPAWYTGRGIRPVGRF-NH2 |

-continued beta-hArg =

Isovaleryl =

N-Mer =

Orn =

Pqa =

Nle =

Staples

Disclosed herein are peptide conjugates comprising a staple.

In some embodiments, the staple attached to the peptide is of Formula (I):

Formula (I)

wherein

A is an optionally substituted alkylene, optionally substituted arylene, optionally substituted heteroarylene, optionally substituted —NR$^3$-alkylene-NR$^3$—, or —N—;

X$^1$ and X$^2$ are independently a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;

wherein X$^1$ is attached to a first amino acid of the peptide, and X$^2$ is attached to a second amino acid of the peptide;

R is hydrogen or -(L)$_s$-Y;

each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;

v is 2-20;

each R$^1$ or R$^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O)NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$, or R$^1$ and R$^2$ are taken together to form a C$_1$-C$_6$ cycloalkyl or C$_1$-C$_6$ heterocycloalkyl;

each R$^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

Y is hydrogen, $C_1$-$C_6$ alkyl, —$CO_2H$, —$CO_2(C_1$-$C_6$ alkyl), —$CO_2NH_2$, —$CO_2N(alkyl)_2$, or —$CO_2NH(alkyl)$; and s is 0-20;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —$NH_2$.

In some embodiments, the staple attached to the peptide is of Formula (I):

Formula (I)

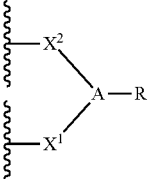

wherein

A is —N—;

$X^1$ and $X^2$ are a bond, —$C(=O)$—, -alkylene-$C(=O)$—, —$C(=O)$-alkylene-, -alkylene-$C(=O)NR^3$—, -alkylene-$NR^3C(=O)$—, —$C(=O)NR^3$-alkylene-, —$NR^3C(=O)$-alkylene-, -alkylene-$C(=O)NR^3$-alkylene-, or -alkylene-$NR^3C(=O)$-alkylene-;

wherein $X^1$ is attached to a first amino acid of the peptide, $X^2$ is attached to a second amino acid of the peptide, and $X^1$ and $X^2$ are identical;

R is hydrogen or -$(L)_s$-Y;

each L is independently —$(CR^1R^2)_v$—, -alkylene-O—, —O-alkylene-, —$C(=O)$-alkylene-, -alkylene-C $(=O)$—, —$NR^3$-alkylene-, -alkylene-$NR^3$—, —S-alkylene-, -alkylene-S—, —$S(=O)$-alkylene-, -alkylene-$S(=O)$—, —$S(=O)_2$-alkylene, -alkylene-$S(=O)_2$—, —$C(=O)$—, —$C(=O)NR^3$—, —$NR^3C(=O)$—, —$NR^3C(=O)NR^3$—, —$NR^3C(=O)NR^3$-alkylene-, —$NR^3C(=O)$-alkylene-$NR^3$—, -alkylene-$C(=O)NR^3$—, —$C(=O)NR^3$-alkylene-, -alkylene-$NR^3C(=O)$—, or —$NR^3C(=O)$-alkylene-;

v is 2-20;

each $R^1$ or $R^2$ is independently hydrogen, halogen, —CN, —$OR^a$, —$SR^a$, —$S(=O)R^b$, —$NO_2$, —$NR^cR^d$, —$S(=O)_2R^d$, —$NR^aS(=O)_2R^d$, —$S(=O)_2NR^cR^d$, —$C(=O)R^b$, —$OC(=O)R^b$, —$CO_2R^a$, —$OCO_2R^a$, —$C(=O)NR^cR^d$, —$OC(=O)NR^cR^d$, —$NR^aC(=O)$$NR^cR^d$, —$NR^aC(=O)R^b$, —$NR^aC(=O)OR^a$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

or $R^1$ and $R^2$ are taken together to form a $C_1$-$C_6$ cycloalkyl or $C_1$-$C_6$ heterocycloalkyl;

each $R^3$ is independently hydrogen, —$S(=O)R^b$, —$S(=O)_2R^a$, —$S(=O)_2NR^cR^d$, —$C(=O)R^b$, —$CO_2R^a$, —$C(=O)NR^cR^d$, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —$OR^a$, or —$NR^cR^d$; and the cycloalkyl, heterocycloalkyl, aryl, and heteroaryl is optionally substituted with one, two, or three of halogen, $C_1$-$C_6$ alkyl, $C_1$-$C_6$ haloalkyl, —$OR^a$, or —$NR^cR^d$;

Y is hydrogen, $C_1$-$C_6$ alkyl, —$CO_2H$, —$CO_2(C_1$-$C_6$ alkyl), —$CO_2NH_2$, —$CO_2N(alkyl)_2$, or —$CO_2NH(alkyl)$;

s is 0-20;

$R^a$ is hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

$R^b$ is $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$; and each $R^c$ and $R^d$ is independently hydrogen, $C_1$-$C_6$ alkyl, $C_2$-$C_6$ alkenyl, $C_2$-$C_6$ alkynyl, $C_1$-$C_6$ heteroalkyl, $C_3$-$C_8$ cycloalkyl, $C_2$-$C_8$ heterocycloalkyl, aryl, or heteroaryl; wherein the alkyl, alkenyl, alkynyl, and heteroalkyl is optionally substituted with one, two, or three of halogen, —OH, —OMe, or —$NH_2$; and the cycloalkyl, heterocycloalkyl, aryl, and heteroaryl is optionally substituted with one, two, or three of halogen, $C_1$-$C_6$ alkyl, $C_1$-$C_6$ haloalkyl, —OH, —OMe, or —$NH_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, $C_1$-$C_6$ alkyl, $C_1$-$C_6$ haloalkyl, —OH, —OMe, or —NH$_2$.

In some embodiments, A is optionally substituted alkylene. In some embodiments, A is —(CH$_2$)$_t$—, wherein t is 1-12. In some embodiments, A is —(CH$_2$)$_t$—, wherein t is 1-10. In some embodiments, A is —(CH$_2$)$_t$—, wherein t is 1-8. In some embodiments, A is —(CH$_2$)$_t$—, wherein t is 1-6. In some embodiments, A is —(CH$_2$)$_t$—, wherein t is 1-4.

In some embodiments, A is optionally substituted arylene. In some embodiments, A is arylene optionally substituted with halogen, alkyl, or haloalkyl. In some embodiments, A is unsubstituted arylene.

In some embodiments, A is —NR$^3$-alkylene-NR$^3$—. In some embodiments, A is —N—.

In some embodiments, X$^1$ and X$^2$ are identical. In some embodiments, X$^1$ and X$^2$ are different.

In some embodiments, X$^1$ and X$^2$ are —C(=O)—. In some embodiments, X$^1$ and X$^2$ are independently -alkylene-C(=O)— or —C(=O)alkylene-. In some embodiments, X$^1$ and X$^2$ are independently —CH$_2$—C(=O)— or —C(=O)—CH$_2$—. In some embodiments, X$^1$ and X$^2$ are independently -alkylene-C(=O)NR$^3$— or —C(=O)NR$^3$-alkylene-. In some embodiments, X$^1$ and X$^2$ are independently —CH$_2$—C(=O)NR$^3$— or —C(=O)NR$^3$—CH$_2$—. In some embodiments, X$^1$ and X$^2$ are independently -alkylene-C(=O)NR$^3$-alkylene- or -alkylene-NR$^3$C(=O)-alkylene-. In some embodiments, X$^1$ and X$^2$ are independently —CH$_2$—C(=O)NR$^3$—CH$_2$CH$_2$— or —CH$_2$—NR$^3$C(=O)—CH$_2$CH$_2$—. In some embodiments, X$^1$ and X$^2$ are independently —CH$_2$—C(=O)NH—CH$_2$CH$_2$— or —CH$_2$—NHC(=O)—CH$_2$CH$_2$—.

In some embodiments, each R$^3$ is independently hydrogen or $C_1$-$C_6$ alkyl. In some embodiments, each R$^3$ is hydrogen.

In some embodiments, >A-R has the following structure:

wherein r1 and r2 are each independently 0-4.

In some embodiments, r1 and r2 are each independently 0-2. In some embodiments, r1 and r2 are each 0. In some embodiments, r1 and r2 are each 1. In some embodiments, r1 and r2 are each 3. In some embodiments, r1 and r2 are each 2.

In some embodiments, >A-R has the following structure:

In some embodiments, >A-R has the following structure:

wherein p1 is 1-5.

In some embodiments, p1 is 1-3. In some embodiments, p1 is 1-2. In some embodiments, p1 is 1. In some embodiments, p1 is 2. In some embodiments, p1 is 3. In some embodiments, p1 is 4. In some embodiments, p1 is 5.

In some embodiments, >A-R has the following structure:

In some embodiments, >A-R has the following structure:

In some embodiments, s is 1-15. In some embodiments, s is 1-10. In some embodiments, s is 5-15. In some embodiments, s is 5-10. In some embodiments, s is 5-20.

In some embodiments, Y is hydrogen or —CO$_2$H. In some embodiments, Y is hydrogen. In some embodiments, Y is —CO$_2$H.

In some embodiments, each L is independently —(CR$^1$R$^2$)$_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-20.

In some embodiments, each L is independently —(CR$^1$R$^2$)$_v$—, -alkylene-O—, —C(=O)—, —C(=O)NR$^3$—, —NR$^3$C(=O)—, -alkylene-C(=O)NR$^3$—, or -alkylene-NR$^3$C(=O)—; and v is 2-16.

In some embodiments, v is 2-16. In some embodiments, v is 2-5. In some embodiments, v is 5-16. In some embodiments, v is 5 or 16. In some embodiments, v is 2 or 16.

In some embodiments, each R$^1$ or R$^2$ is independently hydrogen, halogen, —CN, —OR$^a$, —NR$^c$R$^d$, —C(=O)R$^b$, —CO$_2$R, —C(=O)NR$^c$R$^d$, or $C_1$-$C_6$ alkyl.

In some embodiments, each R$^1$ or R$^2$ is independently hydrogen, halogen, —CO$_2$R$^a$, —C(=O)NR$^c$R$^d$, or $C_1$-$C_6$ alkyl. In some embodiments, each R$^1$ or R$^2$ is independently hydrogen, —CO$_2$R$^a$, or —C(=O)NR$^c$R$^d$. In some embodiments, each R$^1$ or R$^2$ is independently hydrogen or —CO$_2$R$^a$.

In some embodiments, the staple is

In some embodiments, the staple attached to the peptide is wherein each $L^1$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s1 is 1-15.

In some embodiments, the staple attached to the peptide is wherein each $L^2$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s2 is 1-15.

In some embodiments, the staple attached to the peptide is wherein each $L^3$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s3 is 1-15.

In some embodiments, the staple attached to the peptide is wherein each $L^4$ is independently —$(CR^1R^2)_v$—, -alkylene-O—, —O-alkylene-, —C(=O)NR³—, —NR³C(=O)—, -alkylene-C(=O)NR³—, or -alkylene-NR³C(=O)—; v is 2-20; and s4 is 1-15.

In some embodiments, the staple attached to the peptide is wherein each $L^5$ is independently —$(CR^1R^2)_v$—, —C(=O)NR³—, —NR³C(=O)—, -alkylene-C(=O)NR³—, or -alkylene-NR³C(=O)—; v is 2-20; and s5 is 1-10.

In some embodiments, the staple attached to the peptide is wherein each $L^6$ is independently —$(CR^1R^2)_v$—, —C(=O)NR³—, —NR³C(=O)—, -alkylene-C(=O)NR³—, or -alkylene-NR³C(=O)—; v is 2-20; and s6 is 1-5.

In some embodiments, the staple attached to the peptide is wherein each $L^7$ is independently —$(CR^1R^2)_v$—, —$C(\!=\!O)$NR$^3$—, or —NR$^3$C($\!=\!$O)—; v is 2-20; and s7 is 1-5.

In some embodiments, the staple attached to the peptide is

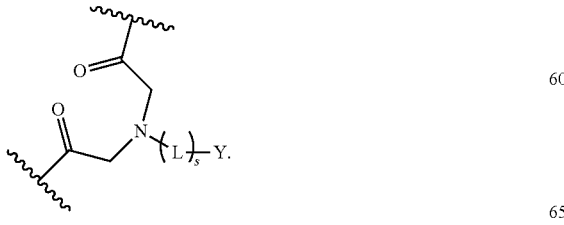

wherein $L^8$ is —$(CR^1R^2)_v$— and v is 10-20.

In some embodiments, the staple attached to the peptide is wherein each $L^9$ is independently —$(CR^1R^2)_v$—, —$C(\!=\!O)$NR$^3$—, —NR$^3$C($\!=\!$O)—, -alkylene-C($\!=\!$O)NR$^3$—, or -al-kylene-NR$^3$C($\!=\!$O)—; v is 2-20; and s9 is 1-5.

In some embodiments, the staple attached to the peptide is wherein $L^{10}$ is —$(CR^1R^2)_v$— and v is 10-20.

In some embodiments, the staple attached to the peptide is

In some embodiments, the staple attached to the peptide is wherein each $L^{11}$ is independently —$(CR^1R^2)_v$—, -alkylene-O—, —O-alkylene-, —$C(=O)NR^3$—, —$NR^3C(=O)$—, -alkylene-$C(=O)NR^3$—, or -alkylene-$NR^3C(=O)$—; v is 2-20; and s11 is 1-15.

In some embodiments, the staple attached to the peptide is wherein each $L^{12}$ is independently —$(CR^1R^2)_v$—, -alkylene-O—, —O-alkylene-, —$C(=O)NR^3$—, —$NR^3C(=O)$—, -alkylene-$C(=O)NR^3$—, or -alkylene-$NR^3C(=O)$—; v is 2-20; and s12 is 1-15.

In some embodiments, the staple attached to the peptide is wherein each $L^{13}$ is independently —$(CR^1R^2)_v$—, -alkylene-O—, —O-alkylene-, —$C(=O)NR^3$—, —$NR^3C(=O)$—, -alkylene-$C(=O)NR^3$—, or -alkylene-$NR^3C(=O)$—; v is 2-20; and s13 is 1-15.

In some embodiments, the staple attached to the peptide is wherein each $L^{14}$ is independently —$(CR^1R^2)_v$—, -alkylene-O—, —O-alkylene-, —C(=O)NR$^3$—, —NR$^3$C(=O)—, -alkylene-C(=O)NR$^3$—, or -alkylene-NR$^3$C(=O)—; v is 2-20; and s14 is 1-15.

In some embodiments, the staple attached to the peptide is wherein each $L^{15}$ is independently —$(CR^1R^2)_v$—, —C(=O)NR$^3$—, —NR$^3$C(=O)—, -alkylene-C(=O)NR$^3$—, or -alkylene-NR$^3$C(=O)—; v is 2-20; and s15 is 1-10.

In some embodiments, the staple attached to the peptide is wherein each $L^{16}$ is independently —$(CR^1R^2)_v$—, —C(=O)NR$^3$—, or —NR$^3$C(=O)—; v is 2-20; and s16 is 1-5.

In some embodiments, the staple attached to the peptide is wherein each $L^{17}$ is independently —$(CR^1R^2)_v$—, —C(=O)NR$^3$—, or —NR$^3$C(=O)—; v is 2-20; and s17 is 1-5.

In some embodiments, the staple attached to the peptide is

15 wherein L$^{18}$ is —(CR$^1$R$^2$)$_v$— and v is 10-20.

In some embodiments, the staple attached to the peptide is

In some embodiments, the staple attached to the peptide is

20

25

30 wherein each L$^{19}$ is independently —(CR$^1$R$^2$)$_v$—, —C(=O)NR$^3$—, —NR$^3$C(=O)—, -alkylene-C(=O) NR$^3$—, or -alkylene-NR$^3$C(=O)—; v is 2-20; and s19 is 1-5.

wherein L$^{20}$ is —(CR$^1$R$^2$)$_v$— and v is 10-20.

In some embodiments, the staple attached to the peptide is:

-continued 53
54

-continued

-continued

-continued the "ʒ-S" being part of a cysteine, homocysteine, 2-amino-5-mercaptopentanoic acid, or 2-amino-6-mercaptohexanoic acid residue and the "ʒ-NH" being part of a lysine, ornith-ine, diaminobutyric acid, diaminopropionic acid, or homoly-sine residue.

In some embodiments, the staple attached to the peptide is:

or

-continued wherein n is 1-4 and is 6-20; the "ξ-S" being part of a cysteine, homocysteine, 2-amino-5-mercaptopentanoic acid, or 2-amino-6-mercaptohexanoic acid residue and the "ξ-NH" being part of a lysine, ornithine, diaminobutyric acid, 0 ξ diaminopropionic acid, or homolysine residue.

In some embodiments, the staple attached to the peptide is:

the "⁊-S" being part of a cysteine, homocysteine, 2-amino-5-mercaptopentanoic acid, or 2-amino-6-mercaptohexanoic acid residue and the "⁊-NH" being part of a lysine, ornithine, diaminobutyric acid, diaminopropionic acid, or homolysine residue.

In some embodiments, the staple attached to the peptide is:

the "ξ-S" being part of a cysteine, homocysteine, 2-amino-5-mercaptopentanoic acid, or 2-amino-6-mercaptohexanoic acid residue.

In some embodiments, the staple attached to the peptide is:

the "ξ-NH" being part of a lysine, ornithine, diaminobutyric acid, diaminopropionic acid, or homolysine residue.

In some embodiments, the staple attached to the peptide is:

the "ξ-NH" being part of a lysine, ornithine, diaminobutyric acid, diaminopropionic acid, or homolysine residue.

In some embodiments, the staple attached to the peptide is:

the "ξ -S" being part of a cysteine, homocysteine, 2-amino-5-mercaptopentanoic acid, or 2-amino-6-mercaptohexanoic acid residue.

In some embodiments, the staple attached to the peptide is:

the "ξ -S" being part of a cysteine, homocysteine, 2-amino-5-mercaptopentanoic acid, or 2-amino-6-mercaptohexanoic acid residue.

In some embodiments, the staple attached to the peptide is:

the "ξ-S" being part of a cysteine, homocysteine, 2-amino-5-mercaptopentanoic acid, or 2-amino-6-mercaptohexanoic acid residue.

In some embodiments, the staple attached to the peptide is:

the "ξ-NH" being part of a lysine, ornithine, diaminobutyric acid, diaminopropionic acid, or homolysine residue.

In some embodiments, the staple attached to the peptide is:

the "ξ-NH" being part of a lysine, ornithine, diaminobutyric acid, diaminopropionic acid, or homolysine residue.

In some embodiments, the staple attached to the peptide is:

the "ξ-NH" being part of a lysine, ornithine, diaminobutyric acid, diaminopropionic acid, or homolysine residue.

Half-Life Extending Moiety (HEM)

Disclosed herein are peptide conjugates comprising a HEM.

In some embodiments, the HEM attached to the peptide is of Formula (II):

$$—X^3\text{-}(L)_s\text{-}Y$$

Formula (II)

wherein $X^3$ is a bond, —C(=O)—, -alkylene-C(=O)—, —C(=O)-alkylene-, -alkylene-C(=O)NR$^3$—, -alkylene-NR$^3$C(=O)—, —C(=O)NR$^3$-alkylene-, —NR$^3$C(=O)-alkylene-, -alkylene-C(=O)NR$^3$-alkylene-, or -alkylene-NR$^3$C(=O)-alkylene-;

wherein $X^3$ is attached to a first amino acid of the peptide;

each L is independently —(CR$^1$R$^2$)$_v$—, -alkylene-O—, —O-alkylene-, —C(=O)-alkylene-, -alkylene-C(=O)—, —NR$^3$-alkylene-, -alkylene-NR$^3$—, —S-alkylene-, -alkylene-S—, —S(=O)-alkylene-, -alkylene-S(=O)—, —S(=O)$_2$-alkylene, -alkylene-S(=O)$_2$—, —C(=O)—, —C(=O)NR$^3$—, —NR$^3$C(=O)—, —NR$^3$C(=O)NR$^3$—, —NR$^3$C(=O)NR$^3$-alkylene-, —NR$^3$C(=O)-alkylene-NR$^3$—, -alkylene-C(=O)NR$^3$—, —C(=O)NR$^3$-alkylene-, -alkylene-NR$^3$C(=O)—, or —NR$^3$C(=O)-alkylene-;

v is 2-20;

each $R^1$ or $R^2$ is independently hydrogen, halogen, —CN, —OR$^a$, —SR$^a$, —S(=O)R$^b$, —NO$_2$, —NR$^c$R$^d$, —S(=O)$_2$R$^d$, —NR$^a$S(=O)$_2$R$^d$, —S(=O)$_2$NR$^c$R$^d$, —C(=O)R$^b$, —OC(=O)R$^b$, —CO$_2$R$^a$, —OCO$_2$R$^a$, —C(=O)NR$^c$R$^d$, —OC(=O)NR$^c$R$^d$, —NR$^a$C(=O) NR$^c$R$^d$, —NR$^a$C(=O)R$^b$, —NR$^a$C(=O)OR$^a$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, —NR$^c$R$^d$, or $R^1$ and $R^2$ are taken together to form a C$_1$-C$_6$ cycloalkyl or C$_1$-C$_6$ heterocycloalkyl;

each $R^3$ is independently hydrogen, —S(=O)R$^b$, —S(=O)$_2$R$^a$, —S(=O)$_2$NR$^c$R$^d$, —C(=O)R$^b$, —CO$_2$R$^a$, —C(=O)NR$^c$R$^d$, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OR$^a$, or —NR$^c$R$^d$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OR$^a$, or —NR$^c$R$^d$;

Y is hydrogen, C$_1$-C$_6$ alkyl, —CO$_2$H, —CO$_2$(C$_1$-C$_6$ alkyl), —CO$_2$NH$_2$, —CO$_2$N(alkyl)$_2$, or —CO$_2$NH(alkyl); and s is 0-20;

$R^a$ is hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

$R^b$ is C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

each $R^c$ and $R^d$ is independently hydrogen, C$_1$-C$_6$ alkyl, C$_2$-C$_6$ alkenyl, C$_2$-C$_6$ alkynyl, C$_1$-C$_6$ heteroalkyl, C$_3$-C$_8$ cycloalkyl, C$_2$-C$_8$ heterocycloalkyl, aryl, or heteroaryl; wherein the alkyl, alkenyl, alkynyl, and heteroalkyl is optionally substituted with one, two, or three of halogen, —OH, —OMe, or —NH$_2$; and the cycloalkyl, heterocycloalkyl, aryl, and heteroaryl is optionally substituted with one, two, or three of halogen, C$_1$-C$_6$ alkyl, C$_1$-C$_6$ haloalkyl, —OH, —OMe, or —NH$_2$;

or $R^c$ and $R^d$, together with the nitrogen atom to which they are attached, form a heterocycloalkyl or heteroaryl; wherein the heterocycloalkyl and heteroaryl is optionally substituted with one, two, or three of halogen, C$_1$-C$_6$ alkyl, C$_1$-C$_6$ haloalkyl, —OH, —OMe, or —NH$_2$.

In some embodiments, $X^3$ is a bond.

In some embodiments, $X^3$ is -alkylene-C(=O)— or —C(=O)alkylene-. In some embodiments, $X^3$ is —CH$_2$—C(=O)— or —C(=O)—CH$_2$—. In some embodiments, $X^3$ is -alkylene-C(=O)NR$^3$— or —C(=O)NR$^3$-alkylene-. In some embodiments, $X^3$ is —CH$_2$—C(=O)NR$^3$— or —C(=O)NR$^3$—CH$_2$—. In some embodiments, $X^3$ is -alkylene-C(=O)NR$^3$-alkylene- or -alkylene-NR$^3$C(=O)-alkylene-. In some embodiments, $X^3$ is —CH$_2$—C(=O) NR$^3$—CH$_2$CH$_2$— or —CH$_2$—NR$^3$C(=O)—CH$_2$CH$_2$—. In some embodiments, $X^3$ is —CH$_2$—C(=O)NH— CH$_2$CH$_2$— or —CH$_2$—NHC(=O)—CH$_2$CH$_2$—.

In some embodiments, each $R^3$ is independently hydrogen or C$_1$-C$_6$ alkyl. In some embodiments, each $R^3$ is hydrogen.

In some embodiments, s is 1-15. In some embodiments, s is 1-10. In some embodiments, s is 5-15. In some embodiments, s is 5-10. In some embodiments, s is 5-20.

In some embodiments, Y is hydrogen or —CO$_2$H. In some embodiments, Y is hydrogen. In some embodiments, Y is —CO$_2$H.

In some embodiments, each L is independently —(CR$^1$R$^2$)$_v$—, -alkylene-O—, —C(=O)—, —C(=O) NR$^3$—, —NR$^3$C(=O)—, -alkylene-C(=O)NR$^3$—, or -alkylene-NR$^3$C(=O)—; and v is 2-20.

In some embodiments, each L is independently —(CR$^1$R$^2$)$_v$—, -alkylene-O—, —C(=O)—, —C(=O) NR$^3$—, —NR$^3$C(=O)—, -alkylene-C(=O)NR$^3$—, or -alkylene-NR$^3$C(=O)—; and v is 2-16.

In some embodiments, v is 2-16. In some embodiments, v is 2-5. In some embodiments, v is 5-16. In some embodiments, v is 5 or 16. In some embodiments, v is 2 or 16.

In some embodiments, each $R^1$ or $R^2$ is independently hydrogen, halogen, —CN, —OR$^a$, —NR$^c$R$^d$, —C(=O)R$^b$, —CO$_2$R, —C(=O)NR$^c$R$^d$, or C$_1$-C$_6$ alkyl.

In some embodiments, each $R^1$ or $R^2$ is independently hydrogen, halogen, —CO$_2$R$^a$, —C(=O)NR$^c$R$^d$, or C$_1$-C$_6$ alkyl. In some embodiments, each $R^1$ or $R^2$ is independently hydrogen, —CO$_2$R$^a$, or —C(=O)NR$^c$R$^d$. In some embodiments, each $R^1$ or $R^2$ is independently hydrogen or —CO$_2$R$^a$.

In some embodiments, the HEM attached to the peptide is:

the "ᔔ -S" being part of a cysteine, homocysteine, 2-amino-5-mercaptopentanoic acid, or 2-amino-6-mercaptohexanoic acid residue.

In some embodiments, the HEM attached to the peptide is:

wherein n is 1-4 and m is 6-20; the "ᔔ -S" being part of a cysteine, homocysteine, 2-amino-5-mercaptopentanoic acid, or 2-amino-6-mercaptohexanoic acid residue.

Peptide Conjugates with a Staple

In one aspect, disclosed herein are peptide conjugates comprising: (a) a peptide selected from a peptide that modulates the PYY receptor, a peptide that modulates both the GLP-1 receptor and the GCG receptor, a peptide that modulates both the GLP-1 receptor and the GIP receptor, and a peptide that modulates the GLP-1 receptor; and (b) a staple attached to the peptide at a first amino acid and a second amino acid.

In some embodiments, the peptide conjugates comprise (a) a peptide that modulates the PYY receptor; and (b) a staple attached to the peptide at a first amino acid and a second amino acid.

In some embodiments, the peptide conjugates comprise (a) a peptide that modulates both the GLP-1 receptor and the GCG receptor; and (b) a staple attached to the peptide at a first amino acid and a second amino acid.

In some embodiments, the peptide conjugates comprise (a) a peptide that modulates both the GLP-1 receptor and the GIP receptor; and (b) a staple attached to the peptide at a first amino acid and a second amino acid.

In some embodiments, the peptide conjugates comprise (a) a peptide that modulates the GLP-1 receptor; and (b) a staple attached to the peptide at a first amino acid and a second amino acid.

Non-limiting examples of amino acids for use in conjugation include cysteine, homocysteine, 2-amino-5-mercaptopentanoic acid, 2-amino-6-mercaptohexanoic acid, lysine, ornithine, diaminobutyric acid, diaminopropionic acid, homolysine, other sulfhydryl containing amino acids, or other amine containing amino acids. In some embodiments, the two amino acids connected by a staple are about or at least about 3, 4, 5, 6, 7, 8, 9, 10, 11, 12, 13, 14, 15, 16, or more amino acids apart. For example, the first amino acid has position i, and the second amino acid has position i+7, i+11, i+13, i+15, or i+16. For example, the first amino acid has a position i in the peptide and the second amino acid has a position i+n in the peptide, wherein n is 4-16. In some embodiments, the first amino acid is at the 14 position and the second amino acid is at the 21 position in the peptide. In some embodiments, the first amino acid is at the 17 position and the second amino acid is at the 24 position in the peptide.

For example, the first amino acid has a position i in the peptide and the second amino acid has a position i+4 in the peptide. For example, the first amino acid has a position i in the peptide and the second amino acid has a position i+5 in the peptide. For example, the first amino acid has a position i in the peptide and the second amino acid has a position i+6 in the peptide. For example, the first amino acid has a position i in the peptide and the second amino acid has a position i+7 in the peptide. For example, the first amino acid has a position i in the peptide and the second amino acid has a position i+8 in the peptide. For example, the first amino acid has a position i in the peptide and the second amino acid has a position i+9 in the peptide. For example, the first amino acid has a position i in the peptide and the second amino acid has a position i+10 in the peptide. For example, the first amino acid has a position i in the peptide and the second amino acid has a position i+11 in the peptide. For example, the first amino acid has a position i in the peptide and the second amino acid has a position i+12 in the peptide. For example, the first amino acid has a position i in the peptide and the second amino acid has a position i+13 in the peptide. For example, the first amino acid has a position i in the peptide and the second amino acid has a position i+14 in the peptide. For example, the first amino acid has a position i in the peptide and the second amino acid has a position i+15 in the peptide. For example, the first amino acid has a position i in the peptide and the second amino acid has a position i+16 in the peptide.

In some embodiments, the first amino acid and the second amino acid are independently selected from the group consisting of an amine-containing amino acid and a sulfhydryl-containing amino acid.

In some embodiments, the first amino acid and second amino acid is independently selected from cysteine, homocysteine, 2-amino-5-mercaptopentanoic acid, and 2-amino-6-mercaptohexanoic acid. In some embodiments, the first amino acid and second amino acid are cysteines.

In some embodiments, the first amino acid and second amino acid is independently selected from lysine, ornithine, diaminobutyric acid, diaminopropionic acid and homolysine.

In some embodiments, the first amino acid and second amino acid are lysines.

In some embodiments, the first amino acid and second amino acid are ornithines.

In some embodiments, the peptide conjugate further comprises a half-life extending molecule attached to a sulfhydryl containing amino acid or an amine-containing amino acid residue in the peptide.

In some embodiments, the amine-containing amino acid is selected from lysine, ornithine, diaminobutyric acid, diaminopropionic acid, and homolysine.

In some embodiments, the amine-containing amino acid is lysine.

In some embodiments, the sulfhydryl-containing amino acid is selected from cysteine, homocysteine, 2-amino-5-mercaptopentanoic acid, and 2-amino-6-mercaptohexanoic acid.

In some embodiments, the sulfhydryl-containing amino acid is cysteine.

Peptide Conjugates with Half-Life Extending Moiety

In one aspect, disclosed herein are peptide conjugates comprising: (a) a peptide selected from a peptide that modulates the PYY receptor, a peptide that modulates both the GLP-1 receptor and the GCG receptor, a peptide that modulates both the GLP-1 receptor and the GIP receptor, and a peptide that modulates the GLP-1 receptor; and (b) a half-life extending moiety (HEM) attached to the peptide at a first amino acid.

In some embodiments, the peptide conjugates comprise (a) a peptide that modulates the PYY receptor; and (b) a half-life extending moiety (HEM) attached to the peptide at a first amino acid.

In some embodiments, the peptide conjugates comprise (a) a peptide that modulates both the GLP-1 receptor and the GCG receptor; and (b) a half-life extending moiety (HEM) attached to the peptide at a first amino acid.

In some embodiments, the peptide conjugates comprise (a) a peptide that modulates both the GLP-1 receptor and the GIP receptor; and (b) a half-life extending moiety (HEM) attached to the peptide at a first amino acid.

In some embodiments, the peptide conjugates comprise (a) a peptide that modulates the GLP-1 receptor; and (b) a half-life extending moiety (HEM) attached to the peptide at a first amino acid.

Non-limiting examples of amino acids for use in conjugation include cysteine, homocysteine, 2-amino-5-mercaptopentanoic acid, 2-amino-6-mercaptohexanoic acid, lysine, ornithine, diaminobutyric acid, diaminopropionic acid, homolysine, other sulfhydryl containing amino acids, or other amine containing amino acids. In some embodiments, the first amino acid is selected from the group consisting of an amine-containing amino acid and a sulfhydryl-containing amino acid. In some embodiments, the first amino acid is selected from cysteine, homocysteine, 2-amino-5-mercaptopentanoic acid, and 2-amino-6-mercaptohexanoic acid. In some embodiments, the first amino acid is cysteine. In some embodiments, the first amino acid is selected from lysine, ornithine, diaminobutyric acid, diaminopropionic acid and homolysine. In some embodiments, the first amino acid is lysine. In some embodiments, the first amino acid is ornithine. In some embodiments, the peptide conjugate further comprises a second half-life extending moiety attached to a sulfhydryl containing amino acid or an amine-containing amino acid residue in the peptide. In some embodiments, the amine-containing amino acid is selected from lysine, ornithine, diaminobutyric acid, diaminopropionic acid, and homolysine. In some embodiments, the amine-containing amino acid is lysine. In some embodiments, the sulfhydryl-containing amino acid is selected from cysteine, homocysteine, 2-amino-5-mercaptopentanoic acid, and 2-amino-6-mercaptohexanoic acid. In some embodiments, the sulfhydryl-containing amino acid is cysteine.

In some embodiments, the peptide conjugate comprises:
a) a peptide that modulates the PYY receptor comprising a peptide sequence having at least about 95% identity to any one of SEQ ID NOs: 3, 5, 6, 8, 14-30, 36, or 37; and
b) a staple attached to the peptide at a first amino acid and a second amino acid.

In some embodiments, the peptide that modulates the PYY receptor comprises a peptide sequence having at least about 99% identity to any one of SEQ ID NOs: 3, 5, 6, 8, 14-30, 36, or 37.

In some embodiments, the peptide that modulates the PYY receptor comprises a peptide sequence that is SEQ ID NOs: 3, 5, 6, 8, 14-30, 36, or 37.

In some embodiments, the peptide that modulates the PYY receptor comprises a sequence having at least about 99% identity to SEQ ID NO: 6.

In some embodiments, the peptide that modulates the PYY receptor comprises a sequence that is SEQ ID NO: 6.

In some embodiments, the peptide conjugate comprises:
a) a peptide that modulates both the GLP-1 receptor and the GCGR receptor comprising a peptide sequence having at least about 95% identity to any one of SEQ ID NOs: 50-59; and
b) a staple attached to the peptide at a first amino acid and a second amino acid.

In some embodiments, the peptide that modulates both the GLP-1 receptor and the GCG receptor comprises a peptide sequence having at least about 99% identity to any one of SEQ ID NOs: 50-59.

In some embodiments, the peptide that modulates both the GLP-1 receptor and the GCG receptor comprises a peptide sequence selected from SEQ ID NOs: 50-59.

In some embodiments, the peptide conjugate comprises:
a) a peptide that modulates both the GLP-1 receptor and the GIP receptor comprising a peptide sequence having at least about 95% identity to any one of SEQ ID NOs: 62-71; and
b) a staple attached to the peptide at a first amino acid and a second amino acid.

In some embodiments, the peptide that modulates both the GLP-1 receptor and the GIP receptor comprises a peptide sequence having at least about 99% identity to any one of SEQ ID NOs: 62-71.

In some embodiments, the peptide that modulates both the GLP-1 receptor and the GIP receptor comprises a peptide sequence selected from SEQ ID NOs: 62-71.

In some embodiments, the peptide that modulates both the GLP-1 receptor and the GIP receptor comprises a sequence having at least about 99% identity to SEQ ID NO: 63.

In some embodiments, the peptide that modulates both the GLP-1 receptor and the GIP receptor comprises a sequence that is SEQ ID NO: 63.

In some embodiments, the peptide conjugate comprises:
a) a peptide that modulates the GLP-1 receptor comprising a peptide sequence having at least about 95% identity to any one of SEQ ID NOs: 74 or 79; and
b) a staple attached to the peptide at a first amino acid and a second amino acid.

In some embodiments, the peptide that modulates the GLP-1 receptor comprises a peptide sequence having at least about 99% identity to any one of SEQ ID NOs: 74 or 79.

In some embodiments, the peptide that modulates the GLP-1 receptor comprises a peptide sequence selected from SEQ ID NOs: 74 or 79.

In some embodiments, the peptide conjugate comprises:

a) a peptide that modulates the PYY receptor comprising a peptide sequence that is SEQ ID NO: 6; and b) a staple attached to the peptide at a first cysteine and a second cysteine having the following structure ("ξ -S" being part of the cysteine residues):

In some embodiments, the peptide conjugate comprises:

a) a peptide that modulates the PYY receptor comprising a peptide sequence that is SEQ ID NO: 10; and b) a HEM attached to the peptide at a first cysteine having the following structure ("ξ -S" being part of the cysteine residues):

In some embodiments, the peptide conjugate comprises:

a) a peptide that modulates both the GLP-1 receptor and the GCG receptor comprising a peptide sequence that is SEQ ID NO: 48; and b) a staple attached to the peptide at a first lysine and a second lysine having the following structure ("ξ -NH" being part of the lysine residues):

In some embodiments, the peptide conjugate comprises:

a) a peptide that modulates both the GLP-1 receptor and the GCG receptor comprising a peptide sequence that is SEQ ID NO: 60; and b) a staple attached to the peptide at a first cysteine and a second cysteine having the following structure ("ξ -S" being part of the cysteine residues):

In some embodiments, the peptide conjugate comprises:

a) a peptide that modulates both the GLP-1 receptor and the GIP receptor comprising a peptide sequence that is SEQ ID NO: 63; and b) a staple attached to the peptide at a first lysine and a second lysine having the following structure ("$\xi$ -NH" being part of the lysine residues):

In some embodiments, the peptide conjugate comprises:

a) a peptide that modulates the GLP-1 receptor comprising a peptide sequence that is SEQ ID NO: 76; and b) a staple attached to the peptide at a first cysteine and a second cysteine having the following structure ("$\xi$ -S" being part of the cysteine residues):

In some embodiments, the peptide conjugate comprises:

a) a peptide that modulates the GLP-1 receptor comprising a peptide sequence that is SEQ ID NO: 77; and b) a staple attached to the peptide at a first cysteine and a second cysteine having the following structure ("$\xi$ -S" being part of the cysteine residues):

US 12,583,900 B2

81

Prolactin-Releasing Peptide (PrRP) Peptide Conjugates

In one aspect, disclosed herein are peptide conjugates comprising a prolactin-releasing peptide (PrRP). In exemplary cases, the prolactin-releasing peptide (PrRP) comprises two amino acids connected by a staple. Non-limiting examples of amino acids for use in conjugation include cysteine, homocysteine, 2-amino-5-mercaptopentanoic acid, 2-amino-6-mercaptohexanoic acid, or other sulfhydryl containing amino acids. For the prolactin-releasing peptide (PrRP) comprising two amino acids connected by a staple, the two amino acids are about or at least about 3, 4, 5, 6, 7, 8, 9, 10, 11, 12, 13, 14, or more amino acids apart. For example, the first amino acid has position i, and the second amino acid has position i+7, i+11, i+13, i+15, or i+16. For example, the first amino acid has a position i in the peptide and the second amino acid has a position i+n in the peptide, wherein n is 4-16. For example, the first amino acid has a position i in the peptide and the second amino acid has a position i+7 in the peptide. For example, the first amino acid has a position i in the peptide and the second amino acid has a position i+11 in the peptide. For example, the first amino acid has a position i in the peptide and the second amino acid has a position i+15 in the peptide. For example, the first amino acid has a position i in the peptide and the second amino acid has a position i+16 in the peptide.

Disclosed herein are peptide conjugates comprising:
a) a prolactin-releasing peptide (PrRP); and
b) a half-life extending molecule attached to a staple, wherein the staple is attached to the peptide at a first amino acid and a second amino acid.

In some embodiments, the first amino acid and the second amino acid are independently selected from sulfhydryl-containing amino acids.

In some embodiments, the first amino acid and second amino acid is independently selected from cysteine, homocysteine, 2-amino-5-mercaptopentanoic acid, and 2-amino-6-mercaptohexanoic acid. In some embodiments, the first amino acid and second amino acid are cysteines.

In some embodiments of a prolactin-releasing peptide (PrRP) and a half-life extending molecule attached to a staple, the peptide conjugate comprises:
a) a prolactin-releasing peptide (PrRP) comprising a peptide sequence selected from SEQ ID NOS: 83-105; and
b) one half-life extending molecule attached to a staple, wherein the staple is attached to the peptide at a first cysteine and a second cysteine;
the half-life extending molecule attached to a staple having the following structure ("ξ -S" being part of the cysteine residue):

83 84

-continued

-continued

In some embodiments of a prolactin-releasing peptide (PrRP) and a half-life extending molecule attached to a staple, the peptide conjugate comprises:

a) a prolactin-releasing peptide (PrRP) comprising a peptide sequence selected from SEQ ID NOs 83-105; and b) one half-life extending molecule attached to a staple, wherein the staple is attached to the peptide at a first cysteine and a second cysteine;

the half-life extending molecule attached to a staple having the following structure ("S" being part of the cysteine residue):

-continued

-continued

In some embodiments of a prolactin-releasing peptide (PrRP) and a half-life extending molecule attached to a staple, the peptide conjugate comprises:

a) a prolactin-releasing peptide (PrRP) comprising a peptide sequence selected from SEQ ID NOs 83-105; and b) one half-life extending molecule attached to a staple, wherein the staple is attached to the peptide at a first cysteine and a second cysteine;

the half-life extending molecule attached to a staple having the following structure ("S" being part of the cysteine residue):

-continued

In some embodiments of a prolactin-releasing peptide (PrRP) and a half-life extending molecule attached to a staple, the peptide conjugate comprises:

a) a prolactin-releasing peptide (PrRP) comprising a peptide sequence selected from SEQ ID NOs 83-105; and b) one half-life extending molecule attached to a staple, wherein the staple is attached to the peptide at a first cysteine and a second cysteine;

the half-life extending molecule attached to a staple having the following structure ("S" being part of the cysteine residue):

In some embodiments of a prolactin-releasing peptide (PrRP) and a half-life extending molecule attached to a staple, the peptide conjugate comprises:

a) a prolactin-releasing peptide (PrRP) comprising a peptide sequence selected from SEQ ID NOs 83-105; and b) one half-life extending molecule attached to a staple, wherein the staple is attached to the peptide at a first cysteine and a second cysteine;

the half-life extending molecule attached to a staple having the following structure ("S" being part of the cysteine residue):

In some embodiments of a prolactin-releasing peptide (PrRP) and a half-life extending molecule attached to a staple, the peptide conjugate comprises:

a) a prolactin-releasing peptide (PrRP) comprising a peptide sequence selected from SEQ ID NOs 83-105; and b) one half-life extending molecule attached to a staple, wherein the staple is attached to the peptide at a first cysteine and a second cysteine;

the half-life extending molecule attached to a staple having the following structure ("S" being part of the cysteine residue):

In some embodiments of a prolactin-releasing peptide (PrRP), the peptide conjugate comprises:

a) a prolactin-releasing peptide (PrRP) comprising a peptide sequence selected from SEQ ID NOs 83-105; and b) a staple attached to the peptide at a first cysteine and a second cysteine;

the half-life extending molecule attached to a staple having the following structure ("S" being part of the cysteine residue):

Pharmacokinetics

Mechanisms by which peptide conjugates positively influence pharmacokinetic or pharmacodynamic behavior include, but are not limited to, (i) preventing or mitigating in vivo proteolytic degradation or other activity-diminishing chemical modification of the therapeutic agent; (ii) improving half-life or other pharmacokinetic properties by reducing renal filtration, decreasing receptor-mediated clearance or increasing bioavailability; (iii) reducing toxicity; (iv) improving solubility; and/or (v) increasing biological activity and/or target selectivity of the unconjugated therapeutic agent. The therapeutic agent may comprise a PYY receptor modulator, GLP-1 receptor modulator, a GCG receptor modulator, a GIP receptor modulator, or an agent, e.g., peptide, that modulates a combination thereof.

Peptide conjugates may enhance one or more pharmacokinetic properties of a therapeutic agent when attached to the therapeutic agent. Peptide conjugates disclosed herein may enhance the one or more pharmacokinetic properties of the therapeutic agent by at least about 200% as measured by pharmacodynamics when compared to the therapeutic agent or unmodified therapeutic peptide alone. Peptide conjugates disclosed herein may enhance the one or more pharmacokinetic properties of the therapeutic agent by at least about 300%, 400%, 500%, 600%, 700%, 800%, 900%, 1000% as measured by pharmacodynamics when compared to the therapeutic agent or unmodified therapeutic peptide alone.

The pharmacokinetic properties may comprise a half-life. The half-life of the peptide conjugate may be at least about two-fold longer compared to the half-life of the unmodified peptide alone. The half-life of the peptide conjugate disclosed herein may be at least about 3-fold, 4-fold, 5-fold, or 10-fold longer compared to the half-life of the therapeutic agent or unmodified therapeutic peptide alone. The half-life of a peptide conjugate disclosed herein may be at least about 6-, 7-, 8-, 9-, 10-, 15-, 20-, 25-, 30-, 35-, 40-, 45-, or 50-fold longer compared to the half-life of the unmodified peptide alone.

In some embodiments, the half-life of the peptide conjugate is at least about 2-fold greater than the half-life of an unmodified form of the peptide. In some embodiments, the half-life of the peptide conjugate is at least about 5-fold greater than the half-life of an unmodified form of the peptide. In some embodiments, the half-life of the peptide conjugate is at least about 10-fold greater than the half-life of an unmodified form of the peptide.

In addition, a peptide conjugate as described herein may have a positive effect on terms of increasing manufacturability, and/or reducing immunogenicity of the peptide, compared to an unconjugated form of the unmodified therapeutic peptide.

Therapeutic Use

In one aspect, peptide conjugates disclosed herein are useful for treating, alleviating, inhibiting and/or preventing one or more diseases and/or conditions. The disease and/or condition may be a chronic disease or condition. Alternatively, the disease and/or condition is an acute disease or condition. The disease or condition may be recurrent, refractory, accelerated, or in remission. The disease or condition may affect one or more cell types. The one or more diseases and/or conditions may be an autoimmune disease, inflammatory disease, or metabolic disease.

Disclosed herein are methods for treating a disease or condition in a subject in need thereof, the method comprising administering to the subject a peptide conjugate described herein. The disease or condition may be diabetes or obesity, or a medical condition associated with diabetes or obesity. The disease or condition may be non-alcoholic fatty liver disease (NAFLD), nonalcoholic steatohepatitis (NASH), or cardiovascular disease. The disease or condition may be an autoimmune disorder. The disease or condition may be Crohn's disease or ulcerative colitis. The disease or condition may be short bowel syndrome (SBS). The disease or condition may be inflammatory bowel disease (IBD), inflammatory bowel syndrome (IBS), or psoriasis. The disease or condition may be Alzheimer's disease, Parkinson's disease or Huntington's disease. The PLC may be administered with one or more additional therapeutic agents. Disclosed herein are methods of treating a disease or condition in a subject in need thereof, the method comprising administering to the subject a composition disclosed herein comprising one or more peptide conjugates.

Provided herein is a method of preventing or treating a metabolic disease or condition in a subject in need thereof, the method comprising administering to the subject a peptide conjugate described herein. The metabolic disease or condition may be diabetes. The metabolic disease or condition may be obesity. The metabolic disease or condition may be glycogen storage disease, phenylketonuria, maple syrup urine disease, glutaric acidemia type 1, Carbamoyl phosphate synthetase I deficiency, alcaptonuria, Medium-chain acyl-coenzyme A dehydrogenase deficiency (MCADD), acute intermittent porphyria, Lesch-Nyhan syndrome, lipoid congenital adrenal hyperplasia, congenital adrenal hyperplasia, POMPC deficiency, LEPR deficiency, Bardet Biedl syndrome, Alstrome syndrome, Prader-Willi Syndrome, Kearns-Sayre syndrome, Zellweger syndrome, Gaucher's disease, or Niemann Pick disease.

Provided herein is a method of preventing or treating NAFLD, NASH, or cardiovascular disease in a subject in need thereof, the method comprising administering to the subject a peptide conjugate described herein.

Provided herein is a method of preventing or treating short bowel syndrome (SBS) in a subject in need thereof, the method comprising administering to the subject a peptide conjugate described herein.

Provided herein is a method of preventing or treating inflammatory bowel disease (IBD), inflammatory bowel syndrome (IBS), or psoriasis in a subject in need thereof, the method comprising administering to the subject a peptide conjugate described herein.

Provided herein is a method of preventing or treating Crohn's disease or ulcerative colitis in a subject in need thereof, the method comprising administering to the subject a peptide conjugate described herein.

Provided herein is a method of preventing or treating a sleep disorder.

Provided herein is a method of preventing or treating absence seizure.

Provided herein is a method of preventing or treating chronic kidney disease (for example complication of diabetes). Provided herein is a method of preventing or treating diabetic heart disease.

Provided herein is a method of preventing or treating cardiovascular events.

Provided herein is a method of preventing or treating Alzheimer's disease, Parkinson's disease or Huntington's disease in a subject in need thereof, the method comprising administering to the subject a peptide conjugate described herein.

Provided herein is a method of preventing or treating stomach and bowel-related disorders, such as the treatment of neonatals with compromised intestine function, osteoporosis, and DPP-IV (dipeptidylpeptidase-IV) mediated conditions. By way of example, the stomach and bowel-related disorders include ulcers, gastritis, digestion disorders, malabsorption syndromes, short-gut syndrome, cul-de-sac syndrome, inflammatory bowel disease, celiac sprue (for example arising from gluten induced enteropathy or celiac disease), tropical sprue, hypogammaglobulinemia sprue, enteritis, regional enteritis (Crohn's disease), ulcerative colitis, irritable bowel syndrome associated with diarrhea, Small intestine damage and short bowel syndrome.

Provided herein is a method of preventing or treating radiation enteritis, infectious or post-infectious enteritis, and small intestinal damage due to toxic or other chemotherapeutic agents. This may require administration of the peptide conjugate prior to, concurrently with or following a course of chemotherapy or radiation therapy in order to reduce side effects of chemotherapy such as diarrhea, abdominal cramping and vomiting, and reduce the consequent structural and functional damage of the intestinal epithelium resulting from the chemotherapy or radiation therapy.

Provided herein is a method of preventing or treating malnutrition, for example conditions such as the wasting syndrome cachexia and anorexia.

Provided herein is a method of preventing or treating a disease or condition which benefits from a modulator of a PYY receptor in a subject in need thereof comprising administering to the subject a peptide conjugate described herein.

Provided herein is a method of preventing or treating a disease or condition which benefits from a modulator of a GLP-1 receptor in a subject in need thereof comprising administering to the subject a peptide conjugate described herein.

Provided herein is a method of preventing or treating a disease or condition which benefits from a modulator of a GLP-1/GIP receptor in a subject in need thereof comprising administering to the subject a peptide conjugate described herein.

Provided herein is a method of preventing or treating a disease or condition which benefits from a modulator of a GLP-1/GCG receptor in a subject in need thereof comprising administering to the subject a peptide conjugate described herein.

Provided herein is a method of preventing or treating a disease or condition which benefits from a modulator of a prolactin-releasing peptide (PrRP) receptor in a subject in need thereof comprising administering to the subject a peptide conjugate described herein.

Combinations

Disclosed herein are pharmaceutical compositions comprising a peptide conjugate described herein and one or more additional therapeutic agents.

The additional therapeutic agents may comprise one or more other diabetes drugs, DPP4 inhibitors, SGLT2 inhibitors, hypoglycemic drugs and biguanidine drugs, insulin secretogogues and sulfonyl urea drugs, TZD drugs, insulin and insulin analogs, FGF21 and analogs, leptin or leptin analogs, amylin and amylin analogs, an anti-inflammatory drug, cyclosporine A or FK506, 5-ASA, or a statin, or any combination thereof. The additional therapeutic agent may be aspirin.

The additional therapeutic agents may comprise a therapeutic incretin or derivative thereof. Non-limiting examples of incretins or derivatives thereof include GLP-1, glucagon, oxyntomodulin, exendin-4, GLP-2, GIP, and combinations thereof.

In some embodiments, combination treatment demonstrates superior glucose control, food intake reduction, and weight loss than administration of a single agent. In some embodiments, combination treatment mimics the beneficial effects of bariatric surgery in an obese patient.

In some embodiments, a modulator of a PYY receptor is administered with a modulator of a GLP-1 receptor.

In some embodiments, a modulator of a PYY receptor is administered with a modulator of a GLP-1/GIP receptor.

In some embodiments, a modulator of a PYY receptor is administered with a modulator of a GLP-1/GCG receptor.

In some embodiments, a modulator of a GLP-1/GIP receptor is administered with a modulator of a GLP-1 receptor.

In some embodiments, a modulator of a GLP-1/GIP receptor is administered with a modulator of a GLP-1/GCG receptor.

In some embodiments, a modulator of a GLP-1/GCG receptor is administered with a modulator of a GLP-1 receptor.

In some embodiments, the combination comprises multiple peptide conjugate describe herein. In some embodiments, the additional therapeutic agent is conjugate 187.

Compositions

Disclosed herein are pharmaceutical compositions comprising a peptide conjugate described herein and a pharmaceutically acceptable excipients or vehicles. Pharmaceutically acceptable excipients or vehicles may include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials, and surfactants.

Neutral buffered saline or saline mixed with serum albumin are exemplary appropriate carriers. The pharmaceutical compositions may include antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics, or polyethylene glycol (PEG). Also by way of example, suitable tonicity enhancing agents include alkali metal halides (preferably sodium or potassium chloride), mannitol, sorbitol, and the like. Suitable preservatives include benzalkonium chloride, thimerosal, phenethyl alcohol, methylparaben, propylparaben, chlorhexidine, sorbic acid and the like. Hydrogen peroxide also may be used as preservative. Suitable cosolvents include glycerin, propylene glycol, and PEG. Suitable complexing agents include caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal, and the like. The buffers may be conventional buffers such as acetate, borate, citrate, phosphate, bicarbonate, or Tris-HCl. Acetate buffer may be about pH 4-5.5, and Tris buffer can be about pH 7-8.5. Additional pharmaceutical agents are set forth in Remington's Pharmaceutical Sciences, 18th Edition, A. R. Gennaro, ed., Mack Publishing Company, 1990.

The composition may be in liquid form or in a lyophilized or freeze-dried form and may include one or more lyoprotectants, excipients, surfactants, high molecular weight structural additives and/or bulking agents. In one embodiment, a lyoprotectant is included, which is a non-reducing sugar such as sucrose, lactose or trehalose. The amount of lyoprotectant generally included is such that, upon reconstitution, the resulting formulation will be isotonic, although hypertonic or slightly hypotonic formulations also may be suitable. In addition, the amount of lyoprotectant should be sufficient to prevent an unacceptable amount of degradation and/or aggregation of the protein upon lyophilization.

Exemplary lyoprotectant concentrations for sugars (e.g., sucrose, lactose, trehalose) in the pre-lyophilized formulation are from about 10 mM to about 400 mM. In another embodiment, a surfactant is included, such as for example, nonionic surfactants and ionic surfactants such as polysorbates (e.g., polysorbate 20, polysorbate 80); poloxamers (e.g., poloxamer 188); poly(ethylene glycol) phenyl ethers (e.g., Triton); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68 etc). Exemplary amounts of surfactant that may be present in the pre-lyophilized formulation are from about 0.001-0.5%. High molecular weight structural additives (e.g., fillers, binders) may include for example, acacia, albumin, alginic acid, calcium phosphate (dibasic), cellulose, carboxymethylcellulose, carboxymethylcellulose sodium, hydroxyethylcellulose, hydroxypropylcellulose, hydroxypropylmethylcellulose, microcrystalline cellulose, dextran, dextrin, dextrates, sucrose, tylose, pregelatinized starch, calcium sulfate, amylose, glycine, bentonite, maltose, sorbitol, ethylcellulose, disodium hydrogen phosphate, disodium phosphate, disodium pyrosulfite, polyvinyl alcohol, gelatin, glucose, guar gum, liquid glucose, compressible sugar, magnesium aluminum silicate, maltodextrin, polyethylene oxide, polymethacrylates, povidone, sodium alginate, tragacanth microcrystalline cellulose, starch, and zein. Exemplary concentrations of high molecular weight structural additives are from 0.10% to 10% by weight. In other embodiments, a bulking agent (e.g., mannitol, glycine) may be included.

Compositions may be suitable for parenteral administration. Exemplary compositions are suitable for injection or infusion into an animal by any route available to the skilled worker, such as intraarticular, subcutaneous, intravenous, intramuscular, intraperitoneal, intracerebral (intraparenchymal), intracerebroventricular, intramuscular, intraocular, intraarterial, or intralesional routes. A parenteral formulation typically may be a sterile, pyrogen-free, isotonic aqueous solution, optionally containing pharmaceutically acceptable preservatives.

Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringers' dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials, anti-oxidants, chelating agents, inert gases and the like. See generally, Remington's Pharmaceutical Science, 16th Ed., Mack Eds., 1980.

Pharmaceutical compositions described herein may be formulated for controlled or sustained delivery in a manner that provides local concentration of the product (e.g., bolus, depot effect) and/or increased stability or half-life in a particular local environment. The compositions can include the formulation of peptide conjugates, polypeptides, nucleic acids, or vectors disclosed herein with particulate preparations of polymeric compounds such as polylactic acid, polyglycolic acid, etc., as well as agents such as a biodegradable matrix, injectable microspheres, microcapsular particles, microcapsules, bioerodible particles beads, liposomes, and implantable delivery devices that provide for the controlled or sustained release of the active agent which then can be delivered as a depot injection.

Techniques for formulating such sustained- or controlled-delivery means are known, and a variety of polymers have been developed and used for the controlled release and delivery of drugs. Such polymers are typically biodegradable and biocompatible. Polymer hydrogels, including those formed by complexation of enantiomeric polymer or polypeptide segments, and hydrogels with temperature or pH sensitive properties, may be desirable for providing drug depot effect because of the mild and aqueous conditions involved in trapping bioactive protein agents (e.g., peptide conjugates).

Suitable and/or preferred pharmaceutical formulations may be determined in view of the present disclosure and general knowledge of formulation technology, depending upon the intended route of administration, delivery format, and desired dosage. Regardless of the manner of administration, an effective dose may be calculated according to patient body weight, body surface area, or organ size.

Further refinement of the calculations for determining the appropriate dosage for treatment involving each of the formulations described herein are routinely made in the art and is within the ambit of tasks routinely performed in the art. Appropriate dosages may be ascertained through use of appropriate dose-response data.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Alkyl" refers to a straight or branched chain hydrocarbon monoradical, which may be fully saturated or unsaturated, having from one to about ten carbon atoms, or from one to six carbon atoms, wherein a sp3-hybridized carbon of the alkyl residue is attached to the rest of the molecule by a single bond. Examples of saturated hydrocarbon monoradical include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. When the alkyl refers to an unsaturated straight or branched chain hydrocarbon monoradical it is known as an "alkenyl" or an "alkynyl". The alkenyl may be in either the cis or trans conformation about the double bond(s), and should be understood to include both isomers. Examples of alkenyls include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms, or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Examples of alkynyl include, but are not limited to ethynyl, 2-propynyl, 2- and the like. Whenever it appears herein, a numerical range such as "$C_2$-$C_6$ alkynyl"

means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_8$ alkynyl, a $C_2$-$C_4$ alkynyl, a $C_2$-$C_3$ alkynyl, or a $C_2$ alkynyl. Unless stated otherwise specifically in the specification, an alkyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —CF$_3$, —OH, —OMe, —NH$_2$, or —NO$_2$. In some embodiments, the alkyl is optionally substituted with oxo, halogen, —CN, —CF$_3$, —OH, or —OMe. In some embodiments, the alkyl is optionally substituted with halogen.

"Alkylene" refers to a straight or branched divalent hydrocarbon chain. Whenever it appears herein, a numerical range such as "$C_1$-$C_6$ alkylene" means that the alkylene consists of 1 carbon atom, 2 carbon atoms, 3 carbon atoms, 4 carbon atoms, 5 carbon atoms, or 6 carbon atoms, although the present definition also covers the occurrence of the term "alkylene" where no numerical range is designated. In some embodiments, the alkylene is a $C_1$-$C_{10}$ alkylene, a $C_1$-$C_9$ alkylene, a $C_1$-$C_8$ alkylene, a $C_1$-$C_7$ alkylene, a $C_1$-$C_6$ alkylene, a $C_1$-$C_5$ alkylene, a $C_1$-$C_4$ alkylene, a $C_1$-$C_3$ alkylene, a $C_1$-$C_2$ alkylene, or a $C_1$ alkylene. Unless stated otherwise specifically in the specification, an alkylene group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkylene is optionally substituted with oxo, halogen, —CN, —CF$_3$, —OH, —OMe, —NH$_2$, or —NO$_2$. In some embodiments, an alkylene is optionally substituted with oxo, halogen, —CN, —CF$_3$, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, aryl, cycloalkyl, heterocycloalkyl, heteroaryl, and the like. In some embodiments, an alkoxy is optionally substituted with oxo, halogen, —CN, —CF$_3$, —OH, —OMe, —NH$_2$, or —NO$_2$. In some embodiments, an alkoxy is optionally substituted with oxo, halogen, —CN, —CF$_3$, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0] nonane, cis-decalin, trans-decalin, bicyclo[2.1.1]hexane, bicyclo[2.2.1]heptane, bicyclo[2.2.2]octane, bicyclo[3.2.2] nonane, and bicyclo[3.3.2]decane, and 7,7-dimethyl-bicyclo [2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro, or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered partially or fully saturated ring radical comprising 2 to 23 carbon atoms and from one to 8 heteroatoms selected from nitrogen, oxygen, phosphorous, and sulfur. Representative heterocycloalkyls include, but are not limited to, heterocycloalkyls having from two to fifteen carbon atoms (C$_2$-C$_{15}$ heterocycloalkyl), from two to ten carbon atoms (C$_2$-C$_{10}$ heterocycloalkyl), from two to eight carbon atoms (C$_2$-C$_8$ heterocycloalkyl), from two to six carbon atoms (C$_2$-C$_6$ heterocycloalkyl), from two to five carbon atoms (C$_2$-C$_5$ heterocycloalkyl), or two to four carbon atoms (C$_2$-C$_4$ heterocycloalkyl). In some embodiments, the heterocycloalkyl is a 3- to 6-membered heterocycloalkyl. In some embodiments, the heterocycloalkyl is a 5- to 6-membered heterocycloalkyl. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkyl radical may be optionally oxidized; the nitrogen atom may be optionally quaternized.

Examples of such heterocycloalkyl radicals include, but are not limited to, aziridinyl, azetidinyl, dioxolanyl, thienyl [1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihy-droisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Partially saturated heterocycloalkyls include, for example dihydropyrrolyl or tetrahydropyridine. Unless stated otherwise specifically in the specification, a heterocycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heterocycloalkyl is optionally substituted with oxo, halogen, methyl, ethyl, —CN, —CF$_3$, —OH, —OMe, —NH$_2$, or —NO$_2$. In some embodiments, a heterocycloalkyl is optionally substituted with oxo, halogen, methyl, ethyl, —CN, —CF$_3$, —OH, or —OMe. In some embodiments, the heterocycloalkyl is optionally substituted with halogen.

"Heteroalkyl" refers to an alkyl group in which one or more skeletal atoms of the alkyl are selected from an atom other than carbon, e.g., oxygen, nitrogen (e.g. —NH—, —N(alkyl)-), sulfur, or combinations thereof. A heteroalkyl is attached to the rest of the molecule at a carbon atom of the heteroalkyl. In one aspect, a heteroalkyl is a C$_1$-C$_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, or combinations thereof wherein the heteroalkyl is attached to the rest of the molecule at a carbon atom of the heteroalkyl. Unless stated otherwise specifically in the specification, a heteroalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heteroaryl" refers to a 5- to 14-membered ring system radical comprising hydrogen atoms, one to thirteen carbon atoms, one to six heteroatoms selected from nitrogen, oxygen, phosphorous, and sulfur, and at least one aromatic ring.

The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 5-membered heteroaryl. In some embodiments, the heteroaryl is a 6-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroaryl is optionally substituted with halogen, methyl, ethyl, —CN, —CF$_3$, —OH, —OMe, —NH$_2$, or —NO$_2$. In some embodiments, a heteroaryl is optionally substituted with halogen, methyl, ethyl, —CN, —CF$_3$, —OH, or —OMe. In some embodiments, the heteroaryl is optionally substituted with halogen.

The term "percent identity" refers to a comparison between two nucleic acid or amino acid sequences. Such comparisons are measured using any number of alignment methods known in the art, including but not limited to global (e.g., Needleman-Wunsch algorithm) or local alignments (e.g., Smith-Waterman, Sellers, or other algorithm). Percent identity often refers to the percentage of matching positions of two sequences for a contiguous section of positions, wherein the two sequences are aligned in such a way to maximize matching positions and minimize gaps of nonmatching positions. In some instances, alignments are conducted wherein there are no gaps between the two sequences. In some instances, the alignment results in less than 5% gaps, less than 3% gaps, or less than 1% gaps. Additional methods of sequence comparison or alignment are also consistent with the disclosure.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that may be administered to a subject, together with at least one antibody of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient, or carrier with which at least one antibody of the present disclosure is administered.

Terms such as "treating" or "treatment" or "to treat" or "alleviating" or "to alleviate" may refer to: 1) therapeutic measures that cure, slow down, lessen symptoms of, and/or halt progression of a diagnosed pathologic condition or disorder; and/or 2) prophylactic or preventative measures that prevent and/or slow the development of a targeted pathologic condition or disorder. "Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, and diminishment of any direct or indirect pathological consequences of the disease, preventing metastasis, decreasing the rate of disease progression, amelioration or palliation of the disease state, and remission or improved prognosis. Thus those in need of treatment may include those already with the disorder; those prone to have the disorder; and those in whom the disorder is to be prevented.

"Amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Disorder" or "disease" refers to a condition that would benefit from treatment with a substance/molecule (e.g., a peptide conjugate disclosed herein) or method disclosed herein. This includes chronic and acute disorders or diseases including those pathological conditions which predispose the mammal to the disorder in question.

"Mammal" for purposes of treatment refers to any animal classified as a mammal, including humans, rodents (e.g., mice and rats), and monkeys; domestic and farm animals; and zoo, sports, laboratory, or pet animals, such as dogs, cats, cattle, horses, sheep, pigs, goats, rabbits, etc. In some embodiments, the mammal is selected from a human, rodent, or monkey.

"Modulate" refers to the ability of a peptide to bind to a protein receptor. In some embodiments, the modulator is a ligand of the receptor. In some embodiments, the modulator is an agonist. In some embodiments, the modulator is an antagonist. For instance, a peptide that modulates the GLP-1 receptor binds to a GLP-1 receptor (GLP-1R). For instance, a peptide that modulates the GCG receptor binds to a GCG receptor (GCGR). For instance, a peptide that modulates the GIP receptor binds to a GIP receptor (GIPR). For instance, a peptide that modulates the PYY receptor binds to a PYY receptor (PYYR). As non-limiting examples, the peptide that modulates the GLP-1 receptor is a GLP-1R agonist. As non-limiting examples, the peptide that modulates both the GLP-1 receptor and the GCG receptor is a dual GLP-1R/GCGR agonist. As non-limiting examples, the peptide that modulates both the GLP-1 receptor and the GIP receptor is a dual GLP-1R/GIPR agonist. As non-limiting examples, the peptide that modulates the PYY receptor is a PYYR agonist.

"Unmodified peptide" refers to either an unmodified sequence (wild type peptide) or a modified sequence without a staple.

EXAMPLES

Peptides were synthesized by standard solid-phase peptide synthesis (SPPS) techniques and purified via HPLC (as described).

Unless otherwise noted, all reagents were purchased from commercial suppliers (Sigma Aldrich, Fisher, Oakwood) and used without further purification. All reactions involving air or moisture sensitive reagents or intermediates were performed under an inert atmosphere of nitrogen or argon. All solvents used were of HPLC grade. Reactions were monitored by LC-MS or by thin-layer chromatography (TLC) on Merck 50×100 mm silica gel 60 aluminum sheets stained using an aqueous solution of $KMnO_4$.

Flash chromatography purifications were performed on silica gel prepacked columns (40 μm, RediSep® Rf from Teledyne Isco) on a CombiFlash® Rf (Teledyne Isco). Purified final compounds were eluted as single and symmetrical peaks (thereby confirming a purity of ≥95%).

Semi-preparative chromatography were performed on a Shimadzu HPLC with a Phenomenex Luna column (C18, 100 Å pore size, 10 μm particle size, 250×10.0 mm, flow: 4 mL/min) or on an Agilent 1200 HPLC with a Phenomenex Luna column (C18, 100 Å pore size, 5 μm particle size, 150×21.2 mm, flow: 20 mL/min).

$^1$H and $^{13}$C NMR spectra were recorded on a Bruker 400 system in $d_6$-DMSO, $CDCl_3$ or $CD_3OD$. Chemical shifts are given in parts per million (ppm) with tetramethylsilane as an internal standard. Abbreviations are used as follows: s=singlet, d=doublet, t=triplet, q=quartet, p=pentet, m=multiplet, dd=doublet of doublets, br=broad. Coupling constants (J values) are given in hertz (Hz). Low resolution mass spectra were recorded on a Waters Acquity UPLC with a Phemomenex Luna Omega C18 column (C18, 100 Å pore size, 1.6 μm particle size, 50×2.1 mm, flow: 0.4 mL/min). Solvents: A—$H_2O$+0.1% formic acid, B—MeCN+0.1% formic acid, gradient: 0-1 min 10-90% B, 1-1.6 min 90% B, 1.6-1.7 min 90-10% B, 1.7-2 min 10% B.

High resolution mass spectra (HRMS) were recorded on an Agilent 1200 Series Accurate Mass Time-of-Flight (TOF) with an Aeris Widepore column (XB-C8, 3.6 μm particle size, 150×2.1 mm, flow: 0.5 mL/min). Solvents: A—$H_2O$+0.1% formic acid, B—MeCN+0.1% formic acid, gradient: 0-2 min 5% B, 2-12 min 5-60% B, 12-13 min 60-80% B, 13-14 min 80-20% B, 14-15 min 20-80% B, 15-16 min 80-20% B, 16-17 min 20-95% B, 17-20 min 95% B, 20-21 min 95-5% B.

General Protocol A for Loading of Chlorotrityl Chloride Resin

Fmoc-Lys(ivDde)-OH (60 mg, 100 μmol) was coupled to 2-chlorotrityl chloride resin (Novabiochem) (100 mg, 80 μmol) by mixing the amino acid, resin, and DIEA (70 μL, 400 μmol) in 5 mL of DMF and stirring for 30 min. The resin was then washed with DMF (3×), DCM (3×) and treated with $CH_3OH$/DCM/DIEA (8:1:1) for 10 min to cap the unreacted trityl chloride sites, dried under vacuum and stored in a desiccator.

General Protocol B for Deprotection of Fmoc Protecting Group

To the resin was added piperidine in DMF (20%). The mixture was shaken for 5 min and drained. Fresh 20% piperidine was added and this time the mixture was shaken for 15 min. Positive ninhydrin and/or TNBS test was observed. The resin was then washed with DMF (3×), DCM (3×).

General Protocol C for Deprotection of ivDde Protecting Group

After washing with DMF and DCM, the resin was treated with 2% hydrazine in DMF (5 mL, 2×15 min). Positive ninhydrin and/or TNBS test was observed. The resin was then washed with DMF (3×), DCM (3×).

General Protocol D for Peptide Coupling

The resin was treated with the carboxylic acid derivative specified (3 eq) using coupling reagent HATU (3.3 eq), and DIEA (3.3 eq) in DMF (5 mL) for 2 h or repeated until a negative ninhydrin and/or TNBS test was observed. The resin was then washed with DMF (3×), DCM (3×).

General Protocol E for On-Resin Bromoacetylation

The resin was then treated with bromoacetic anhydride (2.4 eq), and DIEA (2.6 eq) in 200 mL of DCM for 30 min.

General Protocol F for Cleavage of Peptides from Chlorotrityl Resin

The resin was washed with DCM (3×), the product was cleaved from the resin using 5 mL of 10% TFA in DCM containing 10% $H_2O$ and 10% triisopropylsilane for 1 h.

Example 1: Synthesis of a Fatty Acid Conjugation Reagent (FA2)

FA2a

FA2

Intermediate FA2a. Myristic acid (0.46 g, 2 mmol) was dissolved in 5 mL of DMF. HATU (0.8 g, 2.1 mmol) and DIEA (0.4 mL, 2.2 mmol) were added followed by the addition of Boc-NH-PEG$_2$-COOH (0.5 g, 2 mmol). The reaction mixture was then stirred for 6 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.81 g of tert-butyl (2-(2-(2-tetradecanamidoethoxy)ethoxy)ethyl)carbamate (FA2a) as a white solid in 90% product yield. MS (ES$^+$) m/z 459.6 ([M+H]$^+$), calcd MW 458.4.

FA2. A solution of FA2a (0.23 g, 0.5 mmol) in DCM (10 mL) was treated with TFA (2 mL) for 2 h. The mixture was concentrated, followed by the addition of bromoacetic anhydride (0.14 g, 0.55 mmol) and DIEA (0.17 mL, 1 mmol) in 10 mL of DCM at 0° C. The reaction mixture was then stirred for 2 h, and the solvent was removed. The product was extracted with EtOAc (3×15 mL). The organic layer was successively washed with sat. NaHCO$_3$, cooled HCl (1 M) and brine, dried over Na$_2$SO$_4$, filtered, and concentrated. Purification by flash column chromatography on silica gel provided 0.2 g of FA2 as a white solid in 83% product yield. MS (ES$^+$) m/z 480.4 ([M+H]$^+$), calcd MW 479.5.

Example 2: Synthesis of L1

L1

To a solution of 1,4-diaminobutane (80 μL, 0.795 mmol, 1 eq) in DCM (10 mL) at 0° C. were added DIEA (276 μL, 1.59 mmol, 2 eq) followed by bromoacetic anhydride (413 g, 1.59 mmol, 2 eq) dissolved in 1 mL of DCM. The reaction mixture was then stirred for 30 min at 0° C., 1.5 h at RT, and the solvent was removed. Purification by flash column chromatography on silica gel afforded L1 as a white solid (162 mg, 0.49 mmol, 61%). MS (ES$^+$) m/z 331.0 ([M+H]$^+$). $^1$H NMR (400 MHz, methanol-d$_4$) δ 3.94 (s, 4H), 3.40-3.30 (m, 4H), 1.68 (p, J=3.5 Hz, 4H).

Example 3: Synthesis of L1B

L1B

To a solution of 1,2-ethylenediamine (30 μL, 0.448 mmol, 1 eq) in DCM (5 mL) at 0° C. were added DIEA (172 μL, 0.985 mmol, 2.2 eq) followed by bromoacetic anhydride (233 mg, 0.897 mmol, 2 eq) dissolved in 1 mL of DCM. The reaction mixture was then stirred for 30 min at 0° C., 1.5 h at RT, and the solvent was removed. Purification by flash column chromatography on silica gel provided L1B as a white solid (43.9 mg, 0.145 mmol, 32%). MS (ES$^+$) m/z 302.55 ([M+H]$^+$), 304.54 ([M+H]$^+$). $^1$H NMR (400 MHz, methanol-d$_4$) δ 2.49 (s, 4H), 2.06 (s, 4H).

Example 4: Synthesis of L1C

L1C

To a solution of 1,3-diaminopropane (30 µL, 0.359 mmol, 1 eq) in DCM (5 mL) at 0° C. were added DIEA (138 µL, 0.789 mmol, 2.2 eq) followed by bromoacetic anhydride (186 mg, 0.718 mmol, 2 eq) dissolved in 1 mL of DCM. The reaction mixture was then stirred for 30 min at 0° C., 1.5 h at RT, and the solvent was removed. Purification by flash column chromatography on silica gel afforded L1C as a white solid (60.8 mg, 0.19 mmol, 53%). MS (ES$^+$) m/z 316.32 ([M+H]$^+$), 318.6 ([M+H]$^+$). $^1$H NMR (400 MHz, methanol-d$_4$) δ 3.86 (s, 4H), 3.27 (t, J=6.8 Hz, 4H), 1.74 (p, J=6.8 Hz, 2H).

Example 5: Synthesis of L1D

L1D

To a solution of 1,7-diaminohexane (65 mg, 0.499 mmol, 1 eq) in DCM (15 mL) at 0° C. were added DIEA (208 µL, 1.197 mmol, 2.4 eq) followed by bromoacetic anhydride (259 mg, 0.998 mmol, 2 eq) dissolved in 1 mL of DCM. The reaction mixture was then stirred for 30 min at 0° C., 1.5 h at RT, and the solvent was removed. Purification by flash column chromatography on silica gel afforded L1D as a white solid (120 mg, 0.322 mmol, 64%). MS (ES$^+$) m/z 372.71 ([M+H]$^+$), 374.70 ([M+3H]$^+$). $^1$H NMR (400 MHz, chloroform-d) δ 6.55 (s, 2H), 3.91 (s, 4H), 3.30 (q, J=7.1 Hz, 4H), 1.56 (p, J=7.1 Hz, 4H), 1.45-1.29 (m, 6H).

Example 6: Synthesis of L1E

L1E

To a solution of 1,11-diaminoundecane (48 mg, 0.257 mmol, 1 eq) in DCM (10 mL) at 0° C. were added DIEA (108 µL, 0.616 mmol, 2.4 eq) followed by bromoacetic anhydride (134 mg, 0.515 mmol, 2 eq) dissolved in 1 mL of DCM. The reaction mixture was then stirred for 30 min at 0°

C., 1.5 h at RT, and the solvent was removed. Purification by flash column chromatography on silica gel afforded L1E as a white solid (62.3 mg, 0.145 mmol, 56%). MS (ES$^+$) m/z 428.33 ([M+H]$^+$). $^1$H NMR (400 MHz, chloroform-d) δ 6.53 (s, 2H), 3.91 (s, 4H), 3.30 (q, J=6.8 Hz, 4H), 1.57 (q, J=7.2 Hz, 4H), 1.42-1.20 (m, 14H).

Example 7: Synthesis of L1F

L1F

To a solution of cadaverine (48 mg, 0.257 mmol, 1 eq) in DCM (20 mL) at 0° C. were added DIEA (284 µL, 1.63 mmol, 2.4 eq) followed by bromoacetic anhydride (353 mg, 1.36 mmol, 2 eq) dissolved in 1 mL of DCM. The reaction mixture was then stirred for 30 min at 0° C., 1.5 h at RT, and the solvent was removed. Purification by flash column chromatography on silica gel afforded L1F as a white solid (156 mg, 0.453 mmol, 66%). MS (ES$^+$) m/z 344.65 ([M+H]$^+$), 346.64 ([M+H]$^+$). $^1$H NMR (400 MHz, methanol-d$_4$) δ 3.83 (s, 4H), 3.23 (q, J=6.8 Hz, 4H), 1.57 (p, J=7.2 Hz, 4H), 1.44-1.33 (m, 2H).

Example 8: Synthesis of L1G

L1Ga

L1G

Intermediate L1Ga

To a solution of tert-butyl bis(2-aminoethyl)carbamate (167 mg, 0.82 mmol, 1 eq) in DCM (20 mL) at 0° C. were added DIEA (342 µL, 11.96 mmol, 2.4 eq) followed by bromoacetic anhydride (426 mg, 1.64 mmol, 2 eq) dissolved in 1 mL of DCM. The reaction mixture was then stirred for 30 min at 0° C., 1.5 h at RT, and the solvent was removed. Purification by flash column chromatography on silica gel afforded L1Ga as a white solid (289 mg, 0.65 mmol, 79%). MS (ES$^+$) m/z 445.71 ([M+H]$^+$), 447.7 ([M+H]$^+$). $^1$H NMR (400 MHz, methanol-d$_4$) δ 3.85 (s, 4H), 3.39 (s, 9H), 1.50 (s, 10H).

L1G

Compound L1Ga (20 mg) was dissolved in TFA/DCM (1:1, v/v, 2 mL), agitated 30 min at RT and evaporated (co-evaporation with hexane) to obtain compound L1G as an oil. The product was directly used in further steps. MS (ES$^+$) m/z 345.2 ([M+H]$^+$).

Example 9: Synthesis of L3

Intermediate L3a

Myristic acid (184 mg, 0.805 mmol, 1 eq) was dissolved in 4 mL of DMF. HATU (321 mg, 0.845 mmol, 1.1 eq) and DIEA (154 μL, 0.885 mmol, 1.1 eq) were added followed by the addition of Boc-NH-PEG$_2$-COOH (200 mg, 0.805 mmol, 1 eq). The reaction mixture was then stirred for 1.5 h, and the solvent was removed. The product was dissolved in EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L3a as a white solid (254 mg, 0.55 mmol, 69%). $^1$H NMR (400 MHz, chloroform-d) δ 3.66-3.54 (m, 8H), 3.49 (q, J=5.2 Hz, 2H), 3.35 (d, J=6.1 Hz, 2H), 2.20 (t, J=7.7 Hz, 2H), 1.63-1.58 (m, 2H), 1.47 (s, 8H), 1.33-1.24 (m, 21H), 0.90 (t, J=6.9 Hz, 3H). t$_R$=2.21 min (Agilent). MS (ES$^+$) m/z 459.6 ([M+H]$^+$)

Intermediate L3b

A solution of compound L3a (242 mg, 0.527 mmol, 1 eq) in DCM (2 mL) was treated with TFA (2 mL) for 30 min. The mixture was concentrated, co-evaporated with hexane. To a solution of BocNH-PEG$_2$-CO$_2$H (146 mg, 0.527 mol, 1 eq) dissolved in DMF (5 mL) was added HATU (224 mg, 0.59 mmol, 1.1 eq). Deprotected compound L3a and DIEA (183 μL, 1.05 mmol, 2 eq) in DMF were added to the reaction mixture. The reaction mixture was agitated for 2 h at RT. The product was diluted with EtOAc. The organic layer was successively washed with 1M HCl, sat. NaHCO$_3$, and brine, dried over Na$_2$SO$_4$, filtered, and concentrated.

Purification by flash column chromatography on silica gel provided the desired compound L3b as an oil (129 mg, 0.209 mmol, 40%). $^1$H NMR (400 MHz, chloroform-d) δ 6.76 (s, 1H), 6.19 (s, 1H), 5.29 (s, 1H), 3.76 (t, J=5.8 Hz, 2H), 3.69-3.62 (m, 8H), 3.57 (dt, J=12.3, 5.0 Hz, 6H), 3.48 (dt, J=10.4, 5.5 Hz, 4H), 3.33 (s, 2H), 2.51 (t, J=5.8 Hz, 2H), 2.20 (t, J=7.0 Hz, 2H), 1.90-1.75 (m, 4H), 1.64 (p, J=7.3 Hz, 2H), 1.46 (s, 9H), 1.33-1.22 (m, 17H).

Intermediate L3c

A solution of Compound L3b (129 mg, 0.209 mmol, 1 eq) in DCM (2 mL) was treated with TFA (2 mL) for 30 min. The mixture was concentrated, co-evaporated with hexane. To a solution of Boc-Orn(Boc)-OH (69 mg, 0.209 mmol, 1 eq) dissolved in DMF (5 mL) was added HATU (88 mg, 0.23 mmol 1.1 eq). Deprotected compound L3b and DIEA (73 μL, 0.419 mmol, 2 eq) in DMF were added to the reaction mixture. The reaction mixture was agitated 2 h at RT. The product was diluted with EtOAc. The organic layer was successively washed with 1M HCl, sat. NaHCO$_3$, and brine, dried over Na$_2$SO$_4$, filtered, and concentrated. Purification by flash column chromatography on silica gel provided the desired compound L3c as an oil (137 mg, 0.164 mmol, 78%). t$_R$=4.07 min (Agilent). MS (ES$^+$) m/z 832.9 ([M+H]$^+$). $^1$H NMR (400 MHz, chloroform-d) δ 7.12 (s, 1H), 6.80 (s, 1H), 6.30 (s, 1H), 4.87 (s, 1H), 3.85-3.73 (m, 2H), 3.68-3.61 (m, 7H), 3.58 (p, J=6.1, 5.5 Hz, 7H), 3.53-3.36 (m, 6H), 3.29-3.00 (m, 2H), 2.51 (t, J=5.8 Hz, 2H), 2.20 (t, J=7.7 Hz, 2H), 2.00-1.74 (m, 6H), 1.71-1.51 (m, 5H), 1.45 (s, 18H), 1.35-1.22 (m, 21H).

L3

A solution of Compound L3c (137 mg, 0.165 mmol, 1 eq) in DCM (2 mL) was treated with TFA (2 mL) for 30 min. The mixture was concentrated, co-evaporated with hexane and dissolved in 10 mL of DCM and cooled at 0° C. DIEA (115 µL, 0.66 mmol, 4 eq) was added followed by bromo-acetic anhydride (85.8 g, 0.33 mmol, 2 eq) dissolved in 1 mL of DCM. The reaction mixture was then stirred for 30 min at 0° C., 1.5 h at RT, and the solvent was removed. Purification by flash column chromatography on silica gel afforded L3 as a white solid (56 mg, 0.064 mmol, 39%). $t_R$=3.4 min (Agilent). MS (ES$^+$) m/z 872.4 ([M+H]$^+$), 874.3 ([M+H]$^+$).

Example 10: Synthesis of L4 by flash column chromatography on silica gel provided the desired compound L4a as an oil (558 mg, 1.05 mmol, 58%). MS (ES$^+$) m/z 533.13 ([M+H]$^+$). $^1$H NMR (400 MHz, chloroform-d) δ 6.82 (s, 1H), 5.25 (d, J=8.3 Hz, 1H), 4.75 (s, 1H), 4.19 (s, 1H), 3.76-3.60 (m, 10H), 3.57 (t, J=5.1 Hz, 2H), 3.43 (t, J=4.6 Hz, 2H), 3.30-3.19 (m, 1H), 3.18-3.03 (m, 1H), 1.85 (s, 4H), 1.68-1.49 (m, 2H), 1.45 (s, 18H).

Intermediate L4b

To a solution of compound L4a (548 mg, 1.02 mmol, 1 eq) in anhydrous MeOH (10 mL) and under argon was added Pd/C (10.9 mg, 0.102 mmol, 0.1 eq) and argon was replaced with H$_2$. The reaction mixture was agitated for 6 h at RT, filtrated on celite and evaporated to afford compound L4b as an oil (516 mg, 1.02 mmol, quant). The product was used without any further purification.

Intermediate L4c

L4a

L4b

L4c

L4

Intermediate L4a

To a solution of Boc-Orn(Boc)-OH (595 mg, 1.79 mmol, 1 eq) dissolved in DMF (5 mL) was added HATU (750 mg, 1.79 mmol 1.1 eq), DIEA (343 µL, 1.97 mmol, 1.1 eq) and amine-PEG$_3$-N$_3$ (391 mg, 1.79 mmol, 1 eq) dissolved in 1 mL of DMF. The reaction mixture was agitated 16 h at RT. The product was diluted with EtOAc. The organic layer was successively washed with 1M HCl, sat. NaHCO$_3$, brine, dried over Na$_2$SO$_4$, filtered, and concentrated. Purification To a solution of octadecanedioic acid mono tert-butyl ester (370 mg, 1.02 mmol, 1 eq) dissolved in DMF (5 mL) was added HATU (387 mg, 1.02 mmol 1.1 eq), DIEA (186 µL, 1.07 mmol, 2 eq) and compound L4b (516 mg, 1.02 mmol, 1 eq) dissolved in 1 mL of DMF. The reaction mixture was agitated 3 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L4c as an oil (697 mg, 0.81 mmol, 79%). $^1$H NMR (400 MHz, chloroform-d) δ 6.94 (s, 1H), 6.42 (s, 1H), 4.81 (s, 1H), 4.20 (s, 1H), 3.65 (d, J=6.7 Hz, 8H), 3.59 (dt, J=9.7, 5.1 Hz, 4H), 3.51-3.35 (m, 4H), 3.31-3.18 (m, 1H), 3.17-3.06 (m, 1H), 2.20 (q, J=8.0 Hz, 4H), 1.87 (s, 4H), 1.71-1.53 (m, 6H), 1.45 (s, 26H), 1.26 (s, 24H).

L4

A solution of L4c (422 mg, 0.49 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (327 μL, 1.96 mmol, 4 eq) was added followed by bromoacetic anhydride (254 mg, 0.98 mmol, 2 eq) dissolved in 1 mL of DCM. The reaction mixture was then stirred for 30 min at 0° C., 1.5 h at RT, and the solvent was removed. Purification by flash column chromatography on silica gel afforded L4 as a white solid (53 mg, 0.063 mmol, 12%). MS (ES$^+$) m/z 845.08 ([M+H]$^+$), 847.07 ([M+H]$^+$) $^1$H NMR (400 MHz, methanol-d$_4$) δ 3.68-3.60 (m, 8H), 3.54 (td, J=5.4, 3.4 Hz, 4H), 3.43-3.35 (m, 4H), 3.30-3.16 (m, 2H), 2.27 (t, J=7.5 Hz, 2H), 2.17 (t, J=7.6 Hz, 2H), 1.86-1.73 (m, 1H), 1.72-1.45 (m, 8H), 1.37-1.19 (m, 28H).

Example 11: Synthesis of L4A

L4Aa

L4Ab

L4Ac

L4Ad

L4Ae

-continued

L4A

Intermediate L4Aa

To a solution of tert-butyl bis(2-aminoethyl)carbamate (500 mg, 2.45 mmol, 1 eq) and DIEA (1.02 mL, 5.88 mmol, 2 eq) in DCM (20 mL) at 0° C. was added dropwise bromoacetic anhydride (1.31 g, 5.04 mmol, 2.05 eq in 1 mL DCM). The reaction mixture was agitated 30 min at 0° C., 2 h at RT and evaporated in vacuo. Purification by flash chromatography afforded the product as an oil (883 mg, 81%). $^1$H NMR (400 MHz, methanol-$d_4$) δ 1.50 (s, 9H), 3.39 (s, 8H), 3.85 (s, 4H). $t_R$=1.04 min. MS (ES$^+$) m/z 445.71/447.70 ([M+H]$^+$).

Intermediate L4Ab

A solution of compound L4Aa (1 eq) in DCM/TFA (1:1, v/v) was agitated at RT for 30 min and concentrated in vacuo (co-evaporated with heptane). Compound L4Ab was used directly in further steps without purification. $t_R$=0.58 min. MS (ES$^+$) m/z 345.65/347.67 ([M+H]$^+$).

Intermediate L4Ac

To a solution of mono-tert-butyl succinate (1.05 eq) in DMF was added HATU (1.05 eq). The reaction mixture was agitated at RT for 5 min. Compound L4Ab and DIEA (4 eq) were dissolved in DMF (1 mL) and added to the reaction mixture. The reaction was agitated overnight at RT and diluted with AcOEt. The organic phase was washed with HCl 1N, a solution of saturated NaHCO$_3$, dried over MgSO$_4$ and evaporated. Purification by flash chromatography afforded the product as an oil. $t_R$=1.07 min. MS (ES$^+$) m/z 501.52/503.80 ([M+H]$^+$).

Intermediate L4Ad

A solution of compound L4Ac (1 eq) in DCM/TFA (1:1, v/v) was agitated at RT for 30 min and concentrated in vacuo (co-evaporated with heptane). Compound L4Ad was used directly in further steps without purification. $t_R$=0.57 min. MS (ES$^+$) m/z 445.71/447.73 ([M+H]$^+$).

Intermediate L4Ae

Octadecanedioic acid mono-tert-butyl ester acid (200 mg, 0.54 mmol, 1 eq) was dissolved in 5 mL of DMF. HATU (225 mg, 0.59 mmol, 1.1 eq) and DIEA (103 μL, 0.59 mmol, 1.1 eq) were added followed by the addition of Boc-NH-PEG$_3$-NH$_2$ (157.8 g, 0.54 mmol, 1 eq). The reaction mixture was then stirred for 3 h, and the solvent was removed. The product was dissolved in EtOAc. The organic layer was successively washed with sat. NaHCO$_3$, 1M HCl, brine, dried over Na$_2$SO$_4$, filtered, and concentrated. Purification by flash column chromatography on silica gel provided the desired product L4Ae as a white solid (281 mg, 0.43 mmol, 810%). MS (ES$^+$) m/z 645.5 ([M+H]$^+$). $^1$H NMR (400 MHz, chloroform-d) δ 3.76-3.61 (m, 8H), 3.63-3.54 (m, 4H), 3.48 (q, J=5.1 Hz, 2H), 3.34 (s, 2H), 2.20 (dt, J=9.8, 7.6 Hz, 4H), 1.67-1.55 (m, 4H), 1.49-1.44 (m, 17H), 1.30 (s, 6H), 1.30-1.24 (m, 19H).

L4A

A solution of compound L4Ae in DCM was treated with TFA for 30 min. The mixture was concentrated, co-evaporated with heptane, dissolved in DMF and added to a solution of compound L4Ad, HATU and DIEA in DMF. The reaction mixture was agitated 3 h and purified by semi-preparative HPLC to provide the desired product L4A.

Example 12: Synthesis of L5 octadecanedioic acid mono-tert-butyl ester, HATU, DIEA, DMF

-continued

L5

General Protocol A, B, D (Octadecanedioic Acid Mono-Tert Butyl Ester), C, D (Fmoc-PEG$_2$-Propionic Acid), B, D (Fmoc-PEG$_2$-Propionic Acid), B, D (Fmoc-Orn(Fmoc)-OH), B, E, F.

The crude was purified by semi-preparative HPLC with mass detection to afford the product L5 as a white solid (73 mg, 0.065 mmol, 11%). $^1$H NMR (400 MHz, methanol-d$_4$) δ 4.36 (td, J=8.9, 5.1 Hz, 2H), 3.89 (q, J=11.4 Hz, 2H), 3.82 (s, 2H), 3.74 (t, J=6.2 Hz, 2H), 3.60 (s, 4H), 3.54 (t, J=5.5 Hz, 2H), 3.37 (q, J=5.2 Hz, 2H), 3.29-3.11 (m, 5H), 2.44 (t, J=6.2 Hz, 2H), 2.26 (dt, J=12.3, 7.5 Hz, 4H), 1.89-1.77 (m, 2H), 1.76-1.49 (m, 10H), 1.48-1.38 (m, 2H), 1.37-1.25 (m, 25H).

Example 13: Synthesis of L5A

L5Aa

L5Ab

-continued

L5A

Intermediate L5Aa

A solution of Fmoc-OSu (131 g, 388 mmol) in DCM (200 mL) was added dropwise to a solution of diethylenetriamine (20 g, 194 mmol) in DCM (200 mL) at −40° C. under $N_2$, stirred for 2 h. LCMS showed the reaction was complete. The crude product in solution was not purified and used for the next step directly. $^1$H NMR (400 MHz, DMSO-$d_6$) δ 7.88 (d, J=7.6 Hz, 4H), 7.68 (d, J=7.6 Hz, 4H), 7.43-7.24 (m, 10H), 4.30 (d, J=6.4 Hz, 4H), 4.21 (d, J=6.4 Hz, 2H), 3.06 (d, J=5.6 Hz, 4H), 2.57 (d, J=7.6 Hz, 4H). MS (ES$^+$) m/z 548.2 ([M+H]$^+$).

Intermediate L5Ab

To a solution of compound L5Aa (106 g, 194 mmol) in DCM (400 mL) was added DMAP (4.74 g, 38.8 mmol) and tetrahydrofuran-2,5-dione (67.9 g, 678 mmol), stirred at 25° C. for 14 h. LCMS showed the reaction was complete. To the reaction mixture was added 1 N HCl until pH=5-6, stirred for 15 min, the organic phase was separated, then the organic phase was washed with water and saturated NaCl (500 mL) and the aqueous phase was extracted with DCM (500 mL) twice. The combined DCM was dried over anhydrous $Na_2SO_4$, concentrated under vacuum. The crude product was purified by column chromatography on silica gel using DCM/MeOH (80:0-5:1) as eluent to give compound L5Ab (57.6 g, 45% yield) as a white solid powder. $^1$H NMR (400 MHz, DMSO-$d_6$) δ 12.09 (s, 1H), 7.87 (d, J=7.5 Hz, 4H), 7.66 (d, J=7.0 Hz, 4H), 7.23-7.48 (m, 10H), 4.24-4.33 (m, 4H), 4.14-4.22 (m, 2H), 3.27 (s, 4H), 2.95-3.19 (m, 4H), 2.37-2.44 (m, 4H). MS (ES$^+$) m/z 648.2 ([M+H]$^+$).

L5A

General protocol A, B, D (octadecanedioic acid mono-tert butyl ester), C, D (Fmoc-PEG$_2$-propionic acid), B, D (Fmoc-PEG$_2$-propionic acid), B, D (compound L5Ab), B, E, F.

The crude was purified by HPLC to afford the product L5A as a white solid (5.2 g, 11% yield). MS (ES$^+$) m/z 1188.5 ([M+H]$^+$).

Example 14: Synthesis of L6

-continued

L6

Intermediate L6a

Palmitic acid (235 mg, 0.919 mmol, 1.05 eq) was dissolved in 4 mL of DMF. HATU (349 mg, 0.919 mmol, 1.05 eq) and DIEA (167 μL, 0.963 mmol, 1.1 eq) were added followed by the addition of Boc-NH-PEG$_2$-NH$_2$ (200 mg, 0.875 mmol, 1 eq). The reaction mixture was then stirred for 2 h, and the solvent was removed. The product was dissolved in EtOAc. The organic layer was successively washed with 1M HCl, sat. NaHCO$_3$, HCl and brine, dried over Na$_2$SO$_4$, filtered, and concentrated to provide the desired compound L6a as a white solid (412 mg, 0.84 mmol, 97%). $^1$H NMR (400 MHz, chloroform-d) δ 6.17 (s, 1H), 5.07 (s, 1H), 3.58 (s, 4H), 3.53 (t, J=5.0 Hz, 3H), 3.43 (q, J=5.3 Hz, 2H), 3.36-3.21 (m, 2H), 2.15 (t, J=7.5 Hz, 2H), 1.66-1.54 (m, 2H), 1.32-1.15 (m, 26H), 0.84 (t, J=6.6 Hz, 3H).

Intermediate L6b

A solution of compound L6a (412 mg, 0.84 mmol, 1 eq) in DCM (2 mL) was treated with TFA (2 mL) for 30 min. The mixture was concentrated, co-evaporated with hexane. To a solution of BocNH-PEG$_2$-CO$_2$H (258 mg, 0.931 mmol, 1.1 eq) dissolved in DMF (5 mL) was added HATU (353 mg, 0.931 mmol, 1.1 eq). Deprotected compound L6a and DIEA (294 μL, 1.69 mmol, 2 eq) in DMF were added to the reaction mixture. The reaction mixture was agitated 2 h at RT. The product was diluted with EtOAc. The organic layer was successively washed with 1M HCl, sat. NaHCO$_3$, HCl and brine, dried over Na$_2$SO$_4$, filtered, and concentrated. Purification by flash column chromatography on silica gel provided the desired compound L6b as an oil (329 mg, 0.51 mmol, 60%). $^1$H NMR (400 MHz, chloroform-d) δ 6.79 (s, 1H), 6.28 (s, 1H), 5.28 (s, 1H), 3.68 (t, J=5.8 Hz, 2H), 3.61-3.44 (m, 14H), 3.38 (p, J=5.6 Hz, 4H), 3.24 (q, J=5.5 Hz, 2H), 2.42 (t, J=5.8 Hz, 2H), 2.11 (t, J=7.9 Hz, 2H), 1.55 (p, J=7.2 Hz, 2H), 1.38 (s, 9H), 1.32-1.10 (m, 24H), 0.81 (t, J=6.7 Hz, 3H).

Intermediate L6c

A solution of compound L6b (329 mg, 0.51 mmol, 1 eq) in DCM (2 mL) was treated with TFA (2 mL) for 30 min.

The mixture was concentrated, co-evaporated with hexane. To a solution of Boc-Orn(Boc)-OH (186 mg, 0.56 mmol, 1.1 eq) dissolved in DMF (5 mL) was added HATU (213 mg, 0.56 mmol 1.1 eq). Deprotected compound L6b and DIEA (177 μL, 1.02 mmol, 2 eq) in DMF were added to the reaction mixture. The reaction mixture was agitated 2 h at RT. The product was diluted with EtOAc. The organic layer was successively washed with sat. NaHCO$_3$, 1M HCl and brine, dried over Na$_2$SO$_4$, filtered, and concentrated. Purification by flash column chromatography on silica gel provided the desired compound L6c as an oil (326 mg, 0.37 mmol, 94%). $^1$H NMR (400 MHz, chloroform-d) δ 7.18 (s, 1H), 6.92 (s, 1H), 6.48 (s, 1H), 5.61 (d, J=8.4 Hz, 1H), 5.08 (t, J=5.9 Hz, 1H), 4.13 (s, 1H), 3.73-3.65 (m, 2H), 3.59-3.44 (m, 14H), 3.42-3.29 (m, 8H), 3.19-2.86 (m, 2H), 2.42 (t, J=5.9 Hz, 2H), 2.10 (d, J=7.3 Hz, 2H), 1.78-1.63 (m, 1H), 1.60-1.40 (m, 5H), 1.35 (s, 18H), 1.26-1.09 (m, 22H), 0.80 (t, J=6.7 Hz, 3H).

L6

A solution of compound L6c (100 mg, 0.116 mmol, 1 eq) in DCM (2 mL) was treated with TFA (2 mL) for 30 min. The mixture was concentrated, co-evaporated with hexane and dissolved in 10 mL of DCM and cooled at 0° C. DIEA (80.8 μL, 0.46 mmol, 4 eq) was added followed by bromoacetic anhydride (61.9 mg, 0.238 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L6 as a white solid (50.1 mg, 0.055 mmol, 40%). $^1$H NMR (400 MHz, methanol-d$_4$) δ 4.39 (dd, J=8.4, 5.5 Hz, 1H), 3.91 (q, J=11.4 Hz, 2H), 3.84 (s, 2H), 3.76 (t, J=6.2 Hz, 2H), 3.63 (d, J=7.1 Hz, 8H), 3.57 (q, J=5.5 Hz, 6H), 3.43-3.36 (m, 6H), 3.25 (t, J=13.9, 6.8 Hz, 2H), 2.49 (t, J=6.2 Hz, 2H), 2.21 (t, J=7.5 Hz, 2H), 1.91-1.79 (m, 1H), 1.75-1.53 (m, 5H), 1.42-1.25 (m, 24H), 0.92 (t, J=6.7 Hz, 3H).

Example 15: Synthesis of L7

L7a

US 12,583,900 B2

127                                                                    128

-continued

L7b

L7c

L7

Intermediate L7a

Stearic acid (261 mg, 0.919 mmol, 1.05 eq) was dissolved in 4 mL of DMF. HATU (349 mg, 0.919 mmol, 1.05 eq) and DIEA (167 µL, 0.963 mmol, 1.1 eq) were added followed by the addition of Boc-NH-PEG₂-NH₂ (200 mg, 0.875 mmol, 1 eq). The reaction mixture was then stirred for 2 h, and the solvent was removed. The product was dissolved in EtOAc. The organic layer was successively washed with 1M HCl, sat. NaHCO₃, and brine, dried over Na₂SO₄, filtered, and concentrated to provide the desired compound L7a as a white solid (430 mg, 0.83 mmol, 95%). $^1$H NMR (400 MHz, chloroform-d) δ 3.69-3.59 (m, 4H), 3.56 (t, J=5.1 Hz, 4H), 3.46 (q, J=5.2 Hz, 2H), 3.40-3.23 (m, 2H), 2.18 (t, J=7.6 Hz, 2H), 1.62 (t, J=7.3 Hz, 2H), 1.45 (s, 9H), 1.35-1.19 (m, 30H), 0.88 (t, J=6.7 Hz, 4H).

Intermediate L7b

A solution of compound L7a (426 mg, 0.87 mmol, 1 eq) in DCM (2 mL) was treated with TFA (2 mL) for 30 min. The mixture was concentrated, co-evaporated with hexane. To a solution of BocNH-PEG₂-CO₂H (266 mg, 0.96 mmol, 1.1 eq) dissolved in DMF (5 mL) was added HATU (366 mg, 0.96 mmol, 1.1 eq). Deprotected compound L7a and DIEA (304 µL, 1.75 mmol, 2 eq) in DMF were added to the reaction mixture. The reaction mixture was agitated 2 h at RT. The product was diluted with EtOAc. The organic layer was successively washed with 1M HCl, sat. NaHCO₃, and brine, dried over Na₂SO₄, filtered, and concentrated. Purification by flash column chromatography on silica gel provided the desired compound L7b as an oil (360 mg, 0.53 mmol, 61%). $^1$H NMR (400 MHz, chloroform-d) δ 6.75 (s, 1H), 6.18 (s, 1H), 5.26 (s, 1H), 3.75 (t, J=5.8 Hz, 2H), 3.69-3.52 (m, 14H), 3.47 (p, J=5.4 Hz, 4H), 3.33 (q, J=5.5 Hz, 2H), 2.50 (t, J=5.8 Hz, 2H), 2.19 (t, J=7.5 Hz, 2H), 2.07 (s, 1H), 1.63 (p, J=7.3 Hz, 2H), 1.46 (s, 9H), 1.37-1.19 (m, 29H), 0.89 (t, J=6.7 Hz, 3H).

Intermediate L7c

A solution of compound L7b (360 mg, 0.53 mmol, 1 eq) in DCM (2 mL) was treated with TFA (2 mL) for 30 min.

The mixture was concentrated, co-evaporated with hexane. To a solution of Boc-Orn(Boc)-OH (195 mg, 0.58 mmol, 1.1 eq) dissolved in DMF (5 mL) was added HATU (223 mg, 0.58 mmol 1.1 eq). Deprotected compound L7b and DIEA (186 µL, 1.07 mmol, 2 eq) in DMF were added to the reaction mixture. The reaction mixture was agitated 2 h at RT. The product was diluted with EtOAc. The organic layer was successively washed with 1M HCl, sat. NaHCO₃, and brine, dried over Na₂SO₄, filtered, and concentrated. Purification by flash column chromatography on silica gel provided the desired compound L7c as an oil (373 mg, 0.42 mmol, 78%). $^1$H NMR (400 MHz, chloroform-d) δ 7.14 (s, 1H), 6.84 (s, 1H), 6.35 (s, 1H), 5.53 (d, J=8.2 Hz, 1H), 5.05-4.88 (m, 1H), 4.20 (s, 1H), 3.82-3.69 (m, 2H), 3.65-3.31 (m, 22H), 3.23-3.00 (m, 2H), 2.48 (t, J=5.8 Hz, 2H), 2.17 (t, J=7.8 Hz, 2H), 1.87-1.72 (m, 1H), 1.67-1.48 (m, 5H), 1.42 (s, 18H), 1.34-1.14 (m, 29H), 0.87 (t, J=6.9 Hz, 3H).

L7

A solution of compound L7c (100 mg, 0.112 mmol, 1 eq) in DCM (2 mL) was treated with TFA (2 mL) for 30 min. The mixture was concentrated, co-evaporated with hexane and dissolved in 10 mL of DCM and cooled at 0° C. DIEA (78 µL, 0.44 mmol, 4 eq) was added followed by bromo-acetic anhydride (62 mg, 0.24 mmol, 2.05 eq) dissolved in 1 mL of DCM. The reaction mixture was then stirred for 30 min at 0° C., 1.5 h at RT, and the solvent was removed. The product was dissolved in EtOAc. The organic layer was successively washed with 1M HCl, sat. NaHCO₃, and brine, dried over Na₂SO₄, filtered, and concentrated. Purification by flash column chromatography on silica gel afforded L7 as a white solid (95 mg, 0.10 mmol, 91%). MS (ES⁺) m/z 931.31 ([M+H]⁺), 933.25 ([M+H]⁺). $^1$H NMR (400 MHz, methanol-d₄) δ 4.39 (dd, J=8.5, 5.4 Hz, 1H), 3.91 (q, J=11.3 Hz, 2H), 3.84 (s, 2H), 3.76 (t, J=6.2 Hz, 2H), 3.63 (d, J=7.0 Hz, 8H), 3.57 (t, J=5.5 Hz, 6H), 3.42-3.35 (m, 6H), 3.31-3.13 (m, 4H), 2.49 (t, J=6.2 Hz, 2H), 2.20 (t, J=7.4 Hz, 2H), 1.91-1.79 (m, 1H), 1.75-1.56 (m, 6H), 1.39-1.26 (m, 26H), 0.92 (t, J=6.3 Hz, 3H).

Example 16: Synthesis of L8 hexadecanedioic acid mono-tert-butyl ester, HATU, DIEA, DMF

L8

40

General Protocol A, B, D (Hexadecanedioic Acid Mono-Tert Butyl Ester), C, D (Fmoc-PEG$_2$-Propionic Acid), B, D (Fmoc-PEG$_2$-Propionic Acid), B, D (Fmoc-Orn(Fmoc)-OH), B, E, F.

The crude was purified by semi-preparative HPLC with mass detection to afford the product L8 as a white solid (42.6 mg, 0.038 mmol, 22%). $^1$H NMR (400 MHz, methanol-d$_4$) δ 4.38 (td, J=8.6, 5.1 Hz, 2H), 3.91 (q, J=11.3 Hz, 2H), 3.84 (s, 2H), 3.76 (q, J=6.1 Hz, 4H), 3.65-3.59 (m, 8H), 3.56 (td, J=5.5, 1.7 Hz, 4H), 3.43-3.37 (m, 4H), 3.31-3.16 (m, 4H), 2.48 (dt, J=15.7, 6.2 Hz, 4H), 2.28 (dt, J=12.6, 7.5 Hz, 4H), 1.95-1.79 (m, 1H), 1.77-1.51 (m, 10H), 1.49-1.41 (m, 2H), 1.40-1.26 (m, 31H).

Example 17: Synthesis of L9 heptadecanedioic acid mono-tert-butyl ester, HATU, DIEA, DMF

-continued

L9

General Protocol A, B, D (Heptadecanedioic Acid Mono-Tert Butyl Ester), C, D (Fmoc-PEG$_2$-Propionic Acid), B, D (Fmoc-PEG$_2$-Propionic Acid), B, D (Fmoc-Orn(Fmoc)-OH), B, E, F.

The crude was purified by semi-preparative HPLC with mass detection to afford the product L9 as a white solid (49 mg, 0.089 mmol, 9%). $^1$H NMR (400 MHz, methanol-d$_4$) δ 4.45-4.33 (m, 2H), 3.92 (t, J=10.9 Hz, 2H), 3.85 (d, J=1.1 Hz, 2H), 3.77 (q, J=6.0 Hz, 4H), 3.63 (s, 8H), 3.57 (t, J=5.6 Hz, 4H), 3.40 (t, J=5.5 Hz, 4H), 3.25 (dq, J=22.7, 6.7 Hz, 4H), 2.48 (dt, J=15.6, 6.2 Hz, 4H), 2.29 (dt, J=13.2, 7.4 Hz, 4H), 1.95-1.79 (m, 2H), 1.80-1.50 (m, 10H), 1.51-1.41 (m, 2H), 1.40-1.27 (m, 20H).

Example 18: Synthesis of L12 octadecanedioic acid mono-tert-butyl ester, HATU, DIEA, DMF 133    134

-continued

L12

General Protocol A, B, D (Octadecanedioic Acid), C, D (Fmoc-PEG₂-Propionic Acid), B, D (Fmoc-Orn(Fmoc)-OH), B, E, F.

The crude was purified by semi-preparative HPLC with mass detection to afford the product L12 as a white solid (51.7 mg, 0.054 mmol, 3%). $^1$H NMR (400 MHz, methanol-d₄) δ 4.39 (td, J=9.2, 5.1 Hz, 2H), 3.92 (qd, J=11.4, 1.2 Hz, 2H), 3.85 (s, 2H), 3.76 (t, J=6.2 Hz, 2H), 3.63 (s, 4H), 3.57 (t, J=5.5 Hz, 2H), 3.40 (q, J=5.1 Hz, 2H), 3.30-3.12 (m, 6H), 2.47 (t, J=6.1 Hz, 2H), 2.29 (dt, J=12.1, 7.4 Hz, 4H), 1.95-1.77 (m, 2H), 1.78-1.50 (m, 10H), 1.48-1.40 (m, 2H), 1.39-1.26 (m, 22H).

Example 19: Synthesis of L14

L4b hexadecanedioic acid
mon-tert-butyl ester,
HATU, DIEA, DMF

L14a

1) TFA/DCM
2) Bromoacetic
anhydride
DIEA, DCM

L14

Intermediate L14a

To a solution of hexadecanedioic acid mono tert-butyl ester (102 mg, 0.30 mmol, 1 eq) dissolved in DMF (5 mL) was added HATU (125 mg, 0.33 mmol 1.1 eq), DIEA (51 μL, 0.33 mmol, 1.1 eq) and compound L4b (151.9 mg, 0.3 mmol, 1 eq) dissolved in 1 mL of DMF. The reaction mixture was agitated 3 h at RT. The product was diluted with EtOAc. The organic layer was successively washed with 1M HCl, sat. NaHCO₃, brine, dried over Na₂SO₄, filtered, and concentrated. Purification by flash column chromatography on silica gel provided the desired compound L14a as an oil (147 mg, 0.176 mmol, 59%). ¹H NMR (400 MHz, chloroform-d) δ 6.87 (s, 1H), 6.40 (s, 1H), 5.32 (s, 2H), 4.79 (s, 1H), 4.20 (s, 1H), 3.66 (d, J=7.0 Hz, 8H), 3.60 (dt, J=10.0, 5.1 Hz, 4H), 3.49-3.45 (m, 3H), 3.31-3.18 (m, 1H), 3.13-3.06 (m, 1H), 2.21 (td, J=7.8, 6.0 Hz, 4H), 1.88-1.78 (m, 1H), 1.66-1.53 (m, 7H), 1.51-1.42 (m, 27H), 1.36-1.19 (m, 20H).

L14

A solution of compound L14a (40 mg, 0.048 mmol, 1 eq) in DCM (2 mL) was treated with TFA (2 mL) for 30 min.

The mixture was concentrated, co-evaporated with hexane and dissolved in 20 mL of DCM and cooled at 0° C. DIEA (34 μL, 0.1924 mmol, 4 eq) was added followed by bromoacetic anhydride (23.63 mg, 0.098 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L14 as a white solid (18.3 mg, 0.022 mmol, 46%). MS (ES⁺) m/z 817.1 ([M+H]⁺), 819.09 ([M+H]⁺). ¹H NMR (400 MHz, methanol-d₄) δ 4.38 (dd, J=8.4, 5.5 Hz, 1H), 3.92 (q, J=11.2, 10.6 Hz, 2H), 3.84 (s, 2H), 3.69-3.61 (m, 8H), 3.56 (td, J=5.5, 2.6 Hz, 4H), 3.44-3.36 (m, 4H), 3.30-3.14 (m, 2H), 2.29 (t, J=7.4 Hz, 2H), 2.21 (t, J=7.5 Hz, 2H), 1.91-1.78 (m, 1H), 1.76-1.67 (m, 1H), 1.67-1.54 (m, 6H), 1.40-1.29 (m, 20H).

Example 20: Synthesis of L15

L4b

L15a

L15

Intermediate L15a

To a solution of 20-(tert-butoxy)-20-oxoicosanoic acid (360 mg, 0.90 mmol, 1.05 eq) dissolved in DMF (5 mL) was added HATU (343 mg, 0.90 mmol 1.05 eq), DIEA (300 µL, 1.71 mmol, 2 eq) and compound L4b (435 mg, 0.858 mmol, 1 eq) dissolved in 1 mL of DMF. The reaction mixture was agitated 3 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L15a as an oil (555 mg, 0.625 mmol, 72%). $^1$H NMR (400 MHz, chloroform-d) δ 6.87 (s, 1H), 6.40 (s, 1H), 4.79 (s, 1H), 4.21 (s, 1H), 3.76-3.53 (m, 15H), 3.47 (s, 5H), 3.32-3.05 (m, 3H), 2.29-2.17 (m, 4H), 1.90-1.76 (m, 4H), 1.69-1.53 (m, 2H), 1.52-1.41 (m, 33H), 1.36-1.20 (m, 29H).

L15

A solution of compound L15a (100 mg, 0.112 mmol, 1 eq) in DCM (2 mL) was treated with TFA (2 mL) for 30 min.

The mixture was concentrated, co-evaporated with hexane and dissolved in 20 mL of DCM and cooled at 0° C. DIEA (79 µL, 0.45 mmol, 4 eq) was added followed by bromo-acetic anhydride (60 mg, 0.231 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L15 as a white solid (17.5 mg, 0.02 mmol, 18%). MS (ES$^+$) m/z 873.21 ([M+H]$^+$), 875.20 ([M+H]$^+$) $^1$H NMR (400 MHz, methanol-d$_4$) δ 4.38 (dd, J=8.4, 5.5 Hz, 1H), 3.91 (q, J=11.4 Hz, 2H), 3.84 (s, 2H), 3.72-3.61 (m, 8H), 3.56 (td, J=5.5, 2.7 Hz, 4H), 3.44-3.35 (m, 5H), 3.30-3.17 (m, 2H), 2.29 (t, J=7.4 Hz, 2H), 2.21 (t, J=7.5 Hz, 2H), 1.92-1.77 (m, 1H), 1.75-1.53 (m, 7H), 1.40-1.27 (m, 27H).

Example 21: Synthesis of L16

L16a

L16b

L16c

L16

Intermediate L16a

To a solution of Boc-Orn(Boc)-OH (400 mg, 1.2 mmol, 1 eq) dissolved in DMF (10 mL) was added HATU (504 mg, 1.32 mmol 1.1 eq), DIEA (230 µL, 1.32 mmol, 1.1 eq) and amine-PEG$_2$-N$_3$ (210 mg, 1.20 mmol, 1 eq) dissolved in 1 mL of DMF. The reaction mixture was agitated 4 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L16a as an oil (471 mg, 0.96 mmol, 80%). $^1$H NMR (400 MHz, methanol-d$_4$) δ 4.01 (t, J=6.6 Hz, 1H), 3.71-3.60 (m, 6H), 3.55 (t, J=5.5 Hz, 2H), 3.41-3.37 (m, 3H), 3.04 (t, J=6.2 Hz, 2H), 1.78-1.66 (m, 1H), 1.62-1.48 (m, 3H), 1.48-1.39 (m, 18H).

Intermediate L16b

To a solution of compound L16a (471 mg, 0.9 mmol, 1 eq) in anhydrous MeOH (10 mL) and under argon was added Pd/C (10.2 mg, 0.09 mmol, 0.1 eq) and argon was replaced with H$_2$. The reaction mixture was agitated for 6 h at RT, filtrated on celite and evaporated to afford compound L16b as an oil (295.5 mg, 0.64 mmol, 71%). The product was used without any further purification. MS (ES$^+$) m/z 462.51 ([M+H]$^+$).

Intermediate L16c

To a solution of octadecanedioic acid mono tert-butyl ester (281 mg, 0.76 mmol, 1 eq) dissolved in DMF (5 mL) was added HATU (288 mg, 0.76 mmol, 1 eq), DIEA (132 µL, 0.76 mmol, 1 eq) and compound L16b (351 mg, 0.76 mmol, 1 eq) dissolved in 1 mL of DMF. The reaction mixture was agitated 3 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L16c as an oil (351 mg, 0.43 mmol, 57%). $^1$H NMR (400 MHz, methanol-d$_4$) δ 3.61 (s, 4H), 3.54 (td, J=5.6, 2.3 Hz, 4H), 3.40-3.34 (m, 4H), 3.04 (t, J=6.6 Hz, 2H), 2.20 (td, J=7.6, 5.9 Hz, 4H), 1.77-1.68 (m, 2H), 1.64-1.48 (m, 2H), 1.48-1.42 (m, 28H), 1.35-1.26 (m, 26H).

L16

A solution of compound L16c (31 mg, 0.038 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (27 µL, 0.152 mmol, 4 eq) was added followed by bromo-acetic anhydride (21 mg, 0.078 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L16 as a white solid (12.6 mg, 0.015 mmol, 41%). MS (ES$^+$) m/z 801.13 ([M+H]$^+$), 803.12 ([M+H]$^+$). $^1$H NMR (400 MHz, methanol-d$_4$) δ 4.37 (dd, J=8.5, 5.4 Hz, 1H), 3.91 (q, J=11.3 Hz, 2H), 3.84 (s, 2H), 3.63 (s, 4H), 3.57 (td, J=5.6, 2.6 Hz, 4H), 3.43-3.36 (m, 4H), 3.31-3.17 (m, 1H), 2.29 (t, J=7.4 Hz, 2H), 2.21 (t, J=7.5 Hz, 2H), 1.90-1.79 (m, 1H), 1.76-1.54 (m, 7H), 1.41-1.30 (m, 26H).

Example 22: Synthesis of L17

L17a

L17b

L17c

-continued

L17

Intermediate L17a

To a solution of Boc-Orn(Boc)-OH (400 mg, 1.2 mmol, 1 eq) dissolved in DMF (10 mL) was added HATU (504 mg, 1.32 mmol 1.1 eq), DIEA (230 μL, 1.32 mmol, 1.1 eq) and amine-PEG$_2$-N$_3$ (316 mg, 1.20 mmol, 1 eq) dissolved in 1 mL of DMF. The reaction mixture was agitated 4 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L17a as an oil (454 mg, 0.78 mmol, 66%). $^1$H NMR (400 MHz, methanol-d$_4$) δ 4.04-3.97 (m, 1H), 3.71-3.58 (m, 14H), 3.54 (t, J=5.4 Hz, 2H), 3.37 (t, J=5.0 Hz, 4H), 3.04 (t, J=6.6 Hz, 2H), 1.75-1.67 (m, 1H), 1.62-1.48 (m, 3H), 1.48-1.41 (m, 18H).

Intermediate L17b

To a solution of compound L17a (454 mg, 0.9 mmol, 1 eq) in anhydrous MeOH (10 mL) and under argon was added Pd/C (8.3 mg, 0.078 mmol, 0.1 eq) and argon was replaced with H$_2$. The reaction mixture was agitated for 6 h at RT, filtrated on celite and evaporated to afford compound L17b as an oil (192 mg, 0.35 mmol, 45%). The product was used without any further purification.

Intermediate L17c

To a solution of octadecanedioic acid mono tert-butyl ester (225 mg, 0.61 mmol, 1 eq) dissolved in DMF (5 mL) was added HATU (231 mg, 0.61 mmol 1 eq), DIEA (106 μL, 0.61 mmol, 1 eq) and compound L17b (335 mg, 0.61 mmol, 1 eq) dissolved in 1 mL of DMF. The reaction mixture was agitated 2 h at RT. The product was diluted with EtOAc. The organic layer was successively washed with 1M HCl, sat. NaHCO$_3$, brine, dried over Na$_2$SO$_4$, filtered, and concentrated. Purification by flash column chromatography on silica gel provided the desired compound L17c as an oil (178 mg, 0.20 mmol, 32%). $^1$H NMR (400 MHz, chloroform-d) δ 5.32 (s, 2H), 3.74-3.63 (m, 11H), 3.59 (dt, J=10.9, 5.0 Hz, 4H), 3.52-3.43 (m, 4H), 3.27-3.08 (m, 2H), 2.22 (d, J=7.6 Hz, 4H), 1.69-1.52 (m, 6H), 1.51-1.42 (m, 27H), 1.27 (s, 26H).

L17

A solution of compound L17c (45.6 mg, 0.05 mmol, 1 eq) in DCM (2 mL) was treated with TFA (2 mL) for 30 min. The mixture was concentrated, co-evaporated with hexane and dissolved in 20 mL of DCM and cooled at 0° C. DIEA (36 μL, 0.202 mmol, 4 eq) was added followed by bromo-acetic anhydride (27 mg, 0.103 mmol, 2.05 eq) dissolved in 1 mL of DCM. The reaction mixture was then stirred for 30 min at 0° C., 1.5 h at RT, and the solvent was removed. Purification by flash column chromatography on silica gel afforded L17 as a white solid (14.9 mg, 0.017 mmol, 33%). MS (ES$^+$) m/z 889.18 ([M+H]$^+$), 891.17 ([M+H]$^+$) $^1$H NMR (400 MHz, methanol-d$_4$) δ 4.38 (dd, J=8.3, 5.5 Hz, 1H), 3.92 (q, J=11.3 Hz, 2H), 3.84 (s, 2H), 3.67-3.60 (m, 7H), 3.56 (td, J=5.5, 3.5 Hz, 4H), 3.45-3.35 (m, 5H), 3.32-3.15 (m, 3H), 2.29 (t, J=7.4 Hz, 2H), 2.21 (t, J=7.5 Hz, 2H), 1.90-1.76 (m, 1H), 1.74-1.57 (m, 7H), 1.41-1.26 (m, 25H).

Example 23: Synthesis of L18

-continued

L18

General Protocol A, B, D (Octadecanedioic Acid), C, D (Fmoc-PEG₂-Propionic Acid), B, (Fmoc-PEG₂-Propionic Acid), B, (Fmoc-PEG₂-Propionic Acid), B, D (Fmoc-Orn (Fmoc)-OH), B, E, F.

The crude was purified by semi-preparative HPLC with mass detection to afford the product L18 as a white solid (47 mg, 0.036 mmol, 10%). MS (ES⁺) m/z 1276.39 ([M+H]⁺), 1278.37 ([M+H]⁺).

General Procedure for Bromoacetyl Peptide Stapling/Conjugation

Peptides were dissolved at a concentration of 2 mM with 1.5 eq of bromoacetyl staple in 1:3 (v/v) MeCN/30 mM NH₄HCO₃ buffer (pH 8.5). The pH of the reaction mixture was readjusted with ammonium hydroxide to correct the drop in pH caused by the peptide TFA counterion. More MeCN was added for particularly insoluble peptides. The reaction was stirred at RT for 2-4 h, before acidification to pH 5 via dropwise addition of acetic acid. The resulting solution was lyophilized and purified by reversed-phase HPLC.

General Solid-Phase Protocols for Lactam Stapling

Peptide-resin bearing amine side chain orthogonal protection (Dde/Mmt) at each stapling position was swollen in DMF for 1 h. The Dde protecting group was removed from the first side chain via treatment with 2% hydrazine solution in DMF (2×15 min). Positive TNBS test was observed. The linker building block specified below was coupled as described and a negative TNBS test was observed. The solvent was exchanged for DCM and the Mint group was removed from the second side chain via treatment with 1% TFA in DCM containing 5% TIPS, 5×2 min. The resin was washed with DCM, 10% DIEA in DMF, DMF and a positive TNBS test was observed. The linker was cyclized and the PEG-fatty acid portion of the staple (if applicable) elongated as described below. The complete stapled peptide was cleaved from the resin using 95% TFA, 2.5% TIPS, 2.5% H₂O, 3 h. The peptide cleavage mixture was evaporated to an oil, triturated and washed with diethyl ether and purified via reversed-phase HPLC.

A Dde/Alloc protection scheme can also be used for this approach, which requires the addition of allyl alcohol to the Dde deprotection cocktail as a scavenger to prevent concurrent reduction of the Alloc allyl moiety.

Synthesis of K(Fmoc) Linker

-continued

Ka

K(Fmoc)

Intermediate Ka

Fmoc-β-Ala-OH (1.00 g, 3.21 mmol) and di-tert-butyl iminodiacetate (0.461 g, 2.68 mmol) were suspended in 100 mL DCM. HATU (1.02 g, 2.68 mmol) and DIEA (3.32 mL, 12.8 mmol) were added and the reaction was stirred at RT for 3.5 h. The solvent was evaporated and the residue dissolved in MeOH and purified via flash column chromatography on silica gel (hexane/EtOAc) to afford the product as a white solid (0.802 g, 56%). ¹H NMR (400 MHz, chloroform-d) δ 7.78 (d, J=7.4 Hz, 2H), 7.62 (d, J=7.4 Hz, 2H), 7.42 (t, J=7.4 Hz, 2H), 7.33 (t, J=7.4 Hz, 2H), 5.66 (t, J=5.7 Hz, 1H), 4.35 (d, J=7.3 Hz, 2H), 4.23 (t, J=7.3 Hz, 1H), 4.10 (s, 2H), 4.02 (s, 2H), 3.56 (q, J=5.7 Hz, 2H), 2.55 (t, J=5.7 Hz, 2H), 1.49 (s, 18H).

K(Fmoc) Linker

Compound Ka was treated with 20 mL 1:1 TFA/DCM for 2 h. The solvent was evaporated and the residue triturated and washed with diethyl ether to afford K(Fmoc) linker as a white solid (0.371 g, 58%). MS (ES⁺) m/z 427.15 ([M+H]⁺).

Synthesis of A(Fmoc) Linker

A (Fmoc)

A solution of 5-Aminoisophthalic acid (1.00 g, 5.5 mmol) in 10 mL dioxane was added to a degassed solution of $Na_2CO_3$ (1.46 g, 5.5 mmol) in 15 mL water. The solution was cooled on ice and a solution of Fmoc chloride (1.42 g, 5.5 mmol) in 10 mL dioxane was then added dropwise with stirring over 15 min. The reaction was then stirred for 1 h and then 24 h at RT. The dioxane was removed under vacuum and the remaining aqueous solution acidified with 1M HCl. The resulting solid precipitate was then washed with diethyl ether (4×10 mL), redissolved in EtOAc, filtered, washed with brine, dried over $Na_2SO_4$ filtered and concentrated to give A (Fmoc) linker as a white solid (119 mg, 5%). $^1H$ NMR (500 MHz, DMSO-$d_6$) δ 13.24 (s, 2H), 10.12 (s, 1H), 8.33 (d, J=1.5 Hz, 2H), 8.12 (t, J=1.5 Hz, 1H), 7.91 (d, J=7.6 Hz, 2H), 7.76 (dd, J=7.6, 1.2 Hz, 2H), 7.43 (t, J=7.6 Hz, 2H), 7.36 (td, J=7.6, 1.2 Hz, 2H), 4.50 (d, J=6.8 Hz, 2H), 4.33 (t, J=6.8 Hz, 1H).

General Protocol G for 'A1' and 'K1' Series Simple Lactam Staples

For linker coupling the appropriate diacid building block (2 eq) was attached using HATU (4 eq) and DIEA (4 eq) in DMF, 1×2 h. The cyclization step was achieved using HATU (1 eq) and DIEA (2 eq) in DMF, 1×2 h.

General Protocol H for 'K' PEG-Fatty Acid Trifunctional Lactam Staples

For linker coupling the intramolecular symmetric anhydride of building block K(Fmoc) linker (2 eq) was preformed using DIC (2 eq) and catalytic DMAP in dry DCM for 10 min at RT. The peptide-resin solvent was exchanged for DCM and the anhydride was then added and agitated overnight. The resin was drained, washed with DCM and DMF. The linker was cyclized overnight via treatment with DIC (1 eq) and HOBt or HOAt (1 eq) in DMF, and a negative TNBS was observed. Remaining uncyclized linker was capped via treatment with 10% acetic anhydride in DMF (30 min). The linker Fmoc group was deprotected via treatment with 20% piperidine in DMF (2×10 min). A positive TNBS was observed. Subsequent staple PEG and fatty acid building blocks were attached sequentially to the linker free amine via standard coupling chemistry: building block (3 eq), HATU (3 eq) and DIEA (6 eq) in DMF, 1 h at RT, using 20% piperidine in DMF for deprotection cycles (5+10 min, RT).

General Protocol I for 'A' PEG-Fatty Acid Trifunctional Lactam Staples

For linker coupling the building block A(Fmoc) linker (2 eq) was attached using HATU (4 eq) and DIEA (4 eq) in DMF, 1×2 h. The cyclization step was achieved using HATU (1 eq) and DIEA (2 eq) in DMF, 1×2 h. Remaining uncyclized linker was capped via treatment with 10% acetic anhydride in DMF (30 min). The linker Fmoc group was deprotected via treatment with 20% piperidine in DMF (2×10 min). It was not possible to observe a positive TNBS test for the aniline nitrogen. Fmoc-R-Ala-OH (3 eq) was coupled using HATU (3 eq) and DIEA (6 eq) in DMF, 4×1 h at RT or as the symmetric anhydride using DIC/DMAP in DCM (2 h, RT). Subsequent staple PEG and fatty acid building blocks were attached sequentially to the linker free amine via standard coupling chemistry: building block (3 eq), HATU (3 eq) and DIEA (6 eq) in DMF, 1 h at RT, using 20% piperidine in DMF for deprotection cycles (5+10 min, RT).

In some embodiments, the peptide conjugate described herein comprises a half-life extending moiety or a staple of Table 6.

TABLE 6

| Ex | ID | Structure |
|---|---|---|
| 1 | FA2 | |
| 2 | L1 | |
| 3 | L1B | |

TABLE 6-continued

| Ex | ID | Structure |
|----|----|-----------|
| 4 | L1C | |
| 5 | L1D | |
| 6 | L1E | |
| 7 | L1F | |
| 8 | L1G | |
| | L2 | |
| 9 | L3 | |
| 10 | L4 | |
| 11 | L4A | |

TABLE 6-continued

| Ex | ID | Structure |
|----|----|-----------|
| 12 | L5 | |
| 13 | L5A | |
|  | C20L5A | |
| 14 | L6 | |
| 15 | L7 | |
| 16 | L8 | |
| 17 | L9 | |
| 18 | L12 | |

TABLE 6-continued

| Ex | ID | Structure |
|----|----|-----------|
|    | L13 | |
| 19 | L14 | |
| 20 | L15 | |
| 21 | L16 | |
| 22 | L17 | |
| 23 | L18 | |
|    | L19 | |
|    | K0 | |

TABLE 6-continued

| Ex | ID | Structure |
|----|----|-----------|
| | K1 | |
| | K1C | |
| | K1F | |
| | K1H | |
| | K3 | |
| | K4 | |
| | K5 | |
| | K6 | |

TABLE 6-continued

| Ex | ID | Structure |
|---|---|---|
| | K7 | |
| | K8 | |
| | K9 | |
| | K20 | |
| | A1 | |
| | A5 | |

The "ʡ-S" being part of a cysteine, homocysteine, 2-amino-5-mercaptopentanoic acid, or 2-amino-6-mercaptohexanoic acid residue, and the "ʡ-N" being part of a lysine, ornithine, diaminobutyric acid, diaminopropionic acid, or homolysine residue.

In some embodiments, the PYY peptide conjugates described herein is as shown in Table 7.

TABLE 7

| Conjugate | Sequence | Conjugation position | Staple | Calc mass | Mass found |
|---|---|---|---|---|---|
| | PYY Peptide Conjugates | | | | |
| 1 | IKPEAPGCDASPEECNRYYASLR HYLNLVTRQRY (SEQ ID No. 3) | 8, 15 | L1 | | |
| 2 | IKPEAPGCDASPEECNRYYASLR HYLNLVTRQRY (SEQ ID No. 3) | 8, 15 | L1B | 4153.67 | 4154.12 |
| 3 | IKPEAPGCDASPEECNRYYASLR HYLNLVTRQRY (SEQ ID No. 3) | 8, 15 | L1C | 4167.70 | 4168.23 |
| 4 | IKPEAPGCDASPEECNRYYASLR HYLNLVTRQRY (SEQ ID No. 3) | 8, 15 | L3 | 4725.47 | 4725.90 |
| 5 | IKPEAPGCDASPEECNRYYASLR HYLNLVTRQRY (SEQ ID No. 3) | 8, 15 | L4 | 4696.43 | 4696.90 |
| 6 | IKPEAPGCDASPEECNRYYASLR HYLNLVTRQRY (SEQ ID No. 3) | 8, 15 | L5 | 4968.73 | 4969.20 |
| 7 | IKPEAPGCDASPEECNRYYASLR HYLNLVTRQRY (SEQ ID No. 3) | 8, 15 | L5A | | |
| 8 | IKPEAPGEDASPEELNRYYACLR HYLNCVTRQRY (SEQ ID No. 4) | 21, 28 | L1 | 4223.76 | 4224.02 |
| 9 | IKPEAPGEDASPEELNRYYACLR HYLNCVTRQRY (SEQ ID No. 4) | 21, 28 | L1C | 4209.74 | 4210.00 |
| 10 | IKPEAPGEDASPEELNRYYACLR HYLNCVTRQRY (SEQ ID No. 4) | 21, 28 | L3 | 4767.51 | 4767.89 |
| 11 | IKPEAPGEDASPEELNRYYACLR HYLNCVTRQRY (SEQ ID No. 4) | 21, 28 | L4 | 4738.47 | 4738.97 |
| 12 | IKPEAPGEDASPEELNRYYACLR HYLNCVTRQRY (SEQ ID No. 4) | 21, 28 | L5 | 5010.77 | 5011.18 |
| 13 | IKPEAPGEDASPEELNRYYACLR HYLNCVTRQRY (SEQ ID No. 4) | 21, 28 | L5A | 5081.85 | 5082.30 |
| 14 | IKPEAPGEDASPEELNRYYACLR HYLNCVTRQRY (SEQ ID No. 4) | 21, 28 | L8 | 5038.82 | 5039.30 |
| 15 | PKPEAPGCDASPEECNRYYADLR HYLNWLTRQRY (SEQ ID No. 5) | 8, 15 | L1 | 4280.78 | 4281.20 |
| 16 | PKPEAPGCDASPEECNRYYADLR HYLNWLTRQRY (SEQ ID No. 5) | 8, 15 | L1F | 4294.80 | 4295.00 |
| 17 | PKPEAPGCDASPEECNRYYADLR HYLNWLTRQRY (SEQ ID No. 5) | 8, 15 | L1G | 4295.79 | 4296.10 |
| 18 | PKPEAPGCDASPEECNRYYADLR HYLNWLTRQRY (SEQ ID No. 5) | 8, 15 | L3 | 4824.52 | 4825.00 |
| 19 | PKPEAPGCDASPEECNRYYADLR HYLNWLTRQRY (SEQ ID No. 5) | 8, 15 | L4 | 4795.48 | 4796.10 |

TABLE 7-continued

| Con-jugate | Sequence | Conjugation position | Staple | Calc mass | Mass found |
|---|---|---|---|---|---|
| 20 | PKPEAPGCDASPEECNRYYADLR HYLNWLTRQRY (SEQ ID No. 5) | 8, 15 | L4A | 4863.43 | 4863.39 |
| 21 | PKPEAPGCDASPEECNRYYADLR HYLNWLTRQRY (SEQ ID No. 5) | 8, 15 | L5 | 5067.78 | 5068.30 |
| 22 | PKPEAPGCDASPEECNRYYADLR HYLNWLTRQRY (SEQ ID No. 5) | 8, 15 | L5A | 5138.86 | 5138.51 |
| 23 | PKPEAPGCDASPEECNRYYADLR HYLNWLTRQRY (SEQ ID No. 5) | 8, 15 | L8 | 5095.84 | 5096.30 |
| 24 | PKPEAPGCDASPEECNRYYADLR HYLNWLTRQRY SEQ ID No. 5) | 8, 15 | L9 | 5039.73 | 5040.20 |
| 25 | PKPEAPGCDASPEECNRYYADLR HYLNWLTRQRY (SEQ ID No. 5) | 8, 15 | L12 | 4908.60 | 4909.00 |
| 26 | PKPEAPGCDASPEECNRYYADLR HYLNWLTRQRY (SEQ ID No. 5) | 8, 15 | L13 | | |
| 27 | PKPEAPGCDASPEECNRYYADLR HYLNWLTRQRY (SEQ ID No. 5) | 8, 15 | L14 | 4767.43 | 4767.90 |
| 28 | PKPEAPGCDASPEECNRYYADLR HYLNWLTRQRY (SEQ ID No. 5) | 8, 15 | L15 | 4823.53 | 4824.00 |
| 29 | PKPEAPGCDASPEECNRYYADLR HYLNWLTRQRY (SEQ ID No. 5) | 8, 15 | L16 | 4751.43 | 4751.90 |
| 30 | PKPEAPGCDASPEECNRYYADLR HYLNWLTRQRY (SEQ ID No. 5) | 8, 15 | L17 | 4839.53 | 4840.00 |
| 31 | PKPEAPGCDASPEECNRYYADLR HYLNWLTRQRY (SEQ ID No. 5) | 8, 15 | L18 | 5226.97 | 5227.40 |
| 32 | PKPEAPGKDASPEEWNRYYACL RHYLNCLTRQRY (SEQ ID No. 6) | 21, 28 | L1 | 4293.86 | 4294.34 |
| 33 | PKPEAPGKDASPEEWNRYYACL RHYLNCLTRQRY (SEQ ID No. 6) | 21, 28 | L1C | 4279.84 | 4280.00 |
| 34 | PKPEAPGKDASPEEWNRYYACL RHYLNCLTRQRY (SEQ ID No. 6) | 21, 28 | L1F | 4307.89 | 4308.30 |
| 35 | PKPEAPGKDASPEEWNRYYACL RHYLNCLTRQRY (SEQ ID No. 6) | 21, 28 | L1G | 4308.88 | 4309.00 |
| 36 | PKPEAPGKDASPEEWNRYYACL RHYLNCLTRQRY (SEQ ID No. 6) | 21, 28 | L3 | 4837.61 | 4838.10 |
| 37 | PKPEAPGKDASPEEWNRYYACL RHYLNCLTRQRY (SEQ ID No. 6) | 21, 28 | L4 | 4808.57 | 4809.00 |
| 38 | PKPEAPGKDASPEEWNRYYACL RHYLNCLTRQRY (SEQ ID No. 6) | 21, 28 | L4A | 4876.49 | 4876.46 |
| 39 | PKPEAPGKDASPEEWNRYYACL RHYLNCLTRQRY (SEQ ID No. 6) | 21, 28 | L5 | 5080.87 | 5081.30 |
| 40 | PKPEAPGKDASPEEWNRYYACL RHYLNCLTRQRY (SEQ ID No. 6) | 21, 28 | L5A | 5151.95 | 5152.30 |
| 41 | PKPEAPGKDASPEEWNRYYACL RHYLNCLTRQRY (SEQ ID No. 6) | 21, 28 | L8 | 5108.92 | 5109.30 |
| 42 | PKPEAPGKDASPEEWNRYYACL RHYLNCLTRQRY (SEQ ID No. 6) | 21, 28 | L9 | 5052.81 | 5053.30 |
| 43 | PKPEAPGKDASPEEWNRYYACL RHYLNCLTRQRY (SEQ ID No. 6) | 21, 28 | L12 | 4921.68 | 4922.10 |
| 44 | PKPEAPGKDASPEEWNRYYACL RHYLNCLTRQRY (SEQ ID No. 6) | 21, 28 | L18 | | |

TABLE 7-continued

| Con-jugate | Sequence | Conjugation position | Staple | Calc mass | Mass found |
|---|---|---|---|---|---|
| 45 | PKPEAPGKDASPEEWNRYYACL RHYLNCLTRQRY (SEQ ID No. 6) | 21, 28 | FA2 (x2) | 5724.04 | 5723.99 |
| 46 | PKPEAPGKDASPEEKNRYYADLR HYLNWLTRQRY (SEQ ID No. 7) | 8, 15 | K1 | | |
| 47 | PKPEAPGKDASPEEKNRYYADLR HYLNWLTRQRY (SEQ ID No. 7) | 8, 15 | K3 | | |
| 48 | PKPEAPGKDASPEEKNRYYADLR HYLNWLTRQRY (SEQ ID No. 7) | 8, 15 | K4 | | |
| 49 | PKPEAPGKDASPEEKNRYYADLR HYLNWLTRQRY (SEQ ID No. 7) | 8, 15 | K5 | | |
| 50 | PKPEAPGKDASPEEKNRYYADLR HYLNWLTRQRY (SEQ ID No. 7) | 8, 15 | A5 | | |
| 51 | PKPEAPGKDASPEEWNRYYAKL RHYLNKLTRQRY (SEQ ID No. 8) | 21, 28 | K1 | 4255.18 | 4255.12 |
| 52 | PKPEAPGKDASPEEWNRYYAKL RHYLNKLTRQRY (SEQ ID No. 8) | 21, 28 | K1C | | |
| 53 | PKPEAPGKDASPEEWNRYYAKL RHYLNKLTRQRY (SEQ ID No. 8) | 21, 28 | K1F | 4269.20 | 4269.13 |
| 54 | PKPEAPGKDASPEEWNRYYAKL RHYLNKLTRQRY (SEQ ID No. 8) | 21, 28 | K1H | 4283.21 | 4283.16 |
| 55 | PKPEAPGKDASPEEWNRYYAKL RHYLNKLTRQRY (SEQ ID No. 8) | 21, 28 | K3 | | |
| 56 | PKPEAPGKDASPEEWNRYYAKL RHYLNKLTRQRY (SEQ ID No. 8) | 21, 28 | K4 | | |
| 57 | PKPEAPGKDASPEEWNRYYAKL RHYLNKLTRQRY (SEQ ID No. 8) | 21, 28 | K5 | 5084.69 | 5084.69 |
| 58 | PKPEAPGKDASPEEWNRYYAKL RHYLNKLTRQRY (SEQ ID No. 8) | 21, 28 | A1 | 4303.18 | 4303.15 |
| 59 | PKPEAPGKDASPEEWNRYYAKL RHYLNKLTRQRY (SEQ ID No. 8) | 21, 28 | A5 | 5132.69 | 5132.68 |
| 60 | PKPEAPGKDASPEEWNRYYA[Orn] LRHYLN[Orn]LTRQRY (SEQ ID No. 9) | 21, 28 | K5 | | |
| 61 | PKPEAPGKDASPEEWNRYYA[Orn] LRHYLN[Orn]LTRQRY (SEQ ID No. 9) | 21, 28 | A5 | | |
| 62 | PKPEAPGCDASPEEWNRYYADL RHYLNWLTRQRY (SEQ ID No. 10) | 8 | FA2 | 4996.69 | 4997.10 |
| 63 | PKPEAPGKDASPEECNRYYADLR HYLNWLTRQRY (SEQ ID No. 11) | 15 | FA2 | 4938.65 | 4939.20 |
| 64 | PKPEAPGKDASPEEWNRYYACL RHYLNWLTRQRY (SEQ ID No. 12) | 21 | FA2 | 5009.77 | 5010.20 |
| 65 | PKPEAPGKDASPEEWNRYYADL RHYLNCLTRQRY (SEQ ID No. 13) | 28 | FA2 | 4938.65 | 4939.10 |
| 66 | PKPEAPGCDASPEEWNRYYACLR HYLNCLTRQRY (SEQ ID No. 14) | 8(FA2), 21 + 28 (L1) | L1 + FA2 | 5067.51 | 5066.45 |
| 67 | PKPEAPGCDASPEECNRYYACLR HYLNWLTRQRY (SEQ ID No. 15) | 8 + 15 (L1), 21 (FA2) | L1 + FA2 | | |

TABLE 7-continued

PYY Peptide Conjugates

| Con-jugate | Sequence | Conjugation position | Staple | Calc mass | Mass found |
|---|---|---|---|---|---|
| 68 | HCIKPEAPCEDASPEELNRYYASL RHYLNLVTRQRY (SEQ ID No. 16) | 2 9 | L1 | 4504.09 | 4504.30 |
| 69 | HCIKPEAPCEDASPEELNRYYASL RHYLNLVTRQRY (SEQ ID No. 16) | 2, 9 | L3 | 5047.84 | 5048.20 |
| 70 | HCIKPEAPCEDASPEELNRYYASL RHYLNLVTRQRY (SEQ ID No. 16) | 2, 9 | L4 | 5018.80 | 5019.28 |
| 71 | HCIKPEAPCEDASPEELNRYYASL RHYLNLVTRQRY (SEQ ID No. 16) | 2, 9 | L5 | 5291.10 | 5291.63 |
| 72 | HIKPEAPGCDASPEECNRYYASL RHYLNLVTRQRY (SEQ ID No. 17) | 9, 16 | L1 | 4318.87 | 4319.05 |
| 73 | HIKPEAPGCDASPEECNRYYASL RHYLNLVTRQRY (SEQ ID No. 17) | 9, 16 | L3 | 4725.47 | 4725.90 |
| 74 | HIKPEAPGCDASPEECNRYYASL RHYLNLVTRQRY (SEQ ID No. 17) | 9, 16 | L4 | 4696.43 | 4696.90 |
| 75 | HIKPEAPGCDASPEECNRYYASL RHYLNLVTRQRY (SEQ ID No. 17) | 9, 16 | L5 | 4968.73 | 4969.20 |
| 76 | HIKPEAPGEDASPEECNRYYASC RHYLNLVTRQRY (SEQ ID No. 18) | 16, 23 | L1 | 4334.82 | 4335.10 |
| 77 | HIKPEAPGEDASPEECNRYYASC RHYLNLVTRQRY (SEQ ID No. 18) | 16, 23 | L3 | 4878.57 | 4879.00 |
| 78 | HIKPEAPGEDASPEECNRYYASC RHYLNLVTRQRY (SEQ ID No. 18) | 16, 23 | L4 | 4849.53 | 4849.72 |
| 79 | HIKPEAPGEDASPEECNRYYASC RHYLNLVTRQRY (SEQ ID No. 18) | 16, 23 | L5 | 5121.83 | 5121.90 |
| 80 | IKPEAPGEDASPEELCRYYASLCH YLNLVTRQRY (SEQ ID No. 19) | 16, 23 | L1 | 4153.71 | 4153.98 |
| 81 | IKPEAPGEDASPEELCRYYASLCH YLNLVTRQRY (SEQ ID No. 19) | 16, 23 | L3 | 4697.46 | 4697.88 |
| 82 | IKPEAPGEDASPEELCRYYASLCH YLNLVTRQRY (SEQ ID No. 19) | 16, 23 | L4 | 4668.41 | 4668.90 |
| 83 | IKPEAPGEDASPEELCRYYASLCH YLNLVTRQRY (SEQ ID No. 19) | 16, 23 | L5 | 4940.72 | 4941.10 |
| 84 | IKPEAPGEDASPEELNCYYASLRC YLNLVTRQRY (SEQ ID No. 20) | 17, 24 | L1 | | |
| 85 | HIKPEAPGEDASPEELNRCYASLR HCLNLVTRQRY (SEQ ID No. 21) | 19, 26 | L1 | 4234.79 | 4235.05 |
| 86 | HIKPEAPGEDASPEELNRCYASLR HCLNLVTRQRY (SEQ ID No. 21) | 19, 26 | L3 | 4778.54 | 4778.97 |
| 87 | HIKPEAPGEDASPEELNRCYASLR HCLNLVTRQRY (SEQ ID No. 21) | 19, 26 | L4 | 4749.50 | 4749.80 |
| 88 | HIKPEAPGEDASPEELNRCYASLR HCLNLVTRQRY (SEQ ID No. 21) | 19, 26 | L5 | 5021.80 | 5022.24 |
| 89 | IKPEAPGEDASPEELNRYCASLRH YCNLVTRQRY (SEQ ID No. 22) | 19, 26 | L1 | 4147.67 | 4147.96 |
| 90 | IKPEAPGEDASPEELNRYCASLRH YCNLVTRQRY (SEQ ID No. 22) | 19, 26 | L3 | 4691.41 | 4691.90 |
| 91 | IKPEAPGEDASPEELNRYCASLRH YCNLVTRQRY (SEQ ID No. 22) | 19, 26 | L4 | 4662.37 | 4662.70 |
| 92 | IKPEAPGEDASPEELNRYCASLRH YCNLVTRQRY (SEQ ID No. 22) | 19, 26 | L5 | 4934.67 | 4935.10 |

TABLE 7-continued

| | PYY Peptide Conjugates | | | | |
|---|---|---|---|---|---|
| Con-jugate | Sequence | Conjugation position | Staple | Calc mass | Mass found |
| 93 | IKPEAPGEDASPEELNRYYCSLRH YLCLVTRQRY (SEQ ID No. 23) | 20, 27 | L1 | 4238.82 | 4238.82 |
| 94 | HIKPEAPGEDASPEELNRYYASC RHYLNLCTRQRY (SEQ ID No. 24) | 23, 30 | L1 | 4348.85 | 4349.20 |
| 95 | IKPEAPGCDASPEELNRYCASLRH YLNLVTRQRY (SEQ ID No. 25) | 8, 19 | L1D | 4173.79 | 4174.09 |
| 96 | IKPEAPGEDACPEELNRYYASCR HYLNLVTRQRY (SEQ ID No. 26) | 11, 22 | L1D | 4265.85 | 4266.00 |
| 97 | IKPEAPCEDASPEELNRYYASCRH YLNLVTRQRY (SEQ ID No. 27) | 7, 22 | L1E | 4351.98 | 4351.26 |
| 98 | IKPEAPGEDASPCELNRYYASLR HYLNCVTRQRY (SEQ ID No. 28) | 13, 28 | L1E | 4279.92 | 4280.06 |
| 99 | IKPEAPGEDASCEELNRYYASLR HYLNCVTRQRY (SEQ ID No. 29) | 12, 28 | L1E | | |
| 100 | IKPEAPGEDASPEELNCYYASLRH YLNCVTRQRY (SEQ ID No. 30) | 17, 28 | L1D | 4196.74 | 4196.98 |
| 101 | IKPEAPGCDASPEECNRYYASLR HYLNWVTRQ[N-MeR]Y (SEQ ID No. 33) | 8, 15 | L1 | 4267.80 | 4269.10 |
| 102 | IKPEAPGCDASPEECNRYYASLR HYLNWVTRQ[N-MeR]Y (SEQ ID No. 33) | 8, 15 | L3 | 4811.55 | 4812.94 |
| 103 | IKPEAPGCDASPEECNRYYASLR HYLNWVTRQ[N-MeR]Y (SEQ ID No. 33) | 8, 15 | L4 | 4782.51 | 4783.94 |
| 104 | IKPEAPGCDASPEECNRYYASLR HYLNWVTRQ[N-MeR]Y (SEQ ID No. 33) | 8, 15 | L5 | 5054.81 | 5056.30 |
| 105 | IKPEAPGEDASPEELNRYYACLR HYLNCVTRQ[N-MeR]Y (SEQ ID No. 34) | 21,28 | L1 | 4235.08 | 4235.10 |
| 106 | PKPEAPGCDASPEECNRYYADLR HYLNWLTRQ[N-MeR]Y (SEQ ID No. 35) | 8, 15 | L5 | | |
| 107 | IKPEAPGCDASLEECNRYYASLR HYLNLVTRQRY (SEQ ID No. 36) | 8, 15 | L1 | 4197.77 | 4198.11 |
| 108 | IKPEAPGCDASLEECNRYYASLR HYLNLVTRQRY (SEQ ID No. 36) | 8, 15 | L1B | 4169.72 | 4169.97 |
| 109 | IKPEAPGCDASLEECNRYYASLR HYLNLVTRQRY (SEQ ID No. 36) | 8, 15 | L1C | 4183.74 | 4183.98 |
| 110 | IKPEAPGCDASVEECNRYYASLR HYLNLVTRQRY (SEQ ID No. 37) | 8, 15 | L1 | 4183.74 | 4184.01 |
| 111 | IKPEAPGCDASVEECNRYYASLR HYLNLVTRQRY (SEQ ID No. 37) | 8, 15 | L1B | 4155.69 | 4155.97 |
| 112 | IKPEAPGCDASVEECNRYYASLR HYLNLVTRQRY (SEQ ID No. 37) | 8, 15 | L1C | 4169.72 | 4169.98 |
| 113 | IKPECPGEDASPEELQRYYASLRH YLNWVTRQ[beta-hArg]Y (SEQ ID No. 38) | 5 | FA2 | | |
| 114 | HIKPECPGEDASPEELQRYYASLR HYLNWVTRQ[beta-hArg]Y (SEQ ID No. 39) | 6 | FA2 | 5117.64 | 5117.62 |

TABLE 7-continued

| | PYY Peptide Conjugates | | | | |
|---|---|---|---|---|---|
| Con- jugate | Sequence | Conjugation position | Staple | Calc mass | Mass found |
| 115 | Isovaleryl- RPECPGEDASPEELQRYYASLRH YLNWVTRQ[beta-hArg]Y (SEQ ID No. 40) | 4 | FA2 | | |
| 116 | Ac-IC[Pqa]RHYLNWVTRQ[N-MeR]Y (SEQ ID No. 41) | 2 | FA2 | | |
| 117 | Ac- IK[Ahx]CNRYYASCRHYLNWVTRQ [N-MeR]Y (SEQ ID No. 42) | 4, 11 | L1 | | |
| 118 | Ac- IK[Pqa]CNRYYASCRHYLNWVTRQ [N-MeR]Y (SEQ ID No. 43) | 4, 11 | L1 | | |
| 119 | YESK[Ahx]CARYYSACRHYINLIT RQRY (SEQ ID No. 44) | 6, 13 | L1 | | |
| 120 | YESK[Ahx]CEDLARYCSALRHYI NLITRQRY (SEQ ID No. 45) | 6, 13 | L1 | | |

In some embodiments, the GLP-1R/GCGR Dual Agonists peptide conjugates described herein is as shown in Table 8.

TABLE 8

| | GLP-1R/GCGR Dual Agonists Peptide Conjugates | | | | |
|---|---|---|---|---|---|
| Con- jugate | Sequence | Conjugation position | Staple | Calc mass | Mass found |
| 121 | H[D- Ser]QGTFTSDYSKYLDEKAAKEFIKWL LNGGPSSGAPPPS (SEQ ID No. 48) | 17, 24 | K5 | 1281.66 | 1281.91 |
| 122 | H[D- Ser]QGTFTSDYSKYLDEKAAKEFIKWL LNGGPSSGAPPPS (SEQ ID No. 48) | 17, 24 | K4 | 1220.63 | 1220.87 |
| 123 | H[D- Ser]QGTFTSDYSKYLDEKAAKEFIKWL LRA (SEQ ID No. 49) | 17, 24 | K4 | 1026.05 | 1026.05 |
| 124 | H[D- Ser]QGTFTSDYSKYLDEKAAKEFIKWL LNGGPSSGAPPPS (SEQ ID No. 48) | 17, 24 | K0 | 1095.79 | 1095.79 |
| 125 | H[Aib]QGTFTSDYSKYLDEKAAKEFIK WLLNGRNRNNIA (SEQ ID No. 50) | 17, 24 | K4 | 1221.15 | 1221.40 |
| 126 | H[Aib]QGTFTSDYSKYLDSKKAKEFVK WLLN[Aib]GPSSGAPPPS (SEQ ID No. 51) | 17, 24 | K4 | 1227.40 | 1227.65 |
| 127 | H[Aib]QGTFTSDYSKYLDSKKAQEFVK WLLNGPSSGAPPPS (SEQ ID No. 52) | 17, 24 | K4 | 1206.13 | 1206.38 |
| 128 | H[Aib]QGTFTSDYSKYLDKKAAKEFKQ WLLNGPSSGAPPPS (SEQ ID No. 53) | 16, 23 | K4 | 1209.39 | 1209.39 |
| 129 | H[Aib]QGTFTSDYSKYLDKKKAKEFKQ WLLN[Aib]GRNRNNIA (SEQ ID No. 54) | 16, 23 | K4 | 1260.19 | 1260.19 |
| 130 | H[D-Ser]QGT[D- Phe]TSDYSEYLDEKAAKEFIKWLLNGG PSSGAPPPS (SEQ ID No. 55) | 17, 24 | K4 | 1220.87 | 1220.86 |

TABLE 8-continued

GLP-1R/GCGR Dual Agonists Peptide Conjugates

| Con-jugate | Sequence | Conjugation position | Staple | Calc mass | Mass found |
|---|---|---|---|---|---|
| 131 | H[D-Ser]QGT[D-Phe]TSDYSEYLDEKAAREFIKWLLAGG PSSGAPPPS (SEQ ID No. 56) | 17, 24 | K4 | 1217.12 | 1217.11 |
| 132 | H[D-Ser]QGT[Nle]TSDYSEYLDEKAAKEFIK WLLNGGPSSGAPPPS (SEQ ID No. 57) | 17, 24 | K4 | 1212.37 | 1212.36 |
| 133 | H[D-Ser]QGTLTSDYSEYLDEKAAKEFIKWL LNGGPSSGAPPPS (SEQ ID No. 58) | 17, 24 | K4 | 1212.37 | 1212.37 |
| 134 | H[D-Ser]QGTLTSDYSEYLDSKRAREFVKWL EAGGPSSGAPPPS (SEQ ID No. 59) | 17, 24 | K4 | 1219.87 | 1219.86 |
| 135 | H[D-Ser]QGTFTSDYSKYLDECAAKEFICWL LNGGPSSGAPPPS (SEQ ID No. 60) | 17, 24 | L4A | 1229.61 | 1229.86 |
| 136 | H[D-Ser]QGTFTSDYSKYLDECAAKEFICWL LRA (SEQ ID No. 61) | 17, 24 | L4A | 1035.03 | 1035.04 |
| 137 | H[D-Ser]QGTFTSDYSKYLDECAAKEFICWL LRA (SEQ ID No. 61) | 17, 24 | L5A | 1103.07 | 1103.05 |
| 138 | H[D-Ser]QGTFTSDYSKYLDECAAKEFICWL LNGGPSSGAPPPS (SEQ ID No. 60) | 17, 24 | L5A | 1297.64 | 1297.89 |
| 188 | H[D-Ser]QGTFTSDYSKYLDECAAKEFICWL MNTKRNRNNIA (SEQ ID No. 80) | 17, 24 | L1 | 4524.1 | 1510.0 ($[M + 3H]^3$), 1132.0 ($[M + 4H]^4$) |
| 189 | H[D-Ser]QGTFTSDYSKYLDECAAKEFICWL MNTKRNRNNIA (SEQ ID No. 80) | 17, 24 | L2 | 4952.7 | 1651.8 ($[M + 3H]^3$), 1239.2 ($[M + 4H]^4$) |
| 190 | H[D-Ser]QGTFTSDYSKYLDECAAKEFICWL MNTKRNRNNIA (SEQ ID No. 80) | 17, 24 | L16 | 5038.8 | 1680.3 ($[M + 3H]^3$), 1260.6 ($[M + 4H]^4$) |
| 191 | H[D-Ser]QGTFTSDYSKYLDECAAHDFVCWL LRA (SEQ ID No. 81) | 17, 24 | L1 | 3489.9 | 1164.4 ($[M + 3H]^3$), 873.6 ($[M + 4H]^4$) |
| 192 | H[D-Ser]QGTFTSDYSKYLDECAAHDFVCWL LRA (SEQ ID No. 81) | 17, 24 | L2 | 3918.5 | 1307.2 ($[M + 3H]^3$), 980.6 ($[M + 4H]^4$) |
| 193 | H[D-Ser]QGTFTSDYSKYLDECAAKEFICWL LRA (SEQ ID No. 61) | 17, 24 | L1 | 3509.0 | 1170.6 ($[M + 3H]^3$), 878.2 ($[M + 4H]^4$) |
| 194 | H[D-Ser]QGTFTSDYSKYLDECAAKEFICWL LRA (SEQ ID No. 61) | 17, 24 | L2 | 3937.6 | 1313.6 ($[M + 3H]^3$), 985.4 ($[M + 4H]^4$) |
| 195 | H[D-Ser]QGTFTSDYSKYLDECAAKEFICWL LRA (SEQ ID No. 61) | 17, 24 | L16 | 4065.7 | 1355.6 ($[M + 3H]^{3+}$), 1017.3 ($[M + 4H]^4$) |

TABLE 8-continued

GLP-1R/GCGR Dual Agonists Peptide Conjugates

| Con-jugate | Sequence | Conjugation position | Staple | Calc mass | Mass found |
|---|---|---|---|---|---|
| 196 | H[D-Ser]QGTFTSDYSKYLDECAAKEFICWL LRA (SEQ ID No. 61) | 17, 24 | L19 | 4295.0 | 1432.6 ([M + 3H]$^3$), 1074.7 ([M + 4H]$^4$) |
| 197 | H[D-Ser]QGTFTSDYSKYLDECAAKEFICWL LRA (SEQ ID No. 61) | 17, 24 | L5 | 4296.0 | 1433.0 ([M + 3H]$^3$), 1075.1 ([M + 4H]$^4$) |
| 198 | H[D-Ser]QGTFTSDYSKYLDECAAKEFICWL LRAGPSSGAPPPS (SEQ ID No. 82) | 17, 24 | L16 | 4902.6 | 1635.2 ([M + 3H]$^3$), 1226.6 ([M + 4H]$^4$) |
| 199 | H[D-Ser]QGTFTSDYSKYLDECAAKEFICWL LRAGPSSGAPPPS (SEQ ID No. 82) | 17, 24 | L19 | 5129.9 | 1711.0 ([M + 3H]$^3$), 1284.2 ([M + 4H]$^{4+}$) |
| 200 | H[D-Ser]QGTFTSDYSKYLDECAAKEFICWL LRAGPSSGAPPPS (SEQ ID No. 82) | 17, 24 | L5 | 5130.8 | 1711.3 ([M + 3H]$^3$), 1283.8 ([M + 4H]$^4$ |
| 201 | H[D-Ser]QGTFTSDYSKYLDECAAKEFICWL LNGGPSSGAPPPS (SEQ ID No. 60) | 17, 24 | L16 | 4844.5 | 1615.6 ([M + 3H]$^3$), 1212.2 ([M + 4H]$^4$) |
| 202 | H[D-Ser]QGTFTSDYSKYLDECAAKEFICWL LNGGPSSGAPPPS (SEQ ID No. 60) | 17, 24 | L19 | 5073.7 | 1092.2 ([M + 3H]$^3$), 1269.4 ([M + 4H]$^4$) |
| 203 | H[D-Ser]QGTFTSDYSKYLDECAAKEFICWL LNGGPSSGAPPPS (SEQ ID No. 60) | 17, 24 | L5 | 5074.7 | 1692.6 ([M + 3H]$^3$), 1269.8 ([M + 4H]$^{4+}$) |
| | H[D-Ser]QGTFTSDYSKYLDEKAAKEFIKWL LNGGPSSGAPPPS (SEQ ID No. 48) | 17, 24 | K8 | | |
| | H[D-Ser]QGTFTSDYSKYLDECAAKEFICWL LNGGPSSGAPPPS (SEQ ID No. 60) | 17, 24 | C20L5A | | |
| | H[Aib]QGTFTSDYSEYLDSKKAKEFVK WLLN[Aib]GPSSGAPPPS (SEQ ID No. 108) | 17, 24 | K4 | | |
| | H[Aib]QGTFTSDYSEYLDSKKAKEFVK WLLN[Aib]GPSSGAPPPS (SEQ ID No. 108) | 17, 24 | K5 | | |
| | H[Aib]QGTFTSDYSEYLDSKKAKEFVK WLLN[Aib]GPSSGAPPPS (SEQ ID No. 108) | 17, 24 | K8 | | |
| | H[Aib]QGTFTSDYSEYLDSKKAQEFVK WLLNGGPSSGAPPPS (SEQ ID No. 109) | 17, 24 | K4 | | |
| | H[Aib]QGTFTSDYSEYLDSKKAQEFVK WLLNGGPSSGAPPPS (SEQ ID No. 109) | 17, 24 | K5 | | |
| | H[Aib]QGTFTSDYSEYLDSKKAQEFVK WLLNGGPSSGAPPPS (SEQ ID No. 109) | 17, 24 | K8 | | |
| | H[D-Ser]QGTFTSDYSEYLDEKAAKEFIKWL LNGGPSSGAPPPS (SEQ ID No. 110) | 17, 24 | K4 | | |
| | H[D-Ser]QGTFTSDYSEYLDEKAAKEFIKWL LNGGPSSGAPPPS (SEQ ID No. 110) | 17, 24 | K5 | | |

TABLE 8-continued

| | GLP-1R/GCGR Dual Agonists Peptide Conjugates | | | | |
|---|---|---|---|---|---|
| Con-<br>jugate | Sequence | Conjugation<br>position | Staple | Calc<br>mass | Mass<br>found |
| | H[D-<br>Ser]QGTFTSDYSEYLDEKAAKEFIKWL<br>LNGGPSSGAPPPS (SEQ ID No. 110) | 17, 24 | K8 | | |
| | H[D-Ser]QGT[D-<br>Phe]TSDYSEYLDEKAAKEFIKWLLNGG<br>PSSGAPPPS (SEQ ID No. 55) | 17, 24 | K5 | | |
| | H[D-Ser]QGT[D-<br>Phe]TSDYSEYLDEKAAKEFIKWLLNGG<br>PSSGAPPPS (SEQ ID No. 55) | 17, 24 | K8 | | |
| | H[D-Ser]QGT[D-<br>Phe]TSDYSEYLDEKAAREFIKWLLAGG<br>PSSGAPPPS (SEQ ID No. 56) | 17, 24 | K5 | | |
| | H[D-Ser]QGT[D-<br>Phe]TSDYSEYLDEKAAREFIKWLLAGG<br>PSSGAPPPS (SEQ ID No. 56) | 17, 24 | K8 | | |
| | H[D-<br>Ser]QGTFTSDYSKQLDECAAKEFICWL<br>LQGGPSSGAPPPS (SEQ ID No. 111) | 17, 24 | L5A | | |
| | H[D-<br>Ser]QGTFTSDYSKQLDECAAKEFICWL<br>LQGGPSSGAPPPS (SEQ ID No. 111) | 17, 24 | C20L5A | | |

In some embodiments, the GLP-1R/GIPR Dual Agonists peptide conjugates described herein is as shown in Table 9.

TABLE 9

| | GLP-1R/GIPR Dual Peptide Conjugates | | | | |
|---|---|---|---|---|---|
| Con-<br>jugate | Sequence | Conjugation<br>position | Staple | Calc<br>mass | Mass<br>found |
| 139 | Y[Aib]EGTFTSDYSIYLDKKAA[Aib]EFVKWL<br>LAGGPSSGAPPPS (SEQ ID No. 62) | 17, 24 | K5 | 1258.9 | 1259.16 |
| 140 | Y[Aib]EGTFTSDYSIYLDKKAA[Aib]EFVKWL<br>LAGGPSSGAPPPS (SEQ ID No. 62) | 17, 24 | K4 | 1197.88 | 1197.88 |
| 141 | Y[Aib]EGTFTSDYSIYKDKQAA[Aib]KFVNWL<br>LAGGPSSGAPPPS (SEQ ID No. 63) | 14, 21 | K5 | 1258.9 | 1259.15 |
| 142 | Y[Aib]EGTFTSDYSIYKDKQAA[Aib]KFVNWL<br>LAGGPSSGAPPPS (SEQ ID No. 63) | 14, 21 | K4 | 1197.87 | 1197.87 |
| 143 | Y[Aib]EGTFTSDYSIYLDKKAA[Aib]EFVKWL<br>LAGGPSSGAPPPS (SEQ ID No. 62) | 17, 24 | K9 | 1251.9 | 1252.14 |
| 144 | Y[Aib]EGTFTSDYSIYKDKQAA[Aib]KFVNWL<br>LAGGPSSGAPPPS (SEQ ID No. 63) | 14, 21 | K9 | 1251.89 | 1252.14 |
| 145 | Y[Aib]EGTFTSDYSIYKDKQAA[Aib]KFKNWL<br>KAGGPSSGAPPPS (SEQ ID No. 64) | 23, 27 | K4 | 1208.88 | 1209.38 |
| 146 | Y[Aib]EGTFTSDYSIYLDKKAQ[Aib]AFVKWL<br>IAQGPSSGAPPPS (SEQ ID No. 65) | 17, 24 | K4 | 1215.39 | 1215.89 |
| 147 | Y[Aib]EGTFTSDYSIYLDKKAA[Aib]EFVKWL<br>LAGGPSSGAPPPS (SEQ ID No. 62) | 17, 24 | K6 | 1244.4 | 1244.91 |
| 148 | Y[Aib]EGTFTSDYSIYLDKKAA[Aib]EFVKWL<br>LAGGPSSGAPPPS (SEQ ID No. 62) | 17, 24 | K8 | 1265.91 | 1266.42 |
| 149 | Y[Aib]EGTFTSDYSIYLDKKAA[Aib]EFVKWL<br>LAGGPSSGAPPPS (SEQ ID No. 62) | 17, 24 | K20 | 1237.4 | 1237.89 |

TABLE 9-continued

GLP-1R/GIPR Dual Peptide Conjugates

| Con-jugate | Sequence | Conjugation position | Staple | Calc mass | Mass found |
|---|---|---|---|---|---|
| 150 | Y[Aib]EGTFTSDYSIYLDKKAA[Aib]EFVKWL LAGGPSSGAPPPS (SEQ ID No. 62) | 17, 24 | K7 | 1251.41 | 1251.91 |
| 151 | Y[Aib]EGTFTSDYSIYKDKQAA[Aib]KFVNWL LAGGPSSGAPPPS (SEQ ID No. 63) | 14, 21 | K6 | 1244.4 | 1244.89 |
| 152 | Y[Aib]EGTFTSDYSIYKDKQAA[Aib]KFVNWL LAGGPSSGAPPPS (SEQ ID No. 63) | 14, 21 | K8 | 1265.91 | 1266.41 |
| 153 | Y[Aib]EGTFTSDYSIYKDKQAA[Aib]KFVNWL LAGGPSSGAPPPS (SEQ ID No. 63) | 14, 21 | K20 | 1237.4 | 1237.89 |
| 154 | Y[Aib]EGTFTSDYSIYKDKQAA[Aib]KFVNWL LAGGPSSGAPPPS (SEQ ID No. 63) | 14, 21 | K7 | 1251.41 | 1251.91 |
| 155 | Y[Aib]EGTFTSDYSIYKDKQAA[Aib]KFKNWL KAGGPSSGAPPPS (SEQ ID No. 64) | 23, 27 | K6 | 1255.41 | 1255-91 |
| 156 | Y[Aib]EGTFTSDYSIYKDKQAA[Aib]KFKNWL KAGGPSSGAPPPS (SEQ ID No. 64) | 23, 27 | K8 | 1276.92 | 1277.42 |
| 157 | Y[Aib]EGTFTSDYSIYKDKQAA[Aib]KFKNWL KAGGPSSGAPPPS (SEQ ID No. 64) | 23, 27 | K20 | 1248.40 | 1248.89 |
| 158 | Y[Aib]EGTFTSDYSIYKDKQAA[Aib]KFKNWL KAGGPSSGAPPPS (SEQ ID No. 64) | 23, 27 | K5 | 1269.91 | 1270.41 |
| 159 | Y[Aib]EGTFTSDYSIYKDKQAA[Aib]KFKNWL KAGGPSSGAPPPS (SEQ ID No. 64) | 23, 27 | K9 | 1262.90 | 1263.40 |
| 160 | Y[Aib]EGTFTSDYSIYLDKKAQ[Aib]AFVKWL IAQGPSSGAPPPS (SEQ ID No. 65) | 17, 24 | K6 | 1261.92 | 1262.42 |
| 161 | Y[Aib]EGTFTSDYSIYLDKKAQ[Aib]AFVKWL IAQGPSSGAPPPS (SEQ ID No. 65) | 17, 24 | K8 | 1283.43 | 1283.93 |
| 162 | Y[Aib]EGTFTSDYSIYLDKKAQ[Aib]AFVKWL IAQGPSSGAPPPS (SEQ ID No. 65) | 17, 24 | K20 | 1254.91 | 1255.41 |
| 163 | Y[Aib]EGTFTSDYSIYLDKKAQ[Aib]AFVKWL IAQGPSSGAPPPS (SEQ ID No. 65) | 17, 24 | K5 | 1276.42 | 1276.66 |
| 164 | Y[Aib]EGTFTSDYSIYLDKKAQ[Aib]AFVKWL IAQGPSSGAPPPS (SEQ ID No. 65) | 17, 24 | K9 | 1269.41 | 1269.91 |
| 165 | Y[Aib]EGTFHSDYDIYKDKQAA[Aib]KFVQW LLAGGPSSGAPPPS (SEQ ID No. 66) | 14, 21 | K4 | 1622.83 | 1623.22 |
| 166 | Y[Aib]EGTFHSDYDIYKDKQAA[Aib]KFVQW LLAGGPSSGAPPPS (SEQ ID No. 66) | 14, 21 | K5 | 1704.19 | 1704.6 |
| 167 | Y[Aib]EGTFHSDYDIYKDKQAA[Nle]KFVAW LLAGGPSSGAPPPS (SEQ ID No. 67) | 14, 21 | K4 | 1613.16 | 1613.56 |
| 168 | Y[Aib]EGTFHSDYDIYKDKQAA[Nle]KFVAW LLAGGPSSGAPPPS (SEQ ID No. 67) | 14, 21 | K5 | 1694.53 | 1694.94 |
| 169 | Y[Aib]EGTFT[D-Ser]DY[D-Ser]IYKDKQAA[Nle]KFVAWLLAGGPSSGAPP PS (SEQ ID No. 68) | 14, 21 | K4 | 1591.83 | 1592.23 |
| 170 | Y[Aib]EGTFT[D-Ser]DY[D-Ser]IYKDKQAA[Nle]KFVAWLLAGGPSSGAPP PS (SEQ ID No. 68) | 14, 21 | K5 | 1673.20 | 1673.60 |
| 171 | Y[Aib]EGTFTSDYSIYCDKQAA[Aib]CFVNWL LAGGPSSGAPPPS (SEQ ID No. 69) | 14, 21 | L5A | 1274.88 | 1275.13 |
| 172 | Y[Aib]EGTFTSDYSIYCDKQAA[Aib]CFVNWL LAGGPSSGAPPPS (SEQ ID No. 69) | 14, 21 | L4A | 1206.84 | |
| 173 | YGEGTFTSDYSIYCDKQAAQCFVNWLLAGG PSSGAPPPS (SEQ ID No. 70) | 14, 21 | L4A | 1210.59 | |

TABLE 9-continued

GLP-1R/GIPR Dual Peptide Conjugates

| Con-jugate | Sequence | Conjugation position | Staple | Calc mass | Mass found |
|---|---|---|---|---|---|
| 174 | YGEGTFTSDYSIYCDKQAAQCFVNWLLAGG PSSGAPPPS (SEQ ID No. 70) | 14, 21 | L5A | 1278.62 | |
| 175 | Y[Aib]EGTFTSDYSIYCDKQAAQCFVNWLLA GGPSSGAPPPS (SEQ ID No. 71) | 14, 21 | L4A | 1217.59 | |
| 176 | Y[Aib]EGTFTSDYSIYCDKQAAQCFVNWLLA GGPSSGAPPPS (SEQ ID No. 71) | 14, 21 | L5A | 1285.63 | |
| | Y[Aib]EGTFTSDYSIYCDKQAA[Aib]CFVNWL LAGGPSSGAPPPS (SEQ ID No. 69) | 14, 21 | C20L5A | | |
| | Y[Aib]EGTFTSDYSIYLDKCAA[Aib]EFVCWL LAGGPSSGAPPPS (SEQ ID No. 114) | 17, 24 | L5A | | |
| | Y[Aib]EGTFTSDYSIYLDKCAA[Aib]EFVCWL LAGGPSSGAPPPS (SEQ ID No. 114) | 17, 24 | C20L5A | | |
| | Y[Aib]EGTFTSDYSIYLDKCAQ[Aib]AFVCWLI AQGPSSGAPPPS (SEQ ID No. 115) | 17, 24 | L5A | | |
| | Y[Aib]EGTFTSDYSIYLDKCAQ[Aib]AFVCWLI AQGPSSGAPPPS (SEQ ID No. 115) | 17, 24 | C20L5A | | |
| | Y[Aib]EGTFTSDYSIYCDKQAA[Aib]CFVNWL IAGGPSSGAPPPS (SEQ ID No. 116) | 14, 21 | L5A | | |
| | Y[Aib]EGTFTSDYSIYCDKQAA[Aib]CFVNWL IAGGPSSGAPPPS (SEQ ID No. 116) | 14, 21 | C20L5A | | |
| | Y[Aib]EGTFISDVSIYCDKQAA[Aib]CFVNWLI AGGPSSGAPPPS (SEQ ID No. 117) | 14, 21 | L5A | | |
| | Y[Aib]EGTFISDVSIYCDKQAA[Aib]CFVNWLI AGGPSSGAPPPS (SEQ ID No. 117) | 14, 21 | C20L5A | | |
| | Y[Aib]EGTFISDVSIYLDKCAA[Aib]EFVCWLI AGGPSSGAPPPS (SEQ ID No. 118) | 17, 24 | L5A | | |
| | Y[Aib]EGTFISDVSIYLDKCAA[Aib]EFVCWLI AGGPSSGAPPPS (SEQ ID No. 118) | 17, 24 | C20L5A | | |
| | Y[Aib]EGTFISDLSIYCDKQAA[Aib]CFVQWLI AGGPSSGAPPPS (SEQ ID No. 119) | 14, 21 | L5A | | |
| | Y[Aib]EGTFISDLSIYCDKQAA[Aib]CFVQWLI AGGPSSGAPPPS (SEQ ID No. 119) | 14, 21 | C20L5A | | |
| | Y[Aib]EGTFISDLSIYLDKCAA[Aib]EFVCWLI AGGPASGAPPPS (SEQ ID No. 120) | 17, 24 | L5A | | |
| | Y[Aib]EGTFISDLSIYLDKCAA[Aib]EFVCWLI AGGPASGAPPPS (SEQ ID No. 120) | 17, 24 | C20L5A | | |

In some embodiments, the GLP-1R peptide conjugates described herein is as shown in Table 10.

TABLE 10

GLP-1R Peptide Conjugates

| Con-jugate | Sequence | Con-jugation position | Staple | Calc mass | Mass found |
|---|---|---|---|---|---|
| 177 | HGEGTFTSDLSKQMEEKAVRLFIKWLKNGGPS SGAPPPS (SEQ ID No. 72) | 17, 24 | K5 | 1274.42 | 1274.41 |
| 178 | HGEGTFTSDLSKQMEEKAVRLFIKWLKNGGPS SGAPPPS (SEQ ID No. 72) | 17, 24 | A1 | 1079.04 | 1079.05 |

TABLE 10-continued

| | | | | | |
|---|---|---|---|---|---|
| | | GLP-1R Peptide Conjugates | | | |
| Con-jugate | Sequence | Con-jugation position | Staple | Calc mass | Mass found |
| 179 | HGEGTFTSDLSKQLEEKAVRLFIKWLKNGGPS SGAPPPS (SEQ ID No. 73) | 17, 24 | K5 | 1269.93 | 1269.93 |
| 180 | HGEGTFTSDLSKQ[Nle]EEKAVRLFIKWLKNG GPSSGAPPPS (SEQ ID No. 74) | 17, 24 | K5 | 1269.93 | 1269.93 |
| 181 | H[Aib]EGTFTSDVSSYLEGKAAKEFIKWLVKG RG (SEQ ID No. 75) | 17, 24 | K5 | 1085.08 | 1085.07 |
| 182 | H[Aib]EGTFTSDVSSYLEGKAAKEFIKWLVKG RG (SEQ ID No. 75) | 17, 24 | A1 | 889.70 | 889.70 |
| 183 | HGEGTFTSDLSKQLEECAVRLFICWLKNGGPS SGAPPPS (SEQ ID No. 76) | 17, 24 | L5A | 1285.92 | 1285.92 |
| 184 | HGEGTFTSDLSKQMEECAVRLFICWLKNGGPS SGAPPPS (SEQ ID No. 77) | 17, 24 | L5A | 1290.65 | 1290.40 |
| 185 | HGEGTFTSDVS SYLEGCAAKEFICWLVKGRG (SEQ ID No. 78) | 17, 24 | L5A | 1094.06 | 1094.05 |
| 186 | H[Aib]EGTFTSDVSSYLEGCAAKEFICWLVKGR G (SEQ ID No. 79) | 17, 24 | L5A | 1101.07 | 1101.06 |
| 187 | HGEGTFTSDLSKQMEECAVRLFICWLKNGGPS SGAPPPS (SEQ ID No. 77) | 17, 24 | L5 | 1018.99 | 1018.70 |

In some embodiments, the peptide conjugate described herein is as shown in Tables 11 and 12.

TABLE 11

| | | | | |
|---|---|---|---|---|
| | | Stapled PrRP20 peptide sequences[a] | | |
| Con-jugate | Peptide sequence | Staple/ HEM | Calc mass | Mass found |
| 204 | TCDINPAWCTGRGIRPVGRF-NH2 (SEQ ID NO.: 103) | L1 | 2386.79 | 1194.1, $[M + 2H]^{2+}$ |
| 205 | TPCINPAWYCGRGIRPVGRF-NH2 (SEQ ID NO.: 104) | L1 | 2429.88 | 1216.1, $[M + 2H]^{2+}$ |
| 206 | TPDCNPAWYTCRGIRPVGRF-NH2 (SEQ ID NO.: 105) | L1 | 2475.86 | 1239.1, $[M + 2H]^{2+}$ |
| 207 | TPDICPAWYTGCGIRPVGRF-NH2 (SEQ ID NO.: 83) | L1 | 2376.79 | 1189.1, $[M + 2H]^{2+}$ |
| 208 | TPDINCAWYTGRCIRPVGRF-NH2 (SEQ ID NO.: 84) | L1 | 2491.90 | 831.7, $[M + 3H]^{3+}$ |
| 209 | TPDINPCWYTGRGCRPVGRF-NH2 (SEQ ID NO.: 85) | L1 | 2461.83 | 1232.1, $[M + 2H]^{2+}$ |
| 210 | TPDINPACYTGRGICPVGRF-NH2 (SEQ ID NO.: 86) | L1 | 2304.68 | 1153.1, $[M + 2H]^{2+}$ |
| 211 | TPDINPAWCTGRGIRCVGRF-NH2 (SEQ ID NO.: 87) | L1 | 2385.78 | 1194.1, $[M + 2H]^{2+}$ |
| 212 | TPDINPAWYCGRGIRPCGRF-NH2 (SEQ ID NO.: 88) | L1 | 2446.84 | 1224.1, $[M + 2H]^{2+}$ |
| 213 | TCDINPAWCTGRGIRPVGRF-NH2 (SEQ ID NO.: 103) | L3 | 2930.53 | 1465.8, $[M + 2H]^{2+}$ |
| 214 | TCDINPAWCTGRGIRPVGRF-NH2 (SEQ ID NO.: 103) | L4 | 2901.49 | 967.9, $[M + 3H]^{3+}$ |

TABLE 11-continued

| | Stapled PrRP20 peptide sequences[a] | | | |
|---|---|---|---|---|
| Con-jugate | Peptide sequence | Staple/HEM | Calc mass | Mass found |
| 215 | TCDINPAWCTGRGIRPVGRF-NH2 (SEQ ID NO.: 103) | L5 | 3173.79 | 1058.6, [M + 3H]$^{3+}$ |
| 216 | TPDCNPAWYTCRGIRPVGRF-NH2 (SEQ ID NO.: 105) | L3 | 3019.61 | 1007.5, [M + 3H]$^{3+}$ |
| 217 | TPDCNPAWYTCRGIRPVGRF-NH2 (SEQ ID NO.: 105) | L4 | 2990.56 | 997.9, [M + 3H]$^{3+}$ |
| 218 | TPDCNPAWYTCRGIRPVGRF-NH2 (SEQ ID NO.: 105) | L5 | 3262.86 | 1088.9, [M + 3H]$^{3+}$ |
| 219 | TPDICPAWYTGCGIRPVGRF-NH2 (SEQ ID NO.: 83) | L3 | 2920.53 | 1460.8, [M + 2H]$^{2+}$ |
| 220 | TPDICPAWYTGCGIRPVGRF-NH2 (SEQ ID NO.: 83) | L4 | 2891.49 | 964.5, [M + 3H]$^{3+}$ |
| 221 | TPDICPAWYTGCGIRPVGRF-NH2 (SEQ ID NO.: 83) | L5 | 3163.79 | 1055.6, [M + 3H]$^{3+}$ |
| 222 | TPDINPCWYTGRGCRPVGRF-NH2 (SEQ ID NO.: 85) | L3 | 3005.58 | 1002.8, [M + 3H]$^{3+}$ |
| 223 | TPDINPCWYTGRGCRPVGRF-NH2 (SEQ ID NO.: 85) | L4 | 2976.54 | 993.2, [M + 3H]$^{3+}$ |
| 224 | TPDINPCWYTGRGCRPVGRF-NH2 (SEQ ID NO.: 85) | L5 | 3248.84 | 1084.2, [M + 3H]$^{3+}$ |

[a]All peptides confirmed >95% purity by HPLC (LC-MS).

TABLE 12

| | Stapled PrRP31 peptide sequences[a] | | | |
|---|---|---|---|---|
| Con-jugate | Peptide sequence | Staple/HEM | Calc mass | Mass found |
| 225 | CRAHQHSCETRTPDINPAWYTGRGIR PVGRF-NH2 (SEQ ID NO.: 89) | L1 | 3750.25 | 626.1, [M + 6H]$^{6+}$ |
| 226 | SRAHQCSMETRTCDINPAWYTGRGIR PVGRF-NH2 (SEQ ID NO.: 90) | L1 | 3734.26 | 747.8, [M + 5H]$^{5+}$ |
| 227 | SRAHQHSMCTRTPDICPAWYTGRGIR PVGRF-NH2 (SEQ ID NO.: 91) | L1 | 3725.30 | 621.8, [M + 6H]$^{6+}$ |
| 228 | SRAHQHSMETRTCDINPAWCTGRGIR PVGRF-NH2 (SEQ ID NO.: 92) | L1 | 3708.23 | 619.0, [M + 6H]$^{6+}$ |
| 229 | SRAHQHSMETRTPDCNPAWYTCRGIR PVGRF-NH2 (SEQ ID NO.: 93) | L1 | 3797.30 | 760.6, [M + 5H]$^{5+}$ |
| 230 | SRAHQHSMETRTPDICPAWYTGCGIR PVGRF-NH2 (SEQ ID NO.: 94) | L1 | 3698.23 | 740.6, [M + 5H]$^{5+}$ |
| 231 | SRAHQHSMETRTPDINPCWYTGRGCR PVGRF-NH2 (SEQ ID NO.: 95) | L1 | 3783.27 | 757.8, [M + 5H]$^{5+}$ |
| 232 | SRAHQHSMETRTPDINPAWCTGRGIR CVGRF-NH2 (SEQ ID NO.: 96) | L1 | 3707.22 | 742.6, [M + 5H]$^{5+}$ |

TABLE 12-continued

Stapled PrRP31 peptide sequences[a]

| Con-jugate | Peptide sequence | Staple/HEM | Calc mass | Mass found |
|---|---|---|---|---|
| 233 | CRAHQHSCETRTPDINPAWYTGRGIRPVGRF-NH2 (SEQ ID NO.: 89) | L3 | 4294.00 | 4294.2, $[M + H]^+$ |
| 234 | CRAHQHSCETRTPDINPAWYTGRGIRPVGRF-NH2 (SEQ ID NO.: 89) | L4 | 4264.95 | 4265.3, $[M + H]^+$ |
| 235 | CRAHQHSCETRTPDINPAWYTGRGIRPVGRF-NH2 (SEQ ID NO.: 89) | L5 | 4537.26 | 4537.5, $[M + H]^+$ |
| 236 | SRAHQCSMETRTCDINPAWYTGRGIRPVGRF-NH2 (SEQ ID NO.: 90) | L3 | 4278.01 | 4278.3, $[M + H]^+$ |
| 237 | SRAHQCSMETRTCDINPAWYTGRGIRPVGRF-NH2 (SEQ ID NO.: 90) | L4 | 4248.97 | 4249.3, $[M + H]^+$ |
| 238 | SRAHQCSMETRTCDINPAWYTGRGIRPVGRF-NH2 (SEQ ID NO.: 90) | L5 | 4521.27 | 4521.5, $[M + H]^+$ |
| 239 | SRAHQHSMETRTCDINPAWCTGRGIRPVGRF-NH2 (SEQ ID NO.: 92) | L3 | 4251.97 | 4252.2, $[M + H]^+$ |
| 240 | SRAHQHSMETRTCDINPAWCTGRGIRPVGRF-NH2 (SEQ ID NO.: 92) | L4 | 4222.93 | 4223.1, $[M + H]^+$ |
| 241 | SRAHQHSMETRTCDINPAWCTGRGIRPVGRF-NH2 (SEQ ID NO.: 92) | L5 | 4495.23 | 4495.5, $[M + H]^+$ |
| 242 | SRAHQHSMETRTPDCNPAWYTCRGIRPVGRF-NH2 (SEQ ID NO.: 93) | L3 | 4341.05 | 4342.4, $[M + H]^+$ |
| 243 | SRAHQHSMETRTPDCNPAWYTCRGIRPVGRF-NH2 (SEQ ID NO.: 93) | L4 | 4312.01 | 4313.3, $[M + H]^+$ |
| 244 | SRAHQHSMETRTPDCNPAWYTCRGIRPVGRF-NH2 (SEQ ID NO.: 93) | L5 | 4584.31 | 4585.5, $[M + H]^+$ |
| 245 | SRAHQHSMETRTPDICPAWYTGCGIRPVGRF-NH2 (SEQ ID NO.: 94) | L3 | 4241.97 | 4242.0, $[M + H]^+$ |
| 246 | SRAHQHSMETRTPDICPAWYTGCGIRPVGRF-NH2 (SEQ ID NO.: 94) | L4 | 4212.93 | 4213.1, $[M + H]^+$ |
| 247 | SRAHQHSMETRTPDICPAWYTGCGIRPVGRF-NH2 (SEQ ID NO.: 94) | L5 | 4485.23 | 4485.5, $[M + H]^+$ |
| 248 | SRAHQHSMETRTPDINPCWYTGRGCRPVGRF-NH2 (SEQ ID NO.: 95) | L3 | 4327.02 | 4328.5, $[M + H]^+$ |
| 249 | SRAHQHSMETRTPDINPCWYTGRGCRPVGRF-NH2 (SEQ ID NO.: 95) | L4 | 4297.98 | 4299.4, $[M + H]^+$ |
| 250 | SRAHQHSMETRTPDINPCWYTGRGCRPVGRF-NH2 (SEQ ID NO.: 95) | L5 | 4570.28 | 4571.9, $[M + H]^+$ |
| 251 | SRAHQCS-Nle-ETRTCDINPAWYTG-hArg-GIRPVGRF-NH2 (SEQ ID NO.: 97) | L1 | 3730.26 | 747.0, $[M + 5H]^{5+}$ |

TABLE 12-continued

Stapled PrRP31 peptide sequences[a]

| Con-jugate | Peptide sequence | Staple/HEM | Calc mass | Mass found |
|---|---|---|---|---|
| 252 | SRAHQCS-Nle-ETRTCDINPAWYTG-β-hArg-GIRPVGRF-NH2 (SEQ ID NO.: 98) | L1 | 3730.26 | 747.0, $[M + 5H]^{5+}$ |
| 253 | SRAHQCS-Nle-ETRTCDINPAWYTG-NMe-Arg-GIRPVGRF-NH2 (SEQ ID NO.: 99) | L1 | 3730.26 | 747.0, $[M + 5H]^{5+}$ |
| 254 | SRAHQCS-Nle-ETRTCDINPAWYTGRGIRPVG-NMe-Arg-F-NH2 (SEQ ID NO.: 102) | L1 | 3730.26 | 747.0, $[M + 5H]^{5+}$ |
| 255 | SRAHQCS-Nle-ETRTCDINPAWYTG-hArg-GIRPVGRF-NH2 (SEQ ID NO.: 97) | L3 | 4274.00 | 4274.1, $[M + H]^{+}$ |
| 256 | SRAHQCS-Nle-ETRTCDINPAWYTG-β-hArg-GIRPVGRF-NH2 (SEQ ID NO.: 98) | L3 | 4274.00 | 4274.4, $[M + H]^{+}$ |
| 257 | SRAHQCS-Nle-ETRTCDINPAWYTG-NMe-Arg-GIRPVGRF-NH2 (SEQ ID NO.: 99) | L3 | 4274.00 | 4274.1, $[M + H]^{+}$ |
| 258 | SRAHQCS-Nle-ETRTCDINPAWYTGRGIRPVG-NMe-Arg-F-NH2 (SEQ ID NO.: 102) | L3 | 4274.00 | 4274.3, $[M + H]^{+}$ |
| 259 | SRAHQCS-Nle-ETRTCDINPAWYTG-hArg-GIRPVGRF-NH2 (SEQ ID NO.: 97) | L4 | 4244.96 | 4245.4, $[M + H]^{+}$ |
| 260 | SRAHQCS-Nle-ETRTCDINPAWYTG-β-hArg-GIRPVGRF-NH2 (SEQ ID NO.: 98) | L4 | 4244.96 | 4245.3, $[M + H]^{+}$ |
| 261 | SRAHQCS-Nle-ETRTCDINPAWYTG-NMe-Arg-GIRPVGRF-NH2 (SEQ ID NO.: 99) | L4 | 4244.96 | 4245.4, $[M + H]^{+}$ |
| 262 | SRAHQCS-Nle-ETRTCDINPAWYTGRGIRPVG-NMe-Arg-F-NH2 (SEQ ID NO.: 102) | L4 | 4244.96 | 4245.2, $[M + H]^{+}$ |
| 263 | SRAHQCS-Nle-ETRTCDINPAWYTG-hArg-GIRPVGRF-NH2 (SEQ ID NO.: 97) | L5 | 4517.26 | 753.9, $[M + 6H]^{6+}$ |
| 264 | SRAHQCS-Nle-ETRTCDINPAWYTG-β-hArg-GIRPVGRF-NH2 (SEQ ID NO.: 98) | L5 | 4517.26 | 4517.8, $[M + H]^{+}$ |
| 265 | SRAHQCS-Nle-ETRTCDINPAWYTG-NMe-Arg-GIRPVGRF-NH2 (SEQ ID NO.: 99) | L5 | 4517.26 | 4517.4, $[M + H]^{+}$ |
| 266 | SRAHQCS-Nle-ETRTCDINPAWYTGRGIRPVG-NMe-Arg-F-NH2 (SEQ ID NO.: 102) | L5 | 4517.26 | 4517.8, $[M + H]^{+}$ |
| 267 | SRAHQCS-Nle-ETRTCDINPAWYTG-hArg-GIRPVGRF-NH2 (SEQ ID NO.: 97) | L8 | 4545.31 | 4545.8, $[M + H]^{+}$ |
| 268 | SRAHQCS-Nle-ETRTCDINPAWYTG-hArg-GIRPVGRF-NH2 (SEQ ID NO.: 97) | L9 | 4489.21 | 4489.3, $[M + H]^{+}$ |

TABLE 12-continued

| | Stapled PrRP31 peptide sequences[a] | | | |
|---|---|---|---|---|
| Con-jugate | Peptide sequence | Staple/HEM | Calc mass | Mass found |
| 269 | SRAHQCS-Nle-ETRTCDINPAWYTG-hArg-GIRPVGRF-NH2 (SEQ ID NO.: 97) | L12 | 4358.08 | 4358.4, $[M + H]^+$ |
| 270 | SRAHQCS-Nle-ETRTCDINPAWYTG-hArg-GIRPVGRF-NH2 (SEQ ID NO.: 97) | L6 | 4302.06 | 4302.4, $[M + H]^+$ |
| 271 | SRAHQCS-Nle-ETRTCDINPAWYTG-hArg-GIRPVGRF-NH2 (SEQ ID NO.: 97) | L7 | 4330.11 | 4330.8, $[M + H]^+$ |

[a]All peptides confirmed >95% purity by HPLC (LC-MS).

Biological Assays Protocols

β-Arrestin Recruitment Assay for GPR10 Activation

PathHunter CHO-K1 GPR101 β-Arrestin Orphan GPCR cell line were purchased from DiscoverX. Briefly, cells (20 μL of 5000 cells per well) were seeded in white solid 384 well plate covered with metal lid and incubated overnight. On day 2, the culture medium was replaced by fresh medium (containing no FBS for 0% FBS group). Cells were treated with 5 μL of 12 dilutions of PrRP31 as positive control and sample peptides (with starting concentration of 400 nM and 1:3 serial dilutions) in Protein Dilution Buffer (0.1% BSA) (from PathHunter® detection kit) in triplicate for 90 min at 37° C., 5% $CO_2$. PathHunter® detection kit purchased from DiscoverX was used for detection. 12.5 ul of working detection solution was added per well and incubated for 1 h at room temperature in the dark. The luminescence signal was measured on a ViewLux (PerkinElmer). The value of $EC_{50}$ was obtained using the Prism software.

cAMP Assay for NPFF2R Activation

CHO cells stably overexpressing human NPFF2R (20 μL, 5000 cells per well; obtained from Christopher McCurdy's lab, University of Florida College of Pharmacy) were seeded in white solid 384 well plate covered with metal lid and incubated overnight. On day 2, the culture medium was replaced by fresh medium (containing no FBS for 0% FBS group). Cells were treated with 5 μL of PrRP31 or analogs in 12-point dose-response (with starting concentration of 20 μM and 1:3 serial dilutions thereafter), with 20 μM forskolin as positive control in culture medium and with 0.5 mM IBMX (3-isobutyl-1-methylxanthine) to inhibit cAMP degradation. The assay was carried out in triplicate for 30 min at 37° C., 5% $CO_2$. cAMP dynamic 2 kit from Cisbio was used to detect cAMP level. Briefly, 25 ul of cAMP detection reagent (1:1:38 of cAMP-d2, Cryptate conjugate, lysis buffer) per well was added and incubated at RT for 1 hour. For cell negative control wells, cAMP detection reagent without d2 was added. Plates were then read at Ex320 nm, Em-1 665 nm and, Em-2 615 nm. Graphs were plotted with Ratio or Delta F using Prism software and $EC_{50}$ were then obtained. Ratio=$A_{665\ nm}$/$B_{620\ nm}$×10^4. % Delta F=(Standard or Sample Ratio−$Ratio_{neg}$)/$Ratio_{neg}$×100.

Plasma Peptide Stability

12 μL of a 1 mM peptide stock solution (in DMSO) was added to 300 μL of mouse plasma (final concentration 20 μM). The samples were incubated at 37° C. for 48 h. At specific time intervals (0, 0.25, 0.5, 1, 2, 4, 8, 24 and 48 h), 25 μL of plasma was taken and added to 150 μL of cold acetonitrile/$H_2O$ (9:1, v v)+0.1% TFA to precipitate plasma proteins. Samples were incubated at 0° C. for 30 min and were centrifuged at 17 rpm for 10 min (4° C.). Samples were analyzed using LC-MS (QTOF).

In Vivo Pharmacokinetics Study

In vivo PK was carried out by WuXi AppTec Co., Ltd., in accordance with the WuXi IACUC standard animal procedures along with the IACUC guidelines that are in compliance with the Animal Welfare Act, the Guide for the Care and Use of Laboratory Animals, with applicable WuXi Standard Operating Procedures and generally recognized good laboratory practices. Unfasted male C57 mice (7-9 weeks) from SLAC Laboratory Animal Co. Ltd. or SIPPR/BK Laboratory Animal Co. Ltd. (Shanghai, China) were acclimated for at least 3 days and then dosed by subcutaneous (s.c.) route with 5 mL per kg body weight of a 0.2 mg/mL solution of compound 60 (18-S4) (1 mg/kg dose) dissolved in normal saline (0.9% NaCl). Blood samples (70 μL) were collected from retro-orbital or saphenous vein at the following time points: 0.25, 0.5, 1, 3, 7, 24, 48 and 72 h (n=3 per group, 3 groups). Animals were group housed during acclimation and individually housed during the study. The animal room environment was controlled (18 to 26° C., relative humidity 30 to 70%, 12 h artificial light and 12 h dark). All animals were allowed access to Certified Rodent Diet (SLAC Laboratory Animal Co. Ltd) and water ad libitum. All blood samples were transferred into microcentrifuge tubes containing 2 μL of 0.5 M $K_2EDTA$ anticoagulant and placed on wet ice until centrifugation, which was carried out within 30 min of collection at 3000 g for 15 min (4° C.). Plasma was stored in polypropylene tubes, quick frozen over dry ice and kept at −70° C. until LC-MS/MS analysis.

LC-MS Analysis of Plasma Samples from Pharmacokinetic Study

PK bioanalysis was carried out by WuXi AppTec. An aliquot of 8 μL plasma sample was added to 8 μL 4% $H_3PO_4$ and the plasma proteins precipitated using 160 μL methanol containing 100 ng/mL of glyburide as an internal standard. The mixture was vortexed thoroughly and centrifuged at 3220 g for 15 min (4° C.). 10 μL of the supernatant was injected onto an ACQUITY UPLC® HSS T3 column (1.8 μm, 2.1×50 mm) in line with a SCIEX Triple Quad™ 6500+LC-MS/MS system (ES+). A solvent gradient of 10-60% B over 1 min was used for analysis, where A=0.1% formic acid in water and B=0.1% formic acid in acetonitrile (0.6 mL/min flow rate, 60° C. column temperature). The retention time of compound 60 (18-S4) was 0.96 min. LC-MS data were analyzed using the Analyst 1.6.3 software. A calibration curve was generated using 8 non-zero calibration standards consisting of high, middle and low concentrations, including those at the lower limit of quantification (LLOQ) which was 1-3 ng/mL. Study sample analysis was performed concurrently with a set of calibration standards and two sets of samples using the calibration curve. Plasma concentration versus time data was analyzed by non-compartmental approaches using the Phoenix WinNonlin 6.3 software. Due to volume/sampling limitations in mice, sparse sampling was used. Therefore, a single PK profile was obtained by combining concentrations from various animals and PK parameter estimates were averaged.

Example A: cAMP HTRP Assay (PYY)

To measure the effects of peptide-induced NPY2R-mediated inhibition of cAMP production, cAMP HTRF assay was performed according to manufacturer's instruction (cAMP—Gs Dynamic kit, Cisbio). Briefly, cAMP Hunter CHO cells expressing the NPY2R (DiscoveRx) were seeded overnight in white 384-well plates at 5,000 cells per well in 20 d of F12 medium at 37° C. and 5% $CO_2$. The following day, the medium was removed and replaced with 20 d of Opti-MEM (Gibco) in the presence or absence of 100% FBS. Peptides (prepared as 5× solution in Opti-MEM) of different concentration and forskolin (final concentration is 10 µM, a direct activator of adenylate cyclase enzyme) were added and incubated 30 min at 37° C. Detection reagent was added and further incubated for 60 min at room temperature, and read on a compatible HTRF reader (PHERAstar). Concentration-response curves were determined by nonlinear regression analysis using Prism software (GraphPad Software Inc).

TABLE 13 cAMP HTRP data (SEQ ID NOs)

| SEQ ID | hNPY2R - cAMP 0% FBS/nM | hNPY2R - cAMP 10% FBS/nM |
|---|---|---|
| 1 | 1.2 ± 0.3 | 1.0 ± 0.1 |
| 2 | 0.29 ± 0.07 | 0.5 ± 0.1 |
| 3 | ND | 1.5 |
| 4 | ND | 5.6 |
| 5 | ND | 0.32 |
| 6 | ND | 0.32 |
| 10 | ND | 0.47 |
| 11 | ND | 0.25 |
| 12 | ND | 0.55 |
| 13 | ND | 0.5 |
| 16 | ND | 2.9 |
| 17 | ND | 4.7 |
| 18 | ND | 15 |
| 19 | ND | 750 |
| 20 | ND | 69 |
| 21 | ND | 4.7 |
| 22 | ND | 190 |
| 23 | ND | >10000 |
| 24 | ND | 630 |
| 25 | ND | 18 |
| 26 | ND | 98 |
| 27 | ND | 23 |
| 28 | ND | 7.6 |
| 30 | ND | 7.6 |
| 31 | ND | 0.18 |
| 32 | ND | 0.33 |
| 33 | ND | 92 |
| 34 | ND | 61 |
| 35 | 140 | 82 |
| 36 | ND | 8.9 |
| 37 | ND | 6.3 |

ND = not determined.

TABLE 14 cAMP HTRP data (Peptide Conjugates)

| Conjugate | hNPY2R - cAMP 0% FBS/nM | hNPY2R - cAMP 10% FBS/nM |
|---|---|---|
| 1 | 2.7 | 4.8 |
| 2 | ND | 6.1 |
| 3 | 2.9 | 8.1 |
| 4 | 2.3 | 170 |
| 5 | 22. | 250 |
| 6 | 44 | 310 |
| 8 | 0.95 | 0.9 |
| 10 | 1.2 | 5.6 |
| 11 | 3.1 | 150 |
| 12 | 40 | 340 |
| 13 | 6.9 | 160 |
| 14 | ND | 28 |
| 15 | 0.18 | 0.18 |
| 16 | 0.21 | 0.18 |
| 17 | 0.58 | 0.5 |
| 18 | 0.62 | 5.2 |
| 19 | 0.45 | 21 |
| 20 | 0.27 | ND |
| 21 | 1.2 | 15 |
| 22 | 0.65 | 14 |
| 23 | 5.8 | 160 |
| 24 | 0.85 | 20 |
| 25 | 1.2 | 77 |
| 27 | ND | 1.3 |
| 28 | ND | 32 |
| 29 | ND | 14 |
| 30 | ND | 8.7 |
| 31 | 2.4 | 47 |
| 32 | 0.51 | 0.64 |
| 34 | 0.37 | 0.29 |
| 35 | 0.53 | 0.41 |
| 36 | 0.44 | 4.9 |
| 37 | 0.91 | 9.2 |
| 39 | 3.7 ± 0.7 | 170 ± 20 |
| 40 | 5 ± 2 | 36 ± 5 |
| 41 | ND | 28 |
| 42 | ND | 15 |
| 43 | ND | 24 |
| 44 | ND | ND |
| 45 | 220 | 1600 |
| 51 | 0.4 | 0.38 |
| 53 | 0.2 | 0.21 |
| 54 | 0.56 | 0.51 |
| 57 | 3.4 | 130 |
| 58 | 0.12 | 0.15 |
| 59 | 4.2 | 84 |
| 62 | 1.0 ± 0.5 | 9.2 ± 0.4 |
| 63 | 2.3 ± 0.8 | 40 ± 10 |
| 64 | 1.0 ± 0.4 | 10 ± 1 |
| 65 | 56 ± 6 | 210 |
| 66 | 10 ± 1 | 29 ± 3 |
| 68 | ND | 4.4 |
| 69 | ND | 5.6 |
| 70 | ND | 340 |
| 71 | ND | 1700 |
| 72 | ND | 1.5 |
| 73 | ND | 2.3 |
| 74 | ND | 19 |
| 75 | ND | >10000 |
| 76 | ND | 4.3 |
| 77 | ND | 9.5 |
| 78 | ND | 2700 |
| 79 | ND | >10000 |
| 80 | ND | 2.6 |
| 81 | ND | 6.5 |
| 82 | ND | 40 |
| 83 | ND | 630 |
| 85 | ND | 5.4 |
| 86 | ND | 2.4 |
| 87 | ND | 490 |
| 88 | ND | 520 |
| 89 | ND | 4 |
| 90 | ND | 4.1 |
| 91 | ND | 200 |
| 92 | ND | 660 |

TABLE 14-continued

| | cAMP HTRP data (Peptide Conjugates) | |
| --- | --- | --- |
| Conjugate | hNPY2R - cAMP 0% FBS/nM | hNPY2R - cAMP 10% FBS/nM |
| 93 | ND | 14 |
| 94 | ND | 160 |
| 95 | ND | 3.1 |
| 96 | ND | 22 |
| 97 | ND | 32 |
| 98 | ND | 15 |
| 100 | ND | 8.4 |
| 101 | ND | 9.7 |
| 102 | ND | 45 |
| 103 | ND | 56 |
| 104 | ND | 48 |
| 105 | ND | 0.27 |
| 107 | ND | 3.2 |
| 108 | ND | 1.4 |
| 109 | ND | 0.24 |
| 110 | ND | 2.5 |
| 111 | ND | 1.7 |
| 112 | ND | 0.29 |
| 113 | ND | 90 |
| 114 | 120 | 450 |

ND = not determined.

Example B: In Vivo Studies

Intravenous Infusion

Compounds were dissolved in sterile saline and administered as a 1-hour intravenous infusion to non-fasted male Sprague-Dawley rats (n=3 per group) via femoral vein cannula at a final dose of 0.033 mg/kg. Formulations were administered at a rate of 1.67 mL/kg/h. Blood samples (approximately 250 µL) were collected for pharmacokinetic analysis via a jugular vein cannula at 0.25, 0.5, 0.75, 1, 1.17, 1.33, 1.5, 2, 4, 6, 8, 24, 30 and 48 hr post-start of infusion into microtainer tubes containing K$_2$EDTA as anticoagulant and 25 µL of a protease inhibitor cocktail. Plasma was prepared by centrifugation and stored at −80° C. until analysis.

Plasma Sample Preparation

An aliquot of each plasma sample was placed into to a 96-well plate. To each well, Tween-20 was added to a final concentration of 0.05%. Plates were then vortexed mixed before 3 volumes of 0.1% TFA in 2:1 ethanol:acetonitrile containing an appropriate internal standard was added to each well. Plates were vortex mixed again and then centrifuged for 10 min at 2844×g. Supernatants were placed into a clean 96-well plate and evaporated under a nitrogen stream at 45° C. Residues were reconstituted in 20% acetonitrile (aq) containing 0.10% formic acid.

LC/MS Quantification of Peptides in Plasma

All calibration standards were prepared in control rat plasma containing K$_2$EDTA and protease inhibitor cocktail.

Samples and standards were analyzed by TurboIon-Spray™ UPLC-MS/MS using a system consisting of a CTC HTS PAL auto-injector (Leap, Carrboro, NC), an Agilent Infinity 1290 system with column oven (Palo Alto, CA), a Valco switching valve (Houston, TX), and either an AB Sciex API 5600 TripleTOF™ or Sciex API 4000QTrap mass spectrometer (Framingham, MA). Samples were injected onto a 2.1×50 mm reverse phase C18 analytical column, typically a Waters ACQUITY UPLC HSS T3, 1.8 µm (Waters Corporation, Milford, MA) or similar. Chromatographic separation was achieved with a gradient method using water containing 0.10% formic acid (A) and acetonitrile containing 0.10% formic acid (B) as mobile phase.

Initial conditions consisted of 95% A and 5% B. The organic component was increased to 95% B over a period of 3-4 minutes, depending on the peptide. Typical flow rates were 600 µL/min. The column temperature was held constant at 40 or 45° C. Peptides were quantified my monitoring one or more product ions produced from a multiply charged parent ion.

TABLE 15

| | Half-life and clearance rate in rat (SEQ ID NOs) | |
| --- | --- | --- |
| SEQ ID | Rat T$_{1/2}$/h | Rat CL/(mL/kg/min) |
| 2 | 1.2 | 6.8 |
| 46 | 0.92 | 8.6 |

TABLE 16

| | Half-life and clearance rate in rat (Peptide Conjugates) | |
| --- | --- | --- |
| Conjugate | Rat T$_{1/2}$/h | Rat CL/ (mL/kg/min) |
| 5 | 0.5 ± 0.1 | 12 ± 3 |
| 6 | 5 ± 5 | 2 ± 1 |
| 11 | 2.4 ± 0.2 | 2.4 ± 0.2 |
| 12 | 3.9 ± 0.6 | 0.4 ± 0.1 |
| 19 | 2 ± 1 | 2.9 ± 0.3 |
| 21 | 2.0 ± 0.4 | 0.95 ± 0.07 |
| 37 | 4.5 | 2.2 |
| 39 | 15 | 0.23 |
| 40 | 14 | 0.23 |
| 59 | 8 ± 2 | 20 ± 3 |
| 62 | 12 ± 1 | 0.45 ± 0.04 |
| 63 | 5.7 | 0.78 ± 0.04 |
| 64 | 5 ± 3 | 1.2 ± 0.3 |

Example C: Optimization of the Staple Length and Position in PYY Analogues

The selection of stapling sites on PYY was guided by examination of the structure of the homologous neuropeptide Y (NPY) bound to human G protein-coupled neuropeptide Y receptor Y2 (NPY2R). Residues occurring on the face interacting with the receptor (Y20, L24, Y27 and 128) were avoided when choosing sites for covalent modification, so as to minimize disruption of crucial peptide-receptor interactions. Rapid cleavage at the N-terminus of PYY by dipeptidyl peptidase-4 (DPP-4) following secretion results in the truncated peptide PYY$_{3-36}$ (PYYL: SEQ ID No: 1) being the predominant form in circulation. As PYY1 shows higher specificity toward the Y$_2$ receptor subtype than PYY, we decided to use this truncated form for development. A set of PYY1 analogs was synthesized incorporating di-cysteine mutations at selected stapling positions representing a scan of the entire sequence. Cys substitutions were chosen to enable attachment of bromoacetyl-functionalized staples using the solution-phase chemistry previously described.[40]

A screen of i, i+7 diCys mutants was first carried out to find the best position in the sequence for stapling using the 10-atom staple L1.

To measure peptide-induced NPY2R-mediated inhibition of cAMP production, a cAMP HTRF (cyclic adenosine monophosphate homogenous time resolved fluorescence) assay was performed according to the manufacturer's instructions (cAMP—Gs Dynamic kit, Cisbio). Briefly, cAMP Hunter CHO cells expressing the NPY2R (DiscoveRx) were seeded overnight in white 384-well plates at 5,000 cells per well in 20 μl of F12 medium at 37° C. and 5% $CO_2$. The following day, the medium was removed and replaced with 20 μl of Opti-MEM (Gibco) in the presence or absence of 10% FBS. Peptides (prepared as 5× solution in Opti-MEM) of different concentrations and forskolin (a direct activator of adenylate cyclase enzyme, final concentration 10 μM) were added and incubated for 30 min at 37° C. Detection reagent was added and further incubated for 60 min at room temperature, and read on a compatible HTRF reader (PHERAstar). Concentration-response curves were determined by nonlinear regression analysis using the Prism software (GraphPad Software Inc.).

Multiple diCys substitution positions were tolerated for unstapled PYY1 (2-9, 10-17, 20-27 and 23-30), and stapling at position 23-30 with L1 resulted in subnanomolar potency, similar to that of the native sequence (Table 17). It was also anticipated that longer staples at i, i+11 and i, i+15 positions could potentially enhance proteolytic stability of the peptides, however stapling with the length-matched L1D and L1E respectively adversely affected their activity. In addition, mutations were incorporated into the PYY1 sequence to enhance potency of the native peptide (sequence 'PYY2' or SEQ ID NO. 2). The PYY2 analogs stapled at the 10-17 and 23-30 positions were also found to be potent NPY2R agonists. Staples L1F and L1G (which are slightly longer than L1) are also tolerated at position 10-17. Thus, PYY1 and PYY2 sequences stapled at positions 10-17 and 23-30 were taken forward for fatty acid conjugation for improved serum binding.

TABLE 17

EC50 of stapled PYY analogs

| Sequence | Cysteine substitutions | No staple | L1 10 atom | Other staples | | | | | |
|---|---|---|---|---|---|---|---|---|---|
| | | | | | | | | | |
| | | | | hNPY2R EC50/nM | | | | | |
| PYY1 | None | | 0.97 | | | | | | |
| i, | 2, 9 | 2.9 | 4.4 | | | | | | |
| i + 7 | 10, 17 | 1.5 | 4.8 | L1B (8 atom) | 6.1 | L1C (9 atom) | 8.1 | | |
| | 17, 24 | 15 | 4.3 | | | | | | |
| | 18, 25 | 750 | 2.6 | | | | | | |
| | 19, 26 | 69 | | | | | | | |
| | 20, 27 | 4.7 | 5.4 | | | | | | |
| | 21, 28 | 190 | 4 | | | | | | |
| | 22, 29 | >10000 | 14 | | | | | | |
| | 23, 30 | 5.6 | 0.9 | | | | | | |
| | 24, 31 | 630 | 160 | | | | | | |
| i, i | 10, 21 | 18 | | | | | | | |
| | 13, 24 | 98 | | L1D (13 atom) | 2.2 | | | | |
| | 19, 30 | 7.6 | | " | 8.4 | | | | |
| i, i + 15 | 9, 24 | 23 | | L1E (17 atom) | 32 | | | | |
| | 15, 30 | 7.6 | | " | 15 | | | | |
| PYY2 | None | | 0.45 | | | | | | |
| i, i + 7 | 10, 17 | 0.32 | 0.18 | L1F (11 atom) | 0.18 | L1G (11 atom) | 0.5 | | |
| | 23, 30 | 0.32 | 0.64 | | | | | | |

Example D: Fatty Acid Conjugation Enhances Serum Protein Binding and Extends the Half-Life A library of staples was synthesized incorporating a wide variety of PEG linker and fatty acid types, thus facilitating rapid screening of conjugates. To measure peptide-induced NPY2R-mediated inhibition of cAMP production, a cAMP HTRF (cyclic adenosine monophosphate homogenous time resolved fluorescence) assay was performed according to the manufacturer's instructions (cAMP—Gs Dynamic kit, Cisbio). Briefly, cAMP Hunter CHO cells expressing the NPY2R (DiscoveRx) were seeded overnight in white 384-well plates at 5,000 cells per well in 20 μl of F12 medium at 37° C. and 5% $CO_2$. The following day, the medium was removed and replaced with 20 μl of Opti-MEM (Gibco) in the presence or absence of 10% FBS. Peptides (prepared as 5× solution in Opti-MEM) of different concentrations and forskolin (a direct activator of adenylate cyclase enzyme, final concentration 10 μM) were added and incubated for 30 min at 37° C. Detection reagent was added and further incubated for 60 min at room temperature, and read on a compatible HTRF reader (PHERAstar). Concentration-response curves were determined by nonlinear regression analysis using the Prism software (GraphPad Software Inc.).

Results of this assay are seen in Table 18. In general, a large shift was observed between activity determined in the presence and absence of serum for staples L4 and L5. For example, when comparing PYY1 conjugates tested in conditions with 10% FBS, conjugates with staples L4 and L5 had an $EC_{50}$ of 250 nM and 310 nM, respectively, at the 10-17 positions and an $EC_{50}$ of 150 nM and 340 nM, respectively, at the 23-30 positions compared to an EC50 of 0.97 nM in the unstapled PYY1 tested under the same conditions. Similarly, when comparing PYY2 conjugates at 10% FBS, conjugates with staples L4 and L5 had an $EC_{50}$ of 21 and 15, respectively, at the 10-17 positions and an $EC_{50}$ of 9.2 and 170, respectively, at the 23-30 positions, compared to an $EC_{50}$ of 0.45 nM in the unstapled PYY2 tested under the same conditions.

TABLE 18

NYPYR2 activation of fatty acid stapled PYY conjugates

| Conjugate | Sequence | Cysteine substitution(s) | Staple | hNPY2R EC50/nM cAMP | | |
|---|---|---|---|---|---|---|
| | | | | 0% FBS | 10% FBS | Ratio 10:0% |
| SEQ ID No: 1 | PYY1 | None | — | 1.2 | 0.97 | 0.81 |
| 1 | | 10, 17 | L1 | 2.7 | 4.8 | 1.8 |
| 4 | | | L3 | 2.3 | 170 | 74 |
| 5 | | | L4 | 22 | 250 | 11 |
| 6 | | | L5 | 44 | 310 | 7.0 |
| 8 | | 23, 30 | L1 | 0.95 | 0.9 | 0.95 |
| 10 | | | L3 | 1.2 | 5.6 | 4.7 |
| 11 | | | L4 | 3.1 | 150 | 48 |
| 12 | | | L5 | 40 | 340 | 8.5 |
| SEQ ID No: 2 | PYY2 | None | — | 0.29 | 0.45 | 1.6 |
| 15 | | 10, 17 | L1 | 0.18 | 0.18 | 1 |
| 18 | | | L3 | 0.62 | 5.2 | 8.4 |
| 19 | | | L4 | 0.45 | 21 | 47 |
| 21 | | | L5 | 1.2 | 15 | 13 |
| 32 | | 23, 30 | L1 | 0.51 | 0.64 | 1.3 |
| 36 | | | L3 | 0.44 | 4.9 | 11 |
| 37 | | | L4 | 0.91 | 9.2 | 10 |
| 39 | | | L5 | 3.7 | 170 | 46 |

Example E: Symmetrically-Stapled Conjugates are Potent Against NPY2R

The 'symmetric' staple L5A was introduced to circumvent the formation of regioisomers, which can occur upon stapling with 'asymmetric' L5. To measure peptide-induced NPY2R-mediated inhibition of cAMP production, a cAMP HTRF (cyclic adenosine monophosphate homogenous time resolved fluorescence) assay was performed according to the manufacturer's instructions (cAMP—Gs Dynamic kit, Cisbio). Briefly, cAMP Hunter CHO cells expressing the NPY2R (DiscoveRx) were seeded overnight in white 384-well plates at 5,000 cells per well in 20 µl of F12 medium at 37° C. and 500 $CO_2$. The following day, the medium was removed and replaced with 20 d of Opti-MEM (Gibco) in the presence or absence of 10% FBS. Peptides (prepared as 5× solution in Opti-MEM) of different concentrations and forskolin (a direct activator of adenylate cyclase enzyme, final concentration 10 µM) were added and incubated for 30 min at 37° C. Detection reagent was added and further incubated for 60 min at room temperature, and read on a compatible HTRF reader (PHERAstar). Concentration-response curves were determined by nonlinear regression analysis using the Prism software (GraphPad Software Inc.).

Activity for L5A-stapled conjugates is shown in Table 19. The $EC_{50}$ of symmetrically stapled conjugates was 160 nM at 10% FBS for staples at positions 23, 30 in PYY1. For PYY2, symmetrically stapled conjugates had an $EC_{50}$ of 14 nM and 36 nM at 10% FBS for staples at positions 10-17 and 23-30, respectively.

TABLE 19

Activity of symmetrically-stapled conjugates

| Conjugate | Sequence | Cysteine substitution(s) | Staple/ lipid | hNPY2R $EC_{50}$/nM cAMP | | |
|---|---|---|---|---|---|---|
| | | | | 0% FBS | 10% FBS | Ratio 10:0% |
| SEQ ID No: 1 | PYY1 | None | — | 1.2 | 0.97 | 0.81 |
| 13 | | 23, 30 | L5A | 6.9 | 160 | 23 |
| SEQ ID No: 2 | PYY2 | None | — | 0.29 | 0.45 | 1.6 |
| 22 | | 10, 17 | L5A | 0.65 | 14 | 22 |
| 40 | | 23, 30 | " | 5.3 | 36 | 6.8 |
| 62 | | 10 | FA2 | 1.0 | 9.2 | 9.2 |
| 63 | | 17 | " | 2.3 | 41 | 18 |
| 64 | | 23 | " | 1.0 | 9.7 | 9.7 |
| 65 | | 30 | " | 56 | 210 | 3.8 |

In addition, simple lipidation of the conjugates (without stapling) using FA2 was also found to yield NPY2R agonists with impressive potency. A clear serum shift was observed for fatty acid-conjugated PYY analogs either stapled (diCys mutant40) or lipidated at a single Cys conjugation site (62), as indicated by dose-response curves in the presence and absence of serum, implying enhanced serum binding and longer in vivo half-life.

Example F: PYY Conjugates have an Extended Half-Life

The pharmacokinetic properties of the conjugates were assessed in vivo in order to determine the half-life extension effect. Conjugates were dissolved in sterile saline and administered as a 1 hour intravenous infusion to non-fasted male Sprague-Dawley rats (n=3 per group) via femoral vein cannula at a final dose of 0.033 mg/kg. Formulations were administered at a rate of 1.67 mL/kg/h. Blood samples (approximately 250 µL) were collected for pharmacokinetic analysis via a jugular vein cannula at 0.25, 0.5, 0.75, 1, 1.17, 1.33, 1.5, 2, 4, 6, 8, 24, 30 and 48 h post-start of infusion into microtainer tubes containing $K_2$EDTA as anticoagulant and 25 µL of a protease inhibitor cocktail. Plasma was prepared by centrifugation and stored at −80° C. until analysis.

An aliquot of each plasma sample was placed into to a 96-well plate. To each well, Tween-20 was added to a final concentration of 0.05%. Plates were then vortex mixed before 3 volumes of 0.1% TFA in 2:1 ethanol:acetonitrile containing an appropriate internal standard was added to each well. Plates were vortex mixed again and then centrifuged for 10 min at 2844×g. Supernatants were placed into a clean 96-well plate and evaporated under a nitrogen stream at 45° C. Residues were reconstituted in 20% acetonitrile (aq) containing 0.1% formic acid.

All calibration standards were prepared in control rat plasma containing $K_2$EDTA and protease inhibitor cocktail. Samples and standards were analyzed by TurboIonSpray™ UPLC-MS/MS using a system consisting of a CTC HTS PAL auto-injector (Leap, Carrboro, NC), an Agilent Infinity 1290 system with column oven (Palo Alto, CA), a Valco switching valve (Houston, TX), and either an AB Sciex API 5600 TripleTOF™ or Sciex API 4000QTrap mass spectrometer (Framingham, MA). Samples were injected onto a 2.1×50 mm reverse phase C18 analytical column, typically a Waters ACQUITY UPLC HSS T3, 1.8 µm (Waters Corporation, Milford, MA) or similar. Chromatographic separation was achieved with a gradient method using water containing 0.10% formic acid (A) and acetonitrile containing 0.1% formic acid (B) as mobile phase. Initial conditions consisted of 95% A and 5% B. The organic component was increased to 95% B over a period of 3-4 minutes, depending on the conjugate. Typical flow rates were 600 µL/min. The column temperature was held constant at 40 or 45° C. Conjugates were quantified by monitoring one or more product ions produced from a multiply charged parent ion.

Figure 2:
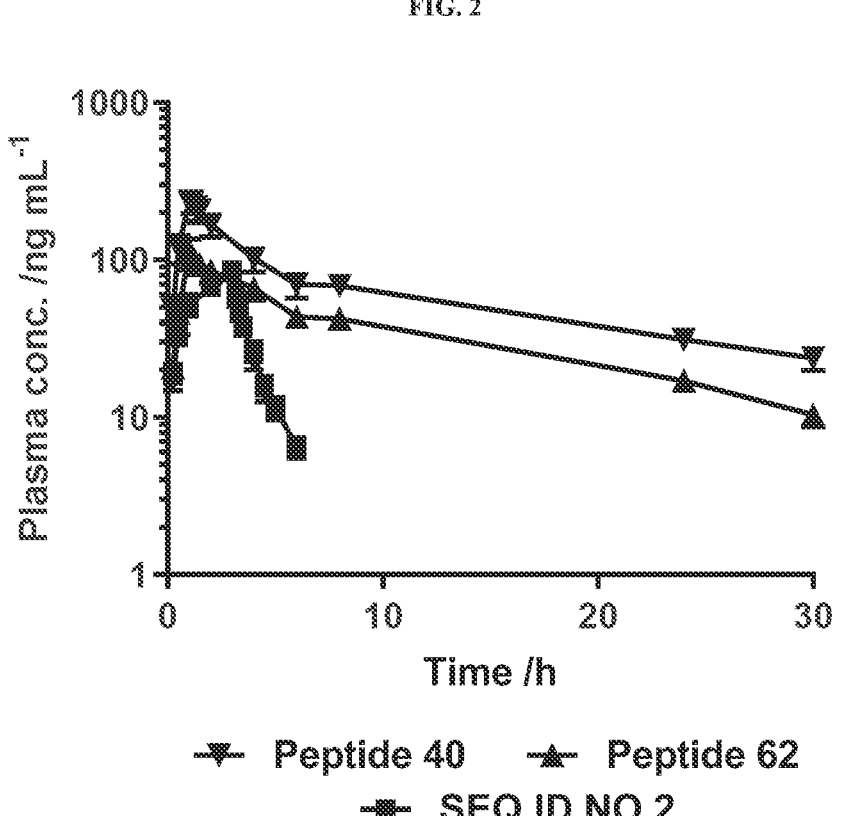
FIG. 2 illustrates the pharmacokinetics of PYY2, conjugate 40, and conjugate 62 in rat.

PYY1 analogues stapled at position 10-17 with L4 and L5 showed half-lives in rat of 0.45 hours and 5.4 hours, respectively, as depicted in Table 20. PYY1 Analogues stapled at positions of 23, 30 with L4 and L5 showed half-lives in rat of 2.4 hours and 3.9 hours, respectively. PYY2 analogs with staples at position 10-17 retain activity with half-lives of 1.9 and 2.0 hours, respectively. PYY2 stapled at position 23-30 exhibited superior long-acting effect, with rat half-lives of up to 15 hours, as depicted in FIG. 2 and Table 21. Lipidation at position 10 also resulted in a prolonged half-life of up to 12 hours.

This effect corresponds with a large in vitro serum shift, and is presumed to result from favorable interaction of the conjugate with serum albumin, as observed for other commercially available lipidated conjugate therapeutics such as semaglutide. Staples L4, L5 and L5A, and lipid FA2 (no staple), all incorporating fatty acid moieties bearing carboxylic acid groups, were found to afford the most favorable pharmacokinetic properties, with L5, FA2, and L5A—decorated with an 'internal' carboxylate on the lysine linker—being superior. While serum shift was taken to be indicative of enhanced albumin binding, the predicted prolonged half-life in vivo was not observed for analogs stapled at the 10-17 position, potentially due to stapling at this position not being protective against proteolytic degradation.

TABLE 20

| | | Cysteine | | hNPY2R (cAMP) | | |
| Conjugate | Sequence | substitution(s) | Staple | $EC_{50}$/nM (0% FBS) | Ratio 10:0% | Rat $T_{1/2}$/h |
|---|---|---|---|---|---|---|
| 4 | PYY1 | 10, 17 | L3 | 2.3 | 74 | INS |
| 5 | | | L4 | 22 | 11 | 0.45 |
| 6 | | | L5 | 44 | 7.0 | 5.4 |
| 10 | | 23, 30 | L3 | 1.2 | 4.7 | INS |
| 11 | | | L4 | 3.1 | 48 | 2.4 |
| 12 | | | L5 | 40 | 8.5 | 3.9 |
| SEQ ID No: 2 | PYY2 | None | — | 0.29 | 1.6 | 1.2 |
| 18 | | 10, 17 | L3 | 0.62 | 8.4 | INS |
| 19 | | | L4 | 0.45 | 47 | 1.9 |
| 21 | | | L5 | 1.2 | 13 | 2.0 |
| 37 | | 23, 30 | L4 | 0.91 | 10 | 4.5 |
| 39 | | | L5 | 3.7 | 46 | 15 |
| 40 | | | L5A | 5.3 | 6.8 | 14 |
| 62 | | 10 | FA2 | 1.0 | 9.2 | 12 |
| 63 | | 17 | " | 2.3 | 18 | 5.7 |
| 64 | | 23 | " | 1.0 | 9.7 | 5.3 |

Detailed pharmacokinetic profiles for long-acting analogs 40 and 62 are shown in Table 21. Both conjugates exhibit a 10-fold or greater increase in half-life, with greatly reduced clearance when compared with the SEQ ID No: 2. This is similar to the fatty acid-conjugated GLP-1R agonist sema-glutide, which is dosed once-weekly in human.

TABLE 21

Rat pharmacokinetic data

| Conjugate | Final dose/ mg kg$^{-1}$ | Infusion/ h | CL/ mL min$^{-1}$ kg$^{-1}$ | $T_{max}$/ h | $C_{max}$/ ng mL$^{-1}$ | $T_{1/2}$/ h | AUC/$_{all}$ h ng mL$^{-1}$ | Pred. human CL/mL min$^{-1}$ kg$^{-1}$ | Pred. human $T_{1/2}$/ days |
|---|---|---|---|---|---|---|---|---|---|
| SEQ ID No: 2- | 0.1 | 3 | 6.76 | 3.00 | 86.2 | 1.21 | 237 | — | — |
| 40 | 0.033 | 1 | 0.234 | 1.11 | 246 | 14.4 | 1870 | 0.027 | 4.5 |
| 62 | 0.033 | 1 | 0.446 | 1.00 | 111 | 11.6 | 1130 | 0.10 | 1.9 |

Example G: The Stapled PYY Conjugates have a Long Predicted Human Plasma Half-Life Conjugate serum albumin binding affinities were measured directly using a Biacore surface plasmon resonance (SPR) assay, which were used to calculate the unbound fraction ($f_u$) for each conjugate. Half-life was calculated using the steady-state volume of distribution ($V_{ss}$) and clearance (CL) using the following equation:

$$T_{\frac{1}{2}} = \frac{\ln 2 \cdot V_{ss}}{CL}$$

For a metabolically stable conjugate, in terms of renal clearance ($CL_R$) and glomerular filtration rate (GFR):

$$CL \cong CL_R = f_u \cdot \text{GFR}$$

Therefore:

$$T_{\frac{1}{2}} = \frac{\ln 2 \cdot V_{ss}}{f_u \cdot GFR}$$

Predicted human half-lives based on allometric scaling corrected for albumin binding are shown in Table 19 alongside experimentally determined parameters for both rat (RSA) and human serum albumin (HSA). All compounds were found to have a relatively high affinity for both RSA and HSA, comparable to that of semaglutide. In addition no large species differences were observed.

moter (Qiagen, Netherlands) and then were selected using 1 µg/mL puromycin (Life Technologies, Carlsbad) for 1 week. The surviving cells (referred to as CRE-HEK293) were expanded and then transfected with a G418 selective mammalian expression plasmid encoding human NPY1R, NPY2R, NPY4R, and NPY5R. The plasmid was transfected into CRE-HEK293 cells using Lipofectamine 2000 and selected with 400 µg/mL geneticin (Life Technologies, Carlsbad, CA). A single colony stable cell line over-expressing both CRE-luciferase and the NPY receptor was then established for the in vitro activity assay for each NPY receptor. These cells were seeded in 384-well plates at a density of 5000 cells per well and cultured for 18 hours in DMEM with 10% FBS at 37° C. and 5% $CO_2$. Cells were treated with conjugates for 24 hours and receptor activation was reported by luminescence intensities, using One-Glo (Promega, WI) luciferase reagent as per the manufacturer's instructions. The $EC_{50}$ of each conjugate was determined using GraphPad Prism 6 software (GraphPad, San Diego, CA).

SEQ ID No: 1, SEQ ID No: 2, and conjugate 21 showed high specificity for NPY2R compared to other NPY receptors, as depicted in Table 23. For the unstapled PYY1 analogue, the $EC_{50}$ was 1900 nM, 6700 nM, and 410 nM against NPY1R, NPY4R, and NPY5R, respectively, compared to an $EC_{50}$ of 0.49 against NPY2R. For the unstapled PYY2 analogue, the $EC_{50}$ was >10000 nM against NPY1R and NPY4R, and 1200 nM against NPY5R, compared to 2.2 nM against NPY2R. For conjugate 21, the PYY2 analogue with staple L5 at positions 10-17, the $EC_{50}$ was 0.39 for NPY2R and >10000 nM for all other NPY receptors tested.

TABLE 22

| | | | | | | | | Predicted human half-lives | | | |
|---|---|---|---|---|---|---|---|---|---|---|---|
| Conjugate | Rat $T_{1/2}$/ h | Rat CL/ mL min⁻¹ kg⁻¹ | Rat $V_{ss}$/ mL kg⁻¹ | $K_d$/µM HSA | $K_d$/µM RSA | $f_u$/% HSA | $f_u$/% RSA | Pred. human $T_{1/2}$/ days | Pred. human CL/mL min⁻¹ kg⁻¹ |
| semaglutide | — | — | — | 4.4 | 17 | 0.69 | 3.3 | — | — |
| 39 | 15 | 0.23 | 270 | 4.4 | 2.3 | 0.69 | 0.47 | 1.4 | 0.095 |
| 40 | 14 | 0.23 | 250 | 0.96 | 1.8 | 0.15 | 0.37 | 4.5 | 0.027 |
| 62 | 12 ± 1 | 0.45 ± 0.04 | 390 | 3.3 | 3.0 | 0.51 | 0.60 | 1.9 | 0.10 |
| 63 | 5.7 | 0.78 ± 0.04 | 230 | 2.5 | 3.8 | 0.40 | 0.37 | 1.0 | 0.11 |
| 64 | 5 ± 3 | 1.2 ± 0.3 | 310 | 3.0 | 1.8 | 0.48 | 0.37 | 0.4 | 0.41 |

Conjugate 40 in particular demonstrated a significantly extended half-life of 14 h in rat, with a projected human half-life of ~4.5 days. Further in vivo studies revealed highly favorable food intake control and significant weight loss effect in a chronic efficacy study in combination with our previously discovered long-acting GLP-1R agonist conjugate 187. Comparison to the approved peptide therapeutic semaglutide suggests the observed rodent half-life is likely to translate to a projected pharmacokinetic profile in humans suitable for once-weekly dosing.

Example H: The PYY Analogues Showed High Specificity for NPY2R

The specificity of the PYY analogues for NPY2R was assessed using a luciferase assay. HEK293 cells were infected with lentivirus encoding firefly luciferase gene under the control of cAMP responsive element (CRE) pro-

TABLE 23

Specificity of PYY analogues against NPY receptors

| | $EC_{50}$/nM | | | |
|---|---|---|---|---|
| Conjugate | NPY1R | NPY2R | NPY4R | NPY5R |
| SEQ ID No: 1 | 1900 | 0.49 | 6700 | 410 |
| SEQ ID No: 2 | >10000 | 2.2 | >10000 | 1200 |
| 21 | >10000 | 0.39 | >10000 | >10000 |

Example I: The PYY Analogues Reduced Food Intake in Mice

Given the well-established anorexigenic effect of PYY administration, a food intake study was carried out in C57BL/6 wild type mice using conjugate 40 at 0.04 and 0.2 mg/kg subcutaneous injection (SC). Conjugate 40 was also tested in combination with a previously published long-acting GLP-1R agonist, conjugate 187.

C57BL/6 wild type male mice (age 15 weeks from Jackson Labs, Bar Harbor, ME) maintained on regular chow diet, were acclimated in reverse light cycle and administered a single dose of conjugate (5 mL/kg) by subcutaneous injection (n=6, group housed 2 per cage). Food intake was monitored at 0 (beginning of dark cycle), 3, 6, 12 and 24 h and body weight at 0 and 48 h post dose.

Figure 3A:
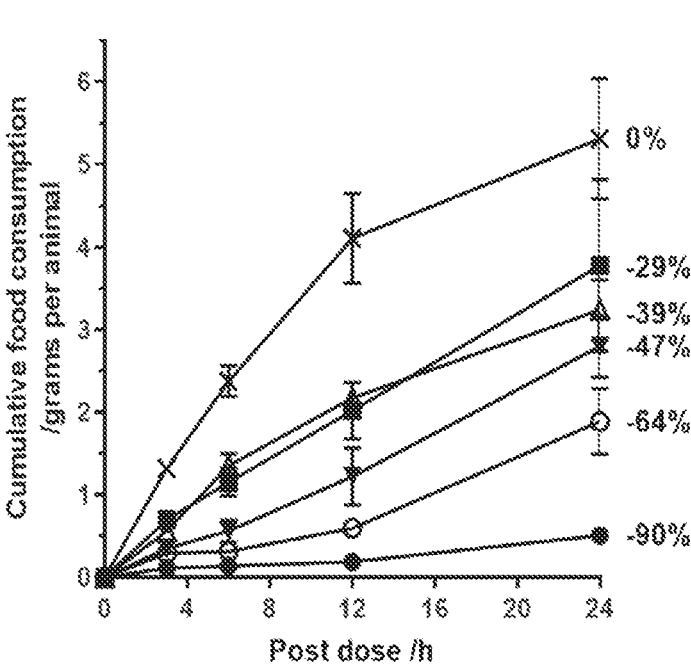
FIG. 3A illustrates the change in food intake over 24 hours of mice treated with a single dose of conjugate 187, conjugate 40, a combination of conjugate 187 and 40, or vehicle alone.
Figure 3B:
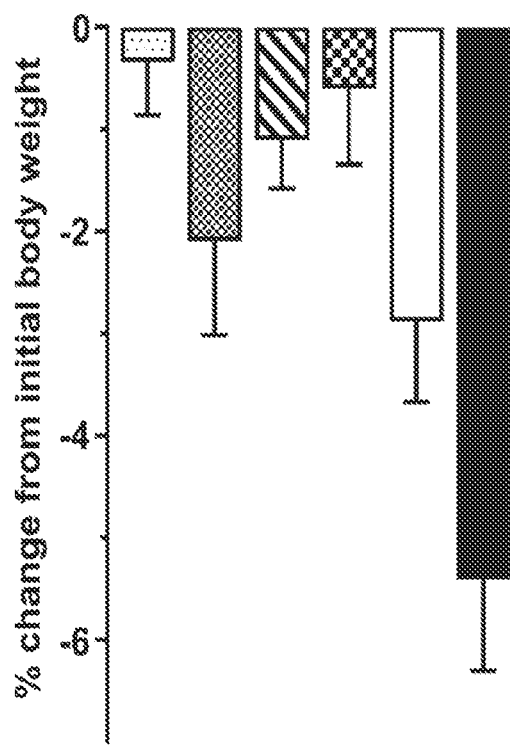
FIG. 3B illustrates the change in body weight over 24 hours of mice treated with a single dose of conjugate 187, conjugate 40, a combination of conjugate 187 and 40, or vehicle alone.

All groups show considerable reduction in food intake, as depicted in FIG. 3A, with dosing of conjugate 40 alone exhibiting a dose-dependent reduction in food consumption in the wild type model. While conjugate 187 dosed at 0.01 mg/kg shows comparable food intake reduction to conjugate 40 dosed at 0.04 mg/kg, the most robust food intake reduction effect was observed when conjugate 187 was used in combination with 40 at both 0.04 and 0.2 mg/kg, resulting in a 64% and 90% reduction in cumulative food intake at 24 h, respectively. A single combined dose of conjugate 187 and 40 produced a significant body weight loss (−5%) observed at 48 hours post dose, as depicted in FIG. 3B, indicating a long-lasting effect.

Example J: Administration of the PYY Analogues Resulted in a Decrease in Body Weight in Mice A two week chronic study to investigate the effect of daily administration of conjugate 40 on body weight and glucose homeostasis, either alone or in combination with conjugate 187, was carried out in a diet-induced obesity (DIO) mouse model.

Diet-induced obesity (DIO) model male mice (age 18 weeks from Taconic Biosciences) maintained on high fat diet (D12492, 60% fat diet) for 12 weeks, were administered conjugate by daily subcutaneous injection for up to 13 days (n=6, group housed 2 per cage, regular light cycle). The average body weight at the beginning of the experiment was 50 g. Mouse body weight was measured on days 0, 2, 4, 6, 8, 10, 12 and 13. Mice were fasted overnight prior to the oral glucose tolerance test (OGTT) on day 14, and then dosed with conjugate. After 6 h, 1 g of glucose solution per kg body weight was administered orally, and mouse tail blood glucose levels were measured before (0 min) and after glucose challenge for 2 h. The data were compared using the unpaired Student's t-test. Where appropriate, data were compared using repeated measures or one-way analysis of variance, followed by the Student-Newman-Keuls post hoc test.

Figure 4A:
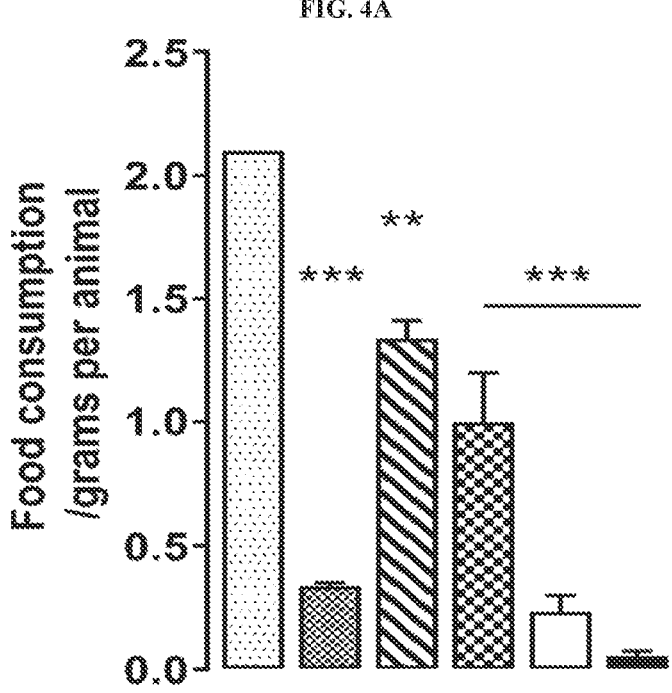
FIG. 4A illustrate the change in food consumption at day 1 of diet-induced obese mice treated with conjugate 187, conjugate 40, a combination of conjugate 187 and 40, or vehicle alone.
Figure 4B:
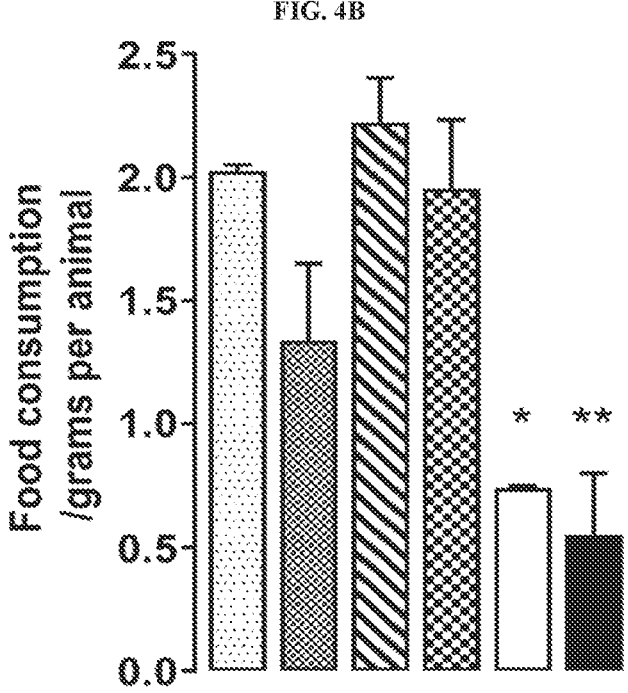
FIG. 4B illustrate the change in food consumption at day 5 of diet-induced obese mice treated with conjugate 187, conjugate 40, a combination of conjugate 187 and 40, or vehicle alone.
Figure 4C:
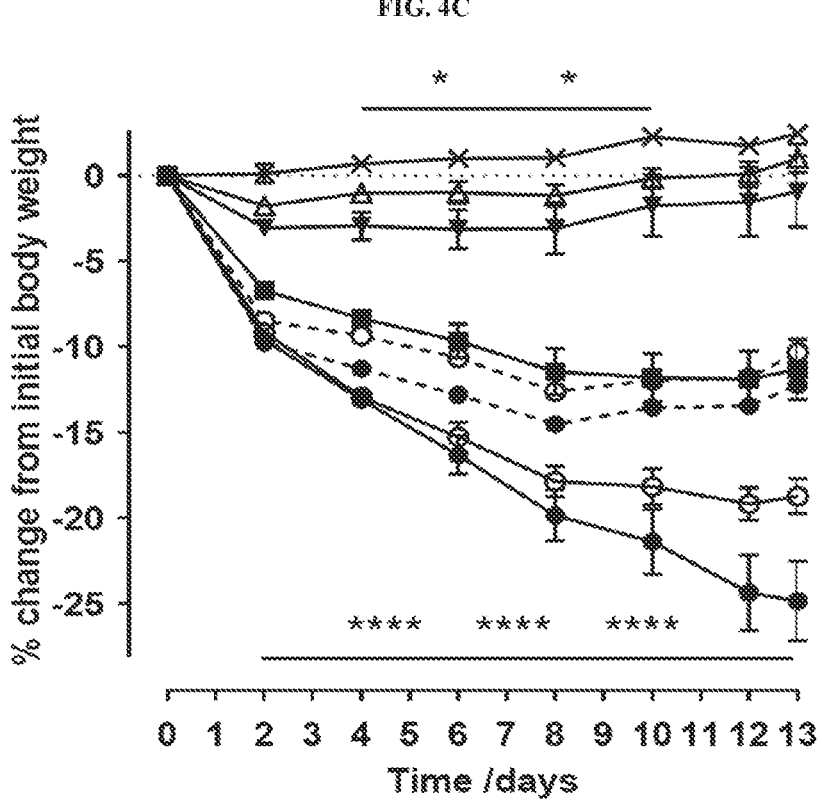
FIG. 4C illustrates the change in body weight over 2 weeks of diet-induced obese mice treated with conjugate 187, conjugate 40, a combination of conjugate 187 and 40, or vehicle alone.

Both doses of the PYY analog (40) alone demonstrated a dose-dependent reduction in food intake at day 1 (FIG. 4A), although this effect appeared to diminish over time (day 5, FIG. 4B). Conjugate 40 alone at high dose also showed significant reduction in body weight compared to the vehicle control, as depicted in FIG. 4C. As observed in the acute food intake study, conjugate 187 alone exhibited some efficacy, but superior body weight reduction was demonstrated in both combination groups. Dosing of 0.01 mg/kg of conjugate 187 in combination with the high dose (0.2 mg/kg) of conjugate 40 resulted in nearly 25% body weight reduction after 13 days. Furthermore, body weight reduction in the combination groups substantially exceeded the predicted profile based on additive effect alone (expected additivity, plotted) suggesting a synergistic enhancement of efficacy upon combination dosing. Similarly, the combination treatment demonstrated greater suppressive effects on food consumption compared to the GLP-1R agonist conjugate 187 alone after day 5 of dosing, as depicted in FIG. 4B.

Figure 4D:
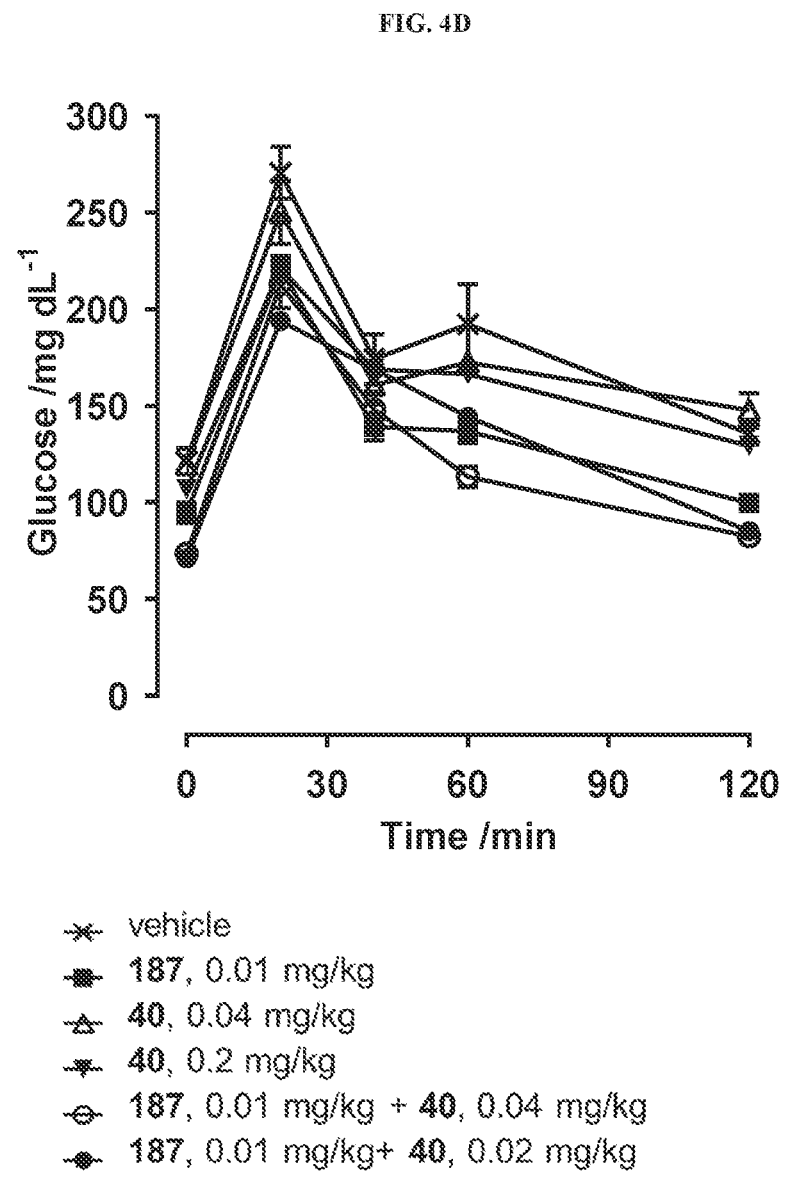
Figure 4E:
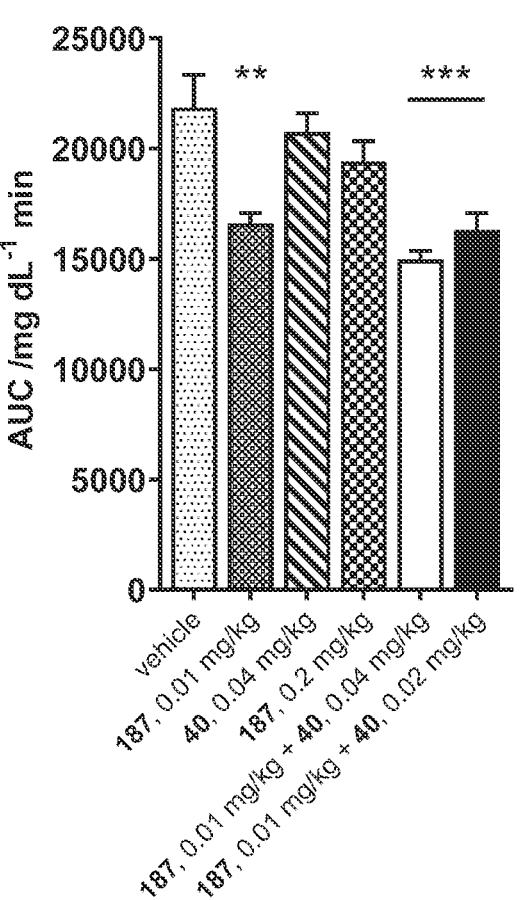
FIG. 4E illustrates the area under the curve for the oral-glucose tolerance test given to diet-induced obese mice treated with conjugate 187, conjugate 40, a combination of conjugate 187 and 40, or vehicle alone after 14 days of treatment.
Figure 4F:
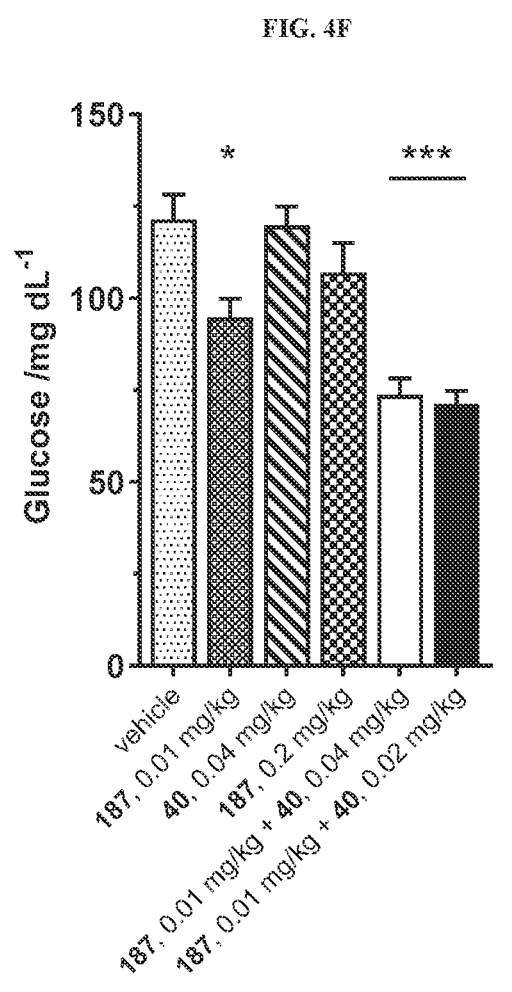

Blood glucose homeostasis at day 14 was evaluated via the oral glucose tolerance test (OGTT, FIGS. 4D-4F). Treatment with PYY analog 40 alone did not have a significant effect on the OGTT result or fasted blood glucose. While significant improvements were observed in the GLP-1R agonist (conjugate 187) dosing groups, as expected, the combination groups yielded slightly superior glucose control. The relatively modest glucose control effect demonstrated was not unexpected, and is potentially due to the somewhat mild hyperglycemia observed in the prediabetic DIO model. The clear discrimination between those groups dosed with conjugate 187 and those without indicates that is it is the effect of the GLP-1R agonist that is driving the glucose control effect in this study. However, the combination groups showed superior effect on fasted glucose levels, as depicted in FIG. 4F, suggesting that combination treatment may exert some sustained additive effect on glucose handling.

Example K: Generation of CRE-Luc Stable Cell Line Overexpressing GLP-1R or GCGR HEK293 cells were infected with lentivirus encoding firefly luciferase gene under the control of cAMP responsive element (CRE) promoter (Qiagen, The Netherlands) and then were selected using 1 µg/mL puromycin (Life Technologies, Carlsbad) for 1 week. The surviving cells (referred to as CRE-HEK293) were expanded and then transfected with a G418 selective mammalian expression plasmid encoding human GLP-1R or GCGR. In brief, GLP-1R or GCGR plasmid was transfected into CRE-HEK293 cells using Lipofectamine 2000 and selected with 400 µg/mL Geneticin (Life Technologies, Carlsbad, CA). Single colony stable cell line overexpressing CRE-luciferase and GLP1R or GCGR (HEK293-GLP-1R-CRE or HEK293-GCGR-CRE) was then established for in vitro activity assay.

Example L: In Vitro Receptor Activation Reporter Assay (Receptor-Mediated cAMP Synthesis)

HEK293-GLP-1R-CRE or HEK293-GCGR-CRE cells were seeded in 384-well plates at a density of 5000 cells per well and cultured for 18 h in DMEM with 10% FBS at 37° C. and 5% $CO_2$. Cells were treated with peptides in a dose dependent manner for 24 h, and receptor activation was reported by luminescence intensities, using One-Glo (Promega, WI) luciferase reagent following manufacturer's instruction. The $EC_{50}$ of each peptide was determined using GraphPad Prism 6 software (GraphPad, San Diego, CA).

TABLE 24

| cAMP data (Peptide Conjugates) | |
| --- | --- |
| | GLP-1R/GCGR - cAMP 0% FBS/nM |
| 121 | 1.357/2.543 |
| 122 | 0.0037/0.070 |
| 123 | 2.371/0.4512 |
| 124 | 0.049/0.319 |
| 125 | 0.210/0.626 |
| 126 | 0.119/0.092 |
| 127 | 0.148/0.009 |
| 128 | 6.640/16.22 |
| 129 | 31.080/55.95 |
| 135 | 0.0075/0.0068 |
| 136 | 2.8735/0.5589 |
| 137 | 2.018/0.4443 |
| 138 | 0.9076/1.4214 |

Example M: cAMP Assay

Figure 5A:
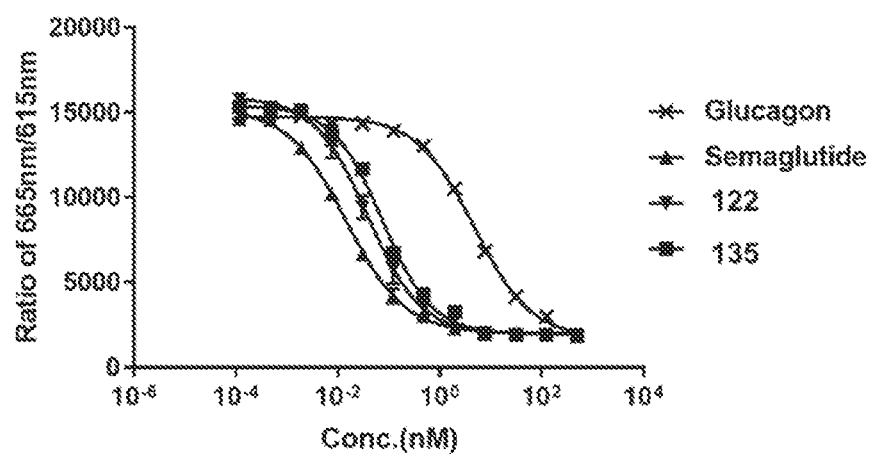
FIG. 5A displays a dose response curve for glucagon, semaglutide, conjugate 122, and conjugate 135 against GLP-1R.
Figure 5B:
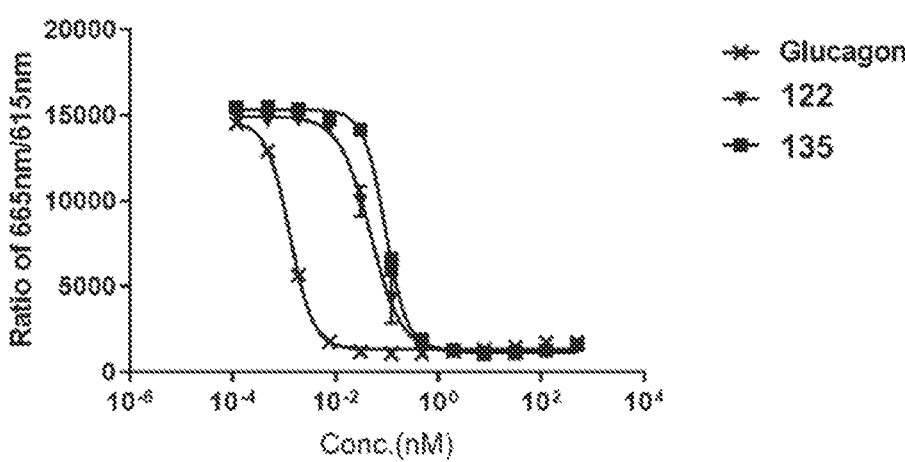
FIG. 5B displays a dose response curve for glucagon, conjugate 122, and conjugate 135 against GCGR.
Figure 5C:
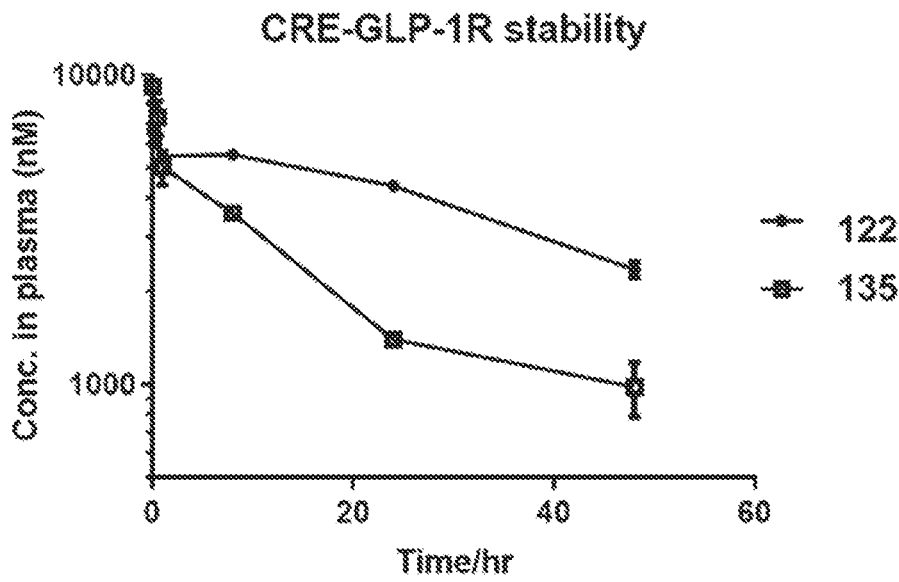
FIG. 5C depicts the stability of conjugates 122 and 135 in 2% plasma over 50 hours.

CHOK1 cells stably overexpressed human GLP-1R or GCGR (20 μL of 5000 cells per well) were seeded in white solid 384 well plate covered with metal lid and incubated for overnight. On day 2, the culture medium was replaced by fresh medium containing no FBS (for 0% FBS group). Cells were treated with 5 μL peptide in 12-point dose response, in culture medium with 0.5 mM IBMX in triplicates for 30 min at 37° C., 5% $CO_2$. cAMP dynamic 2 kit from Cisbio was used to detect cAMP level. Briefly, 25 μL of cAMP detection reagent (1:1:38 of cAMP-d2, Cryptate conjugate, lysis buffer) per well was added and incubated at room temperature for 1 hour. For cell negative control wells, cAMP detection reagent without d2 was added. Plates were then read at Ex320 nm, Em-1 665 nm and, EM-2 615 nm. Graphs were plotted with Ratio or Delta F using Prism software and $EC_{50}$ were then obtained. Ratio=$A_{665\ nm}/B_{620\ nm}\times10^4$. % Delta F=(Standard or Sample Ratio–Ratio$_{neg}$)/Ratio$_{neg}\times100$. Results are seen in FIGS. 5A-5C.

Example N: PK Studies

Female CD-1 mice (n=3 or 4 per group) from Charles River Laboratory were fasted overnight and administered 100 μL of each peptide in phosphate buffered saline (pH=8.2) by intravenous (i.v.) or subcutaneous (s. c.) route. Food was provided to mice after blood collection at 3 h time point. Blood was collected into heparin tubes and centrifuged at 3,000×g for 15 min. The resulting plasma were then stored at −80° C. for peptide concentration determination. The concentrations of peptides in plasma at each time point were determined by in vitro cell based activity assay. Briefly, HEK293-GLP-1R-CRE cells were treated with plasma samples at different time points (5-point dose response, starting from 1:10 to 1:100 dilution of each plasma sample) and incubated for 16 h in DMEM with 1000 FBS at 37° C. with 5% $CO_2$, and the firefly luciferase activity was then measured. Simultaneously, the same peptides were used to obtain standard curves and parameters for Bottom, Top, $EC_{50}$, and Hill Slope. Relative luciferase unit (RLU) for each plasma sample was used to calculate the peptide concentrations in plasma (nmol/L), using parameters derived from the standard curve (RLU=Bottom+(Top−Bottom)/(1+10^((Log $EC_{50}$−Conc.)*Hill Slope)). Peptide concentrations in plasma were obtained and plotted against time points to obtain in vivo half-life of each peptide, using WinNonLin Phoenix software (Pharsight Corp, St. Louis, MO).

Figure 6A:
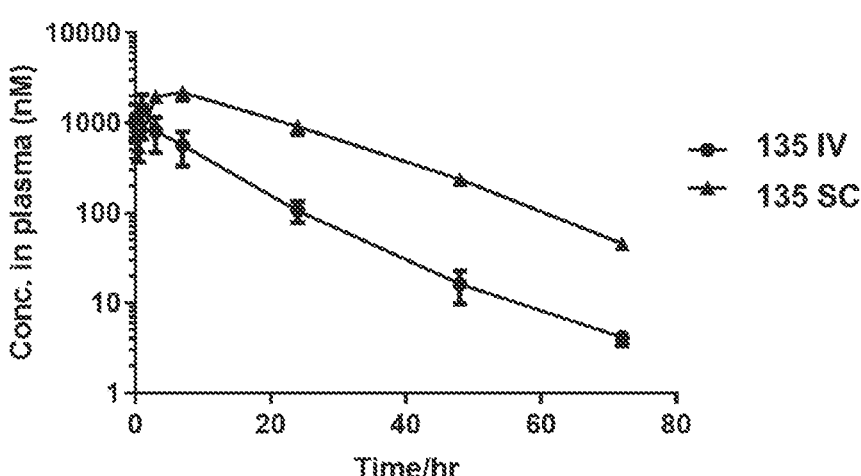
FIG. 6A depicts the pharmacokinetics of conjugate 135 when delivered intravenously and subcutaneously.
Figure 6B:
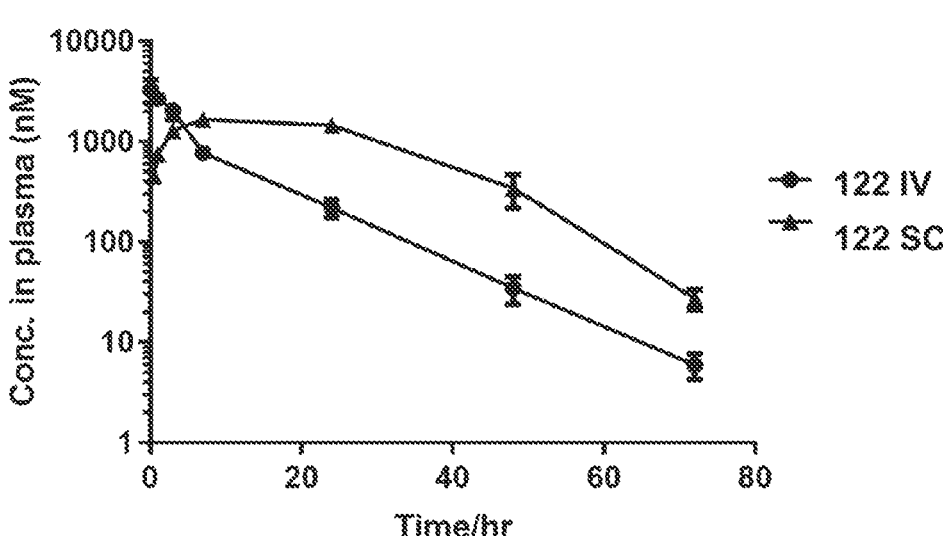
FIG. 6B depicts the pharmacokinetics of conjugate 122 when delivered intravenously and subcutaneously.

Results for peptide 122 and 135 are seen in FIG. 6A-6B and Tables 25a and 25b.

TABLE 25a

| | | | | | | | | |
|---|---|---|---|---|---|---|---|---|
| | | | Pharmacokinetic parameters for analytes administered intravenously | | | | | |
| Peptide | Dose (mg/kg) | Animal | $t_{1/2}$ (h) | $T_{max}$ (h) | $C_{max}$ (ng/mL) | AUC$_{last}$ (h * ng/mL) | AUC$_\infty$ (h * ng/mL) | Cl (mL/h/kg) |
| 122 | 0.3 | AN# 7 | 8.95 | 0.08 | 11800 | 101000 | 101000 | 2.96 |
| | 0.3 | AN# 8 | 8.37 | 1 | 13300 | 97600 | 97800 | 3.07 |
| | 0.3 | AN# 9 | 9.5 | 0.08 | 24700 | 139000 | 140000 | 2.14 |
| | | Mean | 8.94 | 0.389 | 16600 | 113000 | 113000 | 2.72 |
| | | SD | 0.565 | 0.529 | 7060 | 23100 | 23300 | 0.504 |
| 135 | 0.3 | AN# 1 | 10.76 | 1 | 10300 | 78900 | 79300 | 3.78 |
| | 0.3 | AN# 2 | 9.49 | 1 | 9920 | 87100 | 87400 | 3.43 |
| | | Mean | 10.1 | 1 | 10100 | 83000 | 83400 | 3.61 |
| | | SD | 0.896 | 0 | 298 | 5850 | 5780 | 0.25 |

TABLE 25b

| | | | | | | | | | |
|---|---|---|---|---|---|---|---|---|---|
| | | | Pharmacokinetic parameters for analytes administered subcutanously | | | | | | |
| Peptide | Dose (mg/kg) | Animal | $t_{1/2}$ (h) | $T_{max}$ (h) | $C_{max}$ (ng/mL) | AUC$_{last}$ (h * ng/mL) | AUC$_\infty$ (h * ng/mL) | Cl (mL/h/kg) | % F |
| 122 | 1 | AN# 10 | 9.65 | 7 | 9870 | 282000 | 284000 | 3.51 | |
| | 1 | AN# 11 | 8.47 | 24 | 8050 | 276000 | 278000 | 3.59 | |
| | 1 | AN# 12 | 7.09 | 24 | 7990 | 250000 | 250000 | 3.99 | |
| | | Mean | 8.4 | 18.3 | 8630 | 269000 | 271000 | 3.7 | 72% |
| | | SD | 1.28 | 9.81 | 1070 | 17300 | 18200 | 0.257 | |
| 135 | 1 | AN# 4 | 10.61 | 3 | 7650 | 242000 | 246000 | 4.06 | |
| | 1 | AN# 5 | 10.97 | 3 | 12700 | 245000 | 248000 | 4.04 | |
| | 1 | AN# 6 | 11.52 | 7 | 13300 | 260000 | 264000 | 3.79 | |
| | | Mean | 11 | 4.33 | 11200 | 249000 | 253000 | 3.96 | 91% |
| | | SD | 0.457 | 2.31 | 3100 | 9770 | 9760 | 0.15 | |

Figure 6C:
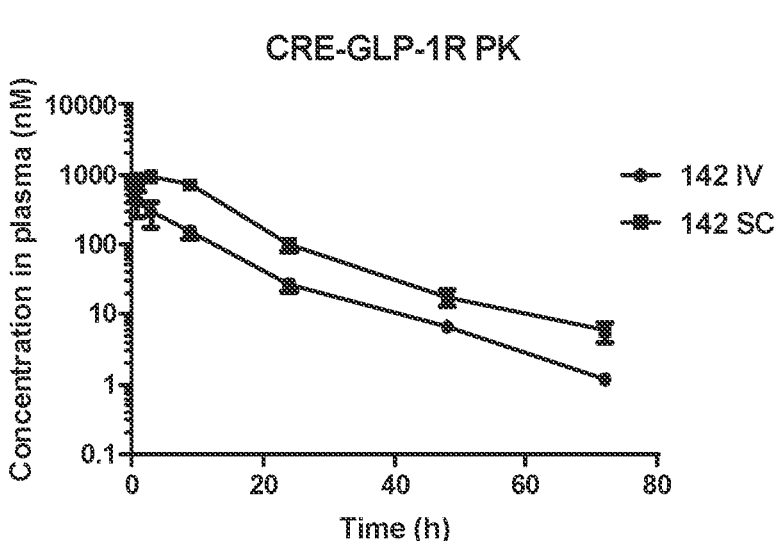
FIG. 6C depicts the pharmacokinetics of mice treated with peptide 142 intravenously and subcutaneously.

The concentration of peptide 142 in plasma over time is depicted in FIG. 6C. The pharmacokinetic parameters are listed in Tables 26a and 26b. Peptide 142 had a mean half life of 10.71 hours when administered intravenously and 11.56 hours when administered subcutaneously.

TABLE 26a

| | Pharmacokinetics for Peptide 142 Administered Intravenously | | | | | | |
|---|---|---|---|---|---|---|---|
| Animal | $T_{1/2}$ (hr) | $T_{max}$ (hr) | $C_{max}$ (ng/mL) | $AUC_{last}$ (hr * ng/mL) | AUCINF_obs (hr * ng/mL) | Vss_obs (L/kg) | Cl_obs (mL/min/kg) |
| 1 | 10.52 | 0.08 | 3900 | 15700 | 15800 | 0.21 | 0.32 |
| 2 | 11.25 | 0.08 | 3550 | 21300 | 21400 | 0.12 | 0.23 |
| 3 | 10.35 | 0.08 | 3930 | 18000 | 18100 | 0.19 | 0.28 |
| Mean | 10.71 | 0.08 | 3790 | 18300 | 18400 | 0.175 | 0.276 |
| SD | 0.478 | 0 | 209 | 2840 | 2850 | 0.05 | 0.042 |
| CV % | 4.5 | 0 | 5.5 | 15.5 | 15.4 | 28.3 | 15.2 |

TABLE 26b

| | Pharmacokinetics for Peptide 142 Administered Subcutaneously | | | | | | |
|---|---|---|---|---|---|---|---|
| Animal | $T_{1/2}$ (hr) | $T_{max}$ (hr) | $C_{max}$ (ng/mL) | $AUC_{last}$ (hr * ng/mL) | AUCINF_obs (hr * ng/mL) | Vss_obs (L/kg) | Cl_obs (mL/min/kg) |
| 4 | 11.15 | 3 | 3980 | 54900 | 55400 | 0.29 | 0.3 |
| 5 | 12.54 | 1 | 4880 | 67100 | 67700 | 0.27 | 0.25 |
| 6 | 10.99 | 3 | 5270 | 55600 | 55900 | 0.28 | 0.3 |
| Mean | 11.56 | 2.33 | 4710 | 59200 | 59700 | 0.28 | 0.282 |
| SD | 0.849 | 1.16 | 659 | 6810 | 6970 | 0.012 | 0.031 |
| CV % | 7.3 | 49.5 | 14 | 11.5 | 11.7 | 4.3 | 10.9 |

Figure 6D:
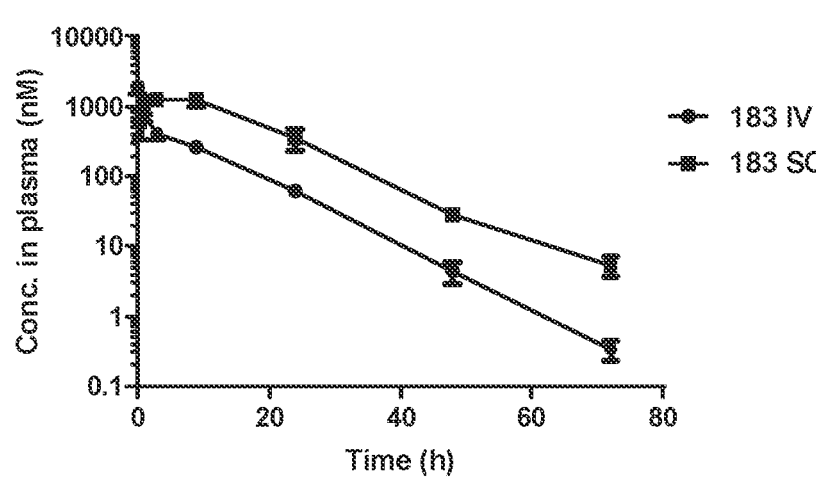
FIG. 6D depicts the pharmacokinetics of mice treated with peptide 183 intravenously and subcutaneously.

The concentration of peptide 183 in plasma over time is depicted in FIG. 6D. The pharmacokinetic parameters are listed in Tables 26c and 26d. Peptide 142 had a mean half life of 6.335 hours when administered intravenously and 7.87 hours when administered subcutaneously.

TABLE 26c

| | Pharmacokinetics for Peptide 183 Administered Intravenously | | | | | | |
|---|---|---|---|---|---|---|---|
| Animal | $T_{1/2}$ (hr) | $T_{max}$ (hr) | $C_{max}$ (ng/mL) | $AUC_{last}$ (hr * ng/mL) | AUCINF_obs (hr * ng/mL) | Vss_obs (L/kg) | Cl_obs (mL/min/kg) |
| 7 | 5.88 | 0.08 | 12000 | 31400 | 31400 | 0.08 | 0.16 |
| 8 | 6.69 | 0.08 | 9720 | 35600 | 35600 | 0.07 | 0.14 |
| 9 | 6.44 | 0.08 | 7970 | 37400 | 37500 | 0.07 | 0.13 |
| Mean | 6.335 | 0.08 | 9890 | 34800 | 34800 | 0.077 | 0.144 |
| SD | 0.413 | 0 | 2010 | 3120 | 3120 | 0.005 | 0.013 |
| CV % | 6.5 | 0 | 20.3 | 9 | 9 | 6.6 | 9.3 |

TABLE 26d

| | Pharmacokinetics for Peptide 183 Administered Subcutaneously | | | | | | |
|---|---|---|---|---|---|---|---|
| Animal | $T_{1/2}$ (hr) | $T_{max}$ (hr) | $C_{max}$ (ng/mL) | $AUC_{last}$ (hr * ng/mL) | AUCINF_obs (hr * ng/mL) | Vss_obs (L/kg) | Cl_obs (mL/min/kg) |
| 10 | 8.23 | 3 | 6220 | 90300 | 90500 | 0.13 | 0.18 |
| 11 | 7.65 | 7 | 8100 | 136000 | 137000 | 0.08 | 0.12 |
| 12 | 8.08 | 3 | 7770 | 139000 | 139000 | 0.08 | 0.12 |
| Mean | 7.987 | 4.33 | 7360 | 122000 | 122000 | 0.098 | 0.142 |
| SD | 0.301 | 2.31 | 1000 | 27400 | 27500 | 0.028 | 0.037 |
| CV % | 3.8 | 53.3 | 13.6 | 22.5 | 22.5 | 28.7 | 25.8 |

Example O: In Vivo Efficacy

C57BL/6J mice (n=6/group) between 10-12 weeks old were fasted overnight and then administrated with 5 mL/kg of each peptide in PBS (pH=8.2) by s.c. route. After 6 hours, mice were orally or intraperitoneally administrated with 2 g of glucose solution per kg body weight and their tail blood glucose levels were measured before (0 min) and after glucose challenge for 2 hours. Follow up OGTT were also performed at 48 h, and 96 h post-original dose in same mice after overnight fast.

The efficacy of the GLP-1R/GCGR dual agonist 135 was then evaluated in an oral glucose tolerance test (OGTT) in wilt type mice. As positive controls, we employed the once-weekly administered, single GLP-1R agonist sema-glutide and the dual GLP-1R/GCGR agonist cotadutide, a once-daily administered peptide currently in Phase II trials by AstraZeneca.

Figure 7G:
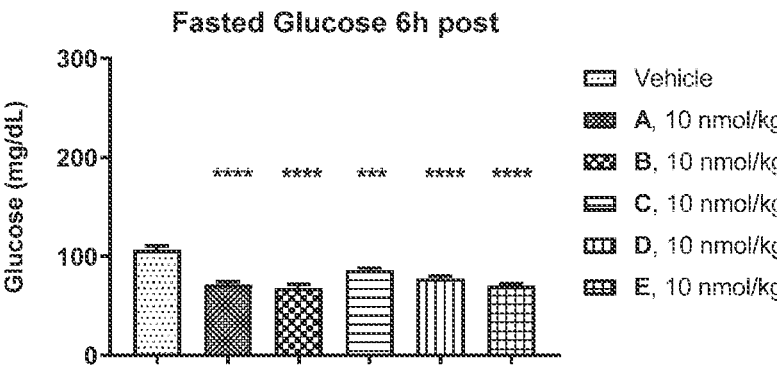
FIG. 7G depicts the effects of the compounds in an oral glucose tolerance test on fasted glucose levels at 6 hours post dose. A: 122, B: 135, C: 138, D: Cotadutide, E: Semaglutide.
Figure 7H:
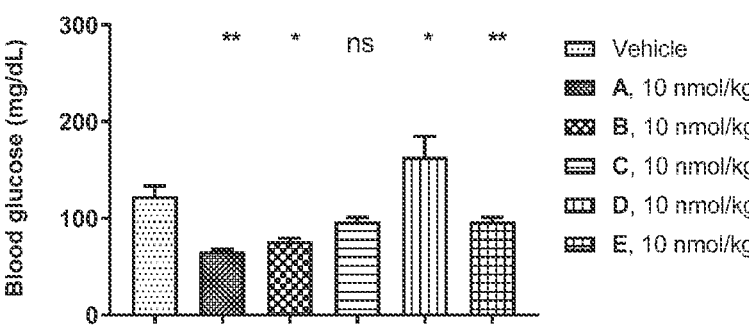
FIG. 7H depicts the effects of the compounds in an oral glucose tolerance test on fasted glucose levels at 48 hours post dose. A: 122, B: 135, C: 138, D: Cotadutide, E: Semaglutide.
Figure 7I:
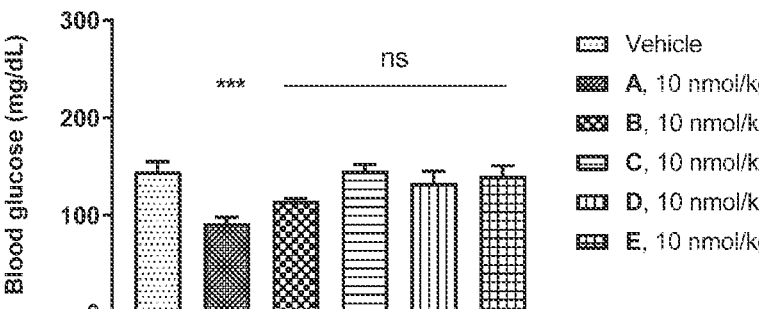
FIG. 7I depicts the effects of the compounds in an oral glucose tolerance test on fasted glucose levels at 96 hours post dose. A: 122, B: 135, C: 138, D: Cotadutide, E: Semaglutide.

The effects of the compounds in oral glucose tolerance test (OGTT) at 6 h, 48 h, and 96 h post dose, compared to vehicle control (PBS pH 8.2), is displayed in FIGS. 7A-7C. FIGS. 7A-7C display the effect of the compounds on blood glucose over time. FIGS. 7D-7F display the effects of the compounds on glucose levels as measured by the area under the curve. FIGS. 7G-7I display the effects of the compounds on fasted glucose. For all figures, A: 122 4, B: 135, C: 138, D: Cotadutide, E: Semaglutide. All peptides significantly decreased blood glucose to a similar level after 6 h of from administration when compared to the vehicle. Similar results were observed for fasted blood glucose for all peptides. However, significant differences in glucose levels were observed after 48 h from administration of the peptides. Cotadutide did not exhibit any improvement over the vehicle after 48 h, consistent with its suitability as a once-daily injection for human subjects. On the other hand, mice treated with conjugate 135 showed more significant improvements in handling glucose after 48 h compared to semaglutide. Moreover, conjugate 135 was able to signifi-cantly reduce fasted glucose levels while the rest of the peptides resulted in no improvements in efficacy. The increased in vivo efficacy of conjugate 135 observed here likely result from both higher dual agonistic activity and the extended in vivo half-life. Assuming a direct relationship between pharmacokinetics and pharmacokinetics, the results of this experiment indicate that peptide conjugate 135 exhib-its a longer half-life than semaglutide, and thus has the potential to be developed as a once-weekly or semi-monthly with an appropriate formulation.

Example P: Generation of CRE-Luc Stable Cell Line Overexpressing GLP-1R or GCGR HEK293 cells were infected with lentivirus encoding firefly luciferase gene under the control of cAMP responsive element (CRE) promoter (Qiagen, The Netherlands) and then were selected using 1 g/mL puromycin (Life Technolo-gies, Carlsbad) for 1 week. The surviving cells (referred to as CRE-HEK293) were expanded and then transfected with a G418 selective mammalian expression plasmid encoding human GLP-1R or GCGR. In brief, GLP-1R or GCGR plasmid was transfected into CRE-HEK293 cells using Lipofectamine 2000 and selected with 400 µg/mL Geneticin (Life Technologies, Carlsbad, CA). Single colony stable cell line overexpressing CRE-luciferase and GLP1R or GIPR (HEK293-GLP-1R-CRE or HEK293-GIPR-CRE) was then established for in vitro activity assay.

Example Q: In Vitro Receptor Activation Reporter Assay (Receptor-Mediated cAMP Synthesis) HEK293

Figure 8A:
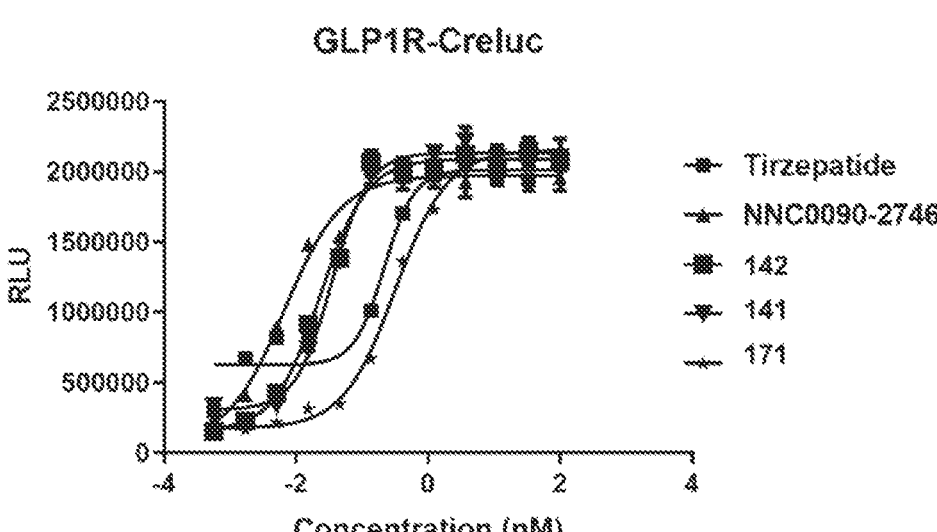
FIG. 8A depicts the results of a GLP1 receptor activation reporter assay for tirzepatide, NNC0090-2746, conjugate 142, 141, and 171.
Figure 8B:
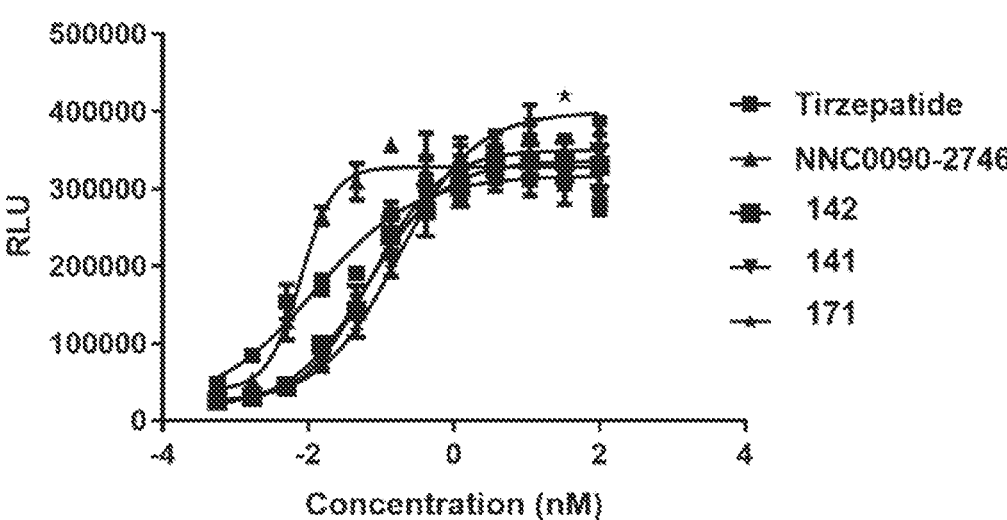
FIG. 8B depicts the results of a GIP receptor activation reporter assay for tirzepatide, NNC0090-2746, conjugate 142, 141, and 171.

GLP-1R-CRE or HEK293-GIPR-CRE cells were seeded in 384-well plates at a density of 5000 cells per well and cultured for 18 h in DMEM with 10% FBS at 37° C. and 5% $CO_2$. Cells were treated with peptides in a dose dependent manner for 24 h, and receptor activation was reported by luminescence intensities, using One-Glo (Promega, WI) luciferase reagent following manufacturer's instruction. The $EC_{50}$ of each peptide was determined using GraphPad Prism 6 software (GraphPad, San Diego, CA). Results are depicted in FIGS. 8A-8B.

TABLE 27

| Creluc data (Peptide Conjugates) | |
| --- | --- |
| | GLP-1R/GIPR - Creluc/nM |
| 141 | 0.01/0.02 |
| 142 | 0.02/0.02 |
| 165 | 13.77/5.31 |
| 166 | 83.92/12.55 |
| 167 | 18.77/20.43 |
| 168 | >1000/303 |
| 169 | 1.32/11.29 |
| 170 | 3.74/15.66 |

Example R: cAMP Assay

CHOK1 cells stably overexpressed human GLP-1R or GIPR (20 µL of 5000 cells per well) were seeded in white solid 384 well plate covered with metal lid and incubated for overnight. On day 2, the culture medium was replaced by fresh medium containing no FBS (for 0% FBS group). Cells were treated with 5 µL peptide in 12-point dose response, in culture medium with 0.5 mM IBMX in triplicates for 30 min at 37° C., 5% $CO_2$. cAMP dynamic 2 kit from Cisbio was used to detect cAMP level. Briefly, 25 µL of cAMP detection reagent (1:1:38 of cAMP-d2, Cryptate conjugate, lysis buf-fer) per well was added and incubated at room temperature for 1 hour. For cell negative control wells, cAMP detection reagent without d2 was added. Plates were then read at Ex320 nm, Em-1 665 nm and, EM-2 615 nm. Graphs were plotted with Ratio or Delta F using Prism software and $EC_{50}$ were then obtained. Ratio=$A_{665\ nm}/B_{620\ nm} \times 10^4$. % Delta F=(Standard or Sample Ratio−$Ratio_{neg}$)/$Ratio_{neg} \times 100$. Results are seen in FIGS. 5A-5C.

TABLE 28

| cAMP data (Peptide Conjugates) | |
| --- | --- |
| | GLP-1R/GIPR - cAMP 0% FBS/nM |
| 139 | 0.061/0.0026 |
| 140 | 0.034/0.0028 |
| 141 | 0.022/0.0048 |
| 142 | 0.026/0.0080 |
| 143 | 0.068/0.0020 |
| 144 | 0.012/0.0022 |
| 145 | 61.37/14.99 |
| 146 | 0.11/0.03 |
| 147 | 0.07/0.02 |
| 148 | 0.46/0.03 |

TABLE 28-continued cAMP data (Peptide Conjugates)

| GLP-1R/GIPR - cAMP 0% FBS/nM | |
|---|---|
| 149 | 0.05/0.01 |
| 150 | 0.06/0.02 |
| 151 | 0.03/0.02 |
| 152 | 0.49/0.05 |
| 153 | 0.05/0.01 |
| 154 | 0.03/0.02 |
| 155 | 4.08/1.66 |
| 156 | 14.64/2.82 |
| 157 | 16.45/ND |
| 158 | 98.29/30.52 |
| 159 | 1179/0.0312 |
| 160 | 0.03/7.297 |
| 161 | 0.4/0.01 |
| 162 | 0.05/0.02 |
| 163 | 0.24/0.05 |
| 164 | 0.14/68.29 |
| 171 | 0.32/017 |
| 272 | 0.46/0.03 |
| 273 | 0.49/0.05 |
| 274 | 0.40/0.01 |

Example S: Oral Glucose Tolerance Test (OGTT)

C57BL/6J mice (n=6/group) between 10-12 weeks old were fasted overnight and then administrated with 5 mL/kg of each peptide in PBS (pH=8.2) by s.c. route. After 6 hours, mice were orally or intraperitoneally administrated with 2 g of glucose solution per kg body weight and their tail blood glucose levels were measured before (0 min) and after glucose challenge for 2 hours. Follow up OGTT were also performed at 72 h, 96 h, and 144 h post-original dose in same mice after overnight fast. For all figures, A: 141, 4, B: 171, C: Tirzepatide, D: 142, E: Semaglutide.

Figure 9A:
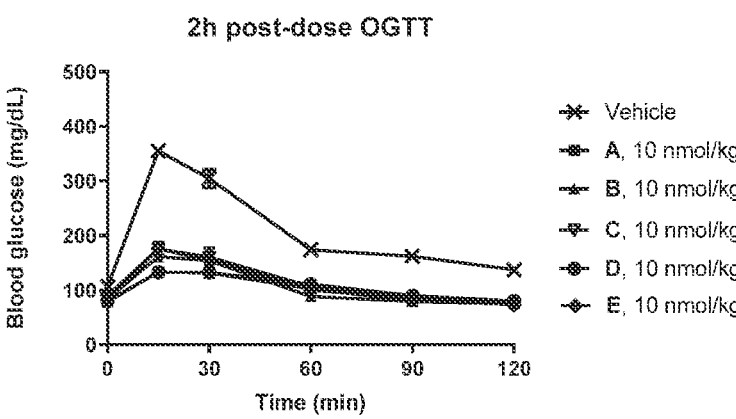
FIG. 9A depicts the effects of treatment with the compounds in an oral glucose tolerance test over time compared to vehicle controls at 2 hours post dose. A: 141, B: 171, C: 142, D: Semaglutide, E: Tirzepatide.
Figure 9B:
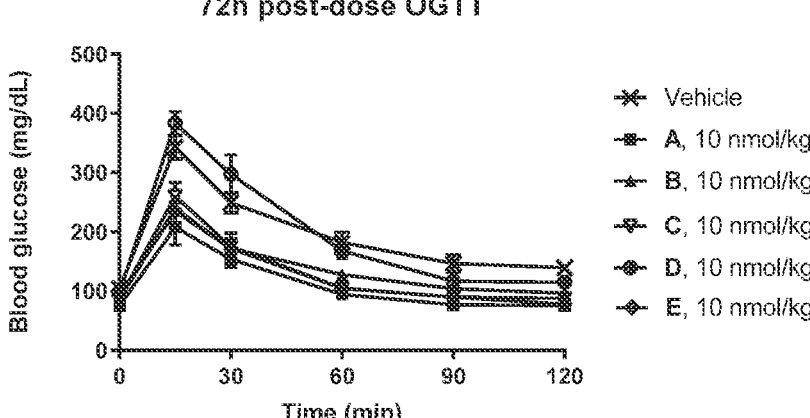
FIG. 9B depicts the effects of treatment with the compounds in an oral glucose tolerance test over time compared to vehicle controls at 72 hours post dose. A: 141, B: 171, C: 142, D: Semaglutide, E: Tirzepatide.
Figure 9C:
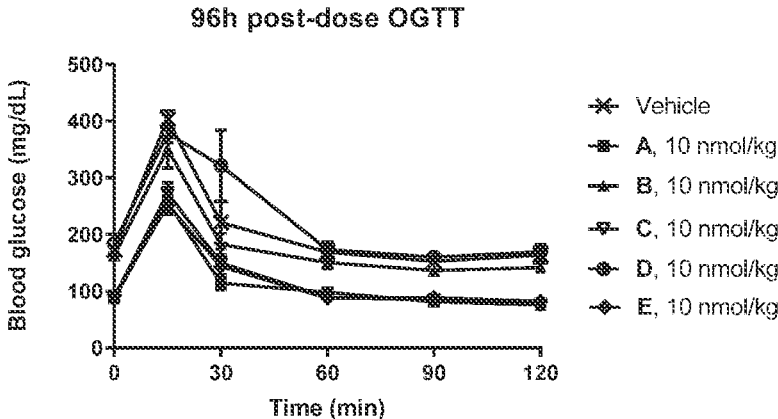
FIG. 9C depicts the effects of treatment with the compounds in an oral glucose tolerance test over time compared to vehicle controls at 96 hours post dose. A: 141, B: 171, C: 142, D: Semaglutide, E: Tirzepatide.
Figure 9D:
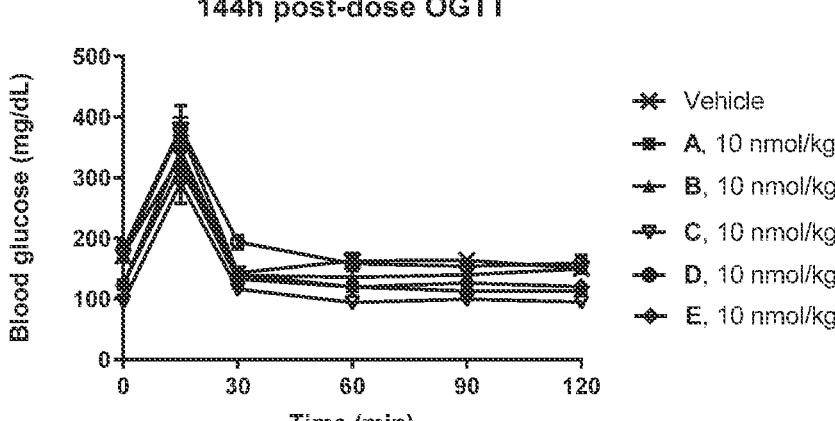
FIG. 9D depicts the effects of treatment with the compounds in an oral glucose tolerance test over time compared to vehicle controls at 144 hours post dose. A: 141, B: 171, C: 142, D: Semaglutide, E: Tirzepatide.
Figure 9E:
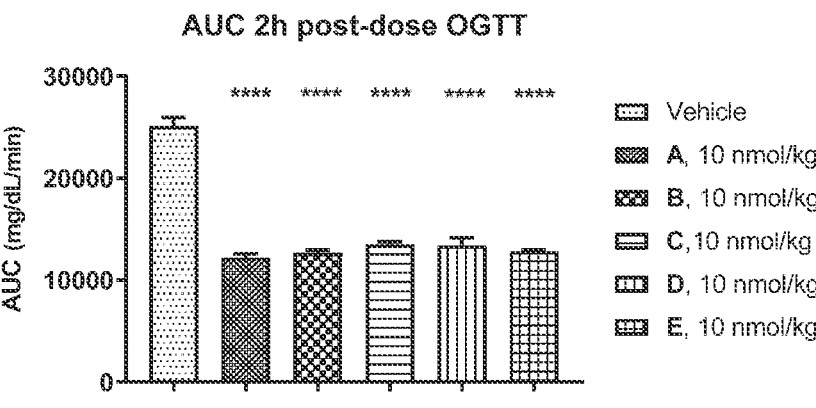
FIG. 9E depicts the effects of treatment with the compounds in an oral glucose tolerance test on blood glucose levels as measured as the area under curve (AUC) compared to vehicle controls at 2 hours post dose. A: 141, B: 171, C: 142, D: Semaglutide, E: Tirzepatide.
Figure 9F:
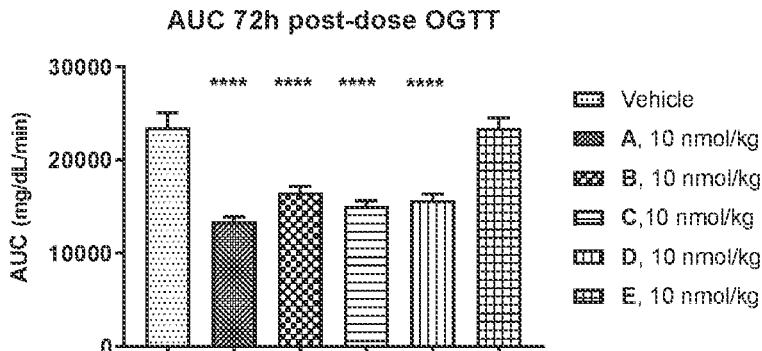
FIG. 9F depicts the effects of treatment with the compounds in an oral glucose tolerance test on blood glucose levels as measured as the area under curve (AUC) compared to vehicle controls at 72 hours post dose. For all figures, A: 141, B: 171, C: 142, D: Semaglutide, E: Tirzepatide.
Figure 9G:
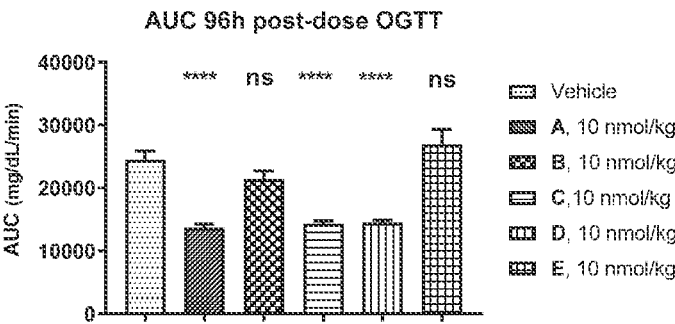
FIG. 9G depicts the effects of treatment with the compounds in an oral glucose tolerance test on blood glucose levels as measured as the area under curve (AUC) compared to vehicle controls at 96 hours post dose. A: 141, B: 171, C: 142, D: Semaglutide, E: Tirzepatide.
Figure 9H:
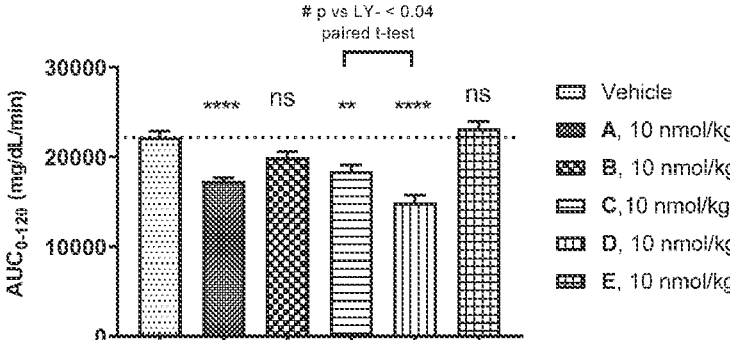
FIG. 9H depicts the effects of treatment with the compounds in an oral glucose tolerance test on blood glucose levels as measured as the area under curve (AUC) compared to vehicle controls at 144 hours post dose. A: 141, B: 171, C: 142, D: Semaglutide, E: Tirzepatide.
Figure 9I:
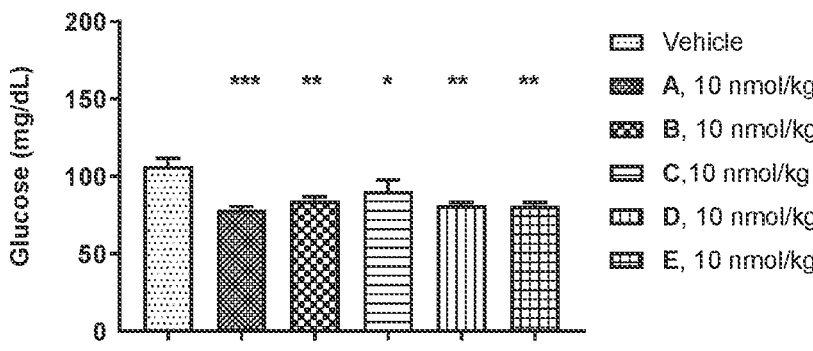
FIG. 9I depicts the effects of treatment with the compounds on fasted glucose as measured as the area under curve (AUC) compared to vehicle controls at 2 hours post dose. A: 141, B: 171, C: 142, D: Semaglutide, E: Tirzepatide.
Figure 9J:
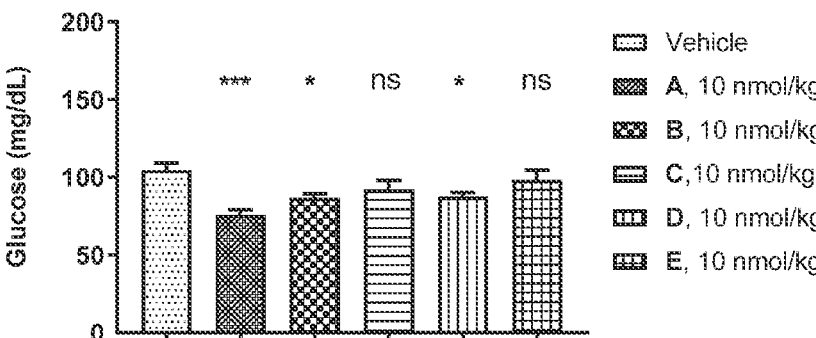
FIG. 9J depicts the effects of treatment with the compounds on fasted glucose as measured as the area under curve (AUC) compared to vehicle controls at 72 hours post dose. A: 141, B: 171, C: 142, D: Semaglutide, E: Tirzepatide.
Figure 9K:
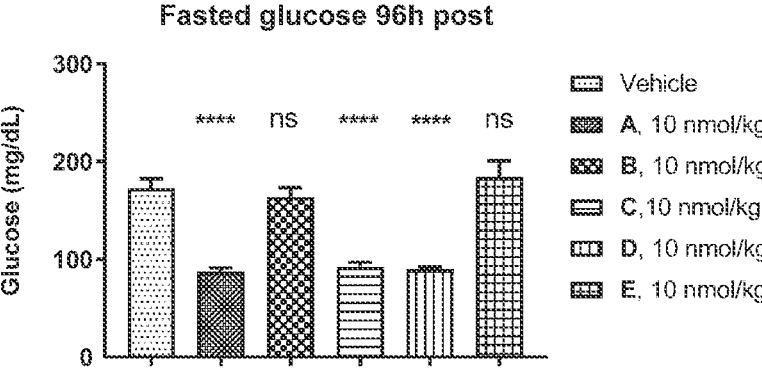
FIG. 9K depicts the effects of treatment with the compounds on fasted glucose as measured as the area under curve (AUC) compared to vehicle controls at 96 hours post dose. A: 141, B: 171, C: 142, D: Semaglutide, E: Tirzepatide.
Figure 9L:
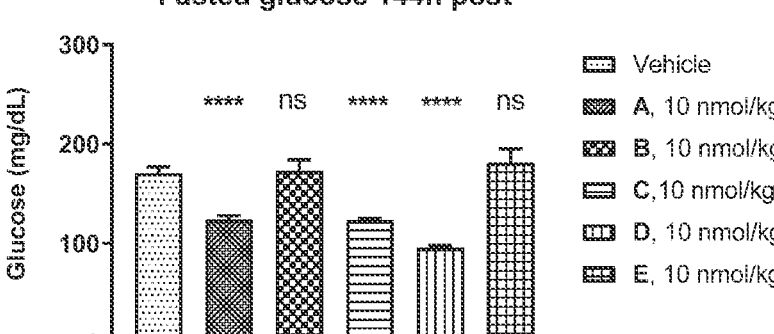
FIG. 9L depicts the effects of treatment with the compounds on fasted glucose as measured as the area under curve (AUC) compared to vehicle controls at 144 hours post dose. A: 141, B: 171, C: 142, D: Semaglutide, E: Tirzepatide.

An oral glucose tolerance test (OGTT) was performed 2 hours, 72 hours 96 hours and 144 hours post dose, as depicted in FIGS. 9A-9D. At 2 hours, there was a significant decrease in blood glucose levels as measured by the AUC in mice treated with compound 141, compound 171, compound 142, semaglutide, and tirzepatide, compared to mice treated with vehicle alone, as depicted in FIG. 9E. In the OGTT performed 72 hours post dose, there was a significant decrease in blood glucose levels as measured by the AUC in mice treated with compound 141, compound 171, compound 142, and semaglutide, compared to mice treated with vehicle alone, as depicted in FIG. 9F. In the OGTT performed 96 hours post dose, there was a significant decrease in blood glucose levels as measured by the AUC in mice treated with compound 141, compound 142, and semaglutide, compared to mice treated with vehicle alone, as depicted in FIG. 9G. In the OGTT performed 144 hours post dose, there was a significant decrease in blood glucose levels as measured by the AUC in mice treated with compound 141, compound 142, and semaglutide, compared to mice treated with vehicle alone, as depicted in FIG. 9F. Treatment with compound 141, compound 171, compound 142, semaglutide, and tirzepatide resulted in a significant decrease in fasted glucose levels at 2 hours post treatment, compared to treatment with vehicle alone, as depicted in FIG. 9I. Treatment with compound 141, compound 171, and semaglutide resulted in a significant decrease in fasted glucose levels 72 hours post treatment, as compared to treatment with vehicle alone, as depicted in FIG. 9J. Treatment with compound 141, compound 142, and semaglutide resulted in a significant decrease in fasted glucose levels at 96 hours and 144 hours post treatment, compared to treatment with vehicle alone, as depicted in FIGS. 9K-9L.

Example T: DIO Mice Study

The results are expressed as means±S.E., and the data were compared using the unpaired Student's t test. Where appropriate, data were compared using repeated measures or one-way analysis of variance, followed by the Student-Newman-Keuls post hoc test. Incremental area under the curve (AUC) analyses for plasma glucose was calculated using GraphPad Prism 6. Groups of data were considered to be significantly different if $p<0.01$.

Body Weight, Food Intake, and Visceral Fat Mass Measurement

DIO mice (C57BL/6, male, 37-week old) were randomized based on their body weight and were treated with daily or twice weekly subcutaneous injections of peptide or vehicle (n=6/group). Body weight and food intake were monitored daily throughout the study.

Figure 10A:
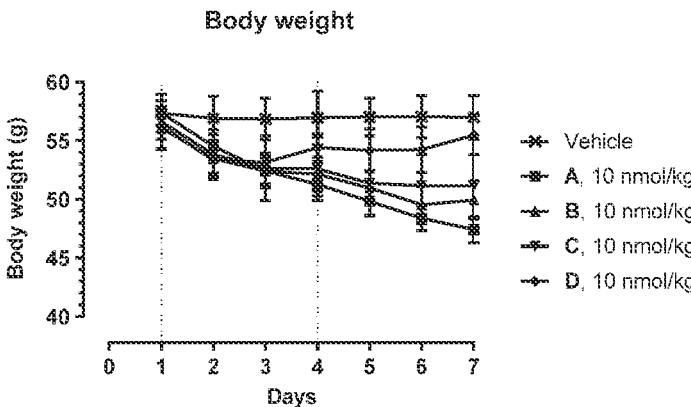
FIG. 10A displays the change in bodyweight of mice dosed daily or twice daily subcutaneously with peptide or vehicle controls. Grey arrows show where the compounds are dosed daily and black arrows for the days where the twice weekly doses are administered. A: 142 (7×/wk), B: 142 (2×/wk), C: Tirzepatide (2×/wk), D: Semaglutide (2×/wk).
Figure 10B:
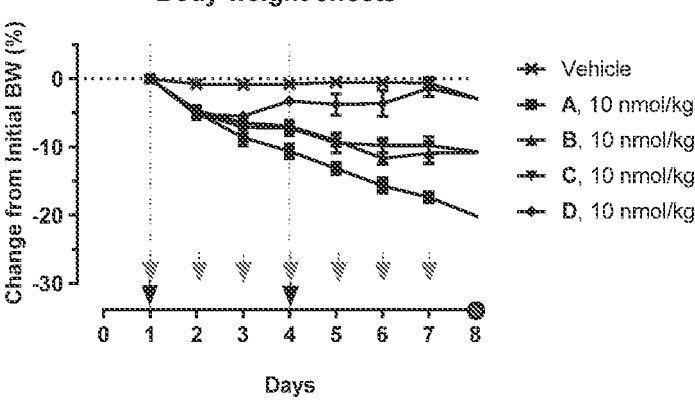
FIG. 10B displays the percent change in bodyweight, respectively, of mice dosed daily or twice daily subcutaneously with peptide or vehicle controls. Grey arrows show where the compounds are dosed daily and black arrows for the days where the twice weekly doses are administered. A: 142 (7×/wk), B: 142 (2×/wk), C: Tirzepatide (2×/wk), D: Semaglutide (2×/wk).
Figure 10C:
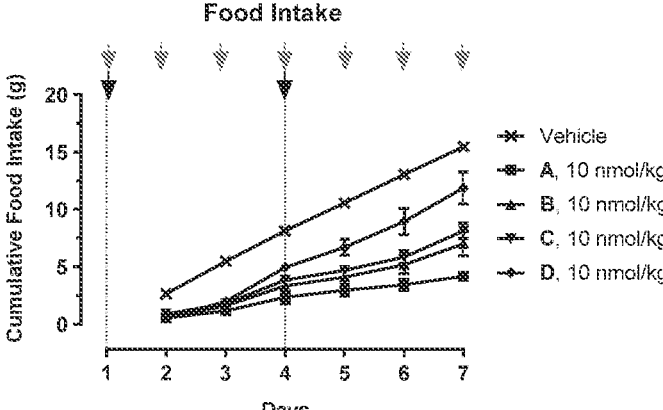
FIG. 10C displays the cumulative food intake in mice over 7 days following subcutaneous dosage of peptide or vehicle control. Grey arrows show where the compounds are dosed daily and black arrows for the days where the twice weekly doses are administered. A: 142 (7×/wk), B: 142 (2×/wk), C: Tirzepatide (2×/wk), D: Semaglutide (2×/wk).

Mice treated with compound 142 or tirzepatide showed a decrease in total bodyweight and percent bodyweight over time, compared to mice treated with vehicle alone, as depicted in FIGS. 10A-10B. Furthermore, mice treated with compound 142 or tirzepatide showed a decrease in cumulative food intake when compared to mice treated with vehicle alone, as depicted in FIG. 10C. In an oral glucose tolerance test (OGTT), blood glucose levels over time were decreased in mice treated with compound 142 or tirzepatide, compared to mice treated with vehicle alone, as depicted in FIG. 10D. Furthermore, there was a significant decrease in total glucose levels as measured by the area under the curve (AUC) in mice that received treatment with compound 142 or tirzepatide, compared to mice treated with vehicle alone. Mice treated with these compound also showed a decrease in glucose levels after overnight fasting at day 8, compared to mice treated with vehicle alone. Mice treated with compound 142 7 times/week showed a 53% decrease in glucose levels, mice treated with compound 142 twice a week showed a 42% decrease in blood glucose levels, and mice treated with tirzepatide showed a 30% decrease in blood glucose levels.

Animals and Statistical Analysis

All animal care and experimental procedures were approved by the Institutional Animal Care and Use Committee (IACUC) of California Institute for Biomedical Research (Calibr) and strictly followed the NIH guidelines for humane treatment of animals. The results are expressed as means S.E., and the data were compared using the unpaired Student's t test. Where appropriate, data were compared using repeated measures or one-way analysis of variance, followed by the Student-Newman-Keuls post hoc test. Incremental area under the curve (AUC) analyses for plasma glucose was calculated using GraphPad Prism 6. Groups of data were considered to be significantly different if $p<0.01$.

Body Weight, Food Intake, and Visceral Fat Mass Measurement

DIO mice (C57BL/6, male, 28-week old) were randomized based on their body weight and were treated with daily subcutaneous injections of peptide or vehicle (n=7/group). Body weight and food intake were monitored daily throughout the study. At the end of the experiment, mice were sacrificed, and visceral fat mass were weighed. Collected plasma was used for cholesterol level determination according to the manufacturer's guide (cholesterol assay kit, Abcam, Cambridge, England) and triglyceride level using a triglyceride colorimetric assay kit (Cayman chemical, Ann Arbor, Michigan).

Cholesterol Level Determination

Collected plasma was used for cholesterol level determination according to the manufacturer's guide (cholesterol assay kit, Abcam, Cambridge, England). Briefly, plasma was diluted using cholesterol assay buffer and then reacted with the same volume of reaction mix containing cholesterol assay buffer, cholesterol probe, enzyme mix and cholesterol esterase. After incubation at 37° C. for 1 hour, the absorbance at 560 nm was measured using an Envision multilabel plate reader (PerkinElmer, Waltham, MA). Subsequently, the concentration of cholesterol in plasma was calculated according to a standard curve.

Triglyceride Level Measurement

Collected plasma was used for triglyceride level determination using a triglyceride colorimetric assay kit (Cayman chemical, Ann Arbor, Michigan). 5 µL of plasma samples or standard were plated into a 384 well plate and followed by adding 75 µL of diluted enzyme buffer to each well. The mixture was incubated at room temperature for 15 min, and the absorbance was read at 560 nm using an Envision plate reader (PerkinElmer, Waltham, MA). The concentration of triglyceride in plasma was calculated using a standard curve.

Biochemical and Histological Analyses

Terminal serum analytes including total cholesterol, triglyceride, alanine aminotransferase (ALT), aspartate aminotransferase (AST), alkaline phosphatase (ALP) were determined by Alfa Wassermann Vet Axcel® clinical analyzer. Hepatic triglycerides were measured in liver homogenates generated with a colorimetric triglyceride kit (Cayman Chemical). Paraformaldehyde-fixed liver were paraffin-embedded, sectioned and stained with hematoxylin-eosin and Picro-Sirius red by HistoTox Labs (Boulder, CO). All histological assessment (steatosis, fibrosis scoring) were performed by a certified histopathologist blind to treatment (HistoTox Labs) based on classification outlined by Kleiner et al.[3]

Results

Figure 11A:
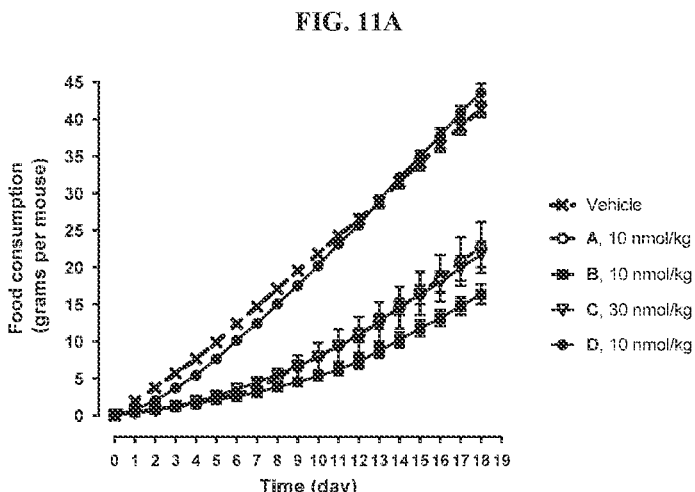
FIG. 11A displays the cumulative food intake of mice treated daily with peptide or vehicle. A: 122, B: 142, C: Semaglutide, D: Cotadutide.
Figure 11B:
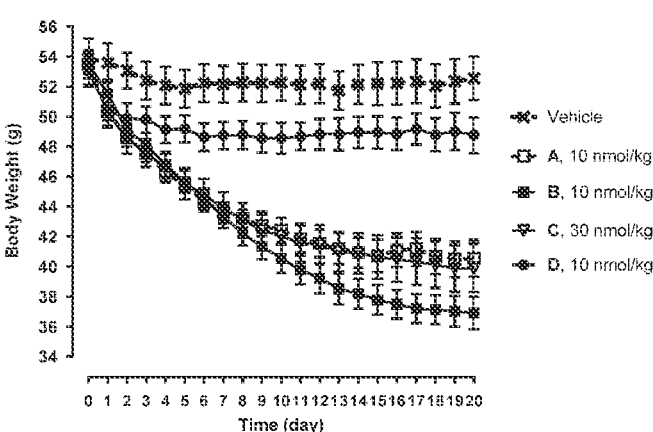
FIG. 11B displays the change in bodyweight of mice treated with peptide or vehicle control over 21 days. A: 122, B: 142, C: Semaglutide, D: Cotadutide.
Figure 11C:
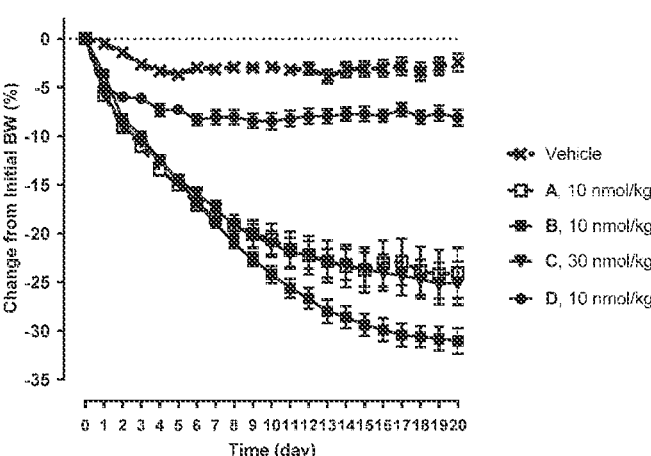
FIG. 11C displays the percent change in bodyweight of mice treated with peptide or vehicle control over 21 days. A: 122, B: 142, C: Semaglutide, D: Cotadutide.
Figure 11D:
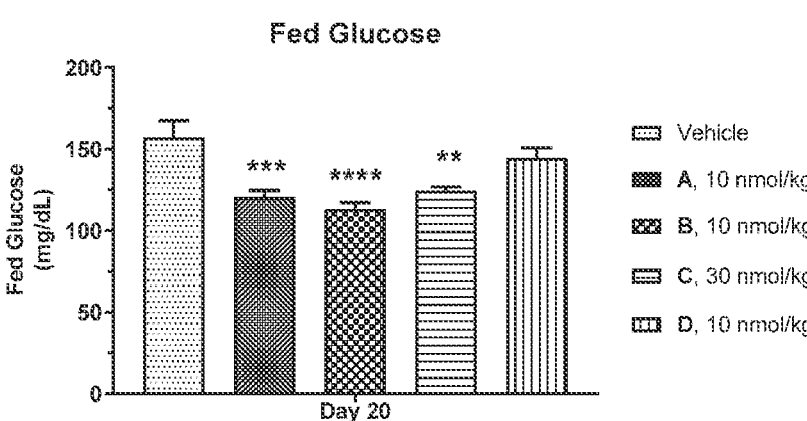
FIG. 11D depicts the effects of the compounds on plasma glucose excursions in fed state at day 20 compared to vehicle controls. A: 122, B: 142, C: Semaglutide, D: Cotadutide.
Figure 11E:
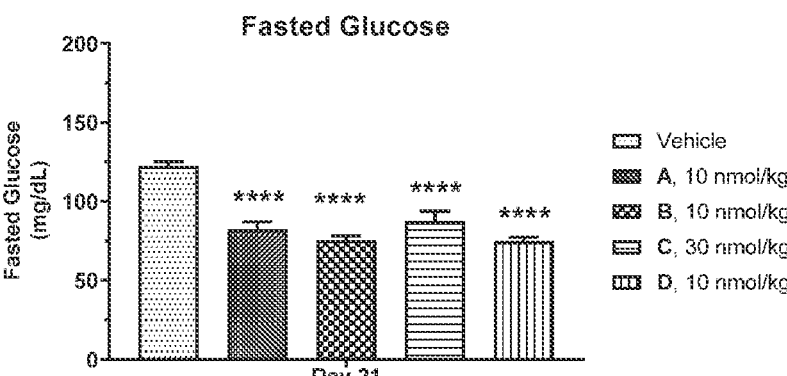
FIG. 11E depicts the effects of the compounds on plasma glucose excursions fasted states at day 20, compared to vehicle controls. A: 122, B: 142, C: Semaglutide, D: Cotadutide.
Figure 11F:
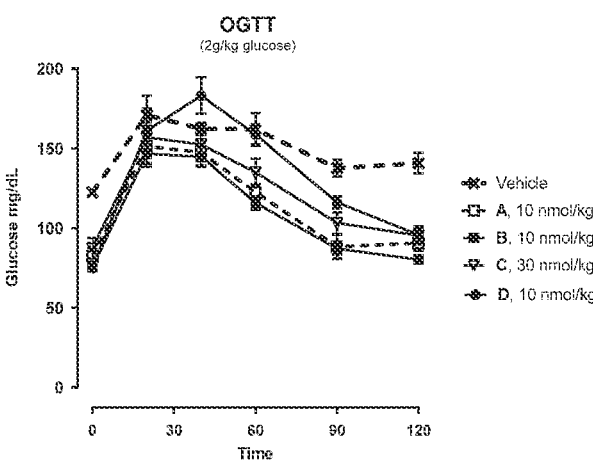
FIG. 11F depicts the effects of treatment with the compounds in an oral glucose tolerance test (OGTT) at day 21 compared to vehicle control. A: 122, B: 142, C: Semaglutide, D: Cotadutide.
Figure 11G:
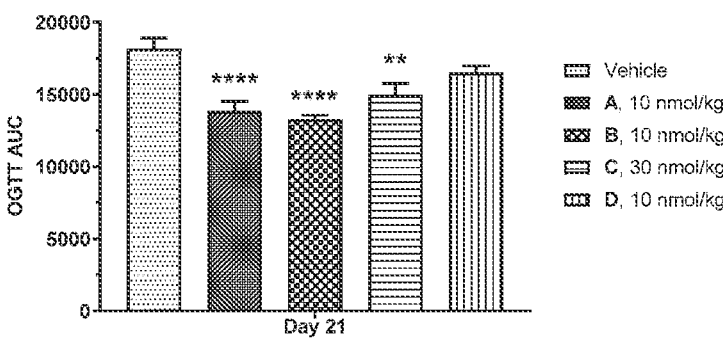
FIG. 11G depicts the levels of glucose as determined by measuring the area under curve (AUC). A: 122, B: 142, C: Semaglutide, D: Cotadutide.
Figure 11H:
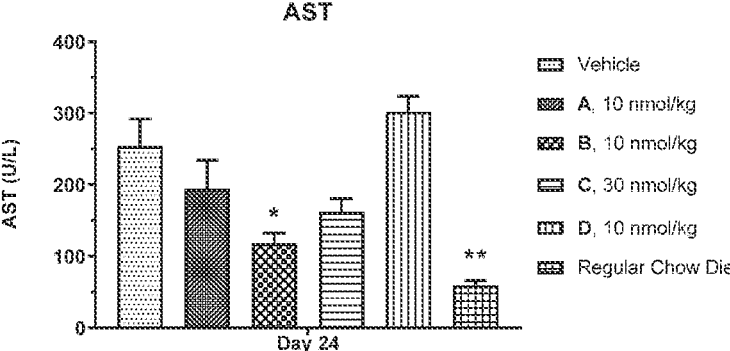
FIG. 11H depicts the effects of treatment with the compounds on plasma levels of aspartate aminotransferase (AST). A: 122, B: 142, C: Semaglutide, D: Cotadutide.
Figure 11I:
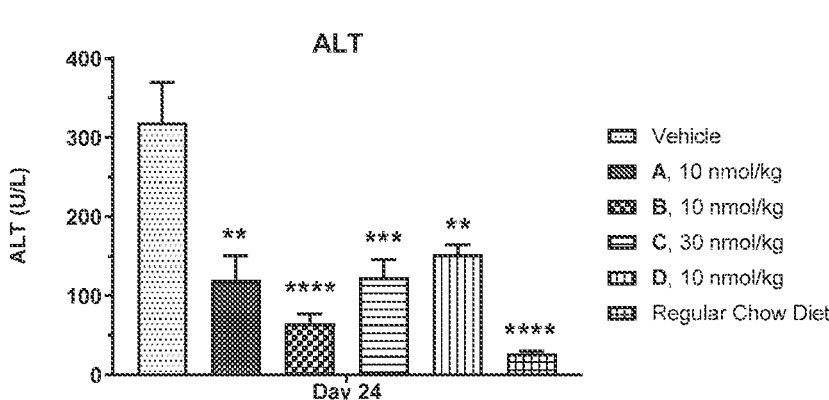
FIG. 11I depicts the effects of treatment with the compounds on plasma levels of alanine aminotransferase (ALT). A: 122, B: 142, C: Semaglutide, D: Cotadutide.
Figure 11J:
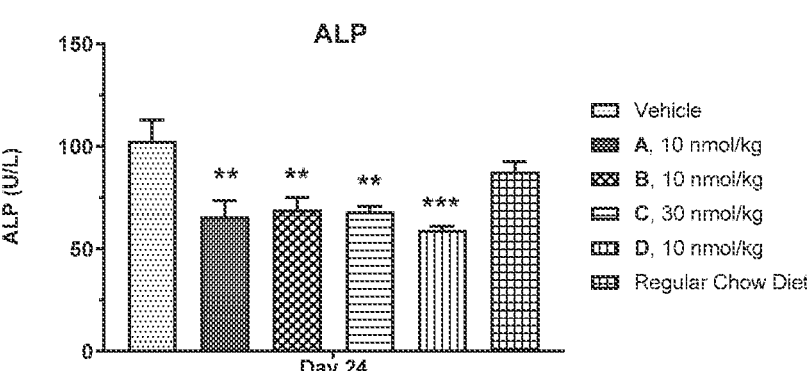
FIG. 11J depicts the effects of treatment with the compounds on plasma levels of alkaline phosphatase (ALP). A: 122, B: 142, C: Semaglutide, D: Cotadutide.
Figure 11K:
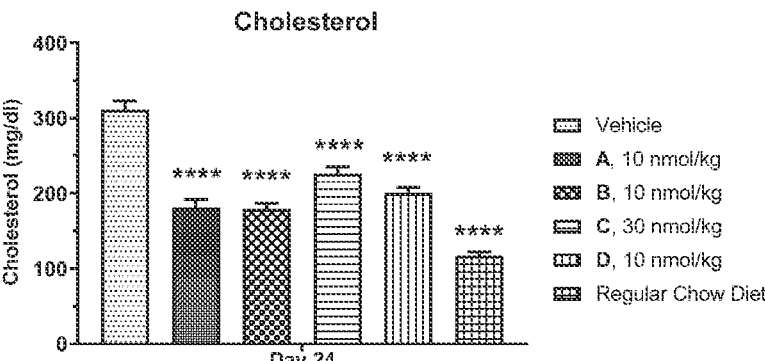
FIG. 11K depicts the effects of treatment with the compounds on plasma levels of cholesterol. A: 122, B: 142, C: Semaglutide, D: Cotadutide.
Figure 11L:
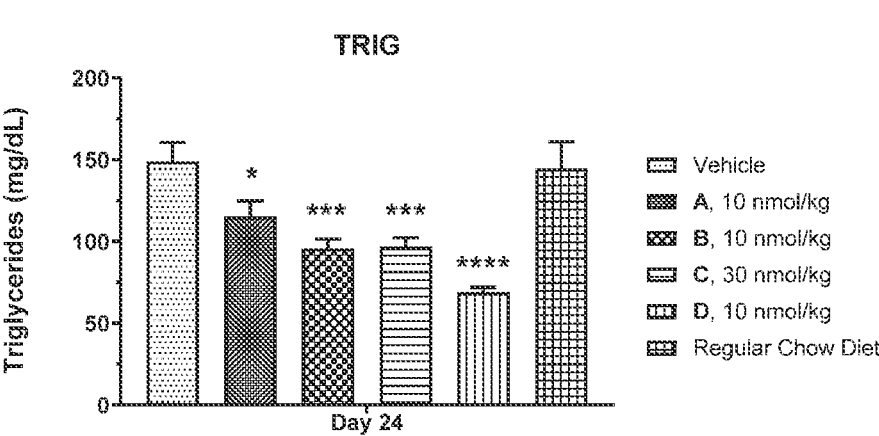
FIG. 11L depicts the effects of treatment with the compounds on plasma levels of triglycerides, respectively. A: 122, B: 142, C: Semaglutide, D: Cotadutide.
Figure 11M:
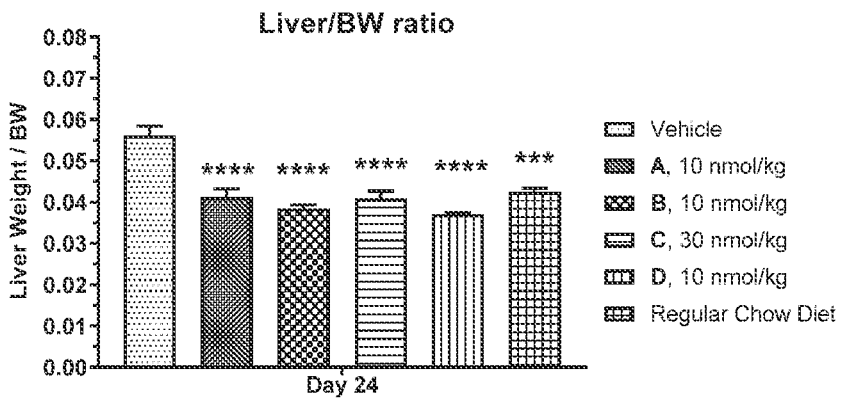
FIG. 11M depicts the effects of treatment with the compounds and vehicle control on the liver to bodyweight ratio. A: 122, B: 142, C: Semaglutide, D: Cotadutide.
Figure 11N:
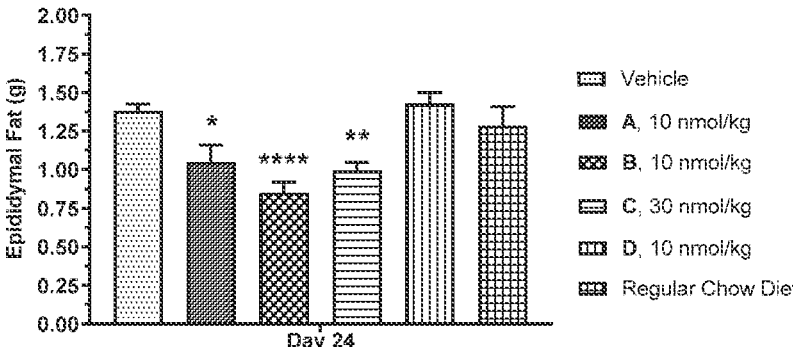
FIG. 11N depicts the effects of treatment with the compounds and vehicle control on the fat weight. A: 122, B: 142, C: Semaglutide, D: Cotadutide.
Figure 11O:
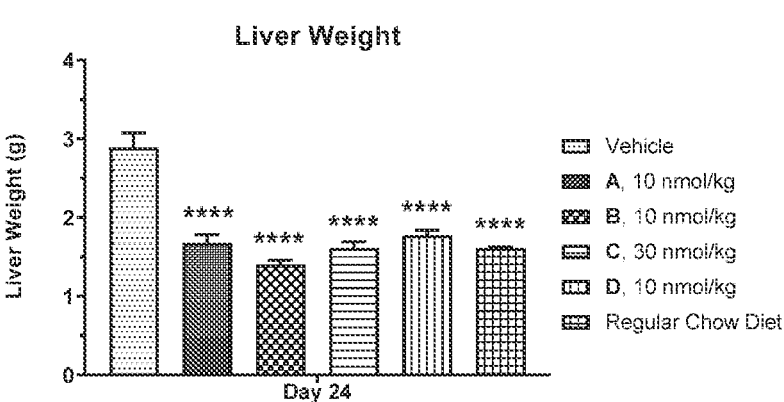
FIG. 11O depicts the effects of treatment with the compounds and vehicle control on the liver weight. A: 122, B: 142, C: Semaglutide, D: Cotadutide.
Figure 11P:
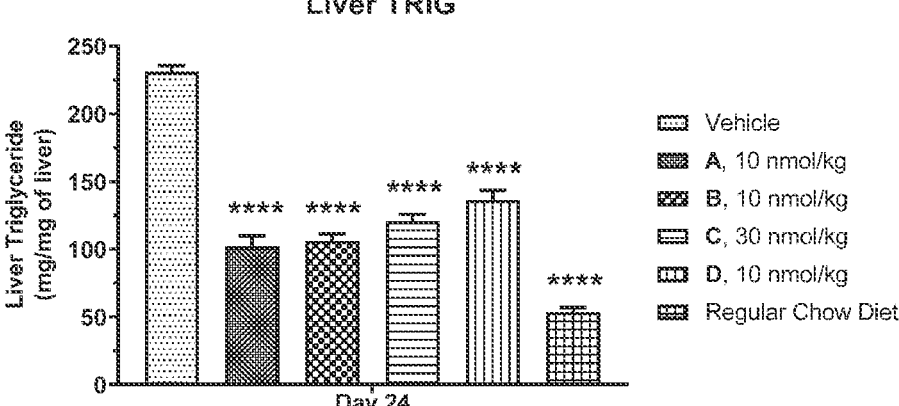
FIG. 11P depicts the effects of treatment with the compounds and vehicle control on liver triglyceride levels. A: 122, B: 142, C: Semaglutide, D: Cotadutide.
Figure 11Q:
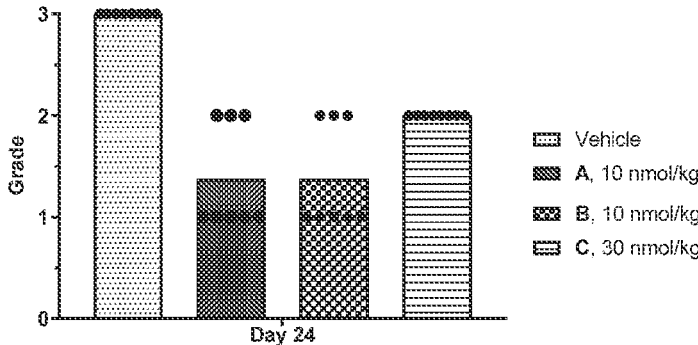
FIG. 11Q depicts the effects of treatment with the compounds and vehicle control on steatosis grade. A: 122, B: 142, C: Semaglutide, D: Cotadutide.

The results are shown in FIGS. 11A-11Q. For all figures, A: 122, B: 142, C: Semaglutide, D: Cotadutide. The vehicle control is PBS with a pH of 8.2. Mice treated with compound 122, compound 142, or semaglutide showed a reduction in food consumption over 20 days, compared to mice treated with vehicle alone, as depicted in FIG. 11A. Furthermore, mice treated with compound 122, compound 142, or semaglutide showed a decrease in both total bodyweight and percent change from initial bodyweight over 21 days when compared to mice treated with vehicle alone, as depicted in FIGS. 11B-11C. Treatment with these compounds also affected glucose levels. As depicted in FIGS. 11D-11E, mice treated with compound 122, compound 142, or semaglutide showed a significant decrease in plasma glucose excursions in a fed state at day 20 and a fasted state at day 21 compared to mice treated with vehicle alone. Mice treated with cotadutide only showed a significant decrease in plasma glucose excursions in a fasted state. In an oral glucose tolerance test (OGTT) performed at day 21, mice treated with compound 122, compound 142 or semaglutide showed a significant decrease in glucose levels over time and as measured by the area under the curve when compared to mice treated with vehicle alone, as depicted in FIGS. 11F-11G.

Treatment with these compounds affects plasma levels of markers of liver function. Treatment with compound 122 or semaglutide significantly reduced levels of ALT, ALP, cholesterol, and triglycerides compared to treatment with vehicle alone, while treatment with compound 142 significantly reduced levels of AST, ALT, ALP, cholesterol, and triglycerides compared to treatment with vehicle alone, as depicted in FIGS. 11J-11L. The liver to bodyweight ratio, liver weight, and liver triglyceride level was significantly decreased in mice treated with compound 122, compound 142, semaglutide, or cotadutide, compared to mice treated with vehicle alone, as depicted in FIGS. 11M, 11O, and 11P. Treatment with compound 122, compound 142, or semaglutide significantly reduced the fat weight, compared to mice treated with vehicle alone, as depicted in FIG. 11N. Steatosis grade was reduced in mice treated with compound 122, compound 142, or semaglutide compared to mice treated with vehicle alone.

Example U: cAMP Assay (GLP-1R Single Agonists)

HEK293 cells were infected with lentivirus encoding firefly luciferase gene under the control of cAMP responsive element (CRE) promoter (Qiagen, Netherlands) and then were selected using 1 g/mL puromycin (Life technologies, Carlsbad) for 1 week. The surviving cells (referred to as CRE-HEK293) were expanded and then transfected with a G418 selective mammalian expression plasmid encoding human GLP-1R. In brief, GLP-1R plasmid was transfected into CRE-HEK293 cells using Lipofectamine 2000 and selected with 400 µg/mL geneticin (Life technologies, Carlsbad, CA). Single colony stable cell line over-expressing both CRE-luciferase and GLP-1R (HEK293-GLP-1R-CRE) was then established for the in vitro activity assay.

HEK293-GLP-1R-CRE cells were seeded in 384-well plates at a density of 5000 cells per well and cultured for 18 hours in DMEM with 1000 FBS at 37° C. and 500 $CO_2$. Cells were treated with peptides in a dose dependent manner for 24 hours, and receptor activation was reported by luminescence intensities, using One-Glo (Promega, WI) luciferase reagent following manufacturer's instruction. The $EC_{50}$ of each peptide was determined using GraphPad Prism 6 software (GraphPad, San Diego, CA).

TABLE 29

| cAMP data (Peptide Conjugates) | | | |
|---|---|---|---|
| | GLP-1R - cAMP 0% FBS/nM | GLP-1R - cAMP 10% FBS/nM | GLP-1R - Cre-Luc/ nM |
| 177 | 0.025 | 6.4 | ND |
| 181 | 0.026 | ND | ND |
| 183 | 0.043 | ND | 0.03 (0.04 recomb.) |
| 184 | 0.047 | 7.8 | ND |
| 186 | ND | ND | 7.3 |

Example A: β-Arrestin Recruitment Assay

The results are shown in Tables 30-32.

TABLE 30

Potency of PrRP20 and PrRP31 Derivatives at the GPR10 Receptor.

| | | | GPR10 $EC_{50}$/nM[a] | | |
|---|---|---|---|---|---|
| SEQ ID NO | Di-Cys | No staple | With S1 | With S2 | With S3 | With S4 |
| 106 (PrRP20) | — | 13 ± 1 | — | — | — | — |
| 103 | 2-9 | 33 ± 3 | 12 ± 1 | 33 ± 4 | 230 ± 30 | 620 ± 60 |
| 104 | 3-10 | 16 ± 2 | 21 ± 2 | N.D. | N.D. | N.D. |
| 105 | 4-11 | 10 ± 1 | 7.3 ± 0.6 | 3.9 ± 0.2 | 77 ± 9 | 81 ± 7 |
| 83 | 5-12 | 44 ± 6 | 13 ± 1 | 25 ± 3 | 610 ± 80 | 840 |
| 84 | 6-13 | 18 ± 2 | 15 ± 2 | N.D. | N.D. | N.D. |
| 85 | 7-14 | 33 ± 4 | 10 ± 1 | 5.2 ± 0.6 | >1000 | >1000 |
| 86 | 8-15 | 6800 | 720 ± 80 | N.D. | N.D. | N.D. |
| 87 | 9-16 | 120 ± 10 | 160 ± 20 | N.D. | N.D. | N.D. |
| 88 | 10-17 | 1600 | >10000 | N.D. | N.D. | N.D. |
| 107 (PrRP31) | — | 12 ± 3 | — | — | — | — |
| 89 | 1-8 | 16 ± 2 | 24 ± 3 | 17 ± 2 | 230 ± 20 | 330 ± 30 |
| 90 | 6-13 | 29 ± 5 | 20 ± 3 | 13 ± 2 | 80 ± 10 | 260 ± 20 |
| 91 | 9-16 | 41 ± 4 | 85 ± 10 | N.D. | N.D. | N.D. |
| 92 | 13-20 | 18 ± 2 | 40 ± 6 | 17 ± 2 | 630 ± 80 | 1500 |
| 93 | 15-22 | 17 ± 2 | 10 ± 1 | 6.1 ± 0.4 | 80 ± 10 | 230 ± 20 |
| 94 | 16-23 | 70 ± 7 | 29 ± 3 | 23 ± 3 | 360 ± 40 | 2800 |
| 95 | 18-25 | 33 ± 4 | 18 ± 2 | 7.5 ± 0.9 | >1000 | >1000 |
| 96 | 20-27 | 920 | 130 ± 20 | N.D. | N.D. | N.D. |

[a]$EC_{50}$ determined in a β-arrestin recruitment assay using GPR10-overexpressing CHO-K1 cells. Cells were treated with the peptides at varying concentrations in triplicate for 90 min at 37° C., 5% $CO_2$. Luminescence was measured and plotted against log agonist concentration. The slope was fitted in Prism to generate the $EC_{50}$, reported as mean ± SEM (n = 3).

TABLE 31

Optimization of Sequence and Staple MEG-FA for C(6-13) PrRP31

| | | | GPR10 $EC_{50}$/nM[a] | | |
|---|---|---|---|---|---|
| SEQ ID NO | No staple | With S1 | With S2 | With S3 | With S4 |
| 107 (PrRP31) | 12 ± 3 | — | — | — | — |
| 90 | 29 ± 5 | 20 ± 3 | 13 ± 2 | 80 ± 10 | 260 ± 20 |
| 97 | 17 ± 2 | 10 ± 1 | 9.1 ± 0.9 | 26 ± 3 | 80 ± 10 |
| 98 | 13 ± 2 | 16 ± 2 | 5.1 ± 0.7 | 60 ± 7 | 81 ± 8 |
| 99 | 44 ± 5 | 34 ± 4 | 8.8 ± 0.8 | 120 ± 20 | 160 ± 20 |
| 100 | >200 | N.D. | N.D. | N.D. | N.D. |
| 101 | >200 | N.D. | N.D. | N.D. | N.D. |
| 102 | 100 ± 10 | 100 ± 10 | 10 ± 1 | 280 ± 30 | 1100 |

[a]$EC_{50}$ determined in a β-arrestin recruitment assay using GPR10-overexpressing CHO-K1 cells. Mean ± SEM (n = 3).

TABLE 32

Optimization of Staple MEG-FA for Nle8, hArg23, C(6-13) PrRP31

| | $EC_{50}$/nM[a] | | Ratio 10%/ | NPFF2R $EC_{50}$/nM[b] | | Ratio |
|---|---|---|---|---|---|---|
| Con-jugate | 10% FBS | 0% FBS | 0% FBS | 10% FBS | 0% FBS | NPFF2R/ GPR10[c] |
| 251 (97-L1) | 10 ± 1 | 5.9 ± 0.8 | 1.7 | 1200 | 920 | 160 |
| 255 (97-L3) | 9.1 ± 0.9 | 8.0 ± 0.7 | 1.1 | 220 ± 20 | 150 | 19 |
| 259 (97-L4) | 26 ± 3 | 12 ± 1 | 2.2 | >10 000 | 470 | 39 |
| 263 (97-L5) | 80 ± 10 | 7.8 ± 0.6 | 10 | >10 000 | 520 | 67 |
| 270 (97-L6) | 42 ± 4 | 12 ± 1 | 3.5 | 310 ± 30 | 270 | 23 |
| 271 (97-L7) | 39 ± 5 | 9 ± 1 | 4.3 | 140 ± 20 | 130 | 14 |

TABLE 32-continued

Optimization of Staple MEG-FA for Nle8, hArg23, C(6-13) PrRP31

| | $EC_{50}$/nM[a] | | Ratio 10%/ | NPFF2R $EC_{50}$/nM[b] | | Ratio |
|---|---|---|---|---|---|---|
| Con-jugate | 10% FBS | 0% FBS | 0% FBS | 10% FBS | 0% FBS | NPFF2R/ GPR10[c] |
| 267 (97-L8) | 830 | 24 ± 3 | 35 | ~10 000 | 560 | 23 |
| 268 (97-L9) | 120 ± 10 | 8.2 ± 0.9 | 15 | >10 000 | 9000 | 1100 |
| 269 (97-L12) | 120 ± 20 | 10 ± 1 | 12 | ~8000 | 1600 | 160 |

[a]$EC_{50}$ determined in β-arrestin recruitment assay using GPR10-overexpressing CHO-K1 cells in the presence (10%) or absence (0%) of FBS.
[b]$EC_{50}$ determined in a cAMP reporter assay using NPFF2R-overexpressing CHO cells in the presence (10%) or absence (0%) of FBS. Mean ± SEM (n = 3). NPFF2R-overexpressing CHO cells were treated with peptides in 12-point dose-response in culture medium and 0.5 mM IBMX (3-isobutyl-1-methylxanthine) to inhibit cAMP degradation, with 20 μM forskolin as positive control. The assay was carried out in triplicate for 30 min at 37° C., 5% $CO_2$, and cAMP detection kit from Cisbio was used to quantify cAMP accumulation. [c]Ratio was calculated using $EC_{50}$s obtained at 0% FBS.

Example B: Plasma Stability

Figure 12:
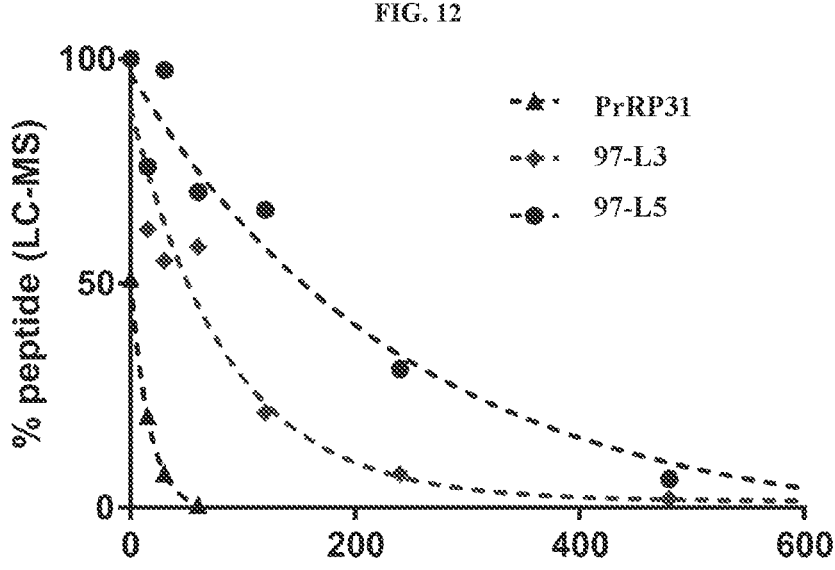
FIG. 12 shows the in vitro plasma stability of PrRP31, conjugate 255 (97-L3) and conjugate 263 (97-L5).

To investigate the stability of the conjugates in plasma, PrRP31, conjugate 255 (97-L3), and conjugate 263 (97-L5) were incubated in mouse plasma for up to 24 h (FIG. 12). The remaining intact peptide levels were quantified by LC-MS (QTOF) after precipitation of the serum proteins. The degradation of PrRP31 in mouse plasma was fast, with a half-life of ~11 min and complete disappearance after 1 h. Stapling with L3 at position 6-13 enhanced the stability, extending the half-life to 30-60 min. When conjugated to staple L5, the half-life was further increased to ~3 h.

Plasma stability was carried out in single replicate with incubation of peptides in mouse plasma at different time points followed by plasma protein precipitation in methanol and quantification via LC-MS.

Example C: Pharmacokinetics Studies

Figure 13:
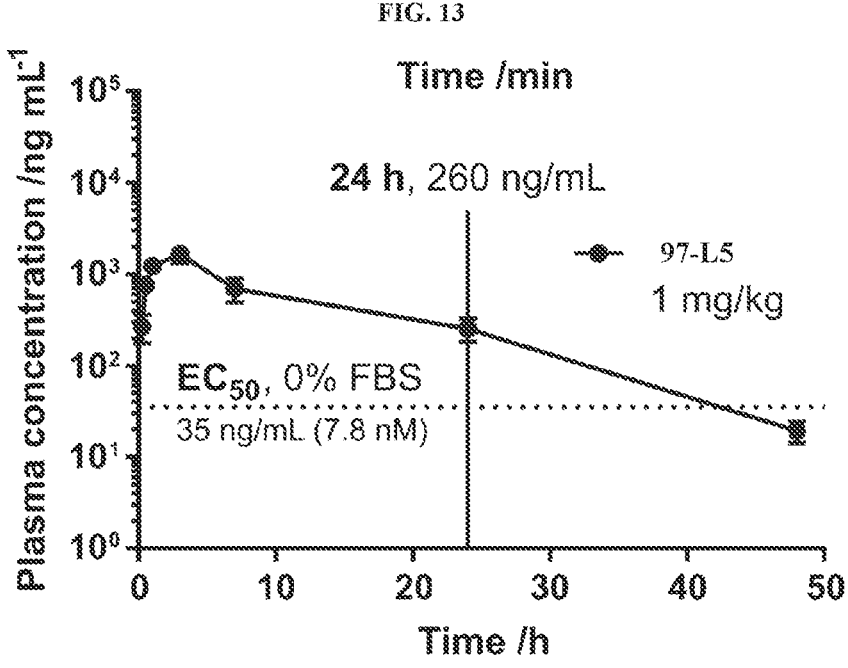
FIG. 13 shows the plasma concentration of conjugate 263 (97-L5) following single s.c. injection of 1 mg/kg in mice.

The pharmacokinetic profile of conjugate 263 (97-L5) was evaluated in male C57 mice upon s.c. injection at 1 mg/kg (FIG. 13). The peptide plasma concentration at various time points (0.25, 0.5, 1, 3, 7, 24, 48 and 72 h) was determined using LC-MS. A $C_{max}$ of ~1.67 µg/mL was reached at ~3 h post administration, with an elimination half-life of 8 h, which is similar to that of semaglutide in rodent.

Mouse PK studies were carried out using single s.c. injection of 1 mg/kg conjugate 263 (97-L5) in mice, and plasma samples were collected at different time points and quantified using LC-MS. PK parameters were calculated via fitting of the data using WinNonlin. Due to volume/sampling limitations in mice, sparse sampling was used. Therefore, a single PK profile was obtained by combining concentrations from various animals and PK parameter estimates were averaged. Therefore SEM is not reported.

Figure 14:
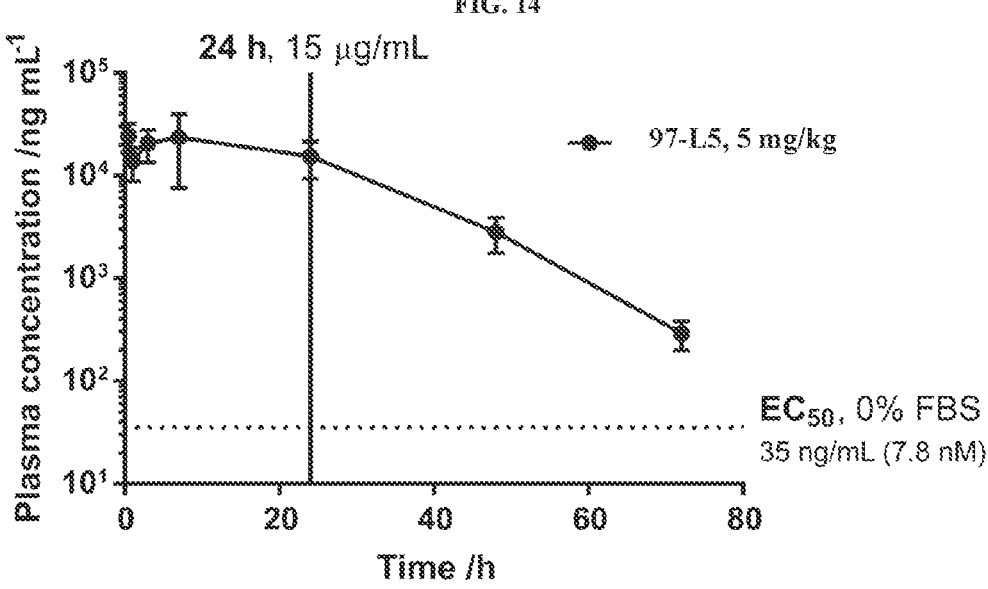
FIG. 14 shows the plasma concentration of conjugate 263 (97-L5) following single s.c. injection of 5 mg/kg in CD-1 female mice (n=4).

An additional PK study was carried out at 5 mg/kg dosing, and a similar pharmacokinetic profile was observed where plasma concentrations were determined using a cell-based functional assay (FIG. 14).

| | $t_{1/2}$/ h | $C_{max}$/ µg mL$^{-1}$ | $AUC_{last}$/h µg mL$^{-1}$ | $AUC_\infty$/h µg mL$^{-1}$ | $AUC_{0-24\,h}$/h µg mL$^{-1}$ |
|---|---|---|---|---|---|
| Mean | 8.44 | 32.4 | 648 | 652 | 444 |
| SD | 0.31 | 7.93 | 92.2 | 92.6 | 113 |
| CV % | 3.78 | 24.4 | 14.2 | 14.2 | 25.5 |

Example D: In Vivo Efficacy Assay

Figure 15:
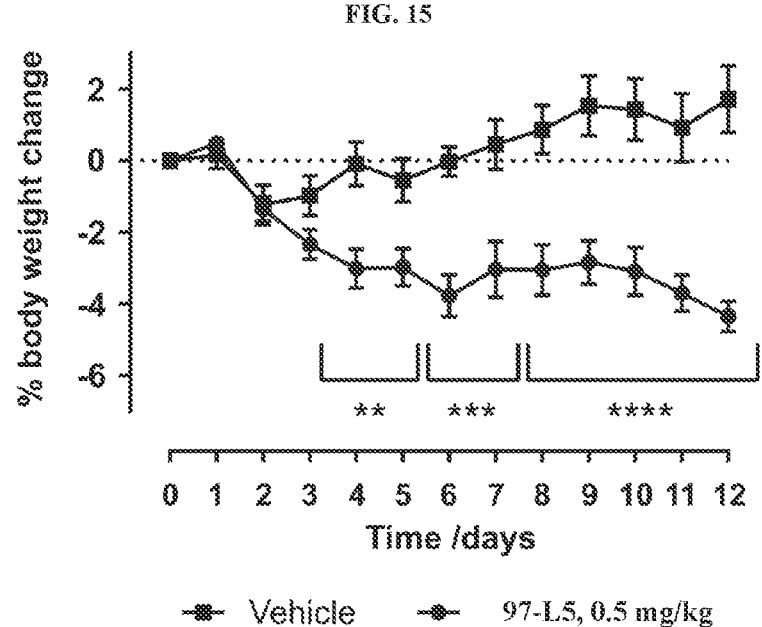
FIG. 15 shows the 12 day body weight study in a diet-induced obesity (DIO) mouse model (n=8 per group), with daily s.c. dosing of conjugate 263 (97-L5).
Figure 16:
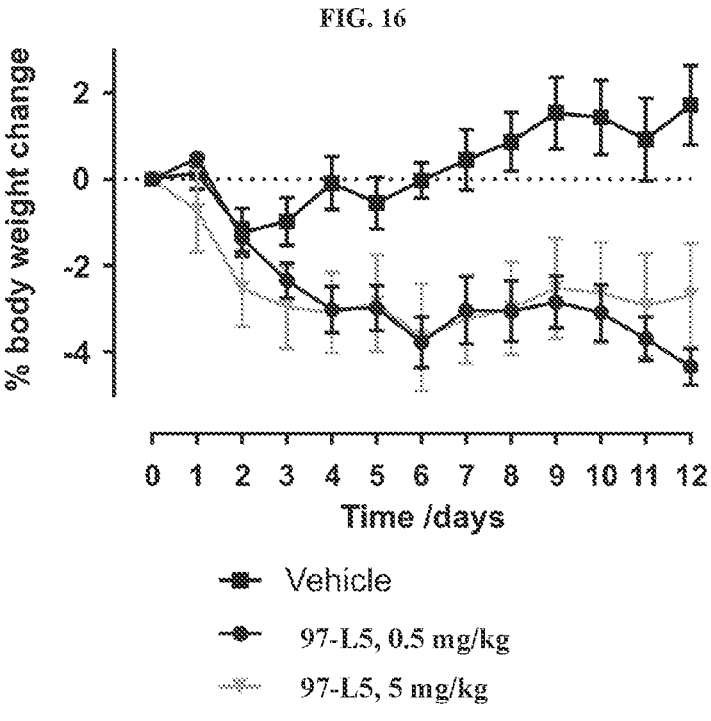
FIG. 16 shows the reduction in body weight of DIO model mice (n=8 per group) over a 12 day period with daily s.c. administration (0.5 and 5 mg/kg) of conjugate 263 (97-L5).

In order to demonstrate translation of extended half-life for conjugate 263 (97-L5) into in vivo efficacy, a 12 day body weight study in a diet-induced obesity (DIO) mouse model (n=8 per group), with daily s.c. dosing (FIG. 15) was carried out. A significant body weight reduction effect was observed for conjugate 263 (97-L5) at 0.5 mg/kg. A higher dose of 5 mg/kg compound 263 (97-L5) daily injection gave similar efficacy to the 0.5 mg/kg dose (FIG. 16), indicating that the $ED_{50}$ for conjugate 263 (97-L5) is lower than 0.5 mg/kg. While this selectivity appears to result in a reduced anorexigenic effect, conjugate 263 (97-L5) is expected to exhibit a more favorable safety profile with regards to undesirable cardiovascular side effects associated with NPFF2R agonism. The 24 h plasma exposures for the 5 mg/kg and 1 mg/kg PK studies are significantly higher than the $EC_{50}$ for conjugate 263 (97-L5), which may indicate that lower doses are required to show a dose-response effect. Detailed dose-response and efficacy studies in more chronic obesity and metabolic disease models are currently underway.

Efficacy was carried out in diet-induced obesity (DIO) mice, dosed daily with conjugate 263 (97-L5) at 0.5 mg/kg s.c. or vehicle over a 12 day period (n=8). Body weight was significantly reduced compared to vehicle treatment; **=$p \leq 0.0001$, *=$p \leq 0.001$, **=$p \leq 0.01$.

Example E: In Vivo Body Weight Study and Oral Glucose Tolerance Test (OGTT)

Figure 17:
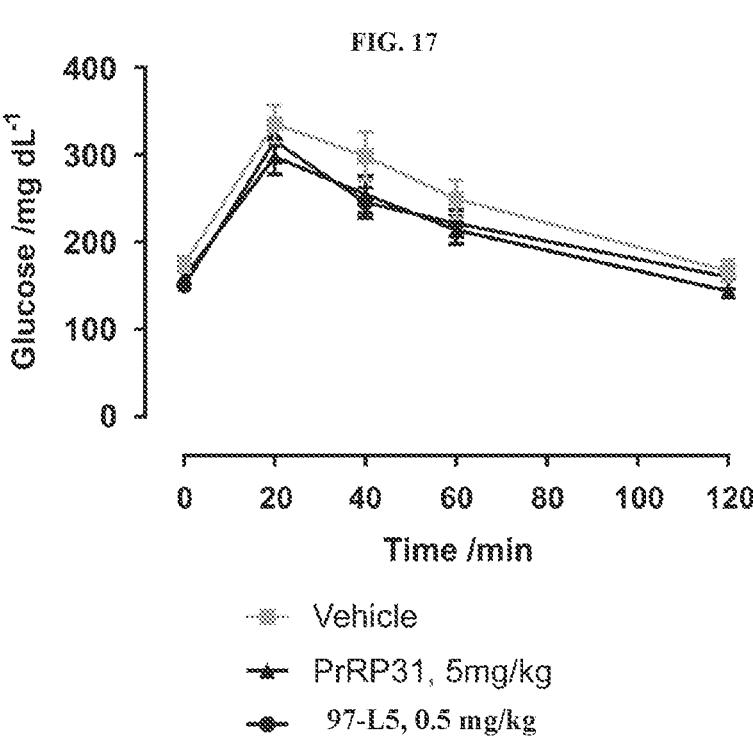
FIG. 17 shows the glucose levels after oral administration of PrRP31 and conjugate 263 (97-L5) in fasted diet-induced obesity (DIO) model mice on day 14 of in vivo body weight study.
Figure 18:
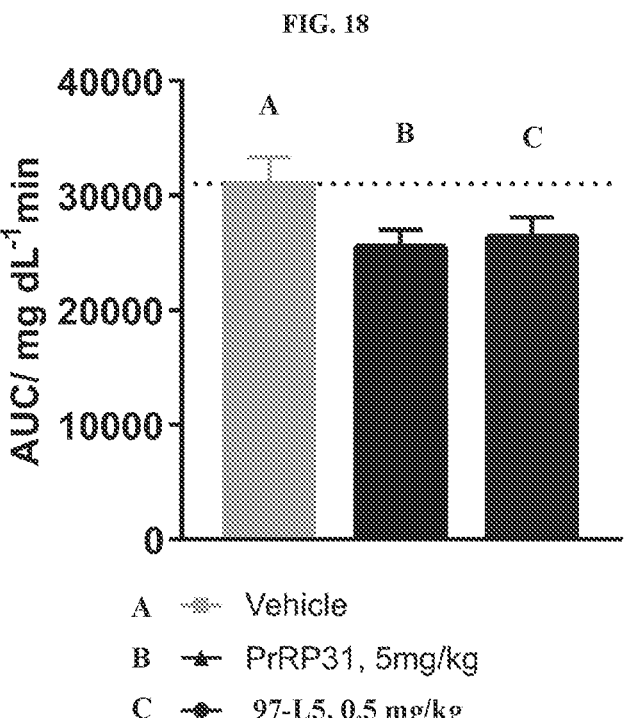
FIG. 18 shows the AUC after oral administration of PrRP31 and conjugate 263 (97-L5) in fasted diet-induced obesity (DIO) model mice on day 14 of in vivo body weight study.

All animal care and experimental procedures were approved by the Institutional Animal Care and Use Committee (IACUC) of the California Institute for Biomedical Research (Calibr) and strictly followed the NIH guidelines for humane treatment of animals. Charles River diet-induced obesity (DIO) model male mice (age 24 weeks from Jackson Labs, Bar Harbor, ME) maintained on high fat diet (D12492, 60% fat diet) for 18 weeks, were administered peptide by daily subcutaneous injection at either 0.5 or 5 mg/kg dose for up to 12 days (group housed 2 per cage). The average body weight at the beginning of the experiment was 50 g. Mouse body weight was monitored daily throughout the study, and food intake on days 1, 2, 6 and 9. Mice were fasted overnight prior to the oral glucose tolerance test (OGTT) on day 14, and then dosed with peptide. After 6 h, 1 g of glucose solution per kg body weight was administered orally, and mouse tail blood glucose levels were measured before (0 min) and after glucose challenge for 2 h. The data were compared using the unpaired Student's t test. Where appropriate, data were compared using repeated measures or one-way analysis of variance, followed by the Student-Newman-Keuls post hoc test. Glucose levels and AUCs are shown in FIG. 17 and FIG. 18 after oral administration of PrRP31 and conjugate 263 (97-L5).

What is claimed is:

1. A peptide conjugate comprising:

a) a peptide comprising SEQ ID NO: 6, or an amino acid sequence having one one amino acid addition, deletion, or substitution relative to the sequence from SEQ ID NO: 6; and b) a staple attached to the peptide at a first amino acid and a second amino acid, wherein the first amino acid and second amino acid is independently cysteine or homo-cysteine, wherein the first amino acid has a position i in the peptide and the second amino acid has a position i+7 in the peptide, wherein the staple is:

wherein
each $L^1$ is independently -alkylene-O—, —O-alkylene-, —C(=O)NH—, —NHC(=O)-, -alkylene-C(=O)NH—, —alkylene-NHC(=O)-, or —(CR$^1$R$^2$)—, wherein each $R^1$ and $R^2$ is independently hydrogen, $C_{1-6}$ alkyl, or —COOH, and v is 2-20;
s1 is 1-15; and
Y is COOH.

2. The peptide conjugate of claim 1, wherein the staple has the structure:

wherein each "⸜-S" is a sulfur atom of the first amino acid or the second amino acid.

3. The peptide conjugate of claim 1, wherein the half-life of the peptide conjugate is at least about 2-fold greater than the half-life of the peptide without conjugation to the staple.

4. The peptide conjugate of claim 1, wherein the staple has the structure:

wherein each "⸜-S" is a sulfur atom of the first amino acid or the second amino acid.

5. The peptide conjugate of claim 1, wherein the staple
has the structure:

wherein each " ⌇ -S" is a sulfur atom of the first amino acid
or the second amino acid.

\* \* \* \* \*